(12) United States Patent
Hirschmann et al.

(10) Patent No.: US 10,208,251 B2
(45) Date of Patent: *Feb. 19, 2019

(54) LIQUID-CRYSTALLINE MEDIUM

(71) Applicant: MERCK PATENT GMBH, Darmstadt (DE)

(72) Inventors: Harald Hirschmann, Darmstadt (DE); Monika Bauer, Seligenstadt (DE); Martina Windhorst, Muenster (DE); Marcus Reuter, Darmstadt (DE); Constanze Brocke, Gross-Gerau (DE); Rocco Fortte, Frankfurt am Main (DE); Matthias Bremer, Darmstadt (DE); Sabine Schoen, Herten (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/337,319

(22) Filed: Oct. 28, 2016

(65) Prior Publication Data

US 2017/0044437 A1 Feb. 16, 2017

Related U.S. Application Data

(62) Division of application No. 14/740,534, filed on Jun. 16, 2015.

(30) Foreign Application Priority Data

Jun. 17, 2014 (DE) .................. 10 2014 008 624
Aug. 29, 2014 (DE) .................. 10 2014 012 565

(51) Int. Cl.
*G02F 1/1333* (2006.01)
*C09K 19/34* (2006.01)
(Continued)

(52) U.S. Cl.
CPC .......... *C09K 19/3491* (2013.01); *C07C 69/52* (2013.01); *C07C 69/602* (2013.01); *C07D 311/18* (2013.01); *C09K 19/0403* (2013.01); *C09K 19/14* (2013.01); *C09K 19/20* (2013.01); *C09K 19/3001* (2013.01); *C09K 19/3003* (2013.01); *C09K 19/3066* (2013.01); *C09K 19/3098* (2013.01); *C09K 19/3405* (2013.01); *C09K 19/3458* (2013.01); *C09K 19/542* (2013.01); *G02F 1/137* (2013.01); *G02F 1/1362* (2013.01); *G02F 1/133723* (2013.01); *C09K 2019/0411* (2013.01); *C09K 2019/122* (2013.01); *C09K 2019/123* (2013.01); *C09K 2019/163* (2013.01); *C09K 2019/301* (2013.01); *C09K 2019/3004* (2013.01); *C09K 2019/3009* (2013.01); *C09K 2019/3016* (2013.01);
(Continued)

(58) Field of Classification Search
CPC ...... C09K 2019/0411; C09K 2019/122; C09K 2019/123; C09K 2019/3004; C09K 2019/301; C09K 2019/3016; C09K 2019/3027; C09K 2019/163; C09K 2019/3408; C09K 2019/548; C09K 2019/3009; C09K 2019/3021; C09K 19/3491; C09K 19/0403; C09K 19/14; C09K 19/20; C09K 19/52; C09K 19/3001; C09K 19/3066; C09K 19/3098; C09K 19/3405; C09K 19/542; C09K 19/3003; C09K 19/3458; G02F 1/133723; G02F 1/137; G02F 1/1362; G02F 1/1333; G02F 2001/133742; C07C 69/52; C07C 69/602; C07D 311/18
USPC .................................................. 252/299.66
See application file for complete search history.

(56) References Cited

U.S. PATENT DOCUMENTS 6,210,761 B1    4/2001  Kondo et al.
6,896,939 B2 *  5/2005  Klasen-Memmer ... C09K 19/42
                                                   252/299.61
(Continued)

FOREIGN PATENT DOCUMENTS

CN    103215046 A    7/2013
CN    103459554 A    12/2013
(Continued)

OTHER PUBLICATIONS

Office Action dated Jan. 5, 2018 issued in copending U.S. Appl. No. 14/740,534 (pp. 1-12).
(Continued)

*Primary Examiner* — Geraldina Visconti
(74) *Attorney, Agent, or Firm* — Millen White Zelano & Branigan, PC

(57) ABSTRACT

The invention relates to a liquid-crystalline medium which comprises at least one compound of the formula I,

I $$R^1-\phantom{X}-Z^1-\phantom{X}(L^3)-Z^2-\phantom{X}(L^2)(L^1)-R^{1*}$$

in which
$R^1$, $R^{1*}$, $Z^1$, $Z^2$ and $L^{1-3}$ have the meanings defined herein, and to the use thereof for an active-matrix display, in particular based on the VA, PSA, PS-VA, PALC, FFS, PS-FFS, PS-IPS or IPS effect.

57 Claims, No Drawings

(51) Int. Cl.
- *C09K 19/04* (2006.01)
- *C09K 19/14* (2006.01)
- *C09K 19/20* (2006.01)
- *C07C 69/52* (2006.01)
- *C07C 69/602* (2006.01)
- *C07D 311/18* (2006.01)
- *C09K 19/30* (2006.01)
- *C09K 19/54* (2006.01)
- *G02F 1/1362* (2006.01)
- *G02F 1/137* (2006.01)
- *G02F 1/1337* (2006.01)
- *C09K 19/12* (2006.01)
- *C09K 19/16* (2006.01)

(52) U.S. Cl.
CPC ........ *C09K 2019/3021* (2013.01); *C09K 2019/3027* (2013.01); *C09K 2019/3408* (2013.01); *C09K 2019/548* (2013.01); *G02F 2001/133742* (2013.01)

(56) References Cited

U.S. PATENT DOCUMENTS

| | | |
|---|---|---|
| 2003/0222245 A1 | 12/2003 | Klasen-Memmer et al. |
| 2013/0183460 A1 | 7/2013 | Klasen-Memmer |
| 2014/0028964 A1 | 1/2014 | Klasen-Memmer |
| 2016/0053178 A1 | 2/2016 | Hirschmann |
| 2016/0152587 A1 | 6/2016 | Hirschmann |
| 2017/0044437 A1 | 2/2017 | Hirschmann |
| 2017/0044438 A1 | 2/2017 | Hirschmann |
| 2018/0030350 A1* | 2/2018 | Hirschmann ...... C09K 19/3098 |

FOREIGN PATENT DOCUMENTS

| | | |
|---|---|---|
| EP | 0945418 A1 | 9/1999 |
| EP | 1352943 A1 | 10/2003 |

OTHER PUBLICATIONS

European Search Report dated Nov. 4, 2015 issued in corresponding application EP 15001562 (pp. 1-7).

Office Action dated Sep. 8, 2017 issued in copending U.S. Appl. No. 14/740,534 (pp. 1-7).

Office Action dated Aug. 28, 2017 issued in copending U.S. Appl. No. 15/337,447 (pp. 1-8).

Office Action dated Mar. 9, 2018 issued in copending U.S. Appl. No. 15/337,447(pp. 1-11).

Office Action dated Sep. 21, 2018 issued in corresponding CN application 20150488845.4 (pp. 1-7).

* cited by examiner

LIQUID-CRYSTALLINE MEDIUM

The invention relates to a liquid-crystalline medium which comprises at least one compound of the formula I,

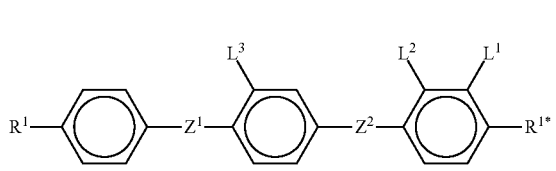

in which

R$^1$ and R$^{1*}$ each, independently of one another, denote an alkyl or alkoxy radical having 1 to 15 C atoms, where, in addition, one or more CH$_2$ groups in these radicals may each optionally be replaced, independently of one another, by —C≡C—, —CF$_2$O—, —CH=CH—,

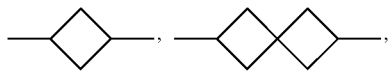

—O—, —CO—O—, —O—CO— in such a way that O atoms are not linked directly to one another, and in which, in addition, one or more H atoms may each optionally be replaced by halogen, Z$^1$ and Z$^2$ each, independently of one another, denote a single bond, —CH$_2$CH$_2$—, —CH=CH—, —CH$_2$O—, —OCH$_2$—, —CF$_2$O—, —OF$_2$—, —COO—, —OCO—, —C$_2$F$_4$—, —C≡C—, —CF=CF—, or —CH=CHCH$_2$O—, L$^{1-3}$ each, independently of one another, denote F, Cl, CF$_3$, OCF$_3$ or CHF$_2$.

Media of this type can be used, in particular, for electro-optical displays having active-matrix addressing based on the ECB effect and for IPS (in-plane switching) displays or FFS (fringe field switching) displays.

The principle of electrically controlled birefringence, the ECB effect or also DAP (deformation of aligned phases) effect, was described for the first time in 1971 (M. F. Schieckel and K. Fahrenschon, "Deformation of nematic liquid crystals with vertical orientation in electrical fields", Appl. Phys. Lett. 19 (1971), 3912). This was followed by papers by J. F. Kahn (Appl. Phys. Lett. 20 (1972), 1193) and G. Labrunie and J. Robert (J. Appl. Phys. 44 (1973), 4869).

The papers by J. Robert and F. Clerc (SID 80 Digest Techn. Papers (1980), 30), J. Duchene (Displays 7 (1986), 3) and H. Schad (SID 82 Digest Techn. Papers (1982), 244) showed that liquid-crystalline phases must have high values for the ratio of the elastic constants K$_3$/K$_1$, high values for the optical anisotropy Δn and values for the dielectric anisotropy of Δ∈≤−0.5 in order to be suitable for use in high-information display elements based on the ECB effect. Electro-optical display elements based on the ECB effect have a homeotropic edge alignment (VA technology=vertically aligned). Dielectrically negative liquid-crystal media can also be used in displays which use the so-called IPS or FFS effect.

Displays which use the ECB effect, as so-called VAN (vertically aligned nematic) displays, for example in the MVA (multi-domain vertical alignment, for example: Yoshide, H. et al., paper 3.1: "MVA LCD for Notebook or Mobile PCs . . . ", SID 2004 International Symposium, Digest of Technical Papers, XXXV, Book I, pp. 6 to 9, and Liu, C. T. et al., paper 15.1: "A 46-inch TFT-LCD HDTV Technology . . . ", SID 2004 International Symposium, Digest of Technical Papers, XXXV, Book II, pp. 750 to 753), PVA (patterned vertical alignment, for example: Kim, Sang Soo, paper 15.4: "Super PVA Sets New State-of-the-Art for LCD-TV", SID 2004 International Symposium, Digest of Technical Papers, XXXV, Book II, pp. 760 to 763), ASV (advanced super view, for example: Shigeta, Mitzuhiro and Fukuoka, Hirofumi, paper 15.2: "Development of High Quality LCDTV", SID 2004 International Symposium, Digest of Technical Papers, XXXV, Book II, pp. 754 to 757) modes, have established themselves as one of the three more recent types of liquid-crystal display that are currently the most important, in particular for television applications, besides IPS (in-plane switching) displays (for example: Yeo, S. D., paper 15.3: "An LC Display for the TV Application", SID 2004 International Symposium, Digest of Technical Papers, XXXV, Book II, pp. 758 & 759) and the long-known TN (twisted nematic) displays. The technologies are compared in general form, for example, in Souk, Jun, SID Seminar 2004, seminar M-6: "Recent Advances in LCD Technology", Seminar Lecture Notes, M-6/1 to M-6/26, and Miller, Ian, SID Seminar 2004, seminar M-7: "LCD-Television", Seminar Lecture Notes, M-7/1 to M-7/32. Although the response times of modern ECB displays have already been significantly improved by addressing methods with overdrive, for example: Kim, Hyeon Kyeong et al., paper 9.1: "A 57-in. Wide UXGA TFT-LCD for HDTV Application", SID 2004 International Symposium, Digest of Technical Papers, XXXV, Book I, pp. 106 to 109, the achievement of video-compatible response times, in particular on switching of grey shades, is still a problem which has not yet been satisfactorily solved.

Industrial application of this effect in electro-optical display elements requires LC phases, which have to satisfy a multiplicity of requirements. Particularly important here are chemical resistance to moisture, air and physical influences, such as heat, infrared, visible and ultraviolet radiation and direct and alternating electric fields.

Furthermore, industrially usable LC phases are required to have a liquid-crystalline mesophase in a suitable temperature range and low viscosity.

None of the hitherto-disclosed series of compounds having a liquid-crystalline mesophase includes a single compound which meets all these requirements. Mixtures of two to 25, preferably three to 18, compounds are therefore generally prepared in order to obtain substances which can be used as LC phases. However, it has not been possible to prepare optimum phases easily in this way since no liquid-crystal materials having significantly negative dielectric anisotropy and adequate long-term stability were hitherto available.

Matrix liquid-crystal displays (MLC displays) are known. Non-linear elements which can be used for individual switching of the individual pixels are, for example, active elements (i.e. transistors). The term "active matrix" is then used, where a distinction can be made between two types:
1. MOS (metal oxide semiconductor) transistors on a silicon wafer as substrate
2. thin-film transistors (TFTs) on a glass plate as substrate.

In the case of type 1, the electro-optical effect used is usually dynamic scattering or the guest-host effect. The use of single-crystal silicon as substrate material restricts the display size, since even modular assembly of various part-displays results in problems at the joints.

In the case of the more promising type 2, which is preferred, the electro-optical effect used is usually the TN effect.

A distinction is made between two technologies: TFTs comprising compound semiconductors, such as, for example, CdSe, or TFTs based on polycrystalline or amorphous silicon. The latter technology is being worked on intensively worldwide.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully color-capable displays, in which a mosaic of red, green and blue filters is arranged in such a way that a filter element is opposite each switchable pixel.

The term MLC displays here encompasses any matrix display with integrated non-linear elements, i.e. besides the active matrix, also displays with passive elements, such as varistors or diodes (MIM=metal-insulator-metal).

MLC displays of this type are particularly suitable for TV applications (for example pocket TVs) or for high-information displays in automobile or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210-288 Matrix LCD Controlled by Double Stage Diode Rings, pp. 141 ff., Paris; STROMER, M., Proc. Eurodisplay 84, September 1984: Design of Thin Film Transistors for Matrix Addressing of Television Liquid Crystal Displays, pp. 145 ff., Paris]. With decreasing resistance, the contrast of an MLC display deteriorates. Since the specific resistance of the liquid-crystal mixture generally drops over the life of an MLC display owing to interaction with the inside surfaces of the display, a high (initial) resistance is very important for displays that have to have acceptable resistance values over a long operating period.

There is still a great demand for MLC displays having very high specific resistance at the same time as a large working-temperature range, short response times and a low threshold voltage, with the aid of which various grey shades can be generated.

The disadvantage of the MLC-TN displays frequently used is due to their comparatively low contrast, the relatively high viewing-angle dependence and the difficulty of generating grey shades in these displays.

VA displays have significantly better viewing-angle dependencies and are therefore principally used for televisions and monitors. However, there continues to be a need to improve the response times here. However, properties such as, for example, the low-temperature stability and the reliability must not be impaired at the same time.

The invention is based on the object of providing liquid-crystal mixtures, in particular for monitor and TV applications, based on the ECB effect or on the IPS or FFS effect, which do not have the disadvantages indicated above, or only do so to a reduced extent. In particular, it must be ensured for monitors and televisions that they also work at extremely high and extremely low temperatures and at the same time have short response times and at the same time have an improved reliability behavior, in particular exhibit no or significantly reduced image sticking after long operating times.

Surprisingly, it is possible to improve the rotational viscosity values and thus the response times if one or more, preferably at least one or two, polar compounds of the general formula I are used in liquid-crystal mixtures, in particular in LC mixtures having negative dielectric anisotropy $\Delta\epsilon$, preferably for VA, IPS and FFS displays. With the aid of the compounds of the formula I, it is possible to prepare liquid-crystal mixtures, preferably VA, PS-VA, PSA, IPS and FFS mixtures which have short response times, at the same time good phase properties and good low-temperature behavior. The liquid-crystalline mixtures according to the invention are distinguished, in particular, by a very good ratio of the rotational viscosities and the elastic constants, preferably $K_3$.

The invention thus relates to a liquid-crystalline medium which comprises at least one compound of the formula I.

The mixtures according to the invention preferably exhibit very broad nematic phase ranges with clearing points $\geq 65°$ C., preferably $\geq 70°$ C., in particular $\geq 75°$ C., very favorable values of the capacitive threshold, relatively high values of the holding ratio and at the same time very good low-temperature stabilities at $-20°$ C. and $-30°$ C., as well as very low rotational viscosity values and short response times. The mixtures according to the invention are furthermore distinguished by the fact that, in addition to the improvement in the rotational viscosity $\gamma_1$, relatively high values of the elastic constants $K_{33}$ for improving the response times can be observed. The compounds of the formula I are suitable, in particular, for the preparation of liquid-crystalline mixtures having a negative $\Delta\epsilon$.

Some preferred embodiments of the mixtures according to the invention are indicated below.

In the compounds of the formula I, $R^1$ preferably denotes straight-chain alkyl, in particular $CH_3$, $C_2H_5$, n-$C_3H_7$, n-$C_4H_9$, n-$O_5H_{11}$ and n-$C_6H_{13}$, furthermore alkenyl and alkoxy In the compounds of the formula I, $R^{1*}$ preferably denotes straight-chain alkoxy, in particular $OC_2H_5$, $OC_3H_7$, $OC_4H_9$, $OC_5H_{11}$, $OC_6H_{13}$, furthermore alkenyloxy, in particular $OCH_2CH=CH_2$, $OCH_2CH=CHCH_3$, $OCH_2CH=CHC_2H_5$, furthermore alkyl, in particular n-$C_3H_7$, n-$C_4H_9$, n-$C_5H_{11}$, n-$C_6H_{13}$.

In the compounds of the formula I, $Z^1$ and $Z^2$ preferably each, independently of one another, denote a single bond.

The radicals $L^1$, $L^2$ and $L^3$, independently of one another, preferably all denote F.

$Z^1$ and $Z^2$ preferably both denote a single bond.

Preferred compounds of the formula I are the compounds of the formulae I-a to I-h,

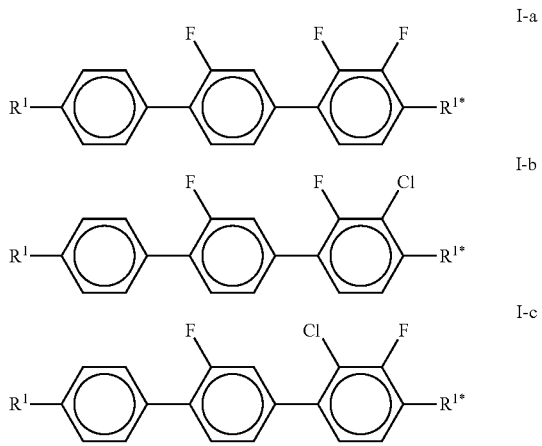

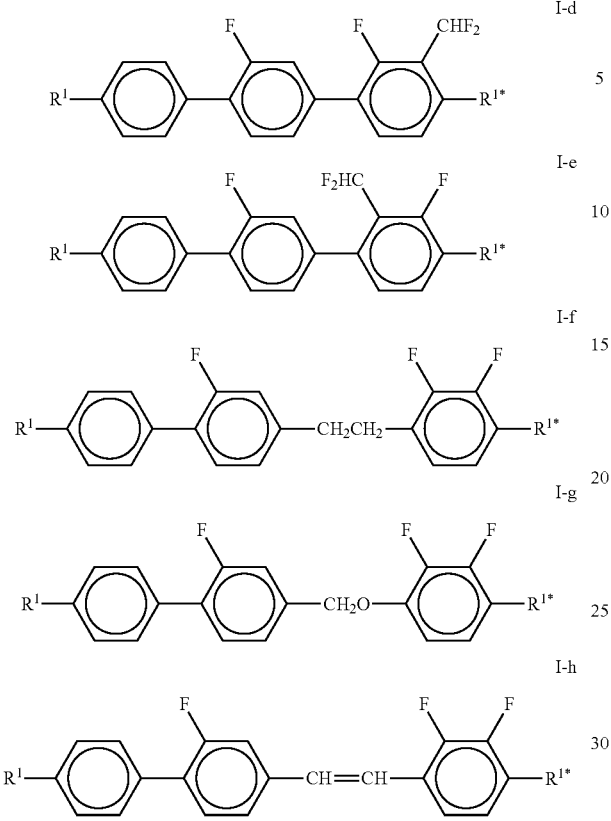
Particular preference is given to the compound of the formula I-a.
Very particularly preferred compounds of the formula I are shown below:
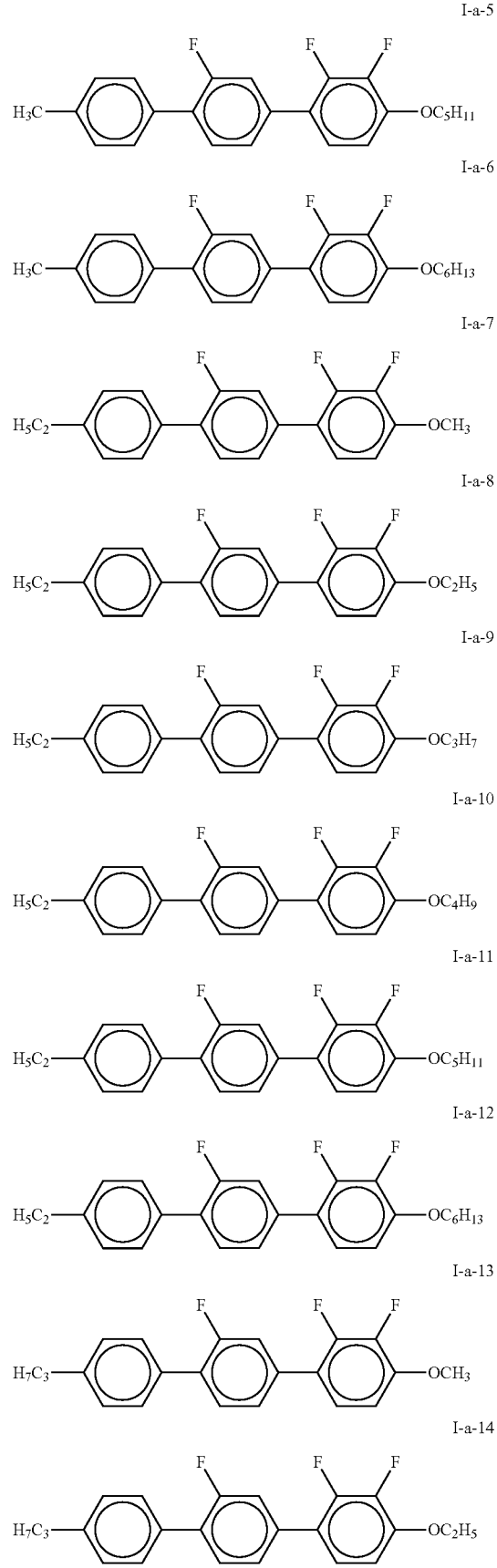

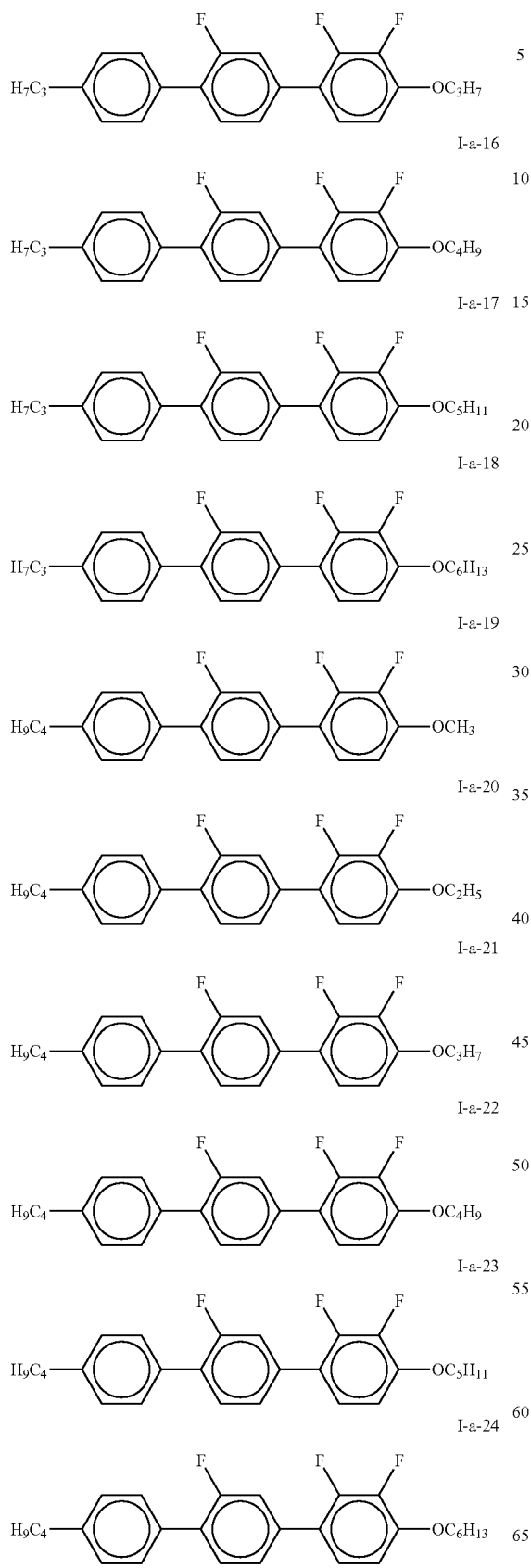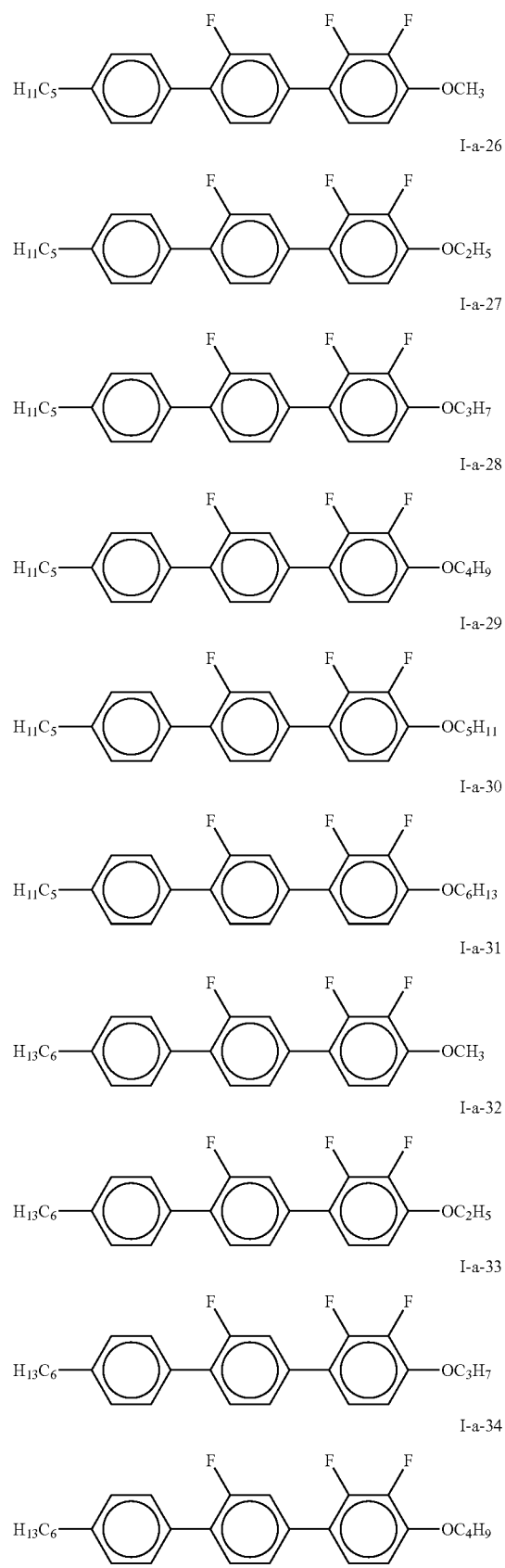

-continued

I-a-35

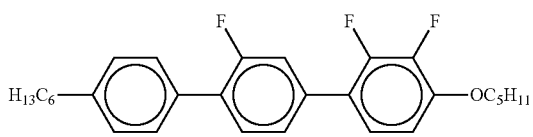

I-a-36

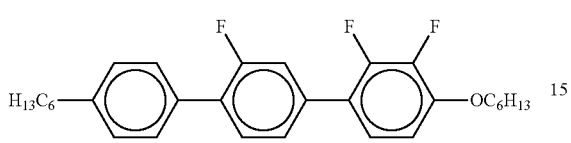

The compounds of the formula I are known, for example, from EP 1 352 943 A1 and can be prepared by known processes.

The compounds of the formula I can be prepared, for example, as follows:

Scheme 1:

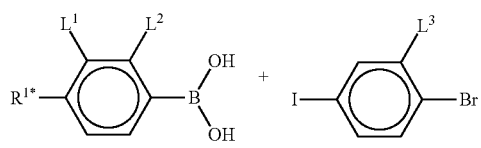

↓ Suzuki coupling

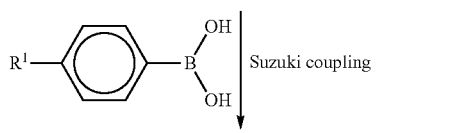

↓ Suzuki coupling

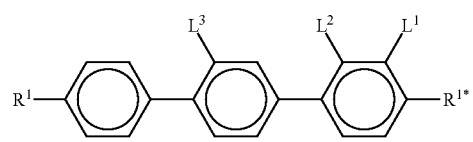

where
R$^1$ and R$^{1*}$: each, independently of one another, denote a straight-chain or branched alkyl or alkoxy radical having 1-15 C atoms, and
L$^{1-3}$: each, independently of one another, denote F, Cl, CF$_3$, OCF$_3$ or CHF$_2$.

Particularly preferred compounds can be prepared, for example, as follows:

Scheme 2

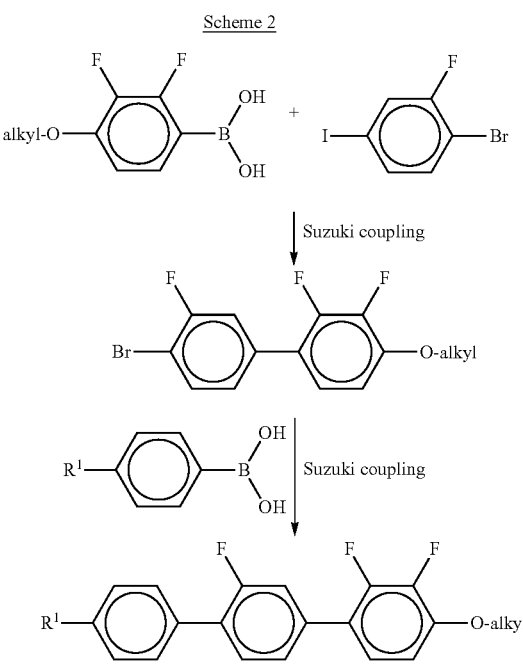

where
R$^1$ denotes a straight-chain or branched alkyl or alkoxy radical having 1-15 C atoms, and
alkyl: denotes an alkyl radical having 1-15 C atoms.

The media according to the invention preferably comprise one, two, three, four or more, preferably one, furthermore two, compound(s) of the formula I.

The compounds of the formula I are preferably employed in the liquid-crystalline medium in amounts of 1-30% by weight, preferably 2-20% by weight and very particularly preferably 3-10% by weight.

Preferred embodiments of the liquid-crystalline medium according to the invention are indicated below:
a) Liquid-crystalline medium which additionally comprises one or more compounds selected from the group of the compounds of the formulae IIA, IIB and IIC,

IIA

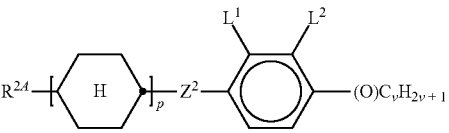

IIB

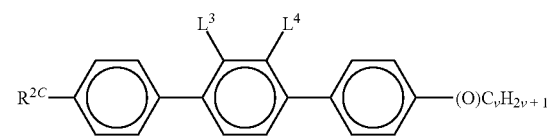

IIC

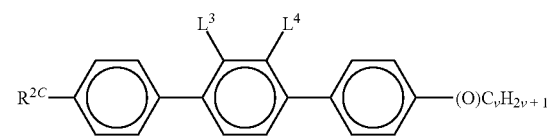

in which
R$^{2A}$, R$^{2B}$ and R$^{2C}$ each, independently of one another, denote H, an alkyl or alkenyl radical having up to 15 C atoms which is unsubstituted, or monosubstituted by CN or CF$_3$ or at least monosubstituted by halogen, where, in addition, one or more CH$_2$ groups in these radicals may each optionally be replaced by —O—, —S—,

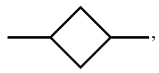

—C≡C—, —CF$_2$O—, —OCF$_2$—, —OC—O— or —O—CO— in such a way that O atoms are not linked directly to one another, L$^{1-4}$ each, independently of one another, denote F, Cl, CF$_3$ or CHF$_2$, Z$^2$ and Z$^{2'}$ each, independently of one another, denote a single bond, —CH$_2$CH$_2$—, —CH=CH—, —CF$_2$O—, —OCF$_2$—, —CH$_2$—O—, —OCH—, —COO—, —OCO—, —C$_2$F$_4$—, —CF=CF—, —C≡C—, or —CH=CHCH$_2$O—, (O) denotes a single bond or —O—, p denotes 0, 1 or 2, a denotes 0 or 1, and v denotes 1 to 6.

In the compounds of the formulae IIA and IIB, Z$^2$ may have identical or different meanings. In the compounds of the formula IIB, Z$^2$ and Z$^{2'}$ may have identical or different meanings.

In the compounds of the formulae IIA, IIB and IIC, R$^{2A}$, R$^{2B}$ and R$^{2C}$ each preferably denote alkyl having 1-6 C atoms, in particular CH$_3$, C$_2$H$_5$, n-C$_3$H$_7$, n-C$_4$H$_9$, n-O$_5$H$_{11}$, furthermore alkenyl having 2-6 C atoms, in particular CH$_2$=CH, CH$_3$CH=CH, C$_2$H$_5$CH=CH, C$_3$H$_7$CH=CH In the compounds of the formulae IIA and IIB, L$^1$, L$^2$, L$^3$ and L$^4$ preferably denote L$^1$=L$^2$=F and L$^3$=L$^4$=F, furthermore L$^1$=F and L$^2$=Cl, L$^1$=Cl and L$^2$=F, L$^3$=F and L$^4$=Cl, L$^3$=Cl and L$^4$=F. Z$^2$ and Z$^{2'}$ in the formulae IIA and IIB preferably each, independently of one another, denote a single bond, furthermore a —CH$_2$O— or —C$_2$H$_4$— bridge.

If in the formula IIB Z$^2$=—C$_2$H$_4$— or —CH$_2$O—, Z$^{2'}$ is preferably a single bond or, if Z$^{2'}$=—C$_2$H$_4$— or —CH$_2$O—, Z$^2$ is preferably a single bond. In the compounds of the formulae IIA and IIB, (O)C$_v$H$_{2v+1}$ preferably denotes OC$_v$H$_{2v+1}$, furthermore C$_v$H$_{2v+1}$. In the compounds of the formula IIC, (O)C$_v$H$_{2v+1}$ preferably denotes C$_v$H$_{2v+1}$. In the compounds of the formula IIC, L$^3$ and L$^4$ preferably each denote F.

Preferred compounds of the formulae IIA, IIB and IIC are indicated below:

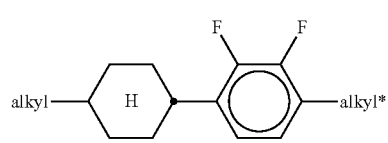

IIA-1

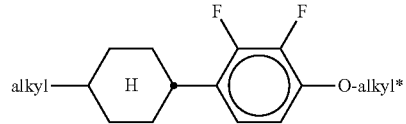

IIA-2

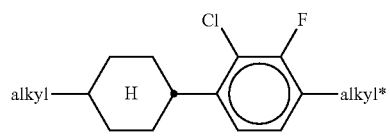

IIA-3

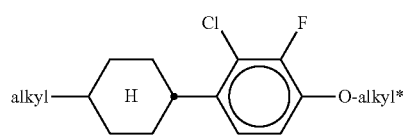

IIA-4

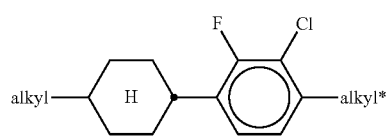

IIA-5

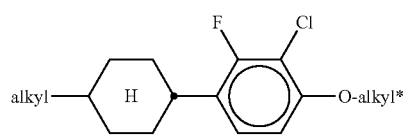

IIA-6

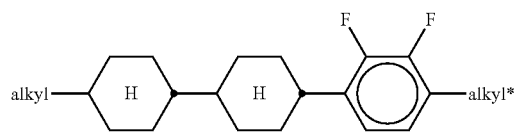

IIA-7

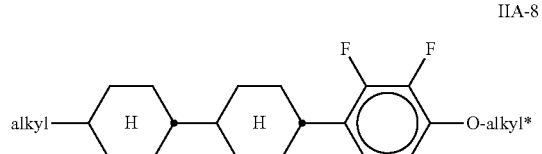

IIA-8

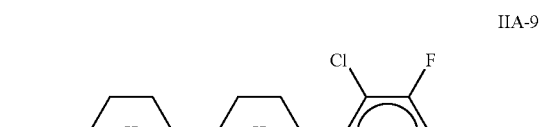

IIA-9

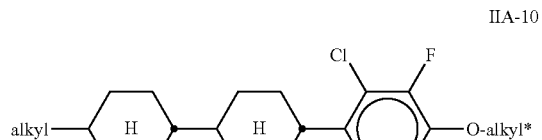

IIA-10

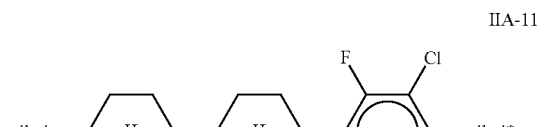

IIA-11

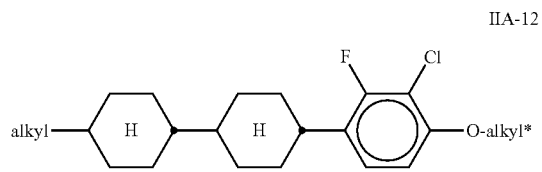

IIA-12

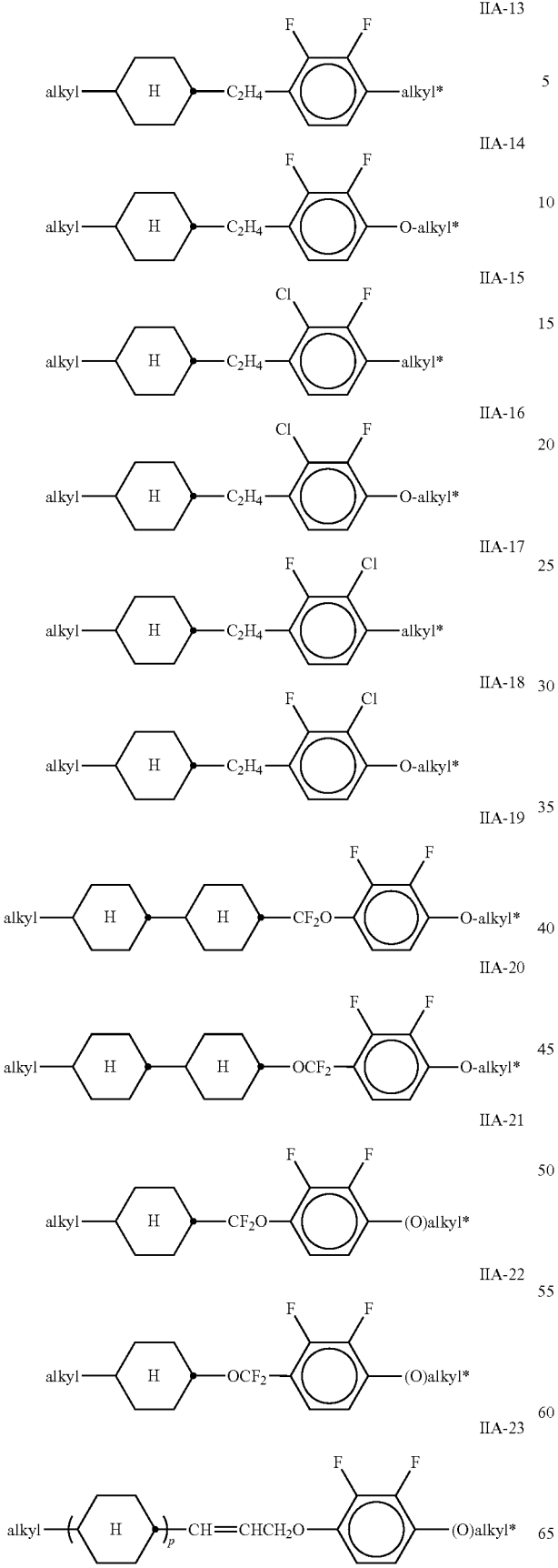
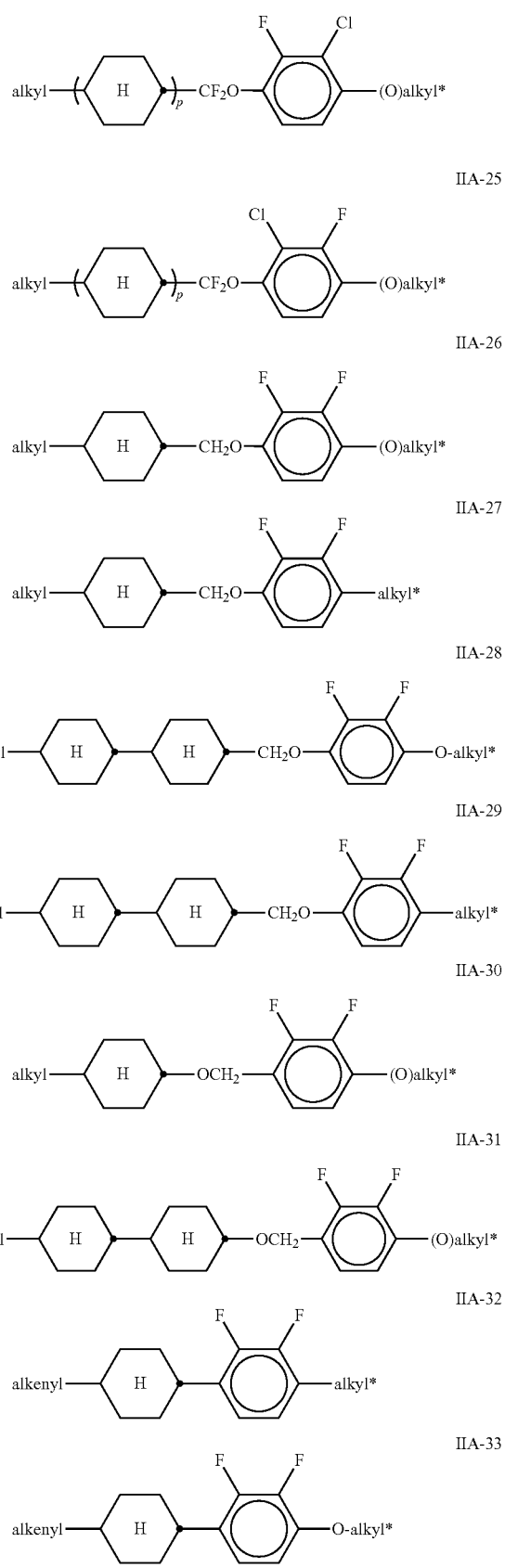

IIA-34
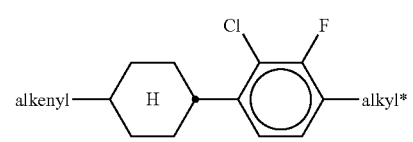
IIA-35
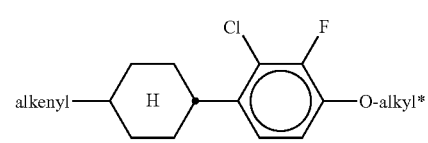
IIA-36
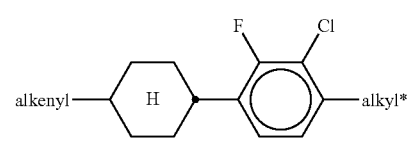
IIA-37
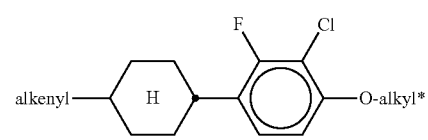
IIA-38
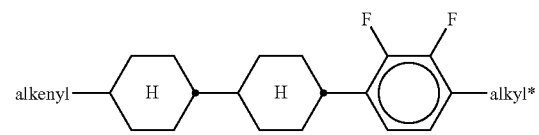
IIA-39
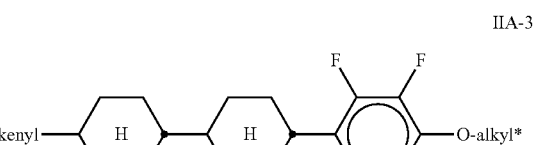
IIA-40
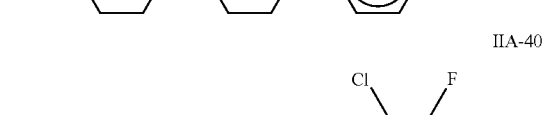
IIA-41
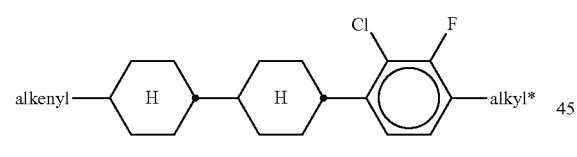
IIA-42

IIA-43
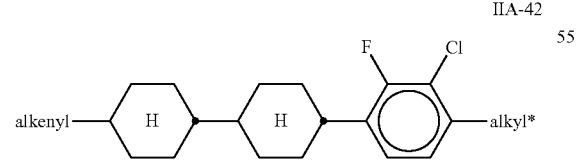
IIA-44
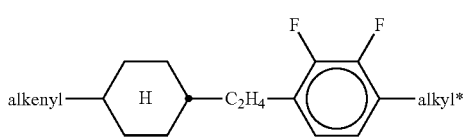
IIA-45
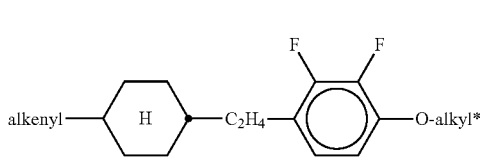
IIA-46
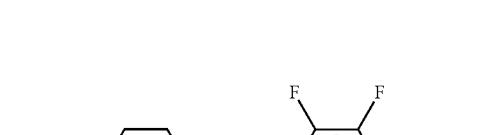
IIA-47
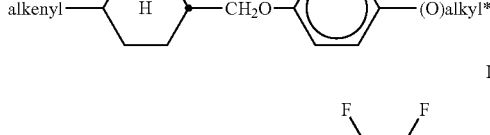
IIA-48
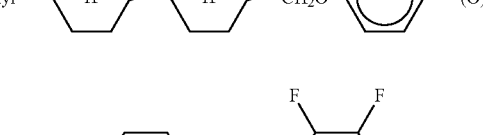
IIA-49
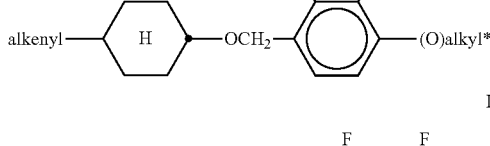
IIA-50
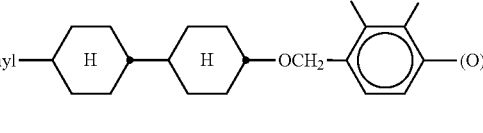
IIA-51
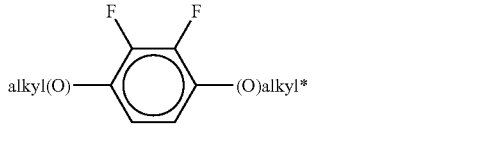
IIA-52
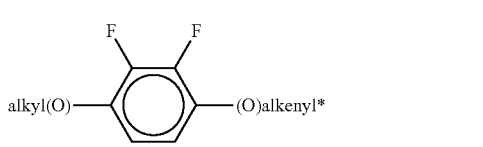
IIB-1
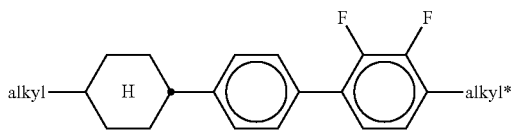

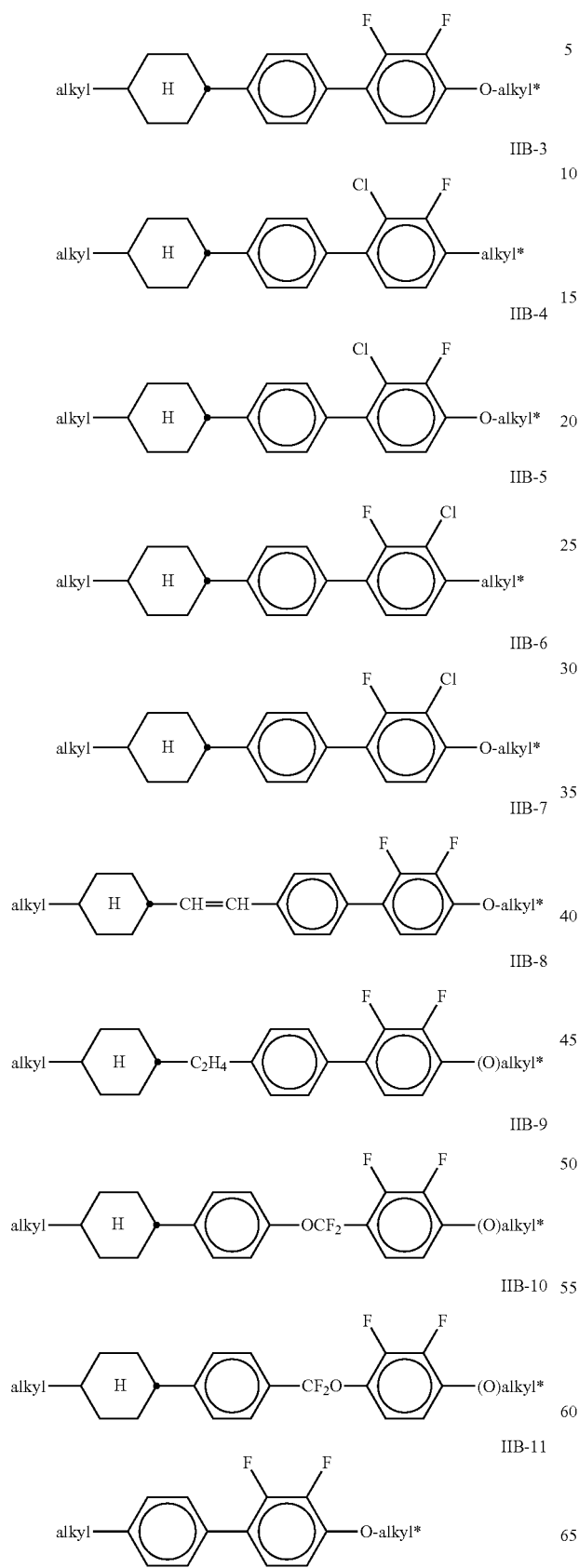
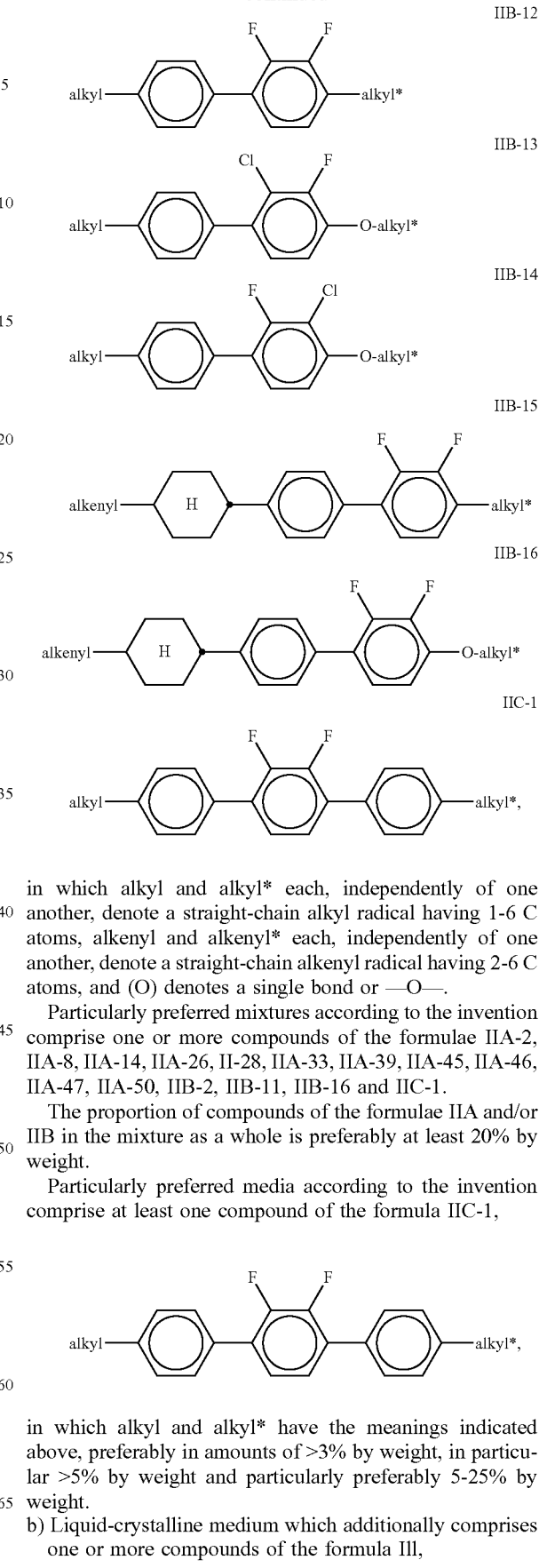

in which alkyl and alkyl* each, independently of one another, denote a straight-chain alkyl radical having 1-6 C atoms, alkenyl and alkenyl* each, independently of one another, denote a straight-chain alkenyl radical having 2-6 C atoms, and (O) denotes a single bond or —O—.

Particularly preferred mixtures according to the invention comprise one or more compounds of the formulae IIA-2, IIA-8, IIA-14, IIA-26, II-28, IIA-33, IIA-39, IIA-45, IIA-46, IIA-47, IIA-50, IIB-2, IIB-11, IIB-16 and IIC-1.

The proportion of compounds of the formulae IIA and/or IIB in the mixture as a whole is preferably at least 20% by weight.

Particularly preferred media according to the invention comprise at least one compound of the formula IIC-1, in which alkyl and alkyl* have the meanings indicated above, preferably in amounts of >3% by weight, in particular >5% by weight and particularly preferably 5-25% by weight.

b) Liquid-crystalline medium which additionally comprises one or more compounds of the formula III,

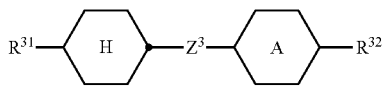
III in which

R$^{31}$ and R$^{32}$ each, independently of one another, denote a straight-chain alkyl, alkoxy, alkenyl, alkoxyalkyl or alkenyloxy radical having up to 12 C atoms, and

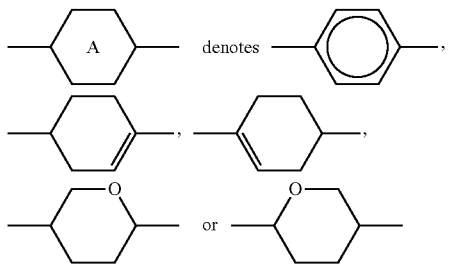

Z$^3$ denotes a single bond, —CH$_2$CH$_2$—, —CH=CH—, —CF$_2$O—, —OCF$_2$—, —CH$_2$O—, —O CH$_2$—, —COO—, —OCO—, —C$_2$F$_4$—, —C$_4$H$_8$—, —C≡C—, or —CF=CF—.

Preferred compounds of the formula Ill are indicated below:

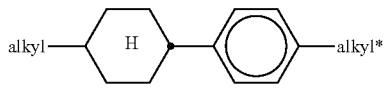
IIIa

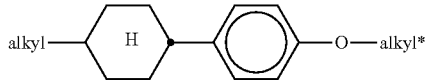
IIIb

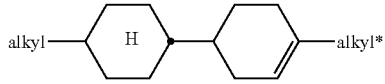
IIIc

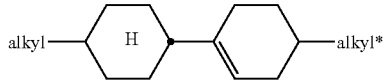
IIId in which alkyl and alkyl* each, independently of one another, denote a straight-chain alkyl radical having 1-6 C atoms.

c) Liquid-crystalline medium which additionally comprises one or more tetracyclic compounds of the formulae

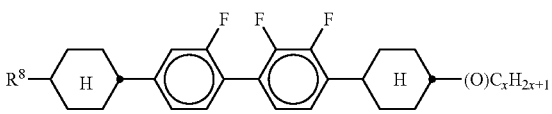
V-1

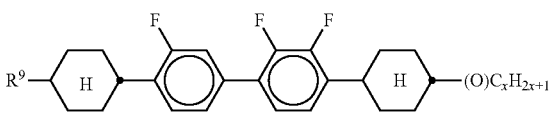
V-2

V-3

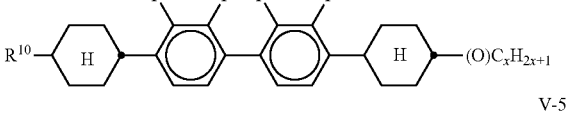
V-4

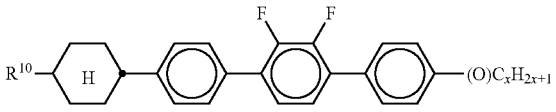
V-5

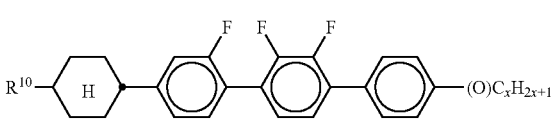
V-6

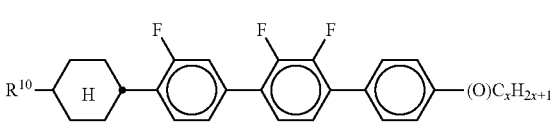
V-7

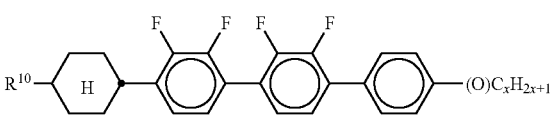
V-8

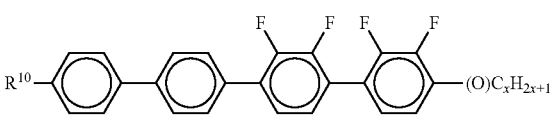
V-9

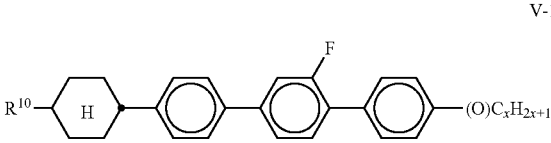
V-10

in which

R$^{7-10}$ each, independently of one another, denote H, an alkyl or alkenyl radical having up to 15 C atoms which is unsubstituted, or monosubstituted by CN or CF$_3$ or at least monosubstituted by halogen, where, in addition, one or more CH$_2$ groups in these radicals may each optionally be replaced by —O—, —S—,

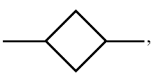

—C≡C—, —CF$_2$O—, —OCF$_2$—, —OC—O— or —O—CO— in such a way that O atoms are not linked directly to one another,
(O) denotes a single bond or —O—, and
w and x each, independently of one another, denote 1 to 6.

Particular preference is given to mixtures comprising at least one compound of the formula V-9 and/or of the formula V-10.

d) Liquid-crystalline medium which additionally comprises one or more compounds of the formulae Y-1 to Y-6,

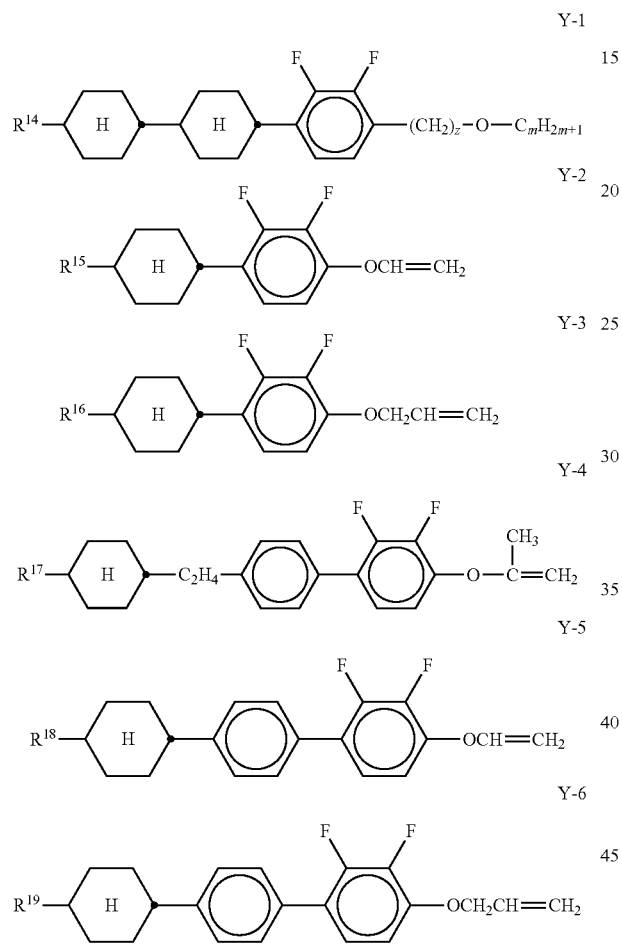

in which R$^{14}$-R$^{19}$ each, independently of one another, denotes an alkyl or alkoxy radical having 1-6 C atoms; and z and m each, independently of one another, denote 1-6.

The medium according to the invention particularly preferably comprises one or more compounds of the formulae Y-1 to Y-6, preferably in amounts of 5% by weight.

e) Liquid-crystalline medium additionally comprising one or more fluorinated terphenyls of the formulae T-1 to T-21,

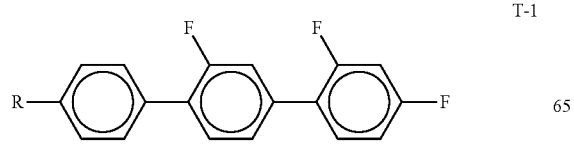

-continued

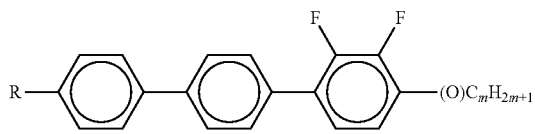

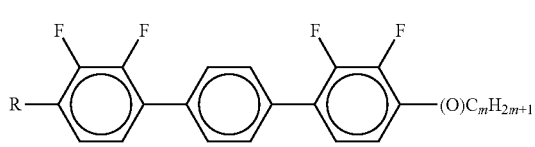

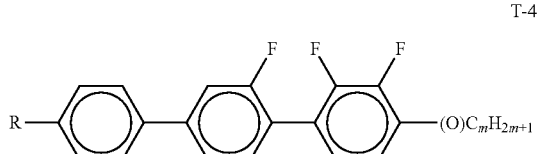

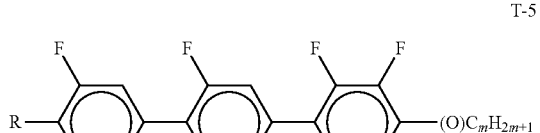

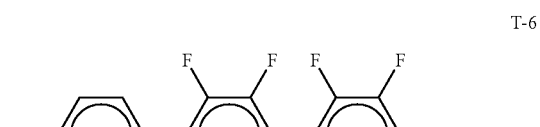

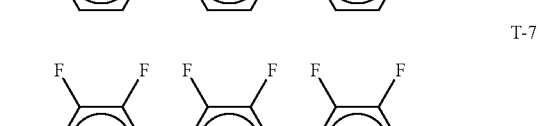

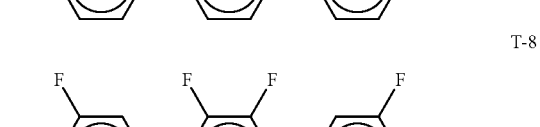

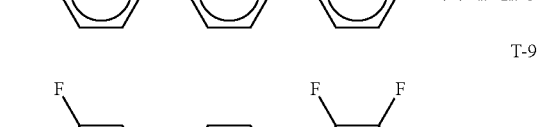

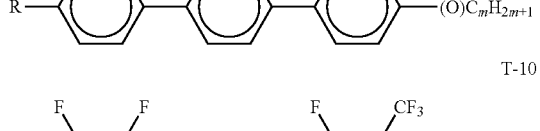

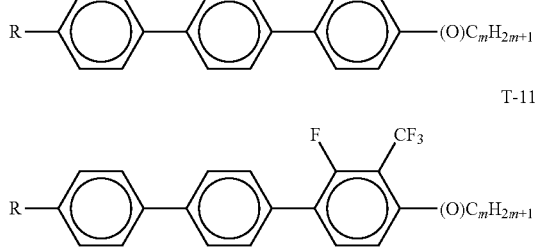

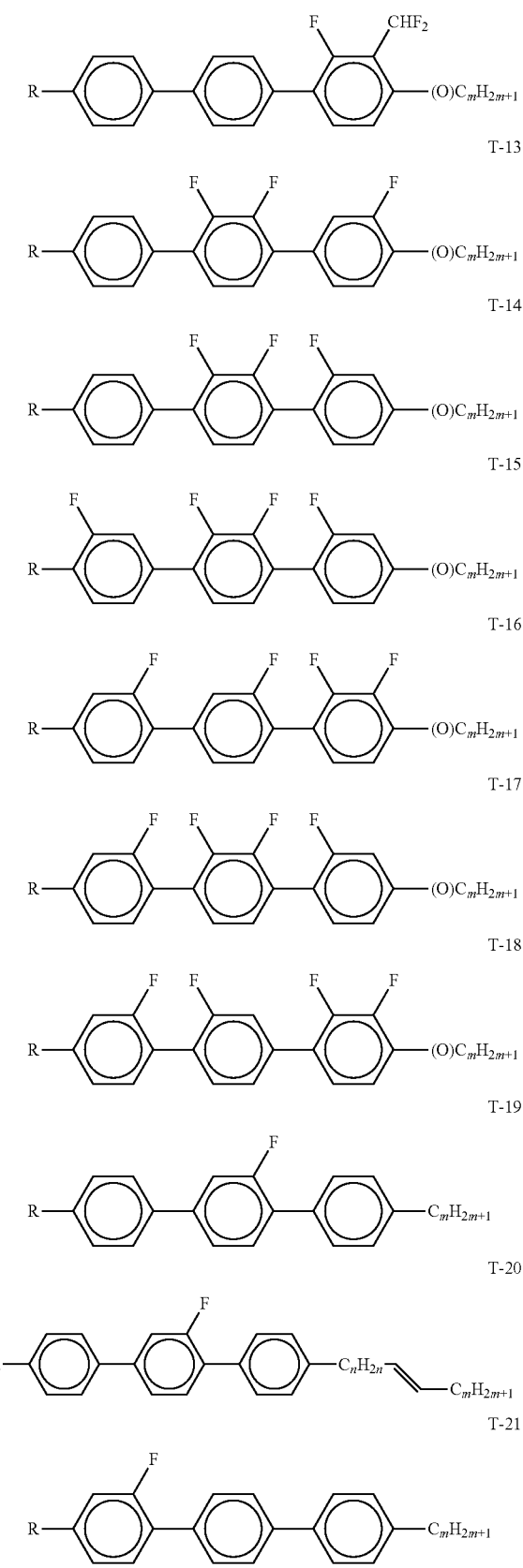

T-12
T-13
T-14
T-15
T-16
T-17
T-18
T-19
T-20
T-21 in which

R denotes a straight-chain alkyl or alkoxy radical having 1-7 C atoms or alkenyl having 2-6 C atoms, (O) denotes a single bond or —O—, and m=0, 1, 2, 3, 4, 5 or 6 and n denotes 0, 1, 2, 3 or 4.

R preferably denotes methyl, ethyl, propyl, butyl, pentyl, hexyl, methoxy, ethoxy, propoxy, butoxy, or pentoxy.

The medium according to the invention preferably comprises the terphenyls of the formulae T-1 to T-21 in amounts of 2-30% by weight, in particular 5-20% by weight.

Particular preference is given to compounds of the formulae T-1, T-2, T-19 and T-20. In these compounds, R preferably denotes alkyl, furthermore alkoxy, each having 1-6 C atoms. In the compounds of the formula T-19, R preferably denotes alkyl or alkenyl, in particular alkyl. In the compound of the formula T-20, R preferably denotes alkyl.

The terphenyls are preferably employed in the mixtures according to the invention if the Δn value of the mixture is to be ≥0.1. Preferred mixtures comprise 2-20% by weight of one or more terphenyl compounds selected from the group of the compounds T-1 to T-21.

f) Liquid-crystalline medium additionally comprising one or more biphenyls of the formulae B-1 to B-3,

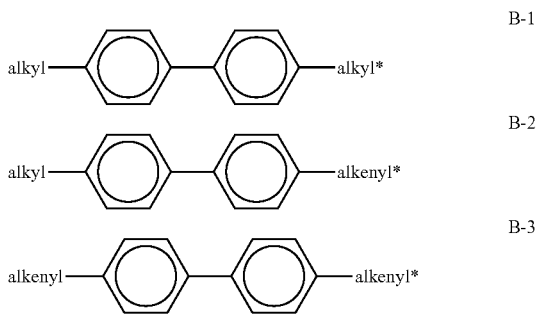

B-1
B-2
B-3 in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms.

The proportion of the biphenyls of the formulae B-1 to B-3 in the mixture as a whole is preferably at least 3% by weight, in particular ≥5% by weight.

Of the compounds of the formulae B-1 to B-3, the compounds of the formulae B-1 and B-2 are particularly preferred.

Particularly preferred biphenyls are

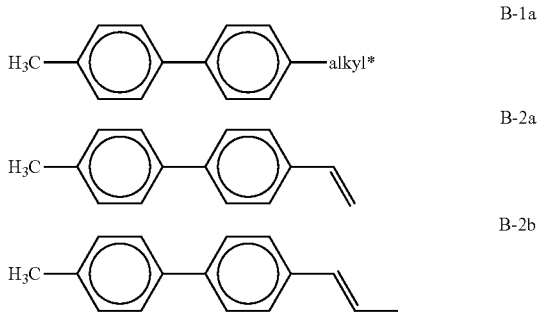

B-1a
B-2a
B-2b

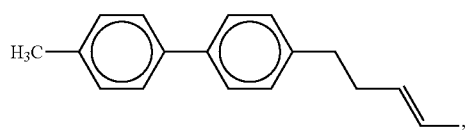

B-2c in which alkyl* denotes an alkyl radical having 1-6 C atoms. The medium according to the invention particularly preferably comprises one or more compounds of the formulae B-1a and/or B-2c.

Preferred compounds of the formula B-1a are, in particular, the compounds of the formulae

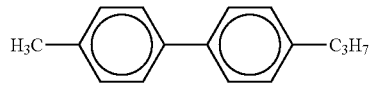

B-1a-1

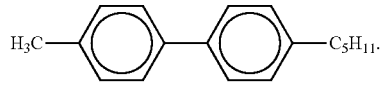

B-1a-2 g) Liquid-crystalline medium additionally comprising at least one compound of the formulae Z-1 to Z-9,

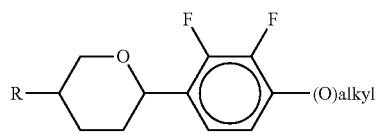

Z-1

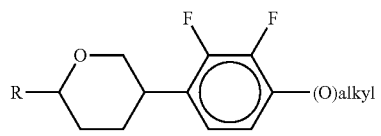

Z-2

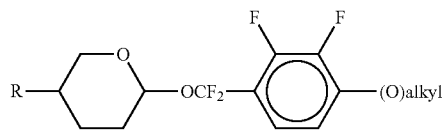

Z-3

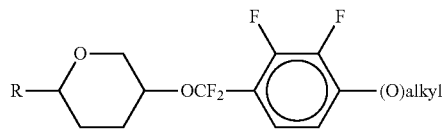

Z-4

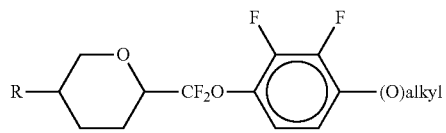

Z-5

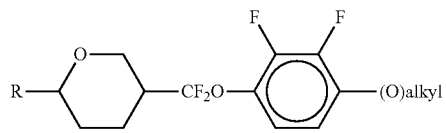

Z-6

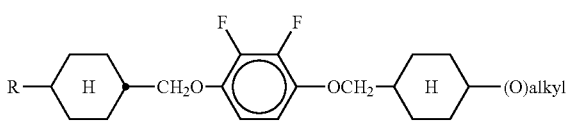

Z-7


Z-8


Z-9 in which

R denotes H, an alkyl or alkenyl radical having up to 15 C atoms which is unsubstituted, or monosubstituted by CN or $CF_3$ or at least monosubstituted by halogen, where, in addition, one or more $CH_2$ groups in these radicals may each optionally be replaced by —O—, —S—,

—C≡C—, —$CF_2$O—, —O$CF_2$—, —OC—O— or —O—CO— in such a way that O atoms are not linked directly to one another, (O) denotes a single bond or —O—, and alkyl denotes an alkyl radical having 1-6 C atoms.

h) Liquid-crystalline medium additionally comprising at least one compound of the formulae O-1 to O-17,

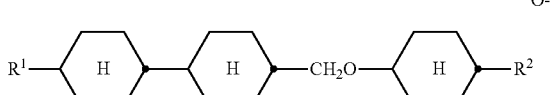

O-1

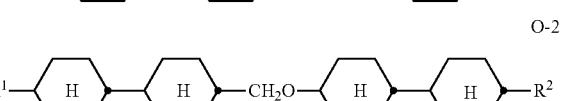

O-2

O-3

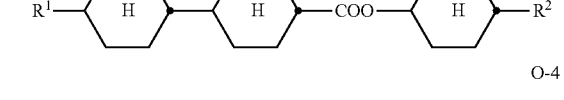

O-4

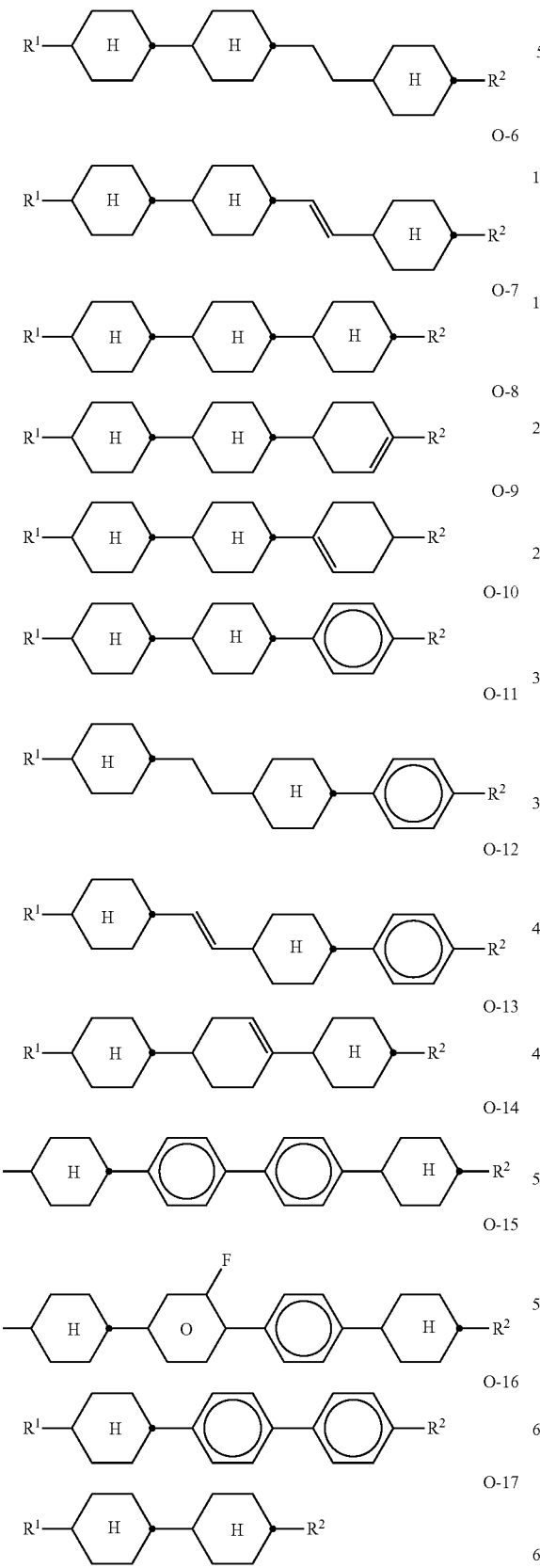

in which
R¹ and R² each, independently of one another, denote H, an alkyl or alkenyl radical having up to 15 C atoms which is unsubstituted, or monosubstituted by CN or $CF_3$ or at least monosubstituted by halogen, where, in addition, one or more $CH_2$ groups in these radicals may each optionally be replaced by —O—, —S—,

—C≡C—, —$CF_2$O—, —O$CF_2$—, —OC—O— or —O—CO— in such a way that O atoms are not linked directly to one another.

R¹ and R² preferably each, independently of one another, denote straight-chain alkyl or alkenyl.

Preferred media comprise one or more compounds of the formulae O-1, O-3, O-4, O-6, O-7, O-10, O-11, O-12, O-14, O-15, O-16 and/or O-17.

Mixtures according to the invention very particularly preferably comprise the compounds of the formula O-10, O-12, O-16 and/or O-17, in particular in amounts of 5-30% by weight.

Preferred compounds of the formula O-17 are selected from the group of the compounds of the formulae

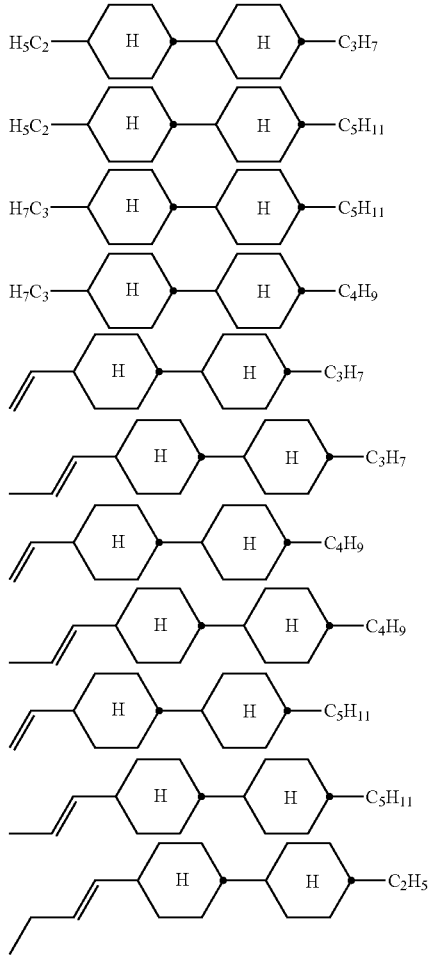

-continued
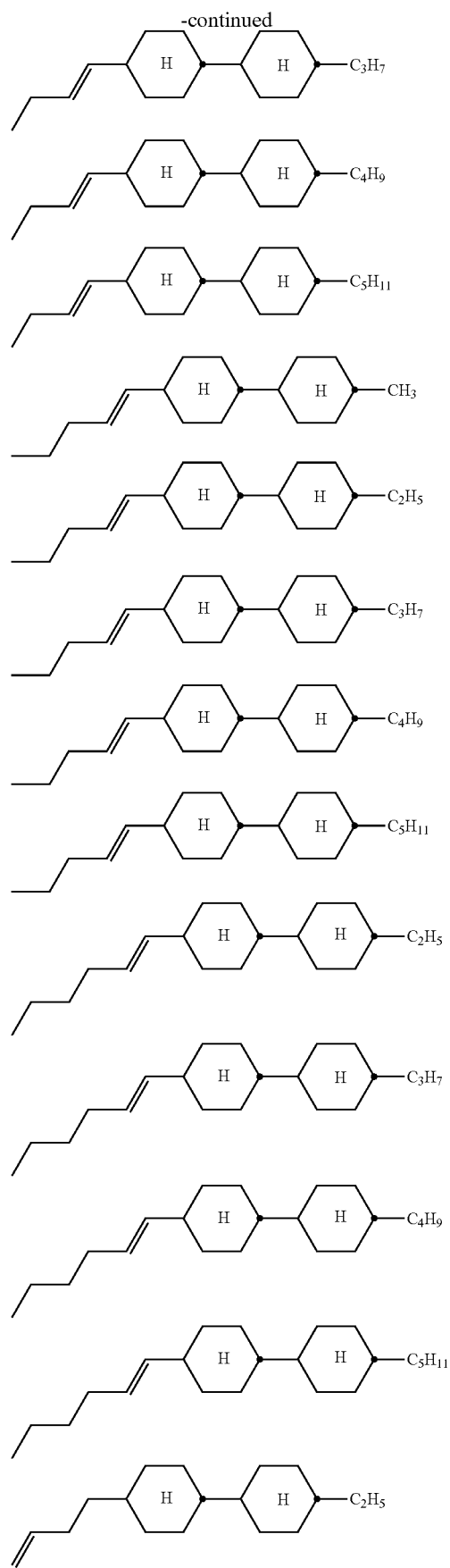
-continued
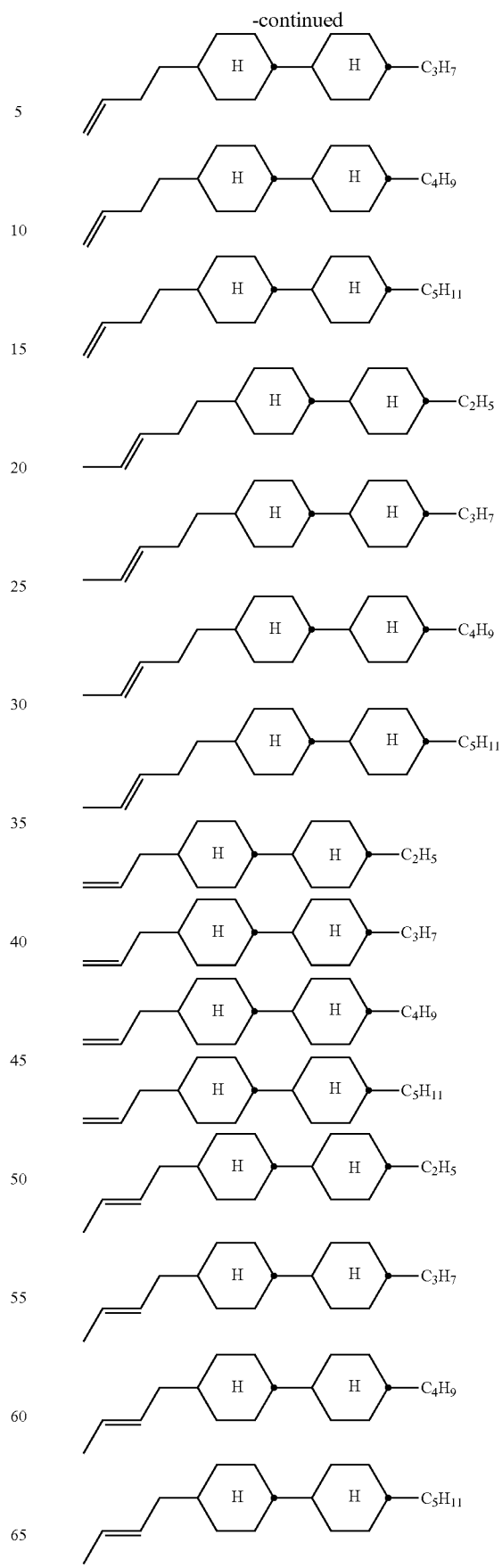

-continued

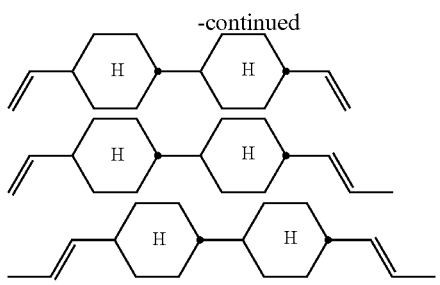

Preference is furthermore given to compounds of the formula O-17 which contain a non-terminal double bond in the alkenyl side chain, particularly the following compounds:

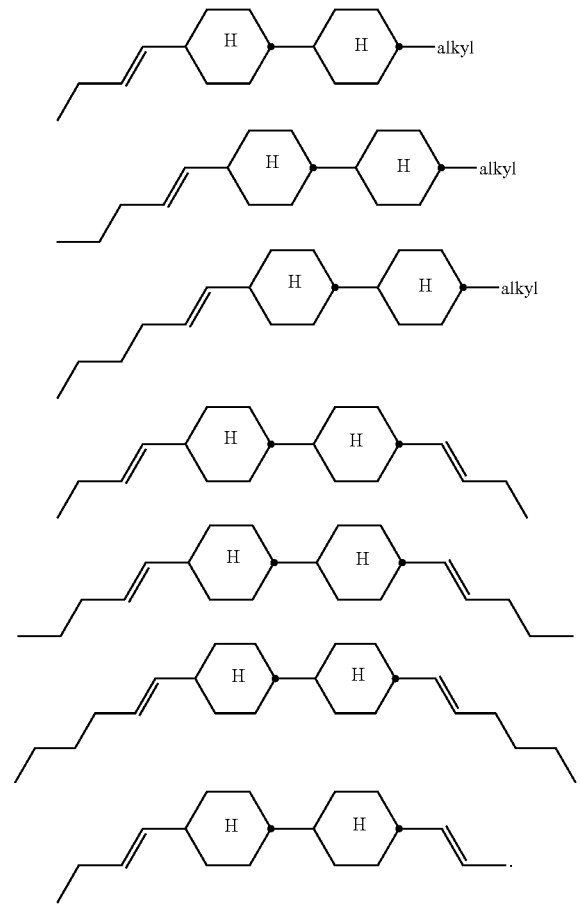

The proportion of compounds of the formula O-17 in the mixture as a whole is preferably at least 5% by weight.

i) Liquid-crystalline medium additionally comprising at least one compound of the formula

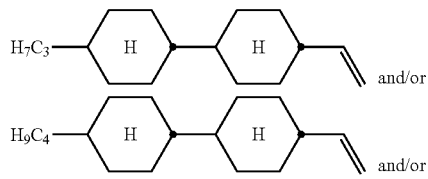

and/or and/or

-continued

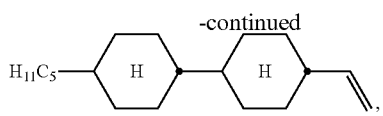

preferably in total amounts of ≥5% by weight, in particular ≥10% by weight.

Preference is furthermore given to mixtures according to the invention

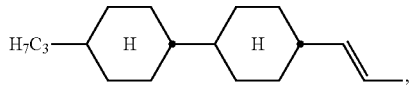

preferably in amounts of 2-15% by weight.

Preferred mixtures comprise 5-60% by weight, preferably 10-55% by weight, in particular 20-50% by weight, of the compound of the formula (acronym: CC-3-V)

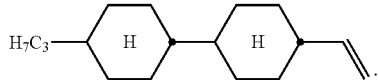

Preference is furthermore given to mixtures which comprise a compound of the formula (acronym: CC-3-V)

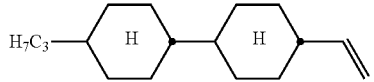

and a compound of the formula (acronym: CC-3-V1)

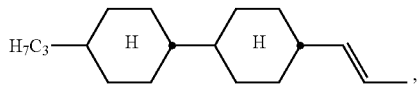

wherein the total amount of CC-3-V and CC-3V-1 combined is preferably in amounts of 10-65% by weight.

j) Liquid-crystalline medium additionally comprising at least one compound of the formula O-10 and at least one compound of the formula O-17 selected from the group of the following compounds:

O-10a

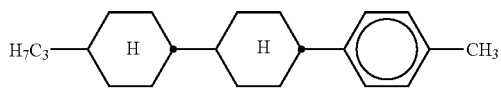

O-10b

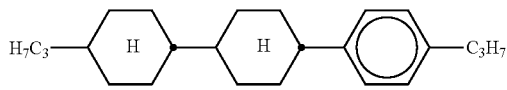

O-17a

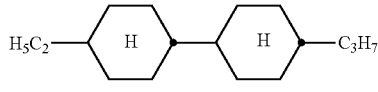

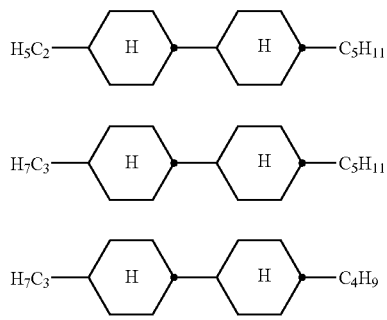

The medium according to the invention particularly preferably comprises the tricyclic compounds of the formula O-10a and/or of the formula O-10b in combination with one or more bicyclic compounds of the formulae O-17a to O-17d. The total proportion of the compounds of the formulae O-10a and/or O-10b in combination with one or more compounds selected from the bicyclic compounds of the formulae O-17a to O-17d is 5-40%, very particularly preferably 15-35%.

Very particularly preferred mixtures comprise compounds O-10a and O-17a:

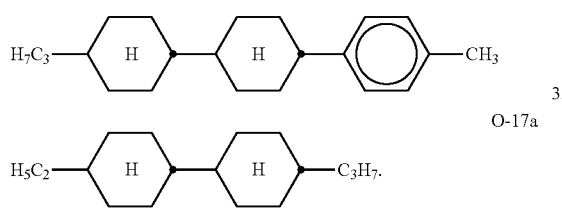

Compounds O-10a and O-17a are preferably present in the mixture in a total concentration of 15-35%, particularly preferably 15-25% and especially preferably 18-22%, based on the mixture as a whole.

Very particularly preferred mixtures comprise the compounds O-10b and O-17a:

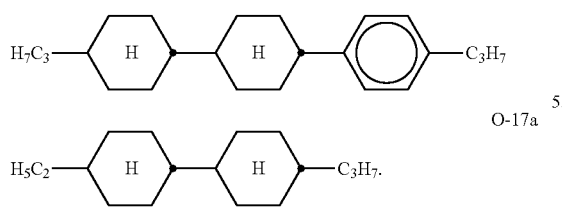

The compounds O-10b and O-17a are preferably present in the mixture in a total concentration of 15-35%, particularly preferably 15-25% and especially preferably 18-22%, based on the mixture as a whole.

Very particularly preferred mixtures comprise the following three compounds:

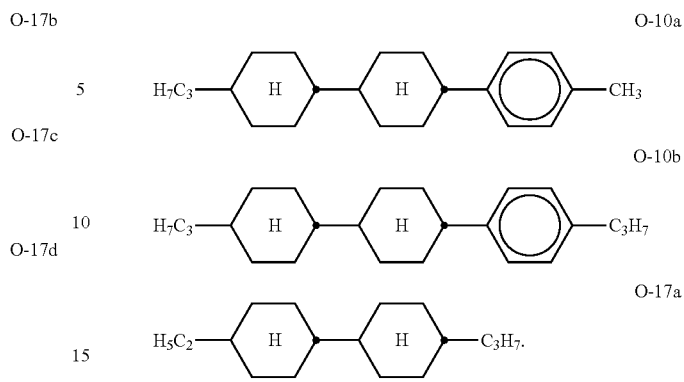

The compounds O-10a, O-10b and O-17a are preferably present in the mixture in a total concentration of 15-35%, particularly preferably 15-25% and especially preferably 18-22%, based on the mixture as a whole.

Preferred mixtures comprise at least one compound selected from the group of the compounds

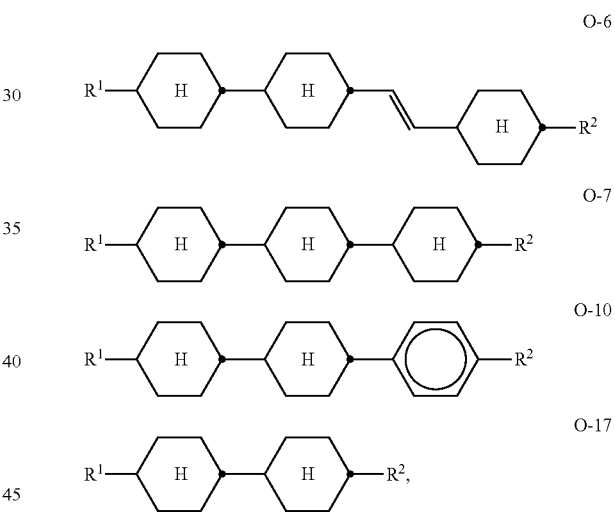

in which $R^1$ and $R^2$ have the meanings indicated above. In the compounds O-6, O-7 and O-17, $R^1$ preferably denotes alkyl or alkenyl having 1-6 or 2-6 C atoms, respectively, and $R^2$ preferably denotes alkenyl having 2-6 C atoms. In the compounds of the formula O-10, $R^1$ preferably denotes alkyl or alkenyl having 1-6 or 2-6 C atoms, respectively, and $R^2$ preferably denotes alkyl having 1-6 C atoms.

Preferred mixtures comprise at least one compound selected from the group of the compounds of the formulae O-6a, O-6b, O-7a, O-7b, O-17e, O-17f, O-17g and O-17h:

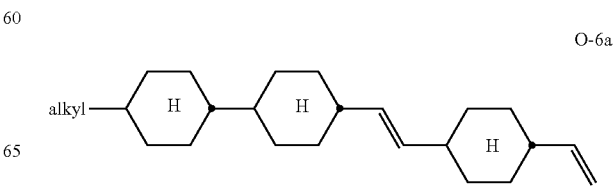

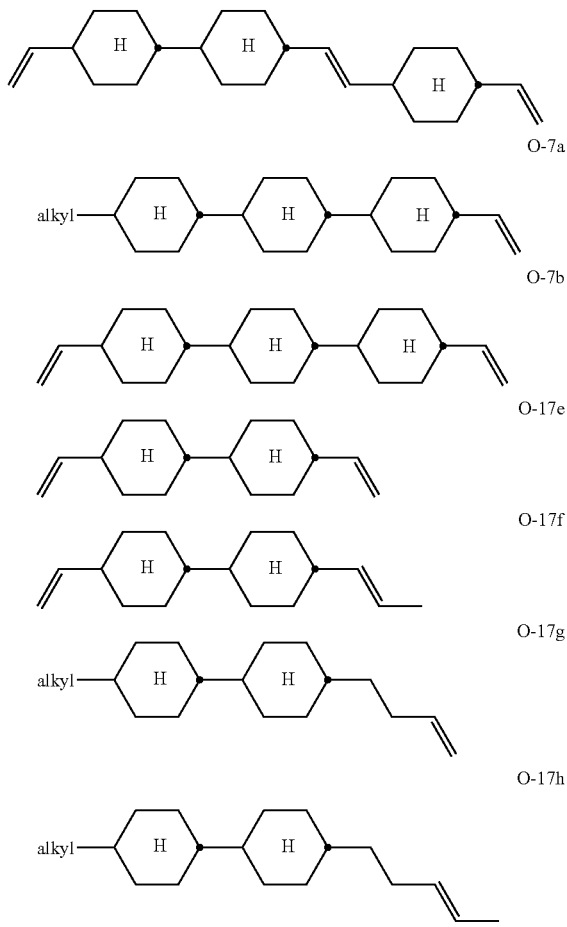

in which alkyl denotes an alkyl radical having 1-6 C atoms.

The compounds of the formulae O-6, O-7 and O-17e-h are preferably present in the mixtures according to the invention in amounts of 1-40% by weight, in particular 2-35% by weight and very particularly preferably 2-30% by weight.

k) Preferred liquid-crystalline media according to the invention comprise one or more substances which contain a tetrahydronaphthyl or naphthyl unit, such as, for example, the compounds of the formulae N-1 to N-5,

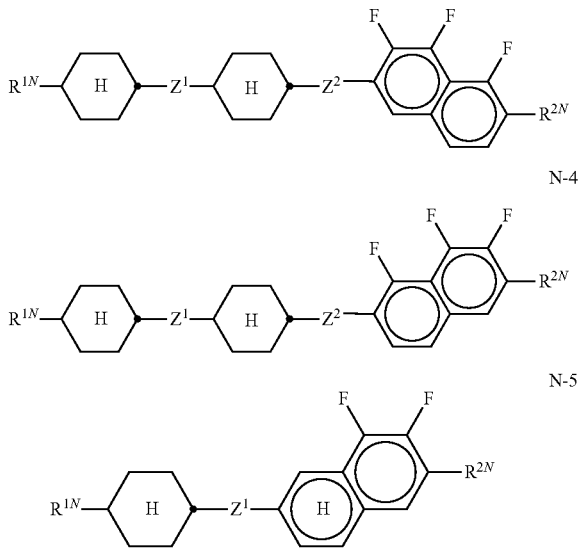

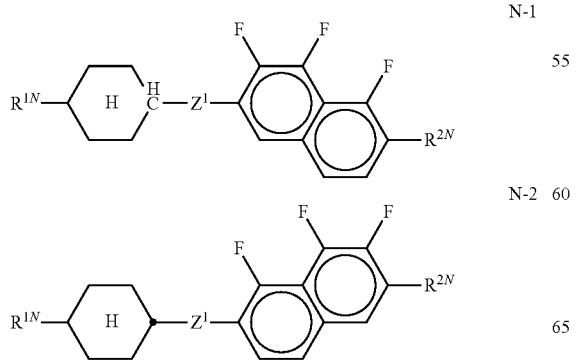

in which $R^{1N}$ and $R^{2N}$ each, independently of one another, denote H, an alkyl or alkenyl radical having up to 15 C atoms which is unsubstituted, or monosubstituted by CN or $CF_3$ or at least monosubstituted by halogen, where, in addition, one or more $CH_2$ groups in these radicals may each optionally be replaced by —O—, —S—,

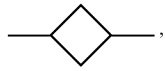

—C≡C—, —$CF_2$O—, —O$CF_2$—, —OC—O— or —O—CO— in such a way that O atoms are not linked directly to one another, $R^{1N}$ and $R^{2N}$ each, independently of one another, preferably denote straight-chain alkyl, straight-chain alkoxy or straight-chain alkenyl, and $Z^1$ and $Z^2$ each, independently of one another, denote —$C_2H_4$—, —CH═CH—, —$(CH_2)_4$—, —$(CH_2)_3$O—, —O$(CH_2)_3$—, —CH═CH$CH_2CH_2$—, —$CH_2CH_2$CH═CH—, —$CH_2$O—, —O$CH_2$—, —CO—O—, —OCO—, —$C_2F_4$—, —CF═CF—, —CF═CH—, —CH═CF—, —C≡C—, —$CF_2$O—, —O$CF_2$—, —$CH_2$— or a single bond.

l) Preferred mixtures comprise one or more compounds selected from the group of the compounds of the formulae BC, CR, PH-1, PH-2, BF-1, BF-2, BS-1 and BS-2,

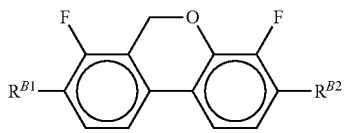

-continued

CR

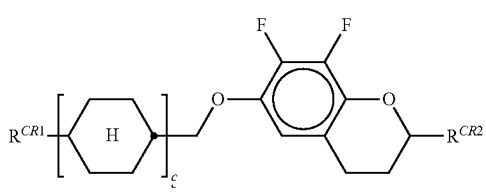

PH-1

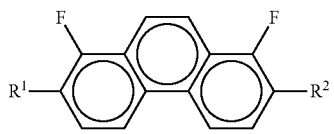

PH-2

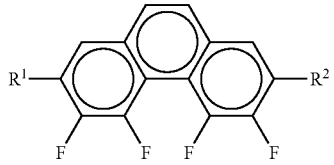

BF-1

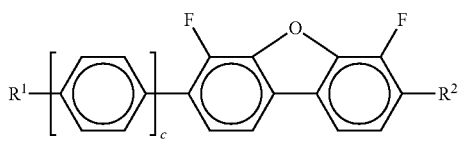

BF-2

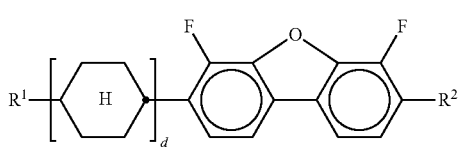

BS-1

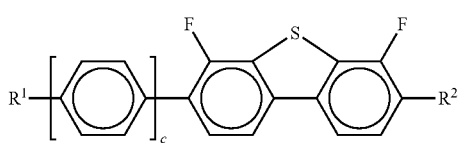

BS-2

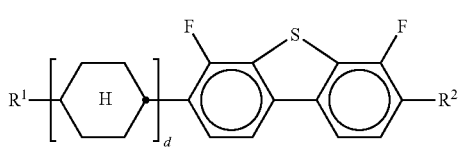

in which $R^{B1}$, $R^{B2}$, $R^{CR1}$, $R^{CR2}$, $R^1$, $R^2$ each, independently of one another, denote H, an alkyl or alkenyl radical having up to 15 C atoms which is unsubstituted, or monosubstituted by CN or $CF_3$ or at least monosubstituted by halogen, where, in addition, one or more $CH_2$ groups in these radicals may each optionally be replaced by —O—, —S—,

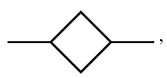

—C≡C—, —$CF_2$O—, —$OCF_2$—, —OC—O— or —O—CO— in such a way that O atoms are not linked directly to one another, c is 0, 1 or 2 and d is 1 or 2.

$R^1$ and $R^2$ preferably, independently of one another, denote alkyl, alkoxy, alkenyl or alkenyloxy having 1 or 2 to 6 C atoms respectively.

The mixtures according to the invention preferably comprise compounds of the formulae BC, CR, PH-1, PH-2, BF-1, BF-2, BS-1 and/or BS-2 in amounts of 3 to 20% by weight, in particular in amounts of 3 to 15% by weight.

Particularly preferred compounds of the formulae BC, CR, BF-1 and BS-1 are the compounds BC-1 to BC-7, CR-1 to CR-5, BF-1a to BF-1c-, BS-1a to BS-1c,

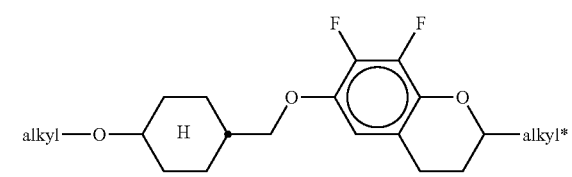

-continued

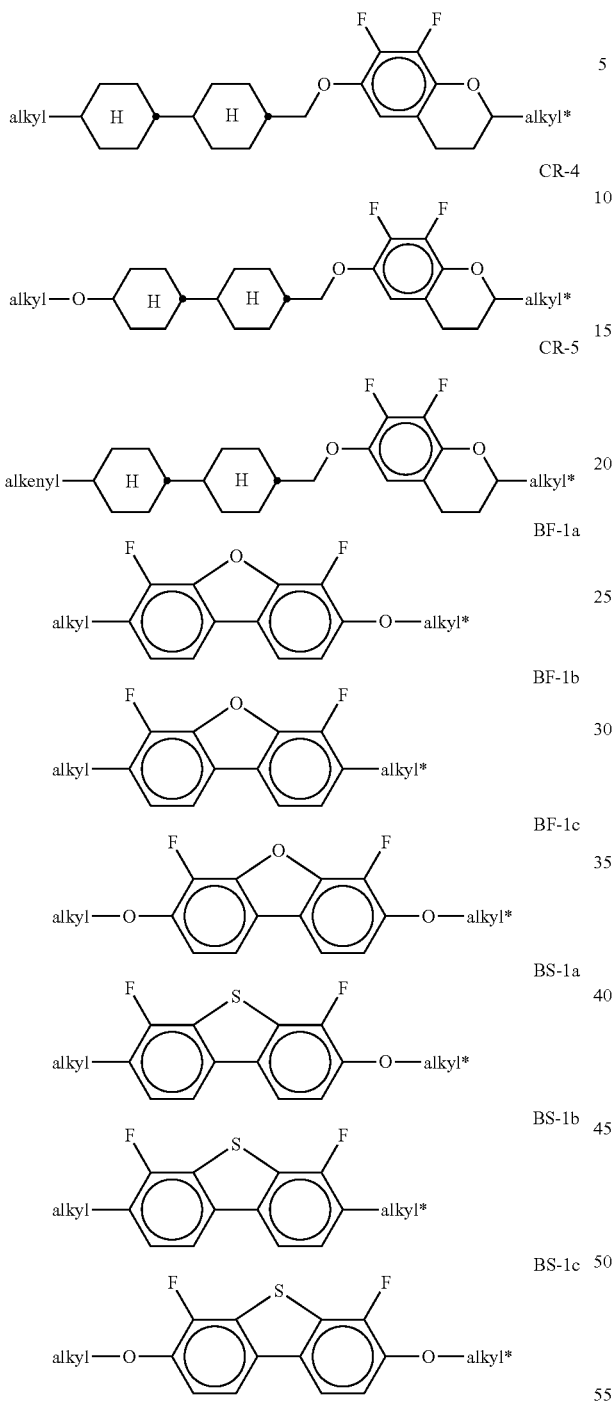

in which
alkyl and alkyl* each, independently of one another, denote a straight-chain alkyl radical having 1-6 C atoms, and
alkenyl and alkenyl* each, independently of one another, denote a straight-chain alkenyl radical having 2-6 C atoms.

Very particular preference is given to mixtures comprising one, two or three compounds of the formula BC-2, BF-1 and/or BF-2.

m) Preferred mixtures comprise one or more indane compounds of the formula In,

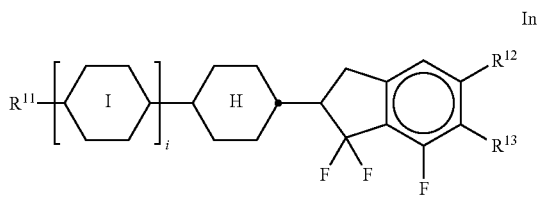

in which
$R^{11}$, $R^{12}$, $R^{13}$ each, independently of one another, denote a straight-chain alkyl, alkoxy, alkoxyalkyl or alkenyl radical having 1-6 C atoms,
$R^{12}$ and $R^{13}$ additionally denote halogen, preferably F,

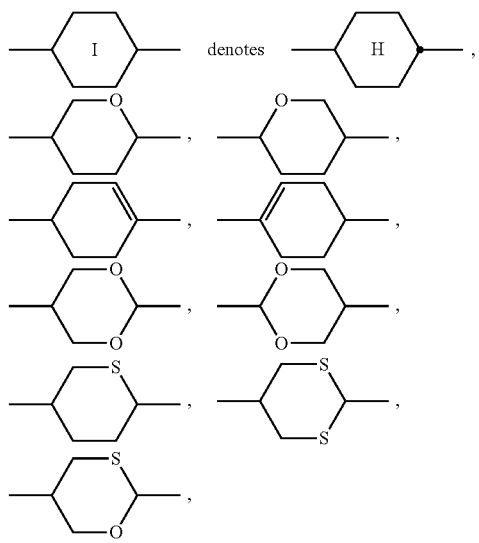

i denotes 0, 1 or 2.

Preferred compounds of the formula In are the compounds of the formulae In-1 to In-16 indicated below:

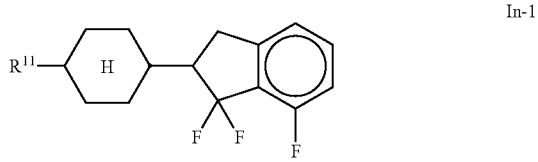

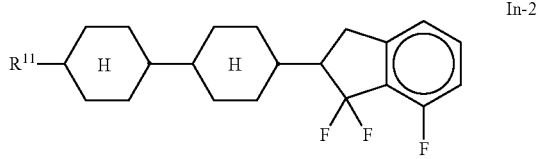

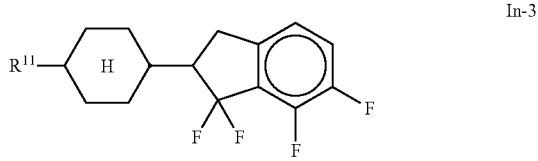

In-4
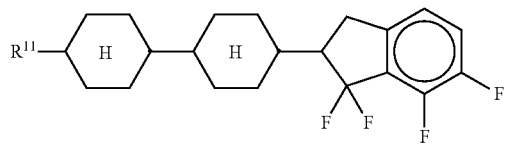

In-5
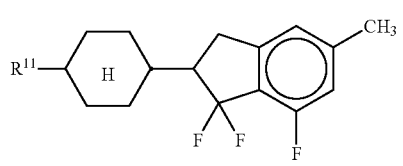

In-6
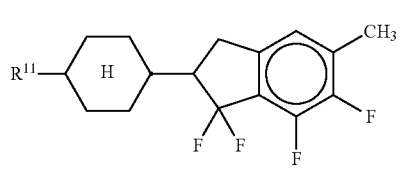

In-7
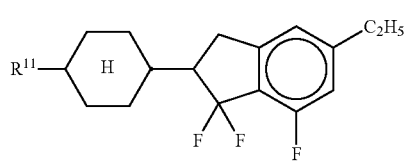

In-8
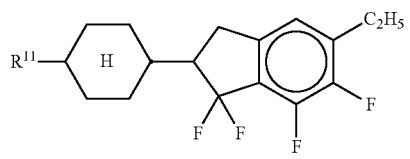

In-9
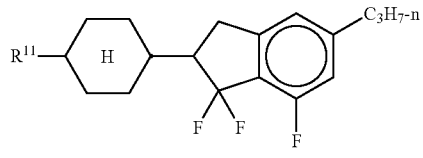

In-10
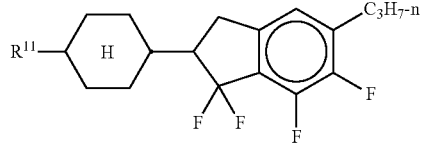

In-11
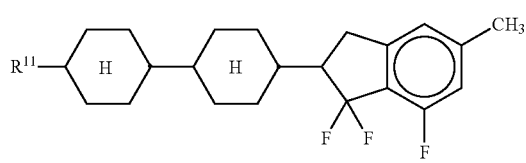

In-12
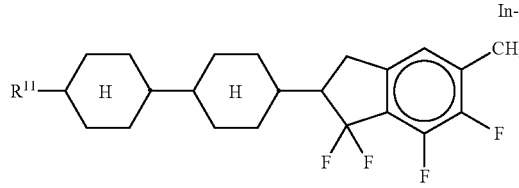

In-13
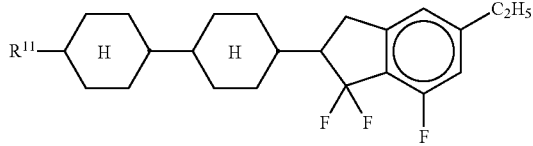

In-14
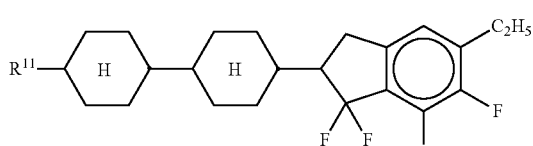

In-15
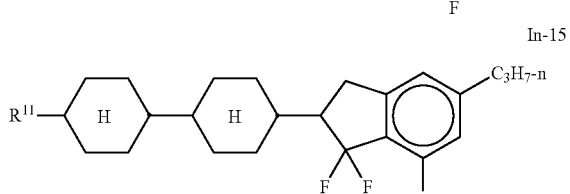

In-16
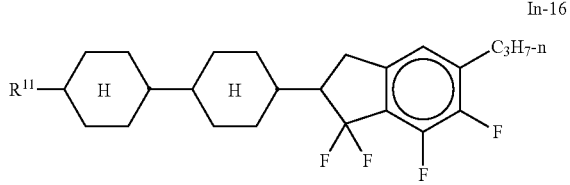

Particular preference is given to the compounds of the formulae In-1, In-2, In-3 and In-4.

The compounds of the formula In and the sub-formulae In-1 to In-16 are preferably employed in the mixtures according to the invention in concentrations ≥5% by weight, in particular 5-30% by weight and very particularly preferably 5-25% by weight.

n) Preferred mixtures additionally comprise one or more compounds of the formulae L-1 to L-11, L-1
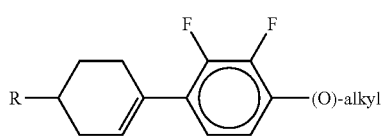

L-2
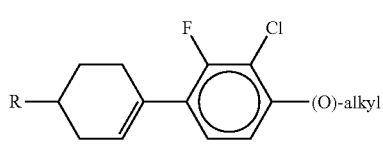

L-3
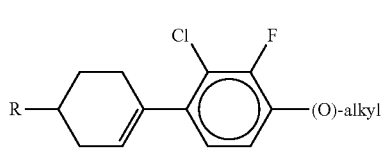

L-4
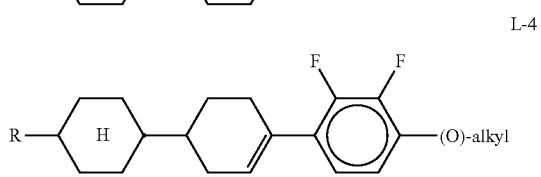

-continued

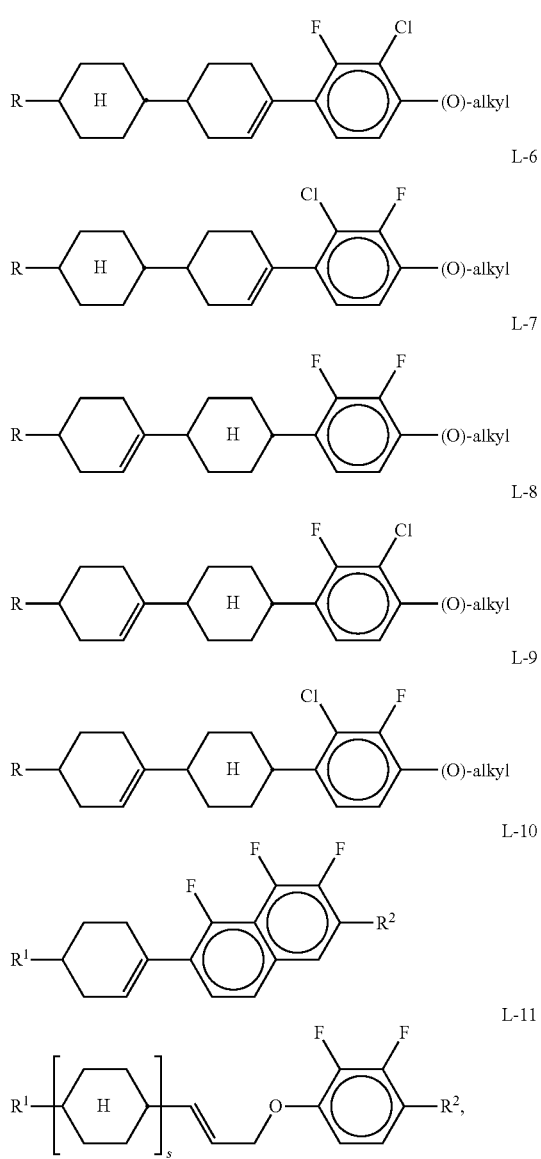

in which

R, R¹ and R² each, independently of one another, denote H, an alkyl or alkenyl radical having up to 15 C atoms which is unsubstituted, or monosubstituted by CN or CF₃ or at least monosubstituted by halogen, where, in addition, one or more CH₂ groups in these radicals may each optionally be replaced by —O—, —S—,

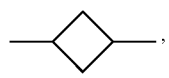

—C≡C—, —CF₂O—, —OCF₂—, —OC—O— or —O—CO— in such a way that O atoms are not linked directly to one another. (O) denotes a single bond or —O—. alkyl denotes an alkyl radical having 1-6 C atoms. s denotes 1 or 2.

Particular preference is given to the compounds of the formulae L-1 and L-4, in particular L-4.

The compounds of the formulae L-1 to L-11 are preferably employed in concentrations of 5-50% by weight, in particular 5-40% by weight and very particularly preferably 10-40% by weight.

Particularly preferred mixture concepts are indicated below: (the acronyms used are explained in Table B. n and m here each, independently of one another, denote 1-15, preferably 1-6).

The mixtures according to the invention preferably comprise
one or more compounds of the formula I in which L¹=L²=F and R¹=R¹*=alkoxy;
CPY-n-Om, in particular CPY-2-O2, CPY-3-O2 and/or CPY-5-O2, preferably in concentrations >5%, in particular 10-30%, based on the mixture as a whole,
and/or
CY-n-Om, preferably CY-3-O2, CY-3-O4, CY-5-O2 and/or CY-5-O4, preferably in concentrations >5%, in particular 15-50%, based on the mixture as a whole,
and/or
CCY-n-Om, preferably CCY-4-O2, CCY-3-O2, CCY-3-O3, CCY-3-O1 and/or CCY-5-O2, preferably in concentrations >5%, in particular 10-30%, based on the mixture as a whole,
and/or
CLY-n-Om, preferably CLY-2-O4, CLY-3-O2 and/or CLY-3-O3, preferably in concentrations >5%, in particular 10-30%, based on the mixture as a whole,
and/or
CK-n-F, preferably CK-3-F, CK-4-F and/or CK-5-F, preferably >5%, in particular 5-25%, based on the mixture as a whole.

Preference is furthermore given to mixtures according to the invention which comprise the following mixture concepts:
(n and m each, independently of one another, denote 1-6.)
CPY-n-Om and CY-n-Om, preferably in concentrations of 10-80%, based on the mixture as a whole,
and/or
CPY-n-Om and CK-n-F, preferably in concentrations of 10-70%, based on the mixture as a whole,
and/or
Y-nO-Om, preferably Y-4O-O4, in particular in concentrations of 2-20% by weight, based on the mixture as a whole,
and/or
CPY-n-Om and PY-n-Om, preferably CPY-2-O2 and/or CPY-3-O2 and PY-3-O2, preferably in concentrations of 10-45%, based on the mixture as a whole,
and/or
CPY-n-Om and CLY-n-Om, preferably in concentrations of 10-80%, based on the mixture as a whole,
and/or
CCVC-n-V, preferably CCVC-3-V, preferably in concentrations of 2-10%, based on the mixture as a whole,
and/or
CCC-n-V, preferably CCC-2-V and/or CCC-3-V, preferably in concentrations of 2-10%, based on the mixture as a whole,
and/or
CC-V-V, preferably in concentrations of 5-50%, based on the mixture as a whole.

In a preferred embodiment, the medium according to the invention, besides one or more compounds of the formula I, comprises at least one compound selected from the group of the compounds of the formulae T-20, T-21, IIA-26, IIA-28, IIIA-33, IIA-39, IIA-50, IIA-51, IIB-16, BF-1, BF-2, V-10, O-6a, L-4, CC-3-V, CC-3-V1, IIB-11 and Z-9:

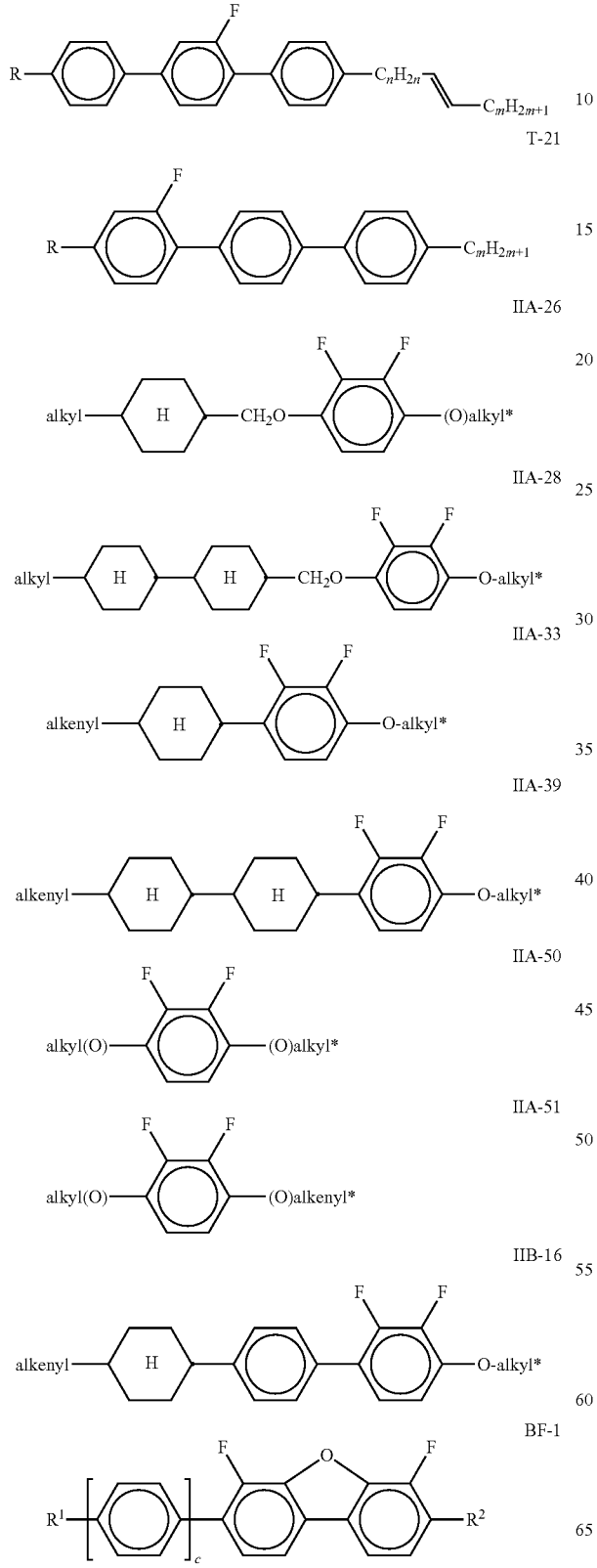

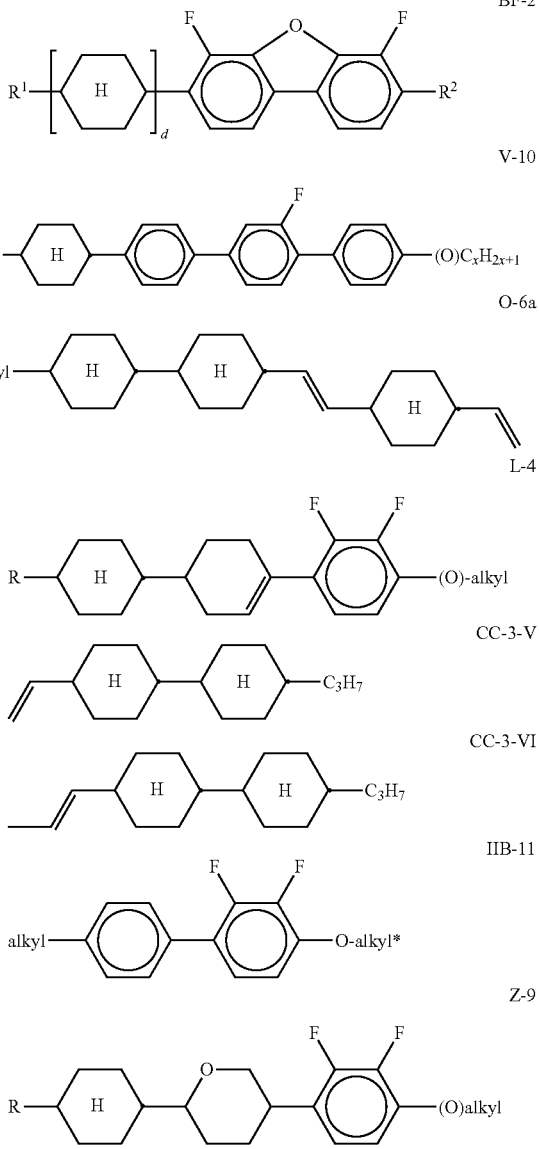

in which
R, $R^1$, $R^2$ and $R^{10}$ each, independently of one another, denote H, an alkyl or alkenyl radical having up to 15 C atoms which is unsubstituted, or monosubstituted by CN or $CF_3$ or at least monosubstituted by halogen, where, in addition, one or more $CH_2$ groups in these radicals may each optionally be replaced by —O—, —S—,

—C≡C—, —$CF_2$O—, —O$CF_2$—, —OC—O— or —O—CO— in such a way that O atoms are not linked directly to one another,
alkyl and alkyl* each, independently of one another, denote a straight-chain alkyl radical having 1-6 C atoms,
alkenyl and alkenyl* each, independently of one another, denote a straight-chain alkenyl radical having 2-6 C atoms, (O)alkyl, (O)-alkyl and
(O)alkyl* each, independently of one another, denote alkyl or O-alkyl
(O)alkenyl* denotes alkenyl or O-alkenyl
m denotes 0, 1, 2, 3, 4, 5 or 6,
n denotes 0, 1, 2, 3 or 4,
x denotes 1 to 6,
c denotes 0, 1 or 2
d 1 or 2.

The invention furthermore relates to an electro-optical display having active-matrix addressing based on the ECB, VA, PS-VA, PA-VA, IPS, PS-IPS, FFS or PS-FFS effect, characterized in that it contains, as dielectric, a liquid-crystalline medium as described above.

The liquid-crystalline medium according to the invention preferably has a nematic phase from ≤−20° C. to ≥70° C., particularly preferably from ≤−30° C. to ≥80° C., very particularly preferably from ≤−40° C. to ≥90° C.

The expression "have a nematic phase" here means on the one hand that no smectic phase and no crystallization are observed at low temperatures at the corresponding temperature and on the other hand that clearing still does not occur on heating from the nematic phase. The investigation at low temperatures is carried out in a flow viscometer at the corresponding temperature and checked by storage in test cells having a layer thickness corresponding to the electro-optical use for at least 100 hours. If the storage stability at a temperature of −20° C. in a corresponding test cell is 1000 h or more, the medium is referred to as stable at this temperature. At temperatures of −30° C. and −40° C., the corresponding times are 500 h and 250 h respectively. At high temperatures, the clearing point is measured by conventional methods in capillaries.

The liquid-crystal mixture preferably has a nematic phase range of at least 60 K and a flow viscosity $v_{20}$ of at most 30 $mm^2 \cdot s^{-1}$ at 20° C.

The values of the birefringence Δn in the liquid-crystal mixture are generally between 0.07 and 0.16, preferably between 0.08 and 0.13.

The liquid-crystal mixture according to the invention has a Δ∈ of −0.5 to −8.0, in particular −2.5 to −6.0, where Δ∈ denotes the dielectric anisotropy.

The rotational viscosity $\gamma_1$ at 20° C. is preferably ≤150 mPa·s, in particular 120 mPa·s.

The liquid-crystal media according to the invention have relatively low values for the threshold voltage ($V_0$). They are preferably in the range from 1.7 V to 3.0 V, particularly preferably ≤2.5 V and very particularly preferably ≤2.3 V.

For the present invention, the term "threshold voltage" relates to the capacitive threshold ($V_0$), also known as the Freedericks threshold, unless explicitly indicated otherwise.

In addition, the liquid-crystal media according to the invention have high values for the voltage holding ratio in liquid-crystal cells.

In general, liquid-crystal media having a low addressing voltage or threshold voltage exhibit a lower voltage holding ratio than those having a higher addressing voltage or threshold voltage and vice versa.

For the present invention, the term "dielectrically positive compounds" denotes compounds having a Δ∈>1.5, the term "dielectrically neutral compounds" denotes those having −1.5≤Δ∈≤1.5 and the term "dielectrically negative compounds" denotes those having Δ∈<−1.5. The dielectric anisotropy of the compounds is determined here by dissolving 10% of the compounds in a liquid-crystalline host and determining the capacitance of the resultant mixture in at least one test cell in each case having a layer thickness of 20 µm with homeotropic and with homogeneous surface alignment at 1 kHz. The measurement voltage is typically 0.5 V to 1.0 V, but is always lower than the capacitive threshold of the respective liquid-crystal mixture investigated.

All temperature values indicated for the present invention are in ° C.

The mixtures according to the invention are suitable for all VA-TFT applications, such as, for example, VAN, MVA, (S)-PVA, ASV, PSA (polymer sustained VA) and PS-VA (polymer stabilized VA). They are furthermore suitable for IPS (in-plane switching) and FFS (fringe field switching) applications having negative Δ∈.

The nematic liquid-crystal mixtures in the displays according to the invention generally comprise two components A and B, which themselves consist of one or more individual compounds.

Component A has significantly negative dielectric anisotropy and gives the nematic phase a dielectric anisotropy of ≤−0.5. Besides one or more compounds of the formula I, it preferably comprises the compounds of the formulae IIA, IIB and/or IIC, furthermore one or more compounds of the formula O-17.

The proportion of component A is preferably between 45 and 100%, in particular between 60 and 100%.

For component A, one (or more) individual compound(s) which has (have) a value of Δ∈≤−0.8 is (are) preferably selected. This value must be more negative, the smaller the proportion of A in the mixture as a whole.

Component B has pronounced nematogeneity and a flow viscosity of not greater than 30 $mm^2 \cdot s^{-1}$, preferably not greater than 25 $mm^2 \cdot s^{-1}$, at 20° C.

A multiplicity of suitable materials is known to the person skilled in the art from the literature. Particular preference is given to compounds of the formula O-17.

Particularly preferred individual compounds in component B are extremely low-viscosity nematic liquid crystals having a flow viscosity of not greater than 18 $mm^2 \cdot s^{-1}$, preferably not greater than 12 $mm^2 \cdot s^{-1}$, at 20° C.

Component B is monotropically or enantiotropically nematic, has no smectic phases and is able to prevent the occurrence of smectic phases down to very low temperatures in liquid-crystal mixtures. For example, if various materials of high nematogeneity are added to a smectic liquid-crystal mixture, the nematogeneity of these materials can be compared through the degree of suppression of smectic phases that is achieved.

The mixture may optionally also comprise a component C, comprising compounds having a dielectric anisotropy of Δ∈≤1.5. These so-called positive compounds are generally present in a mixture of negative dielectric anisotropy in amounts of ≤20% by weight, based on the mixture as a whole.

If the mixture according to the invention comprises one or more compounds having a dielectric anisotropy of Δ∈≤1.5, these are preferably one or more compounds selected from the group of the compounds of the formulae P-1 to P-4,

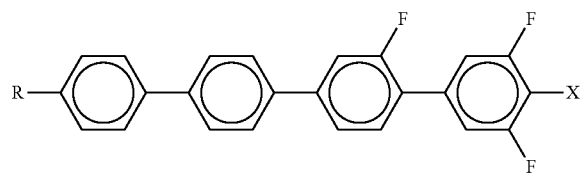

P-1

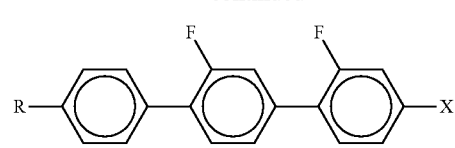

P-2

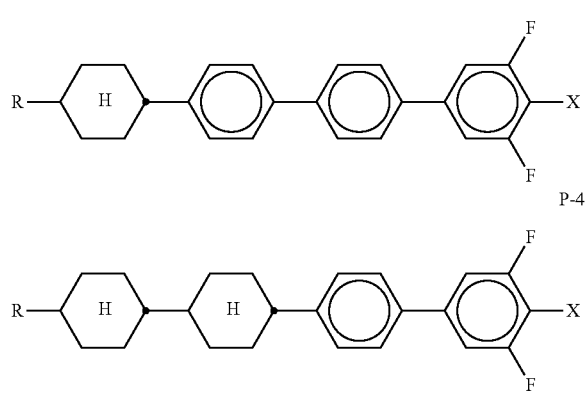

P-3

P-4 in which
R denotes straight-chain alkyl, alkoxy or alkenyl, each having 1 or 2 to 6 C atoms respectively, and
X denotes F, Cl, $CF_3$, $OCF_3$, $OCHFCF_3$ or $CCF_2CHFCF_3$, preferably F or $OCF_3$.

The compounds of the formulae P-1 to P-4 are preferably employed in the mixtures according to the invention in concentrations of 2-15%, in particular 2-10%.

Particular preference is given to the compound of the formula

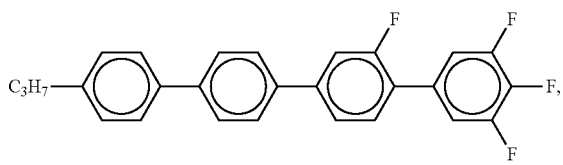

which is preferably employed in the mixtures according to the invention in amounts of 2-15%.

In addition, these liquid-crystal mixtures may also comprise more than 18 components, preferably 18 to 25 components.

Besides one or more compounds of the formula I, the mixtures preferably comprise 4 to 15, in particular 5 to 12, and particularly preferably <10, compounds of the formulae IIA, IIB and/or IIC and optionally one or more compounds of the formula O-17.

Besides compounds of the formula I and the compounds of the formulae IIA, IIB and/or IIC and optionally O-17, other constituents may also be present, for example in an amount of up to 45% of the mixture as a whole, but preferably up to 35%, in particular up to 10%.

The other constituents are preferably selected from nematic or nematogenic substances, in particular known substances, from the classes of the azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-biscyclohexylbiphenyls or cyclohexylpyrimidines, phenyl- or cyclohexyl-dioxanes, optionally halogenated stilbenes, benzyl phenyl ethers, tolans and substituted cinnamic acid esters.

The most important compounds which are suitable as constituents of liquid-crystal phases of this type can be characterized by the formula IV $$R^{20}\text{-L-G-E-}R^{21} \quad \text{IV}$$

in which L and E each denote a carbo- or heterocyclic ring system from the group formed by 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G denotes —CH=CH— —N(O)=N—
—CH=CQ- —CH=N(O)—
—C≡C— —$CH_2$—$CH_2$—
—CO—O— —$CH_2$—O—
—CO—S— —$CH_2$—S—
—CH=N— —COO-Phe-COO—
—$CF_2$O— —CF=CF—
—$OCF_2$— —$OCH_2$—
—$(CH_2)_4$— —$(CH_2)_3$O— or a C—C single bond, Q denotes halogen, preferably chlorine, or —CN, Phe denotes phenylene, and $R^{20}$ and $R^{21}$ each denote alkyl, alkenyl, alkoxy, alkoxyalkyl or alkoxycarbonyloxy having up to 18, preferably up to 8, carbon atoms, or one of these radicals alternatively denotes CN, NC, $NO_2$, NCS, $CF_3$, $SF_5$, $OCF_3$, F, Cl or Br.

In most of these compounds, $R^{20}$ and $R^{21}$ are different from one another, one of these radicals usually being an alkyl or alkoxy group. Other variants of the proposed substituents are also common. Many such substances or also mixtures thereof are commercially available. All these substances can be prepared by methods known from the literature.

It goes without saying for the person skilled in the art that the VA, IPS or FFS mixture according to the invention may also comprise compounds in which, for example, H, N, O, Cl and F have been replaced by the corresponding isotopes.

Polymerizable compounds, so-called reactive mesogens (RMs), for example as disclosed in U.S. Pat. No. 6,861,107, may furthermore be added to the mixtures according to the invention in concentrations of preferably 0.01-5% by weight, particularly preferably 0.2-2% by weight, based on the mixture. These mixtures may optionally also comprise an initiator, as described, for example, in U.S. Pat. No. 6,781,665. The initiator, for example Irganox-1076 from BASF, is preferably added to the mixture comprising polymerizable compounds in amounts of 0-1%. Mixtures of this type can be used for so-called polymer-stabilized VA modes (PS-VA) or PSA (polymer sustained VA), in which polymerization of the reactive mesogens is intended to take place in the liquid-crystalline mixture. The prerequisite for this is that the liquid-crystal mixture itself does not comprise any polymerizable components which likewise polymerize under the conditions where the RMs polymerize.

The polymerization is preferably carried out under the following conditions:

The polymerizable components are polymerized in a cell using a UV-A lamp of defined intensity for a defined period and applied voltage (typically 10 V to 30 V alternating voltage, frequencies in the range from 60 Hz to 1 kHz). The UV-A light source employed is typically a metal-halide vapor lamp or high-pressure mercury lamp having an intensity of 50 mW/cm².

These are conditions where, for example, liquid-crystalline compounds containing an alkenyl or alkenyloxy side chain, such as, for example, of the

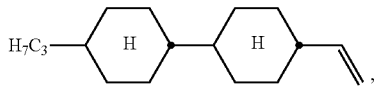

do not polymerize.

In a preferred embodiment of the invention, the polymerizable compounds are selected from the compounds of the formula M

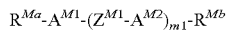   M in which the individual radicals have the following meaning:
$R^{Ma}$ and $R^{Mb}$ each, independently of one another, denote P, P-Sp-, H, F, Cl, Br, I, —CN, —NO$_2$, —NCO, —NCS, —OCN, —SCN, SF$_5$ or an alkyl, alkenyl or alkynyl group having 1 to 25 C atoms wherein in the alkyl group one or more non-adjacent CH$_2$ groups may each optionally be replaced, independently of one another, by —C(R$^0$)=C (R$^{00}$)—, —C≡C—, —N(R$^{00}$)—, —O—, —S—, —CO—, —CO—O—, —O—CO—, —O—CO—O— in such a way that O and/or S atoms are not linked directly to one another, and in which, in addition, one or more H atoms may each optionally be replaced by F, Cl, Br, I, CN, P or P-Sp-, where at least one of the radicals $R^{Ma}$ and $R^{Mb}$ preferably denotes or contains a group P or P-Sp-,
P denotes a polymerizable group,
Sp denotes a spacer group or a single bond,
$A^{M1}$ and $A^{M2}$ each, independently of one another, denote an aromatic, heteroaromatic, alicyclic or heterocyclic group, preferably having 4 to 25 ring atoms, preferably C atoms, which also includes or may contain annellated rings, and which may optionally be mono- or polysubstituted by L,
L denotes P, P-Sp-, OH, CH$_2$OH, F, Cl, Br, I, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl, optionally substituted aryl having 6 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which, in addition, one or more H atoms may each optionally be replaced by F, Cl, P or P-Sp-, and L preferably denotes P, P-Sp-, H, OH, CH$_2$OH, halogen, SF$_5$, NO$_2$, an alkyl, alkenyl or alkynyl group,
Y$^1$ denotes halogen,
$Z^{M1}$ denotes —O—, —S—, —CO—, —CO—O—, —OCO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—, —CF=CF—, —C≡C—, —CH=CH—, —COO—, —OCO—CH=CH—, CR$^0$R$^{00}$ or a single bond,
R$^0$ and R$^{00}$ each, independently of one another, denote H or alkyl having 1 to 12 C atoms,
R$^x$ denotes P, P-Sp-, H, halogen, straight-chain, branched or cyclic alkyl having 1 to 25 C atoms, in which, in addition, one or more non-adjacent CH$_2$ groups may each optionally be replaced by —O—, —S—, —CO—, —CO—O—, —O—CO—, or —O—CO—O— in such a way that O and/or S atoms are not linked directly to one another, and in which, in addition, one or more H atoms may each optionally be replaced by F, Cl, P or P-Sp-, an optionally substituted aryl or aryloxy group having 6 to 40 C atoms, or an optionally substituted heteroaryl or heteroaryloxy group having 2 to 40 C atoms,
m1 denotes 0, 1, 2, 3 or 4 and
n1 denotes 1, 2, 3 or 4,
where at least one, preferably one, two or three, particularly preferably one or two, from the group $R^{Ma}$, $R^{Mb}$ and the substituents L present denotes a group P or P-Sp- or contains at least one group P or P-Sp-.

Particularly preferred compounds of the formula M are those in which
$R^{Ma}$ and $R^{Mb}$ each, independently of one another, denote P, P-Sp-, H, F, Cl, Br, I, —CN, —NO$_2$, —NCO, —NCS, —OCN, —SCN, SF$_5$ or straight-chain or branched alkyl having 1 to 25 C atoms, in which, in addition, one or more non-adjacent CH$_2$ groups may each optionally be replaced, independently of one another, by —C(R$^0$)=C (R$^{00}$)—, —C≡C—, —N(R$^{00}$)—, —O—, —S—, —CO—, —CO—O—, —O—CO—, —O—CO—O— in such a way that O and/or S atoms are not linked directly to one another, and in which, in addition, one or more H atoms may each optionally be replaced by F, Cl, Br, I, CN, P or P-Sp-, where at least one of the radicals $R^{Ma}$ and $R^{Mb}$ preferably denotes or contains a group P or P-Sp-,
$A^{M1}$ and $A^{M2}$ each, independently of one another, denote 1,4-phenylene, naphthalene-1,4-diyl, naphthalene-2,6-diyl, phenanthrene-2,7-diyl, anthracene-2,7-diyl, fluorene-2,7-diyl, coumarine, flavone, where, in addition, one or more CH groups in these groups may each optionally be replaced by N, cyclohexane-1,4-diyl, in which, in addition, one or more non-adjacent CH$_2$ groups may each optionally be replaced by O or S, 1,4-cyclohexenylene, bicyclo[1.1.1]pentane-1,3-diyl, bicyclo[2.2.2]octane-1,4-diyl, spiro[3.3]heptane-2,6-diyl, piperidine-1,4-diyl, decahydronaphthalene-2,6-diyl, 1,2,3,4-tetrahydronaphthalene-2,6-diyl, indane-2,5-diyl or octahydro-4,7-methanoindane-2,5-diyl, where all these groups are unsubstituted or mono- or polysubstituted by L,
L denotes P, P-Sp-, OH, CH$_2$OH, F, Cl, Br, I, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl, optionally substituted aryl having 6 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which, in addition, one or more H atoms may each optionally be replaced by F, Cl, P or P-Sp-,
P denotes a polymerizable group,
Y$^1$ denotes halogen,
R$^x$ denotes P, P-Sp-, H, halogen, straight-chain, branched or cyclic alkyl having 1 to 25 C atoms, in which, in addition, one or more non-adjacent CH$_2$ groups may each optionally be replaced by —O—, —S—, —CO—, —CO—O—, —O—CO—, or —O—CO—O— in such a way that O and/or S atoms are not linked directly to one another, and in which, in addition, one or more H atoms may each optionally be replaced by F, Cl, P or P-Sp-, an optionally substituted aryl or aryloxy group having 6 to 40 C atoms, or an optionally substituted heteroaryl or heteroaryloxy group having 2 to 40 C atoms.

Very particular preference is given to compounds of the formula M in which one of $R^{Ma}$ and $R^{Mb}$ or both denote P or P-Sp-.

Suitable and preferred RMs or monomers or comonomers for use in liquid-crystalline media and PS-VA displays or PSA displays according to the invention are selected, for example from the following formulae:

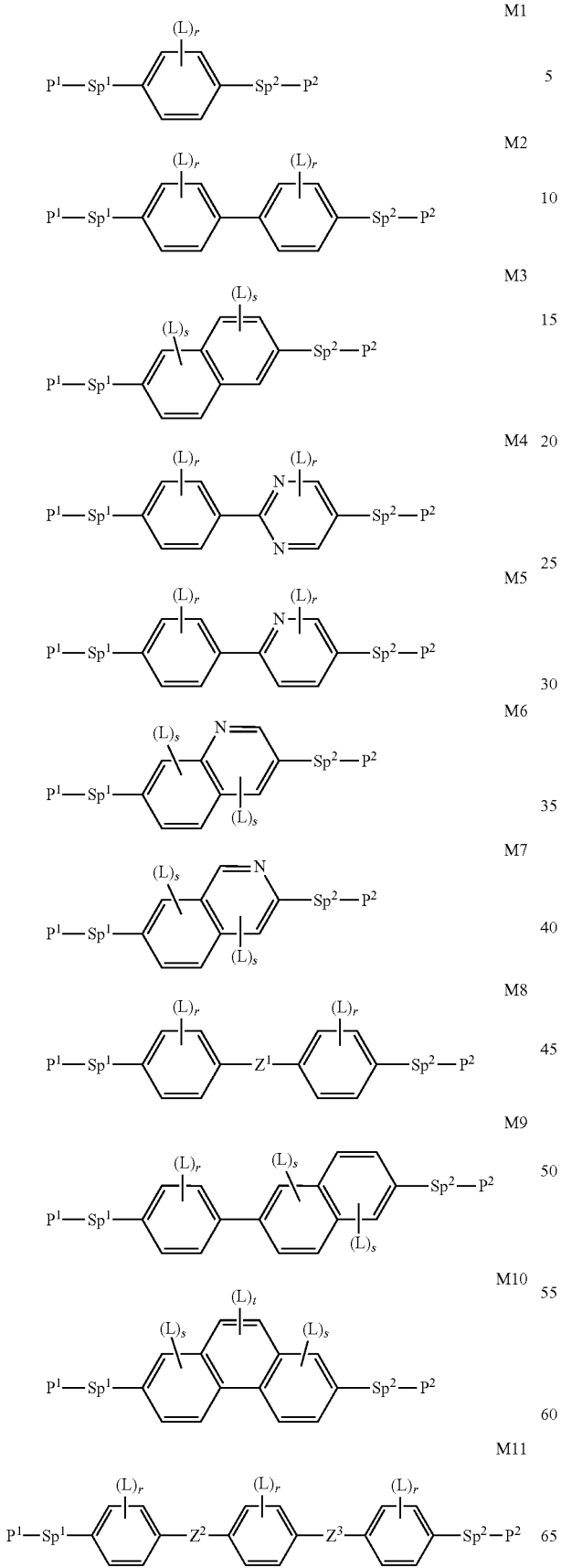
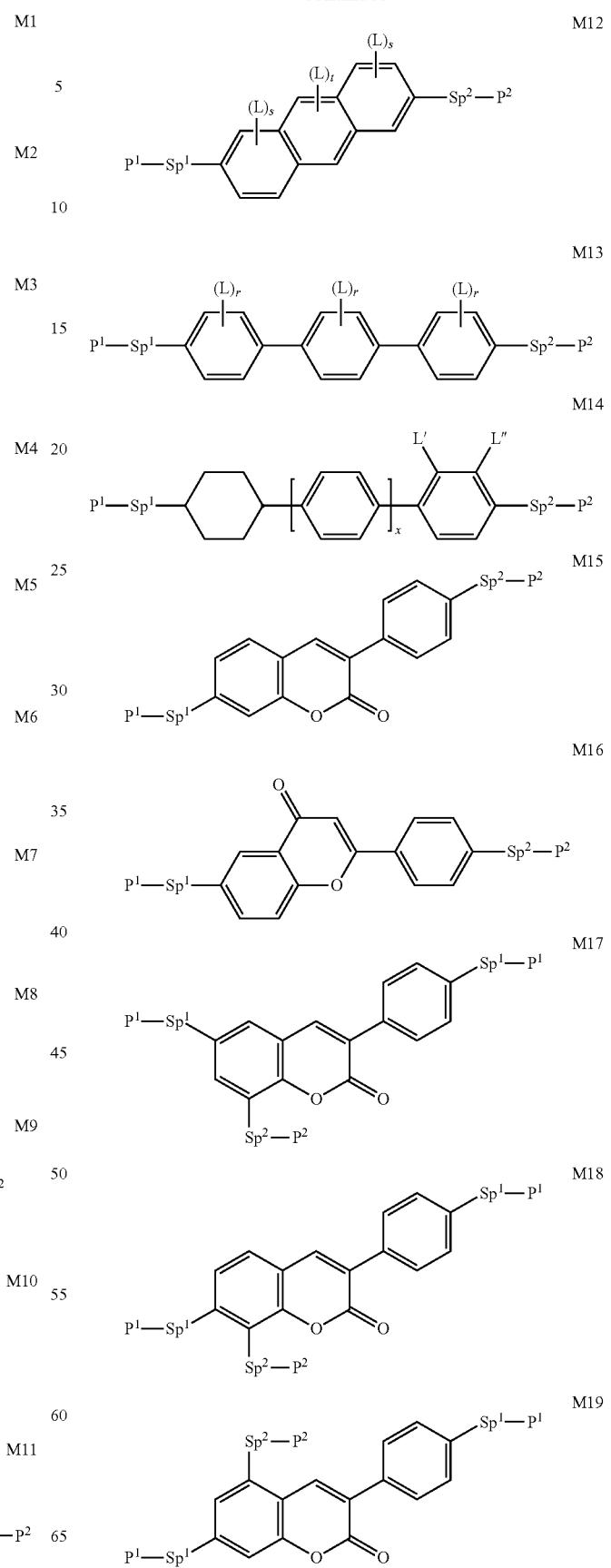

M20
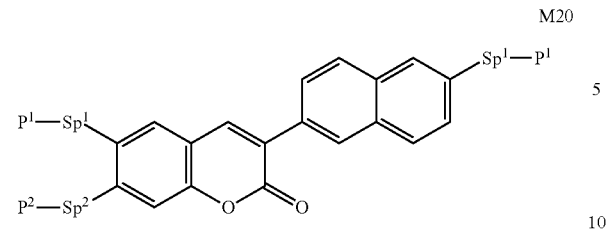
M21
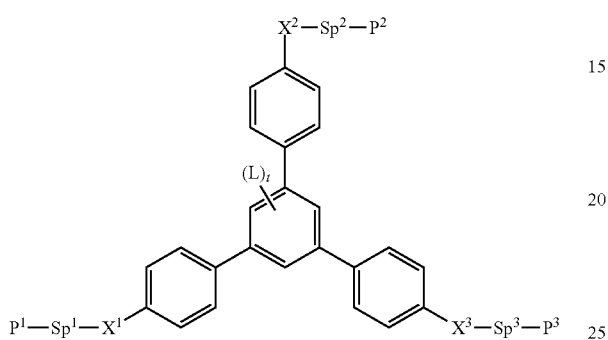
M22
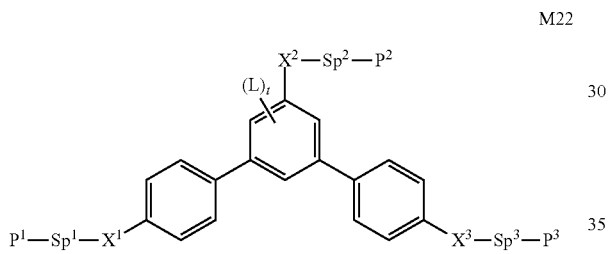
M23
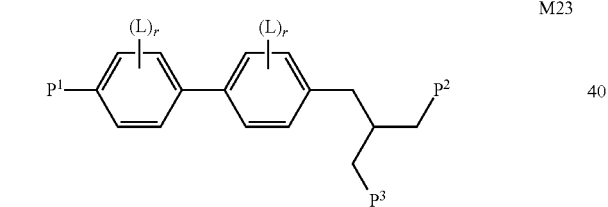
M24
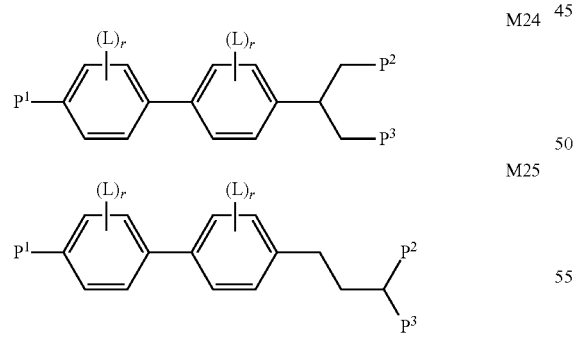
M25
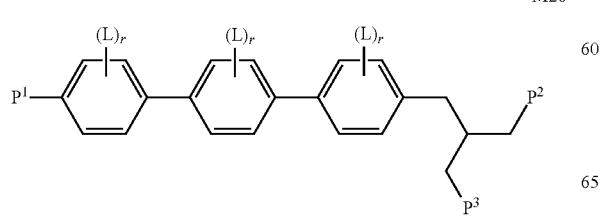
M26
M27
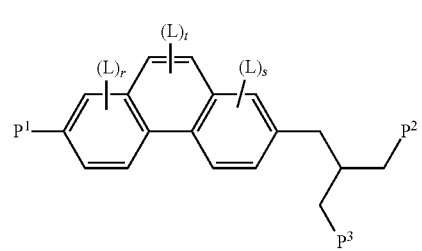
M28
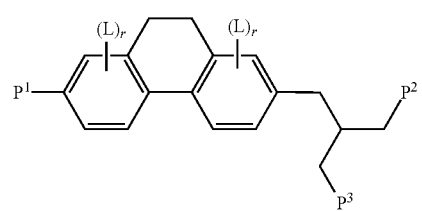
M29
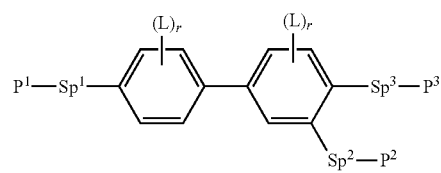
M30
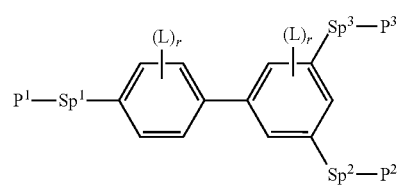
M31
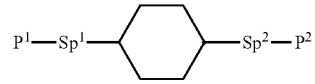
M32
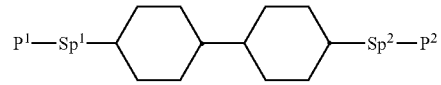
M33
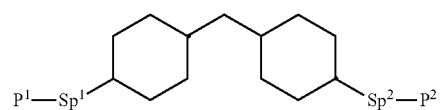
M34
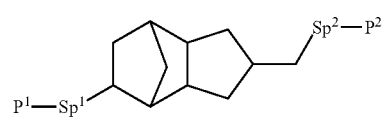
M35
M36
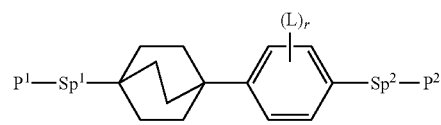
M37
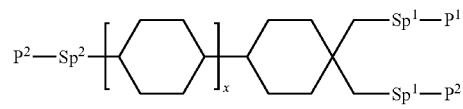

-continued

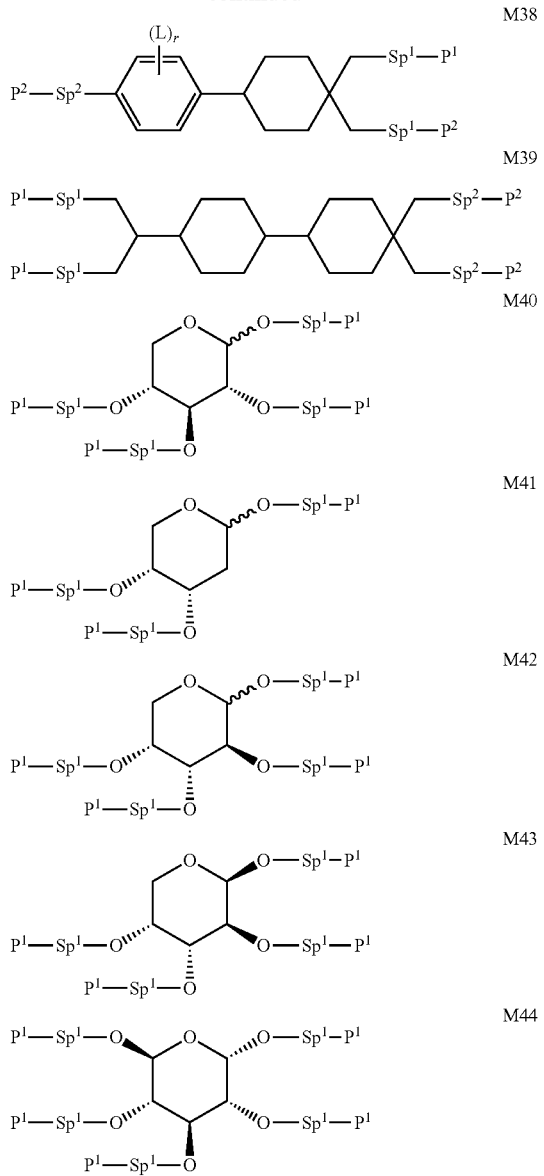

in which the individual radicals have the following meanings:
$P^1$, $P^2$ and $P^3$ each, identically or differently, denote a polymerizable group, preferably having one of the meanings indicated above and below for P, particularly preferably an acrylate, methacrylate, fluoroacrylate, oxetane, vinyloxy or epoxy group,
$Sp^1$, $Sp^2$ and $Sp^3$ each, independently of one another, denote a single bond or a spacer group, preferably having one of the meanings indicated above and below for Sp, and particularly preferably —$(CH_2)_{p1}$—, —$(CH_2)_{p1}$—O—, —$(CH_2)_{p1}$—CO—O— or —$(CH_2)_{p1}$—O—CO—O—, in which p1 is an integer from 1 to 12, and where in the last-mentioned groups the linking to the adjacent ring takes place via the 0 atom,
where one or more of the radicals $P^1$-$Sp^1$-, $P^2$-$Sp^2$- and $P^3$-$Sp^3$- may also denote $R^{aa}$, with the proviso that at least one of the radicals $P^1$-$Sp^1$-, $P^2$-$Sp^2$- and $P^3$-$Sp^3$- present does not denote $R^{aa}$,
$R^{aa}$ denotes H, F, Cl, CN or straight-chain or branched alkyl having 1 to 25 C atoms, in which, in addition, one or more non-adjacent $CH_2$ groups may each optionally be replaced, independently of one another, by $C(R^0)$=C($R^{00}$)—, —C≡C—, —N($R^0$)—, —O—, —S—, —CO—, —CO—O—, —O—CO—, or —O—CO—O— in such a way that O and/or S atoms are not linked directly to one another, and in which, in addition, one or more H atoms may each optionally be replaced by F, Cl, CN or P-Sp-, particularly preferably straight-chain or branched, optionally mono- or polyfluorinated, alkyl, alkoxy, alkenyl, alkynyl, alkylcarbonyl, alkoxycarbonyl or alkylcarbonyloxy having 1 to 12 C atoms (where the alkenyl and alkynyl radicals have at least two and the branched radicals at least three C atoms),
$R^0$, $R^{00}$ each, independently of one another and on each occurrence identically or differently, denote H or alkyl having 1 to 12 C atoms,
$X^1$, $X^2$ and $X^3$ each, independently of one another, denote —CO—O—, O—CO— or a single bond,
$Z^1$ denotes —O—, —CO—, —C($R^yR^z$)— or —$CF_2CF_2$—,
$R^y$ and $R^z$ each, independently of one another, denote H, F, $CH_3$ or $CF_3$,
$Z^2$ and $Z^3$ each, independently of one another, denote —CO—O—, —O—CO—, —$CH_2$O—, —O$CH_2$—, —$OCF_2$— or —$(CH_2)_n$—, where n is 2, 3 or 4,
L on each occurrence, identically or differently, denotes F, Cl, CN, SCN, $SF_5$ or straight-chain or branched, optionally mono- or polyfluorinated, alkyl, alkoxy, alkenyl, alkynyl, alkylcarbonyl, alkoxycarbonyl, alkylcarbonyloxy or alkoxycarbonyloxy having 1 to 12 C atoms, preferably F,
L' and L" each, independently of one another, denote H, F or Cl,
r denotes 0, 1, 2, 3 or 4,
s denotes 0, 1, 2 or 3,
t denotes 0, 1 or 2,
x denotes 0 or 1.

In the compounds of the formulae M1 to M36,

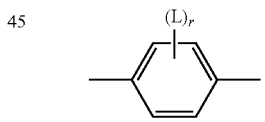

preferably denotes

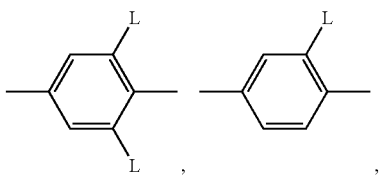

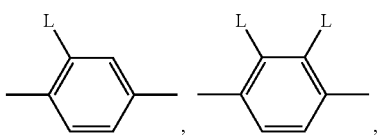

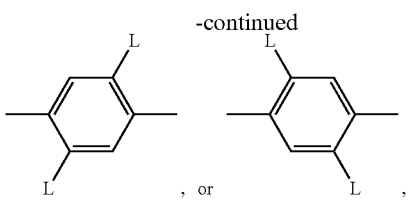

, or in which L, identically or differently on each occurrence, has one of the above meanings and preferably denotes F, Cl, CN, $NO_2$, $CH_3$, $C_2H_5$, $C(CH_3)_3$, $CH(CH_3)_2$, $CH_2CH(CH_3)C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$ or P-Sp-, particularly preferably F, Cl, CN, $CH_3$, $C_2H_5$, $OCH_3$, $COCH_3$, $OCF_3$ or P-Sp-, very particularly preferably F, Cl, $CH_3$, $OCH_3$, $COCH_3$ or $OCF_3$, in particular F or $CH_3$.

Suitable polymerizable compounds are listed, for example, in Table E.

The liquid-crystalline media in accordance with the present application preferably comprise in total 0.1 to 10%, preferably 0.2 to 4.0%, particularly preferably 0.2 to 2.0%, of polymerizable compounds.

Particular preference is given to the polymerizable compounds of the formula M and the formulae RM-1 to RM-98 (see Table E).

The mixtures according to the invention may furthermore comprise conventional additives, such as, for example, stabilizers, antioxidants, UV absorbers, nanoparticles, microparticles, etc.

The structure of the liquid-crystal displays according to the invention corresponds to the usual geometry, as described, for example, in EP-A 0 240 379.

The following examples are intended to explain the invention without limiting it. Above and below, percent data denote percent by weight; all temperatures are indicated in degrees Celsius.

Throughout the patent application, 1,4-cyclohexylene rings and 1,4-phenylene rings are depicted as follows:

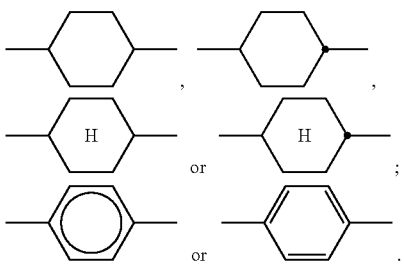

The cyclohexylene rings are trans-1,4-cyclohexylene rings.

Throughout the patent application and in the working examples, the structures of the liquid-crystal compounds are indicated by means of acronyms.

Unless indicated otherwise, the transformation into chemical formulae is carried out in accordance with Tables 1-3. All radicals $C_nH_{2n+1}$, $C_mH_{2m+1}$ and $C_{m'}H_{2m'+1}$ or $C_nH_{2n}$ and $C_mH_{2m}$ are straight-chain alkyl radicals or alkylene radicals respectively, in each case having n, m, m' or z C atoms respectively. n, m, m', z each denote, independently of one another, 1, 2, 3, 4, 5, 6, 7, 8, 9, 10, 11 or 12, preferably 1, 2, 3, 4, 5 or 6. In Table 1 the ring elements of the respective compound are coded, in Table 2 the bridging members are listed, and in Table 3 the meanings of the symbols for the left-hand or right-hand side chains of the compounds are indicated.

TABLE 1

Ring elements

A

AI

B

B(S)

C

D

DI

F

FI

G

GI

TABLE 1-continued

Ring elements

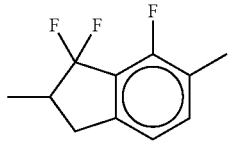 K

 L

 LI

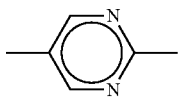 M

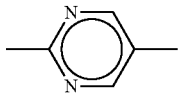 MI

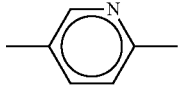 N

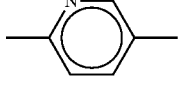 NI

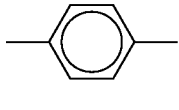 P

 S

TABLE 1-continued

Ring elements

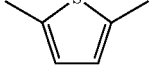 U

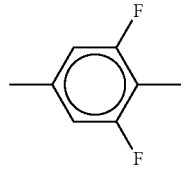 UI

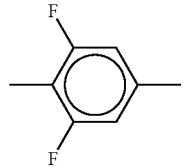 Y

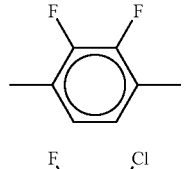 Y(F,Cl)

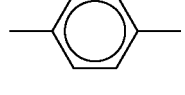 Y(Cl,F)

TABLE 2

| | Bridging members | | |
|---|---|---|---|
| E | —CH$_2$CH$_2$— | | |
| V | —CH=CH— | | |
| T | —C≡C— | | |
| W | —CF$_2$CF$_2$— | | |
| Z | —COO— | ZI | —OCO— |
| O | —CH$_2$O— | OI | —OCH$_2$— |
| Q | —CF$_2$O— | QI | —OCF$_2$— |

TABLE 3

| Side chains | | | |
|---|---|---|---|
| Left-hand side chain | | Right-hand side chain | |
| n- | C$_n$H$_{2n+1}$— | -n | —C$_n$H$_{2n+1}$ |
| nO— | C$_n$H$_{2n+1}$—O— | —On | —O—C$_n$H$_{2n+1}$ |
| V— | CH$_2$=CH— | —V | —CH=CH$_2$ |
| nV— | C$_n$H$_{2n+1}$—CH=CH— | —nV | —C$_n$H$_{2n}$—CH=CH$_2$ |
| Vn— | CH$_2$=CH—C$_n$H$_{2n}$— | —Vn | —CH=CH-C$_n$H$_{2n+1}$ |
| nVm— | C$_n$H$_{2n+1}$—CH=CH—C$_m$H$_{2m}$— | —nVm | —C$_n$H$_{2n}$—CH=CH—C$_m$H$_{2m+1}$ |
| N— | N≡C— | —N | —C≡N |
| F— | F— | —F | —F |
| Cl— | Cl— | —Cl | —Cl |
| M— | CFH$_2$— | —M | —CFH$_2$ |
| D— | CF$_2$H— | —D | —CF$_2$H |
| T— | CF$_3$— | —T | —CF$_3$ |
| MO— | CFH$_2$O— | —OM | —OCFH$_2$ |
| DO— | CF$_2$HO— | —OD | —OCF$_2$H |
| TO— | CF$_3$O— | —OT | —OCF$_3$ |

TABLE 3-continued
| Side chains | | | |
|---|---|---|---|
| Left-hand side chain | | Right-hand side chain | |
| T— | CF$_3$— | —T | —CF$_3$ |
| A— | H—C≡C— | —A | —C≡C—H |
Preferred mixture components are indicated in Tables A and B.
TABLE A
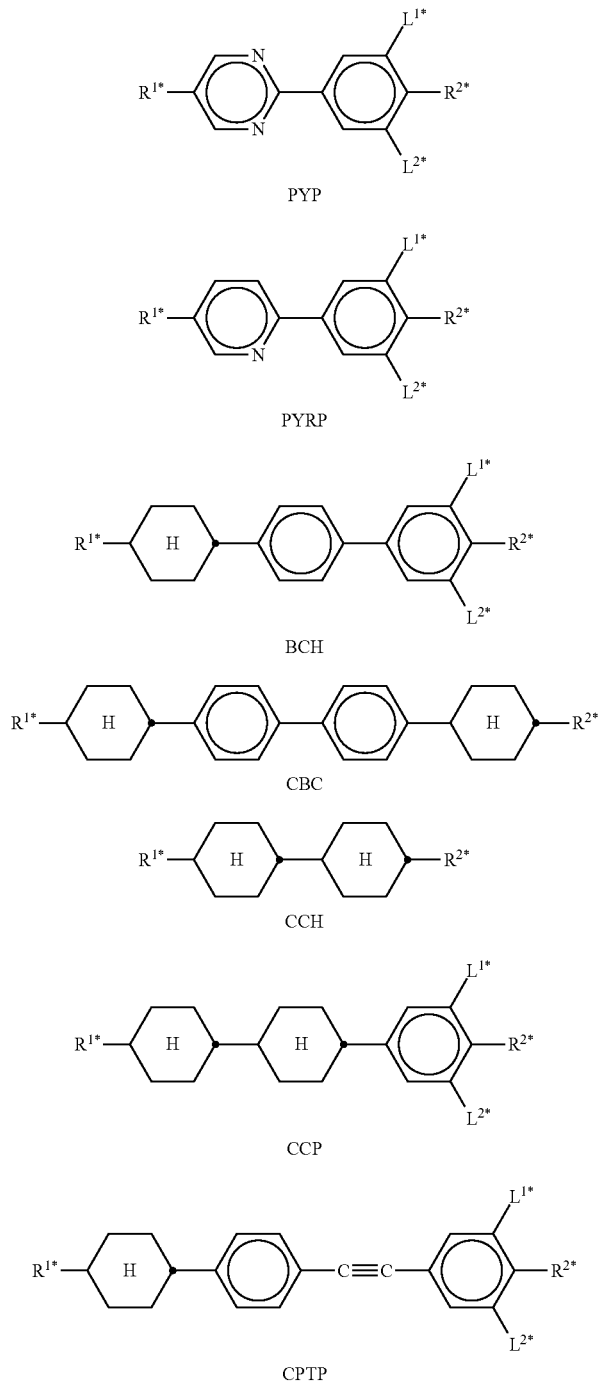
PYP
PYRP
BCH
CBC
CCH
CCP
CPTP TABLE A-continued
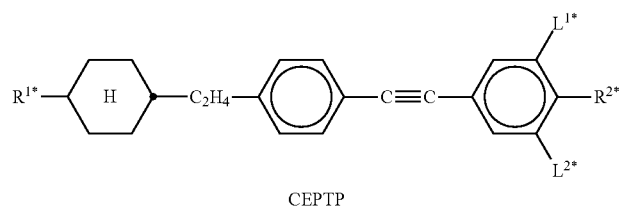
CEPTP
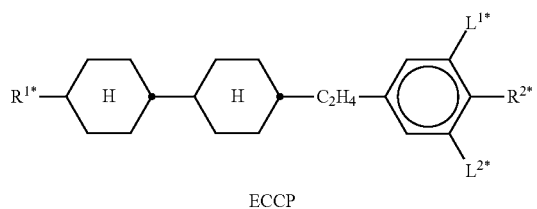
ECCP
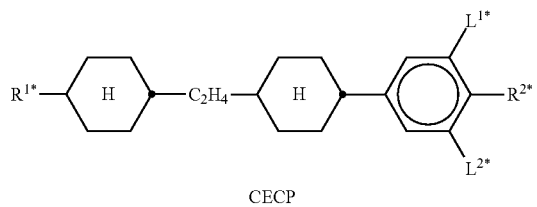
CECP
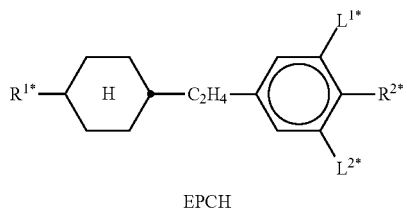
EPCH
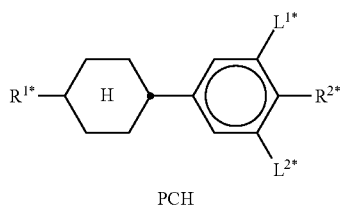
PCH
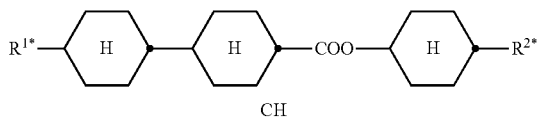
CH
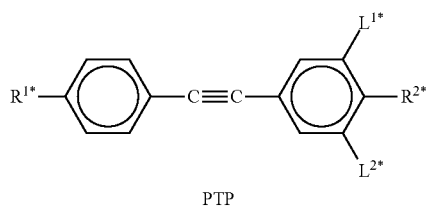
PTP
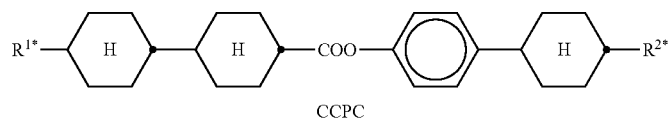
CCPC TABLE A-continued
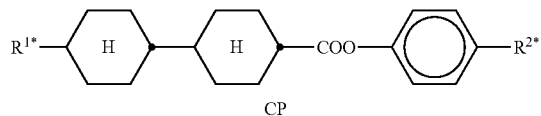
CP
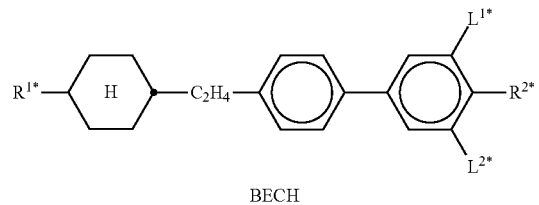
BECH
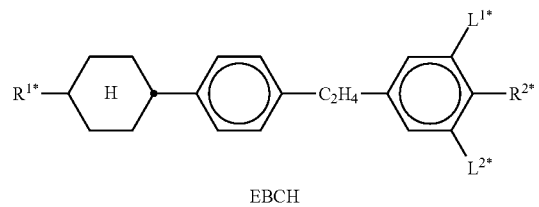
EBCH
CPC
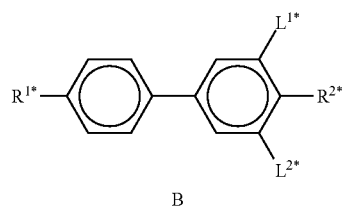
B
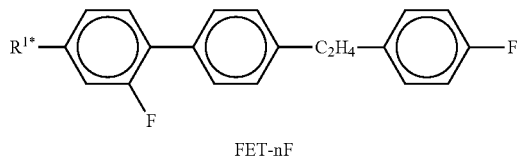
FET-nF
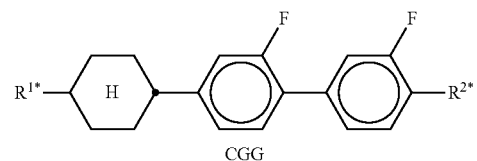
CGG
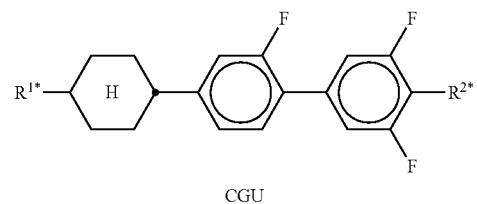
CGU TABLE A-continued
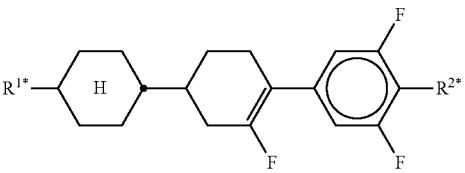
CFU
Besides the compounds of the formula I, the mixtures according to the invention very particularly preferably comprise one or more compounds from Table B.
TABLE B
The following abbreviations are used:
(n, m, m', z: each, independently of one another, 1, 2, 3, 4, 5 or 6;
$(O)C_mH_{2m+1}$ means $OC_mH_{2m+1}$ or $C_mH_{2m+1})$
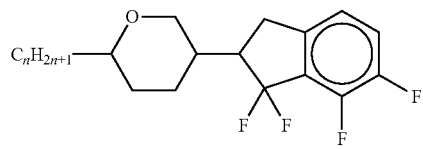
AIK-n-F
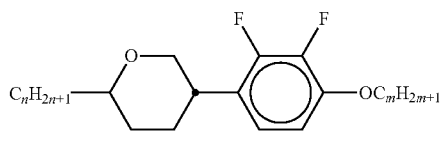
AIY-n-Om
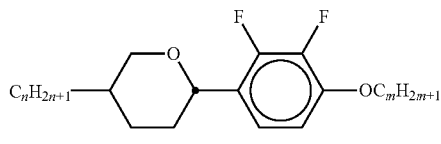
AY-n-Om
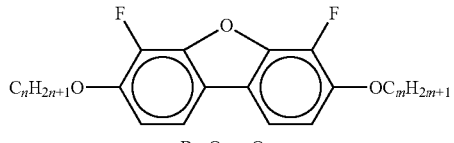
B-nO—Om
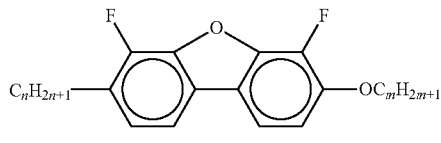
B-n-Om
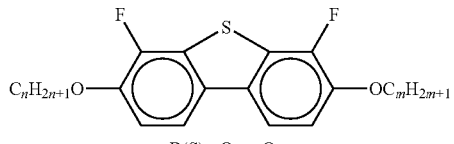
B(S)-nO—Om TABLE B-continued
The following abbreviations are used:
(n, m, m', z: each, independently of one another, 1, 2, 3, 4, 5 or 6;
$(O)C_mH_{2m+1}$ means $OC_mH_{2m+1}$ or $C_mH_{2m+1}$)
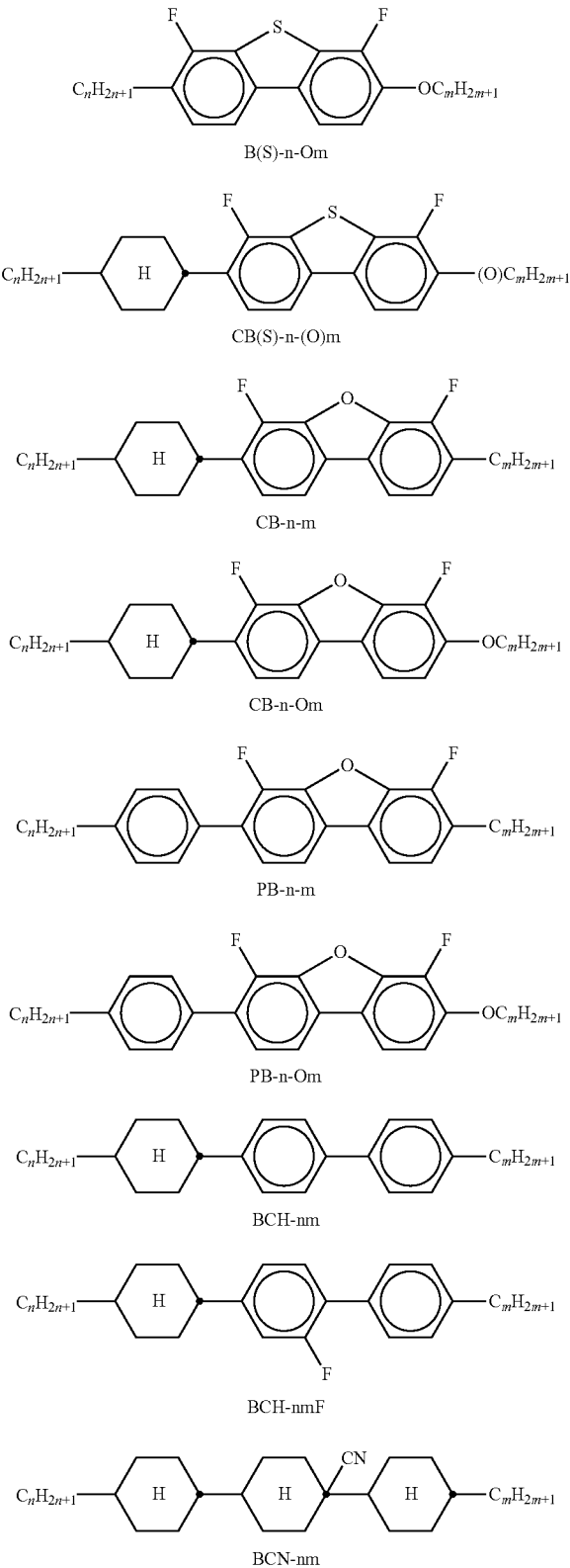

TABLE B-continued
The following abbreviations are used:
(n, m, m', z: each, independently of one another, 1, 2, 3, 4, 5 or 6;
(O)$C_mH_{2m+1}$ means $OC_mH_{2m+1}$ or $C_mH_{2m+1}$)
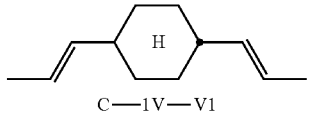
C—1V—V1
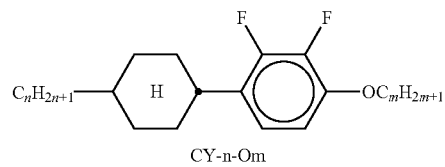
CY-n-Om
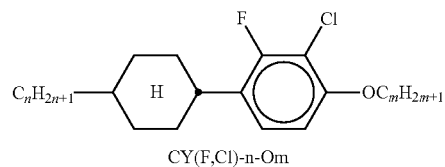
CY(F,Cl)-n-Om
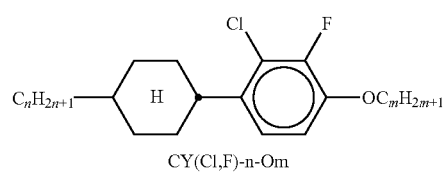
CY(Cl,F)-n-Om
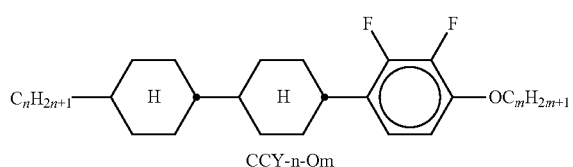
CCY-n-Om
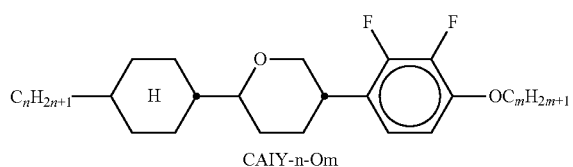
CAIY-n-Om
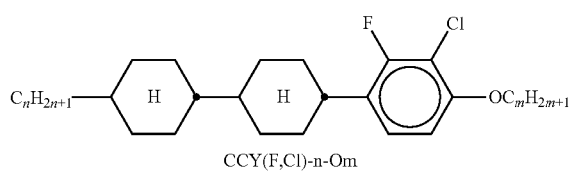
CCY(F,Cl)-n-Om
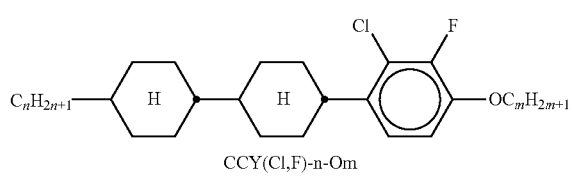
CCY(Cl,F)-n-Om
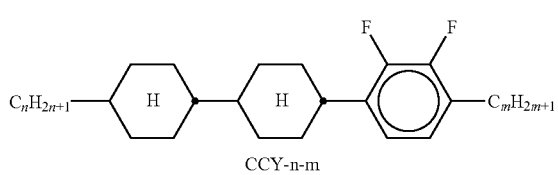
CCY-n-m TABLE B-continued
The following abbreviations are used:
(n, m, m', z: each, independently of one another, 1, 2, 3, 4, 5 or 6;
$(O)C_mH_{2m+1}$ means $OC_mH_{2m+1}$ or $C_mH_{2m+1}$)
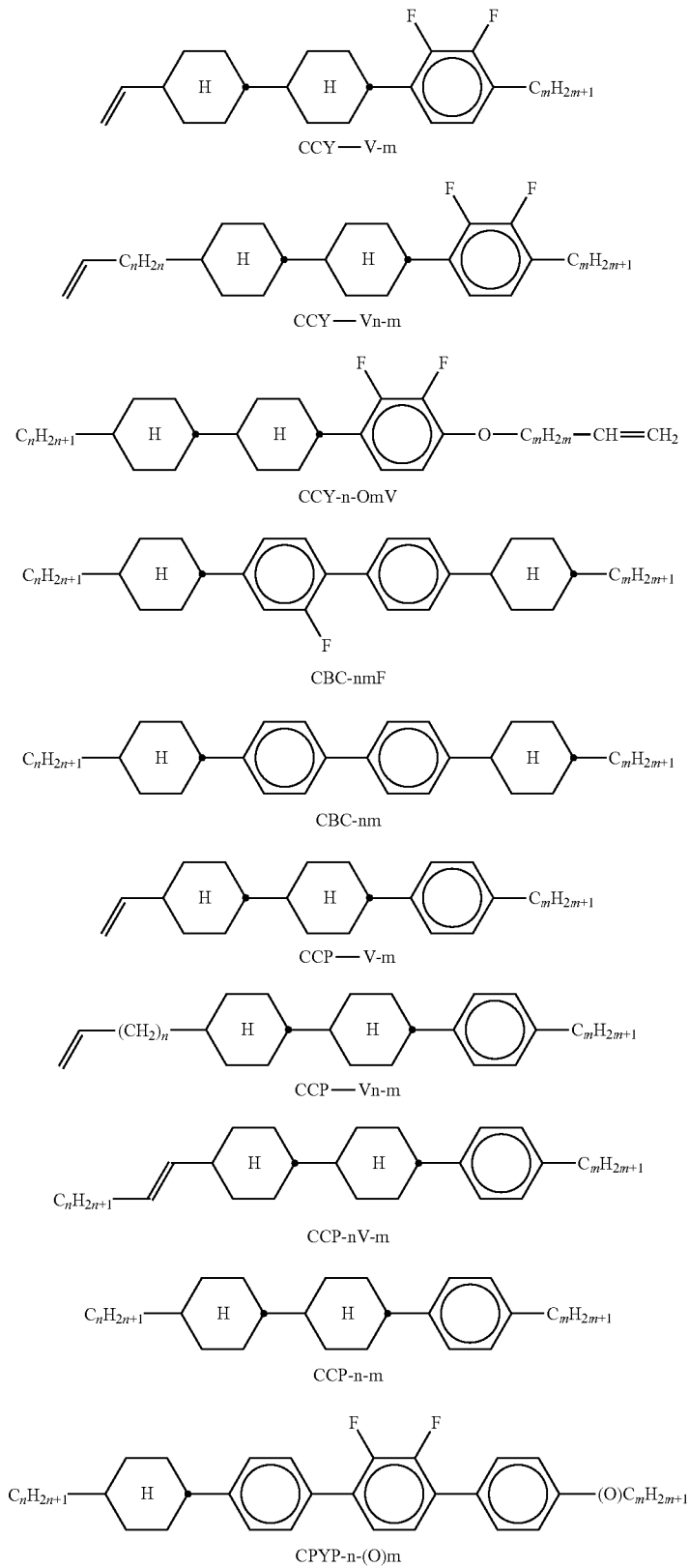

TABLE B-continued
The following abbreviations are used:
(n, m, m', z: each, independently of one another, 1, 2, 3, 4, 5 or 6;
$(O)C_mH_{2m+1}$ means $OC_mH_{2m+1}$ or $C_mH_{2m+1}$)
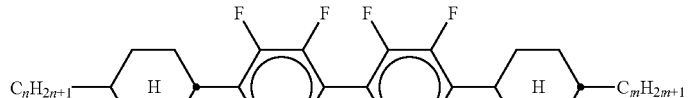
CYYC-n-m
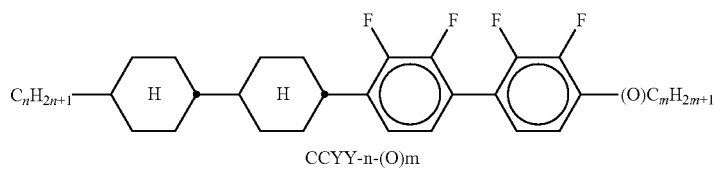
CCYY-n-(O)m
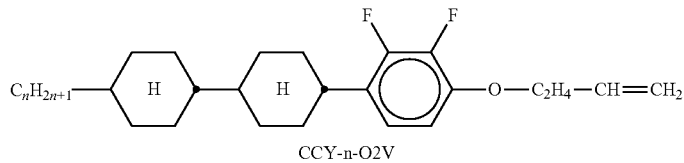
CCY-n-O2V
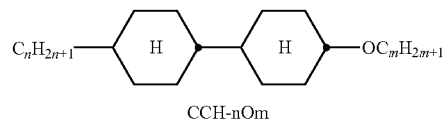
CCH-nOm
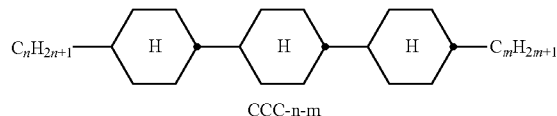
CCC-n-m
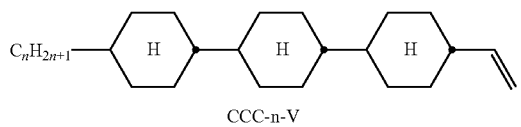
CCC-n-V
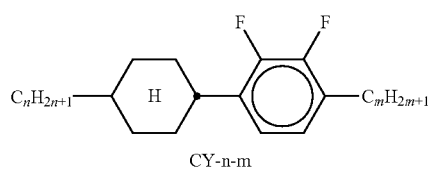
CY-n-m
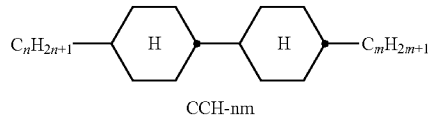
CCH-nm
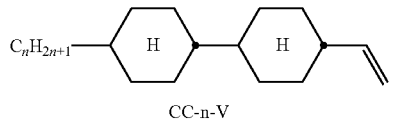
CC-n-V
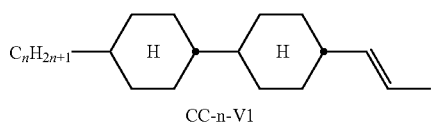
CC-n-V1

TABLE B-continued
The following abbreviations are used:
(n, m, m', z: each, independently of one another, 1, 2, 3, 4, 5 or 6;
(O)$C_mH_{2m+1}$ means $OC_mH_{2m+1}$ or $C_mH_{2m+1}$)
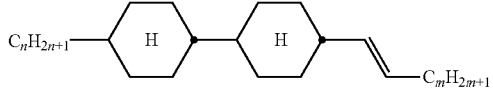
CC-n-Vm
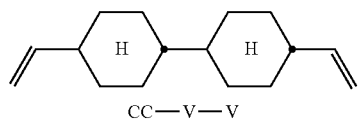
CC—V—V
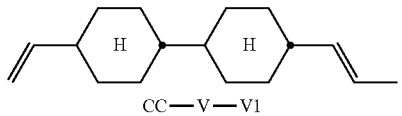
CC—V—V1
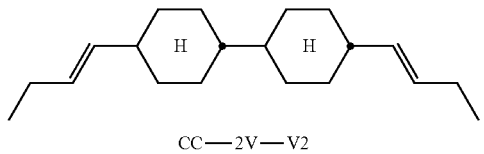
CC—2V—V2
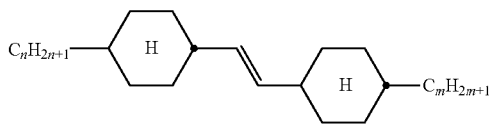
CVC-n-m
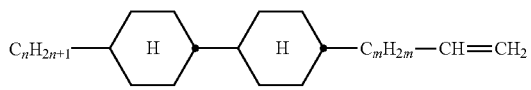
CC-n-mV
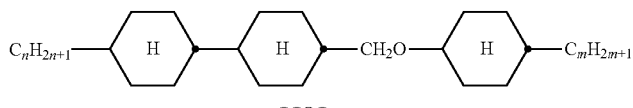
CCOC-n-m
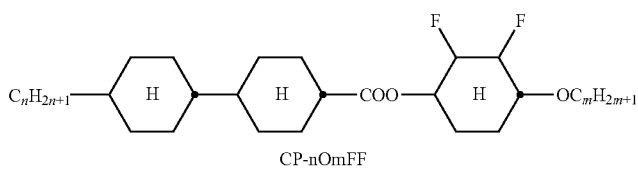
CP-nOmFF
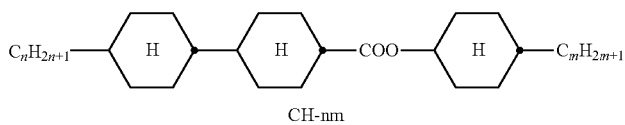
CH-nm
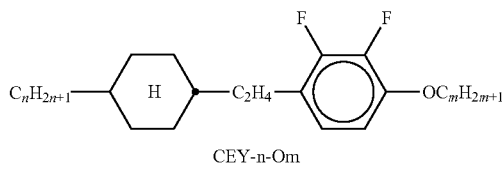
CEY-n-Om TABLE B-continued
The following abbreviations are used:
(n, m, m', z: each, independently of one another, 1, 2, 3, 4, 5 or 6;
$(O)C_mH_{2m+1}$ means $OC_mH_{2m+1}$ or $C_mH_{2m+1}$)
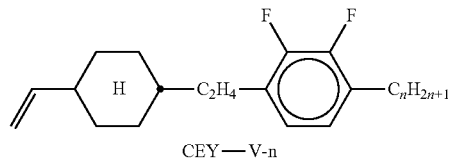
CEY—V-n
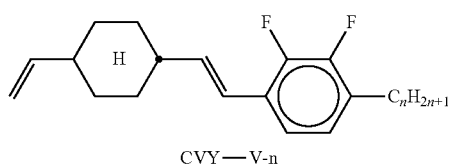
CVY—V-n
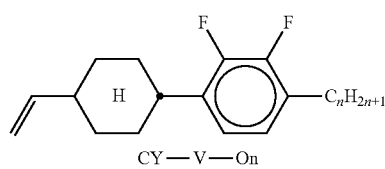
CY—V—On
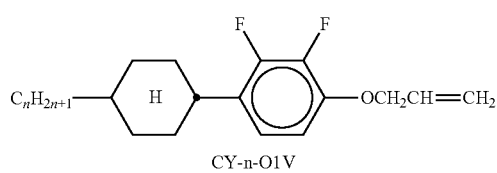
CY-n-O1V
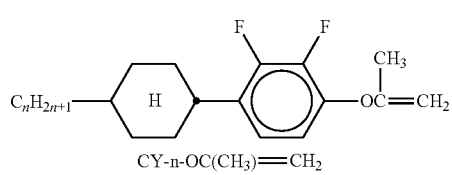
CY-n-OC(CH$_3$)=CH$_2$
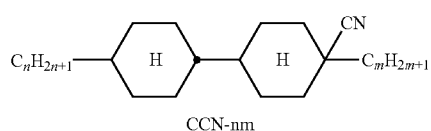
CCN-nm
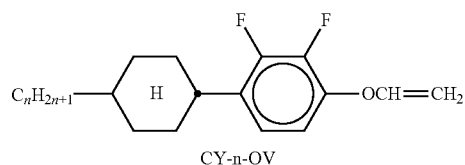
CY-n-OV
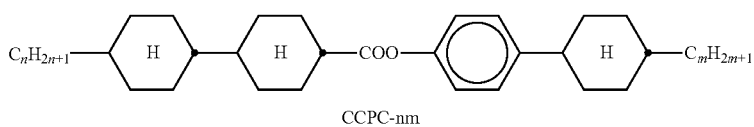
CCPC-nm
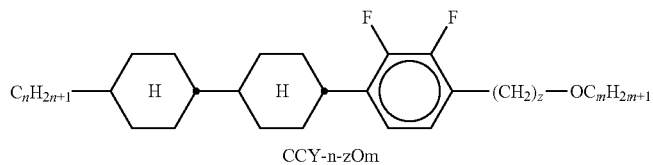
CCY-n-zOm TABLE B-continued
The following abbreviations are used:
(n, m, m', z: each, independently of one another, 1, 2, 3, 4, 5 or 6;
$(O)C_mH_{2m+1}$ means $OC_mH_{2m+1}$ or $C_mH_{2m+1}$)
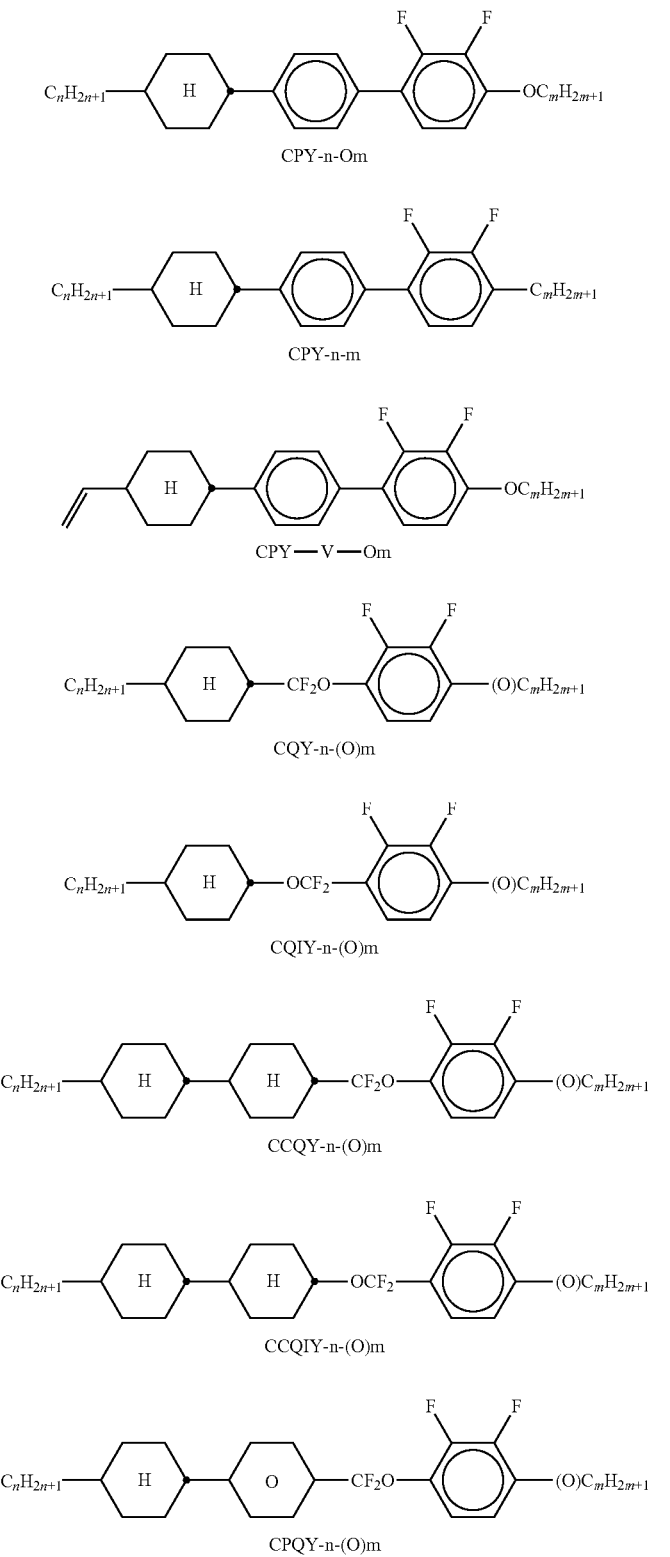
CPY-n-Om
CPY-n-m
CPY—V—Om
CQY-n-(O)m
CQIY-n-(O)m
CCQY-n-(O)m
CCQIY-n-(O)m
CPQY-n-(O)m TABLE B-continued
The following abbreviations are used:
(n, m, m', z: each, independently of one another, 1, 2, 3, 4, 5 or 6;
(O)C$_m$H$_{2m+1}$ means OC$_m$H$_{2m+1}$ or C$_m$H$_{2m+1}$)
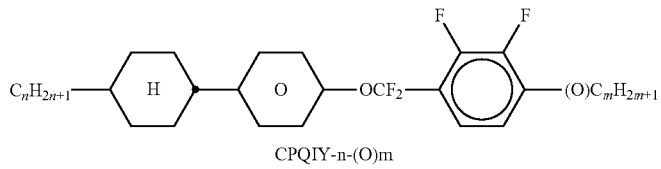
CPQIY-n-(O)m
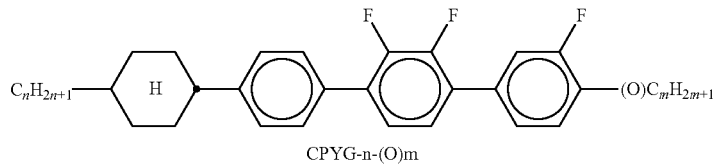
CPYG-n-(O)m
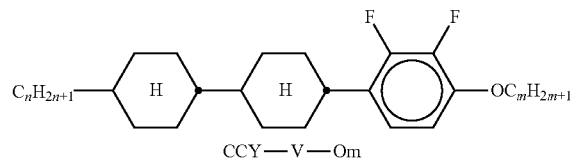
CCY—V—Om
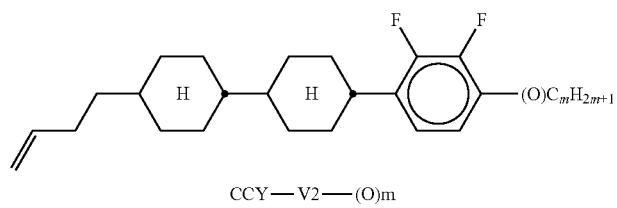
CCY—V2—(O)m
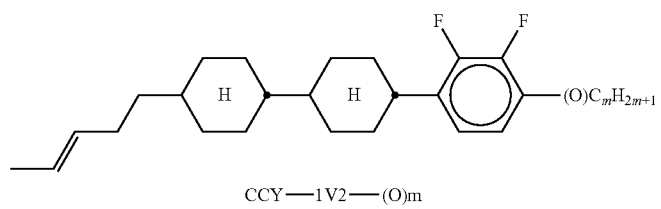
CCY—1V2—(O)m
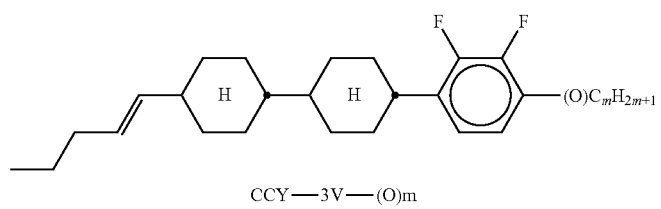
CCY—3V—(O)m
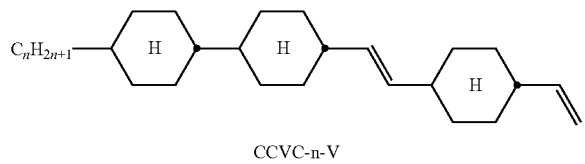
CCVC-n-V
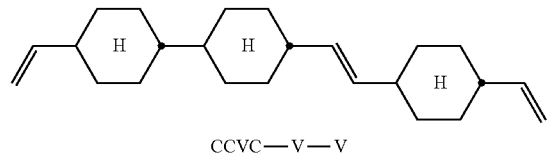
CCVC—V—V TABLE B-continued
The following abbreviations are used:
(n, m, m', z: each, independently of one another, 1, 2, 3, 4, 5 or 6;
$(O)C_mH_{2m+1}$ means $OC_mH_{2m+1}$ or $C_mH_{2m+1}$)
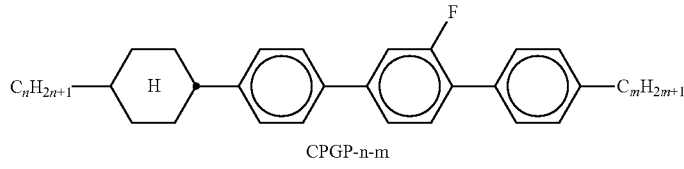
CPGP-n-m
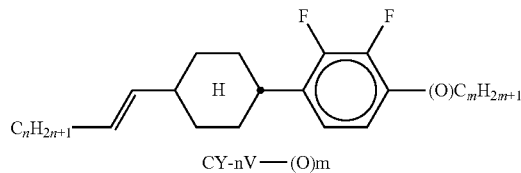
CY-nV—(O)m
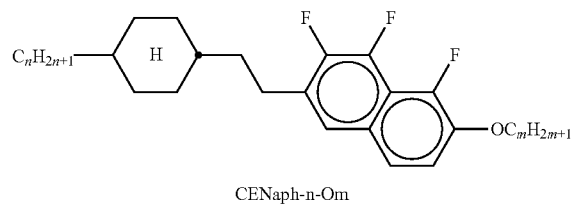
CENaph-n-Om
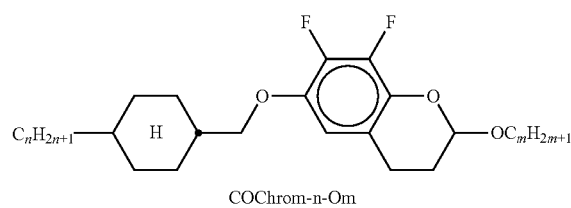
COChrom-n-Om
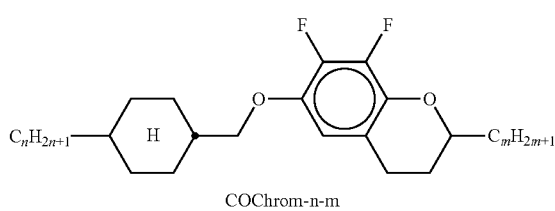
COChrom-n-m
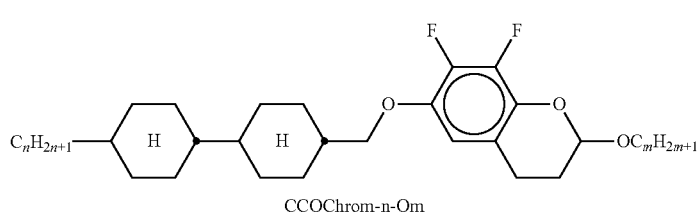
CCOChrom-n-Om
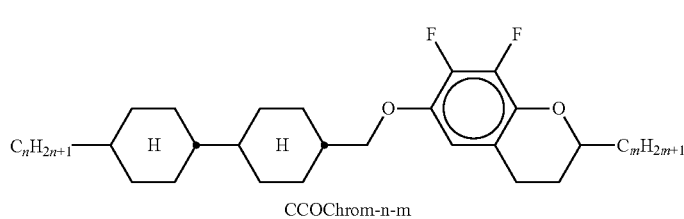
CCOChrom-n-m TABLE B-continued
The following abbreviations are used:
(n, m, m', z: each, independently of one another, 1, 2, 3, 4, 5 or 6;
$(O)C_mH_{2m+1}$ means $OC_mH_{2m+1}$ or $C_mH_{2m+1}$)
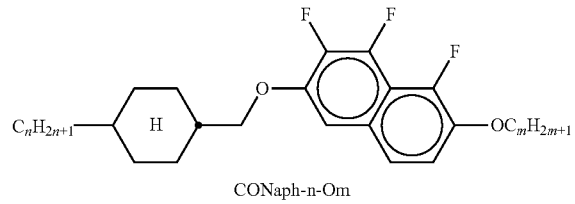
CONaph-n-Om
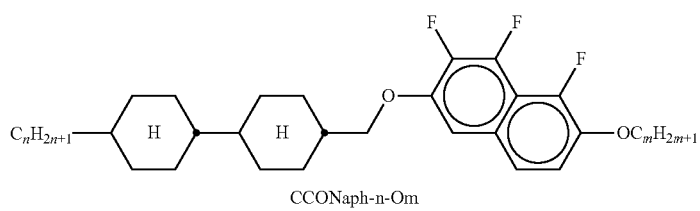
CCONaph-n-Om
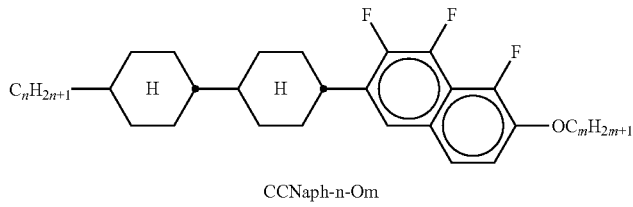
CCNaph-n-Om
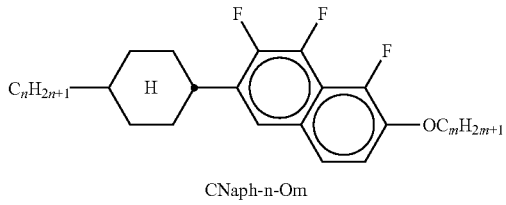
CNaph-n-Om
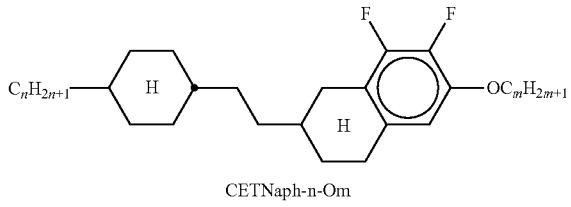
CETNaph-n-Om
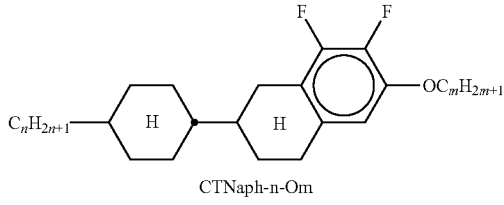
CTNaph-n-Om
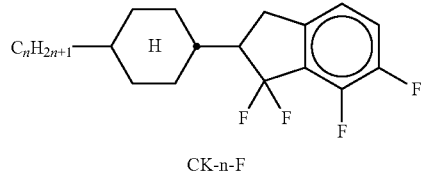
CK-n-F TABLE B-continued
The following abbreviations are used:
(n, m, m', z: each, independently of one another, 1, 2, 3, 4, 5 or 6;
$(O)C_mH_{2m+1}$ means $OC_mH_{2m+1}$ or $C_mH_{2m+1}$)
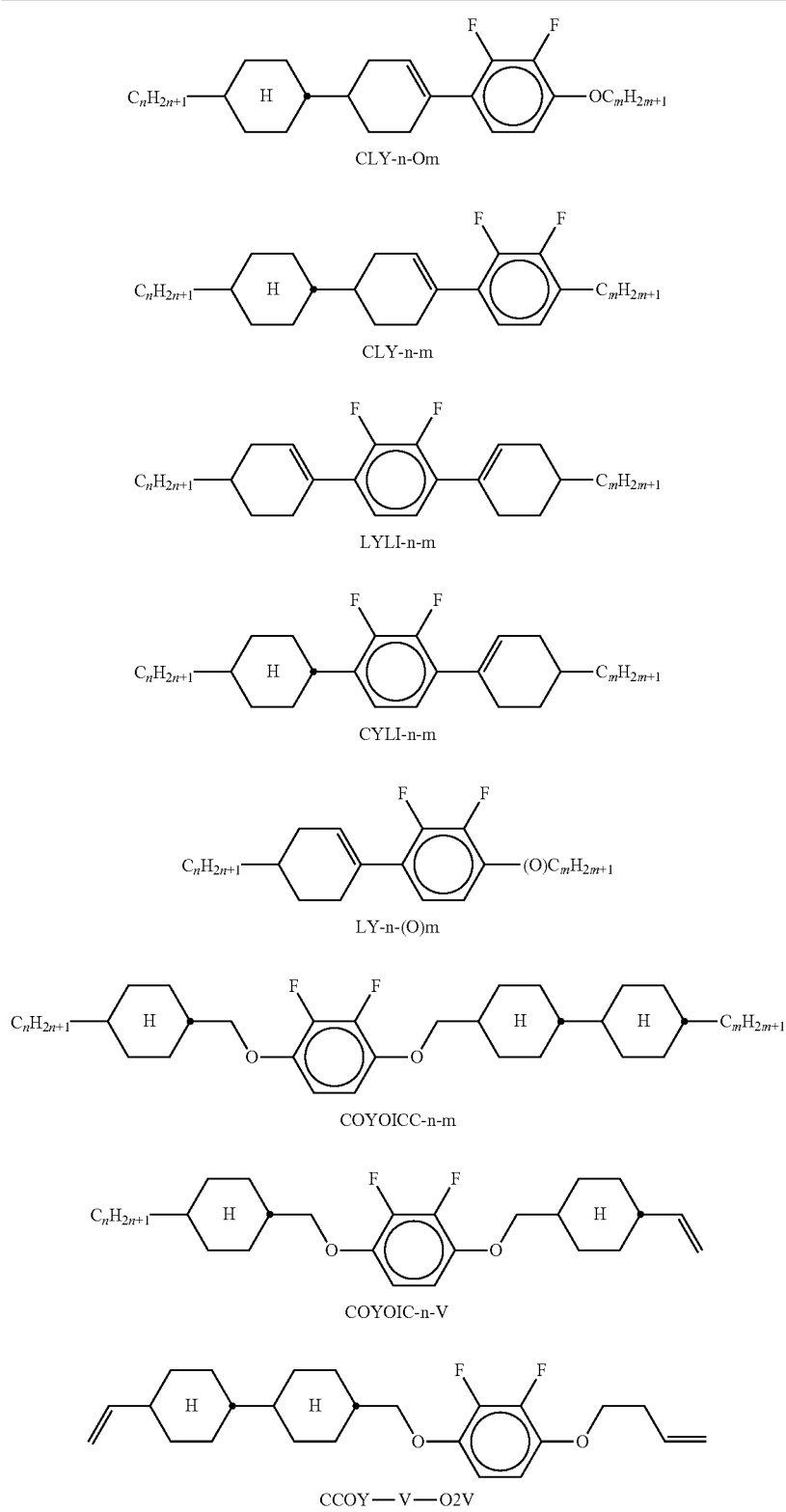
CLY-n-Om
CLY-n-m
LYLI-n-m
CYLI-n-m
LY-n-(O)m
COYOICC-n-m
COYOIC-n-V
CCOY—V—O2V TABLE B-continued
The following abbreviations are used:
(n, m, m', z: each, independently of one another, 1, 2, 3, 4, 5 or 6;
$(O)C_mH_{2m+1}$ means $OC_mH_{2m+1}$ or $C_mH_{2m+1}$)
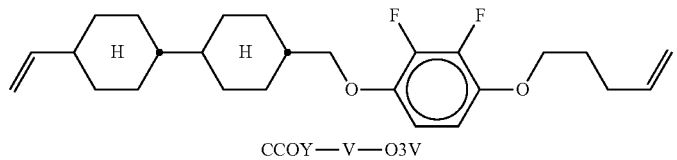
CCOY—V—O3V
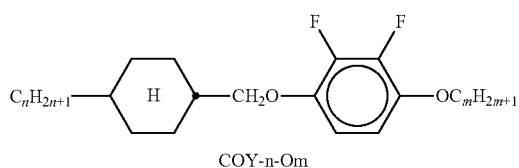
COY-n-Om
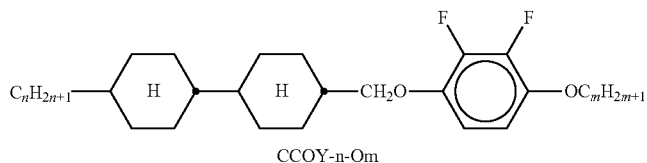
CCOY-n-Om
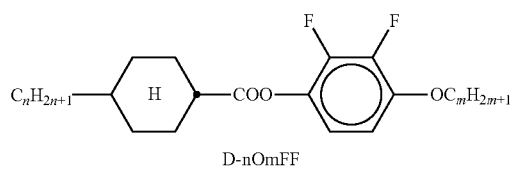
D-nOmFF
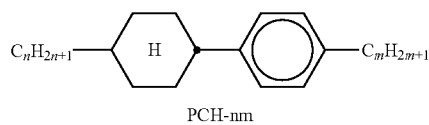
PCH-nm
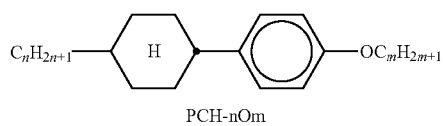
PCH-nOm
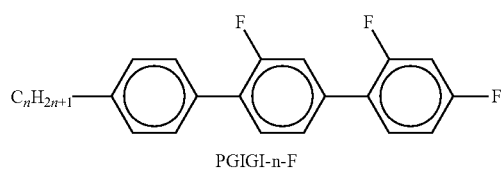
PGIGI-n-F
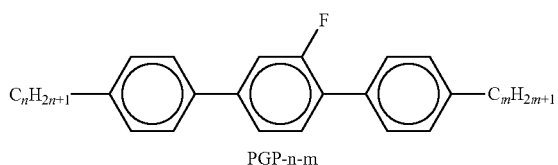
PGP-n-m
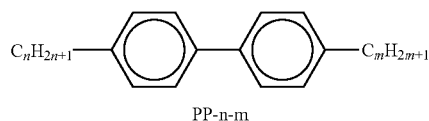
PP-n-m TABLE B-continued
The following abbreviations are used:
(n, m, m', z: each, independently of one another, 1, 2, 3, 4, 5 or 6;
(O)$C_mH_{2m+1}$ means $OC_mH_{2m+1}$ or $C_mH_{2m+1}$)
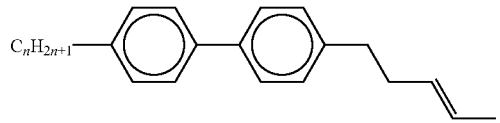
PP-n-2V1
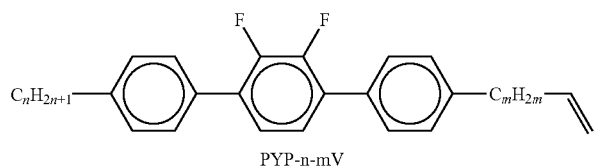
PYP-n-mV
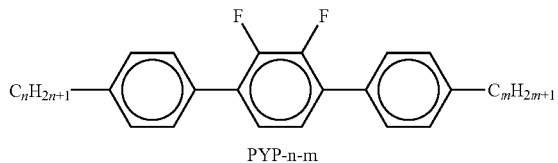
PYP-n-m
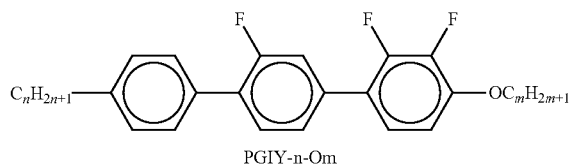
PGIY-n-Om
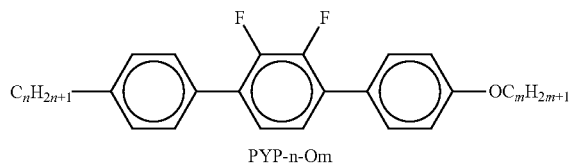
PYP-n-Om
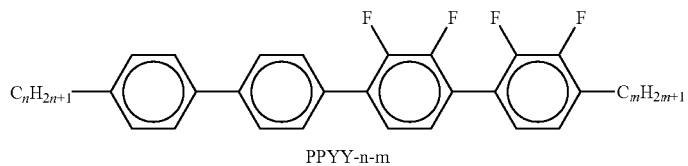
PPYY-n-m
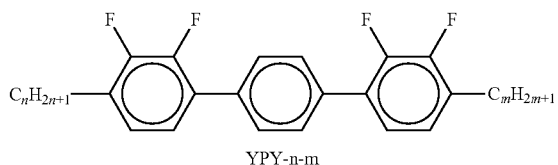
YPY-n-m
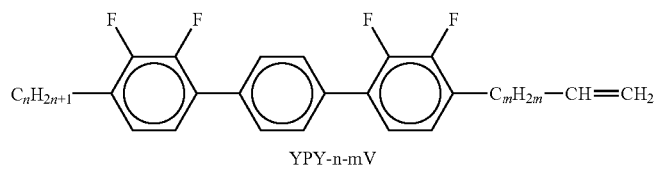
YPY-n-mV TABLE B-continued
The following abbreviations are used:
(n, m, m', z: each, independently of one another, 1, 2, 3, 4, 5 or 6;
(O)$C_mH_{2m+1}$ means $OC_mH_{2m+1}$ or $C_mH_{2m+1}$)
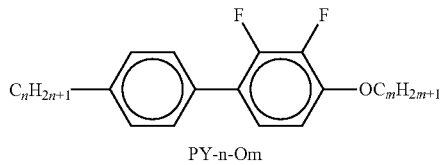
PY-n-Om
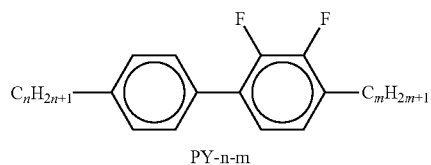
PY-n-m
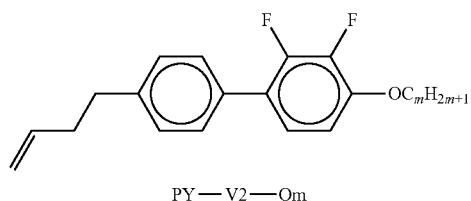
PY—V2—Om
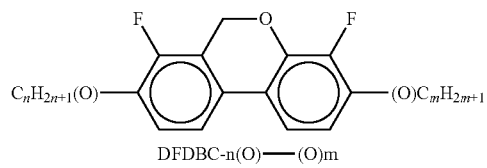
DFDBC-n(O)—(O)m
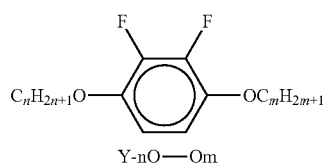
Y-nO—Om
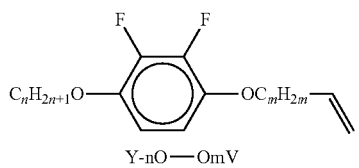
Y-nO—OmV
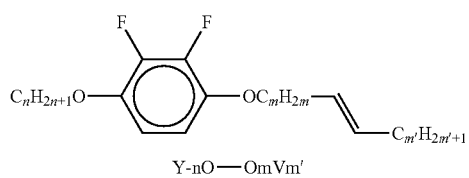
Y-nO—OmVm'
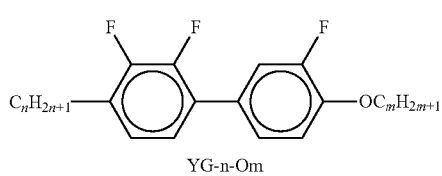
YG-n-Om TABLE B-continued The following abbreviations are used:
(n, m, m', z: each, independently of one another, 1, 2, 3, 4, 5 or 6;
$(O)C_mH_{2m+1}$ means $OC_mH_{2m+1}$ or $C_mH_{2m+1}$)

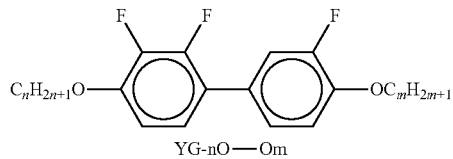
YG-nO—Om

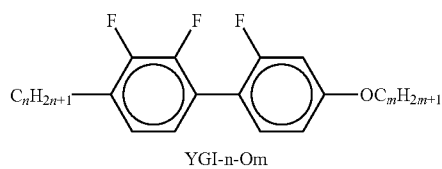
YGI-n-Om

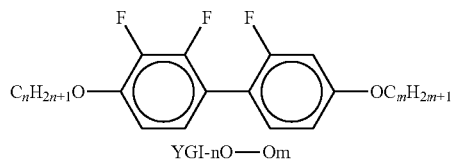
YGI-nO—Om

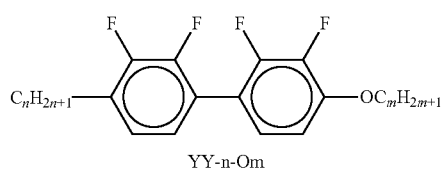
YY-n-Om

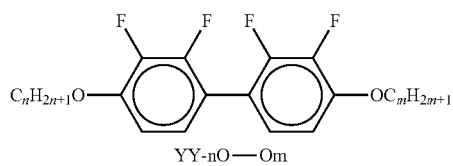
YY-nO—Om

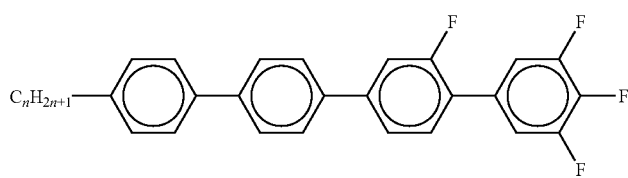
PPGU-n-F

The liquid-crystal mixtures which can be used in accordance with the invention are prepared in a manner which is conventional per se. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing.

By means of suitable additives, the liquid-crystal phases according to the invention can be modified in such a way that they can be employed in any type of, for example, ECB, VAN, IPS, GH or ASM-VA LCD display that has been disclosed to date.

The dielectrics may also comprise further additives known to the person skilled in the art and described in the literature, such as, for example, UV absorbers, antioxidants, nanoparticles and free-radical scavengers. For example, 0-15% of pleochroic dyes, stabilizers, such as, for example, phenols, HALS (hindered amine light stabilizers), for example Tinuvin 770 (=bis(2,2,6,6-tetramethyl-4-piperidyl) sebacate), or chiral dopants may be added. Suitable stabilizers for the mixtures according to the invention are, in particular, those listed in Table D.

For example, O-15% of pleochroic dyes may be added, furthermore conductive salts, preferably ethyldimethyldodecylammonium 4-hexoxybenzoate, tetrabutylammonium tetraphenylboranate or complex salts of crown ethers (cf., for example, Haller et al., Mol. Cryst. Liq. Cryst., Volume 24, pages 249-258 (1973)), may be added in order to improve the conductivity or substances may be added in order to modify the dielectric anisotropy, the viscosity and/or the alignment of the nematic phases. Substances of this type are described, for example, in DE-A 22 09 127, 22 40 864, 23 21 632, 23 38 281, 24 50 088, 26 37 430 and 28 53 728.

Table C shows possible dopants which can be added to the mixtures according to the invention. If the mixtures comprise a dopant, it is employed in amounts of 0.01-4% by weight, preferably 0.1-1.0% by weight.

TABLE C

Table C indicates possible dopants which are generally added to the mixtures according to the invention. The mixture preferably comprises 0-10% by weight, in particular 0.01-5% by weight and particularly preferably 0.01-3% by weight of dopants.

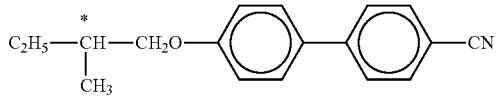

C15

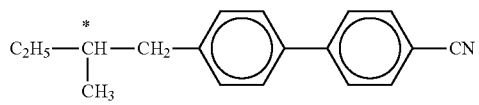

CB 15

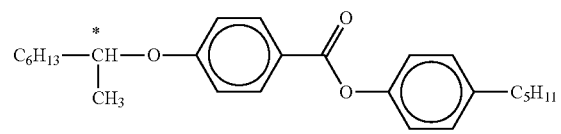

CM 21

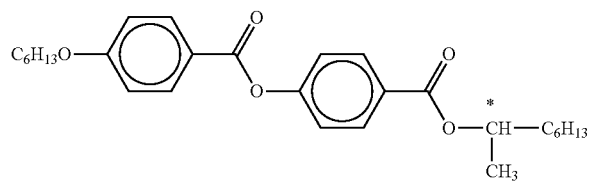

R/S-811

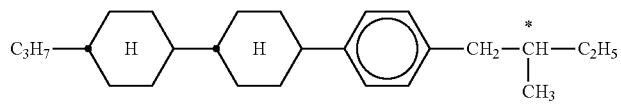

CM 44

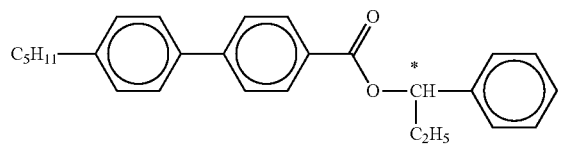

CM 45

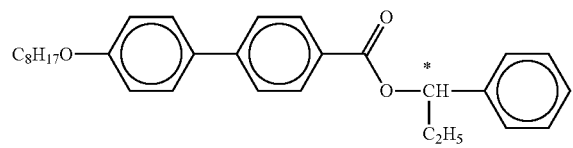

CM 47

TABLE C-continued
Table C indicates possible dopants which are generally added to the mixtures according to the invention. The mixture preferably comprises 0-10% by weight, in particular 0.01-5% by weight and particularly preferably 0.01-3% by weight of dopants.
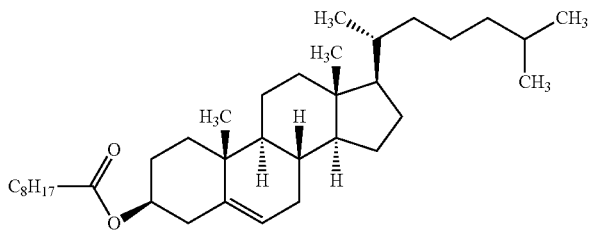
CN
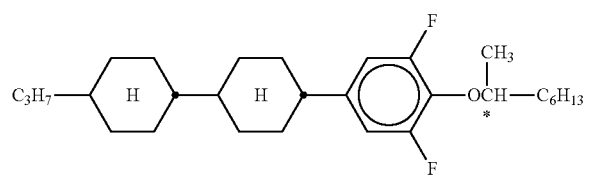
R/S-2011
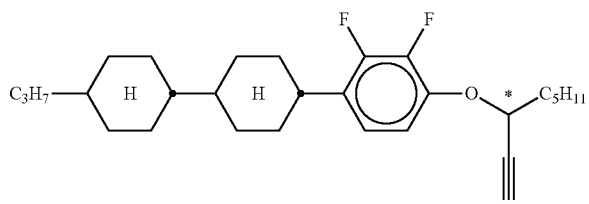
R/S-3011
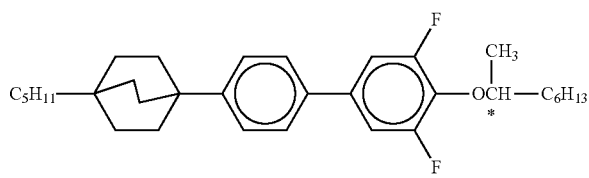
R/S-4011
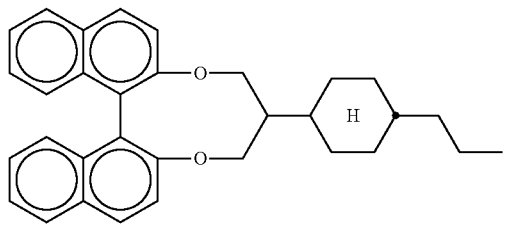
R/S-5011
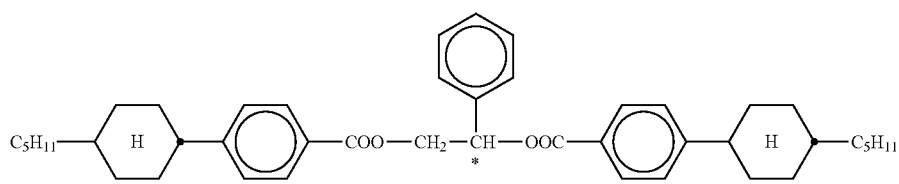
R/S-1011

TABLE D
Stabilizers which can be added, for example, to the mixtures according to the invention in amounts of 0-10% by weight are shown below.
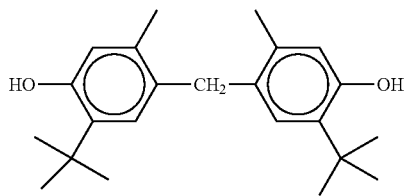
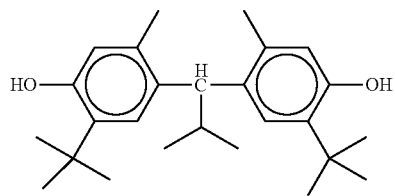
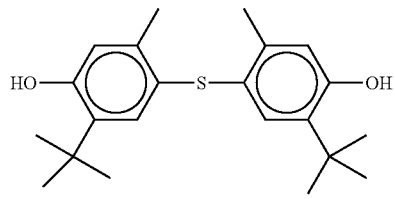
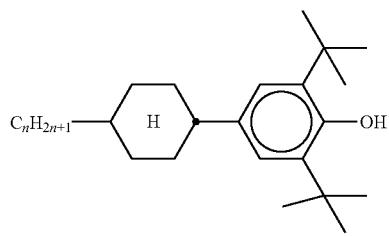
n = 1, 2, 3, 4, 5, 6 or 7
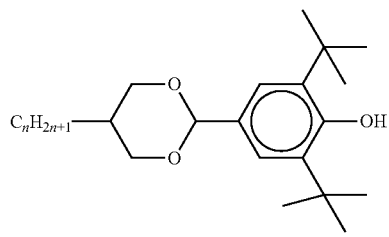
n = 1, 2, 3, 4, 5, 6 or 7
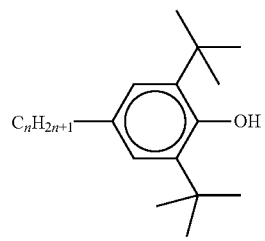
n = 1, 2, 3, 4, 5, 6 or 7

TABLE D-continued
Stabilizers which can be added, for example, to the mixtures according to the invention in amounts of 0-10% by weight are shown below.
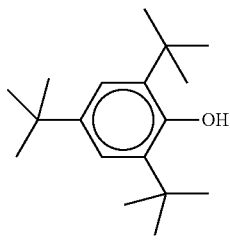
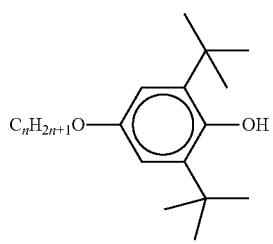
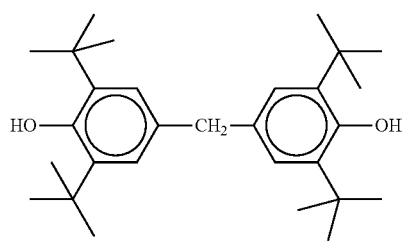
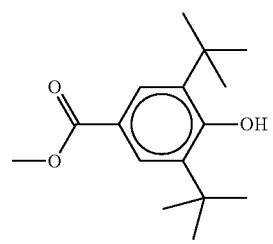
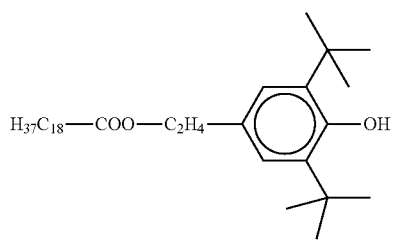
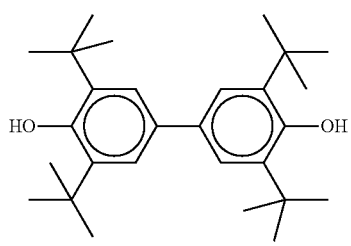

TABLE D-continued
Stabilizers which can be added, for example, to the mixtures according to the invention in amounts of 0-10% by weight are shown below.
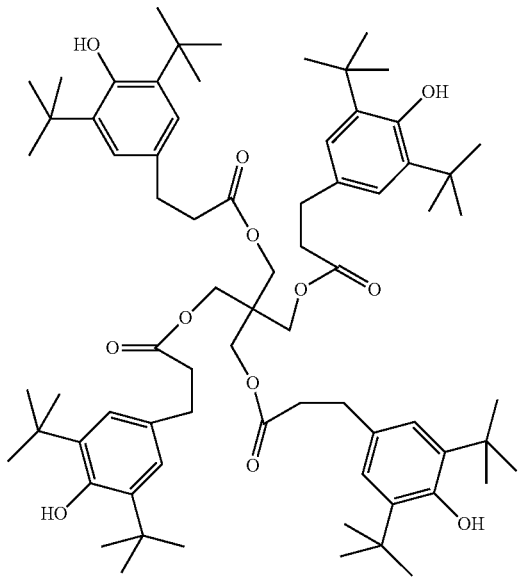 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]
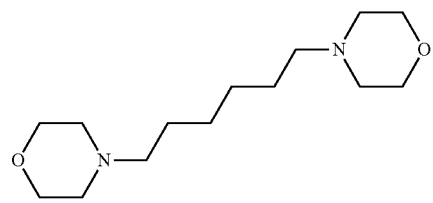 [SMILES: C(CCCN1CCOCC1)CCN1CCOCC1]
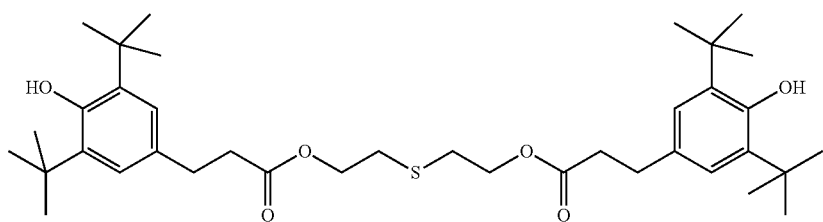 [SMILES: CC(C)(C)c1cc(CCC(=O)OCCSCCOC(=O)CCc2cc(C(C)(C)C)c(O)c(C(C)(C)C)c2)cc(C(C)(C)C)c1O]
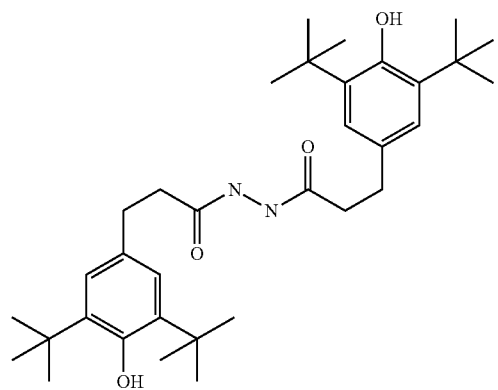 [SMILES: CC(C)(C)c1cc(CCC(=O)NNC(=O)CCc2cc(C(C)(C)C)c(O)c(C(C)(C)C)c2)cc(C(C)(C)C)c1O]

TABLE D-continued
Stabilizers which can be added, for example, to the mixtures according to the invention in amounts of 0-10% by weight are shown below.
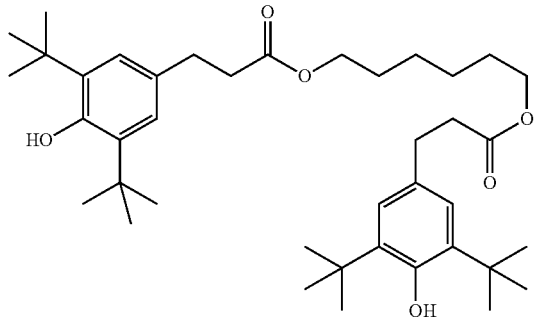 [SMILES: CC(C)(C)c1cc(CCC(=O)OCCCCCCOC(=O)CCc2cc(C(C)(C)C)c(O)c(C(C)(C)C)c2)cc(C(C)(C)C)c1O]
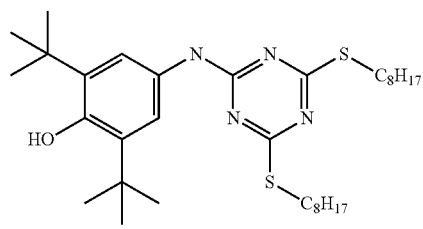
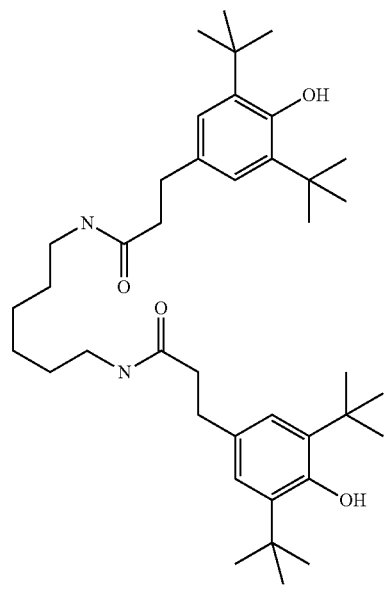 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]

TABLE D-continued
Stabilizers which can be added, for example, to the mixtures according to the invention in amounts of 0-10% by weight are shown below.
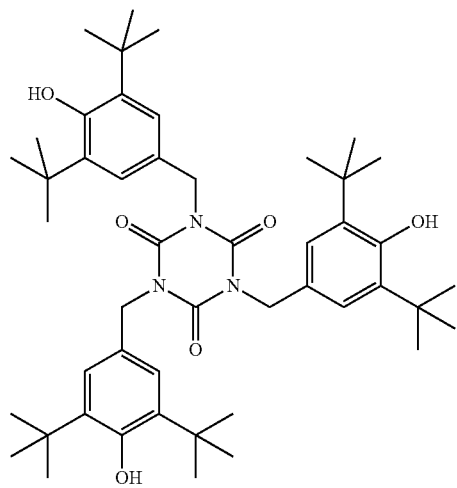 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
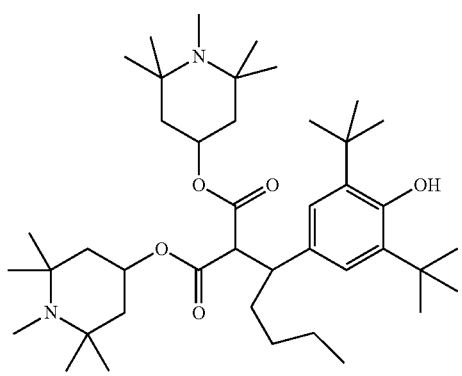 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]
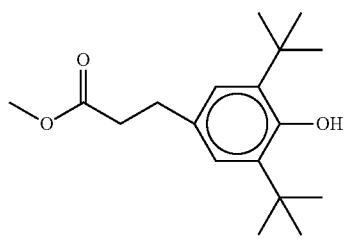
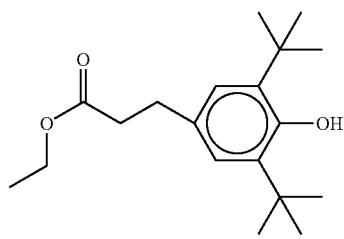
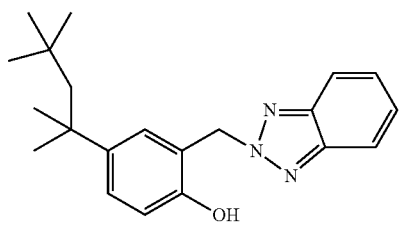 [SMILES: CC(C)(C)CC(C)(C)c1ccc(O)c(Cn2nc3ccccc3n2)c1]

TABLE D-continued
Stabilizers which can be added, for example, to the mixtures according to the invention in amounts of 0-10% by weight are shown below.
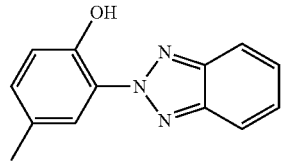 [SMILES: Cc1ccc(O)c(-n2nc3ccccc3n2)c1]
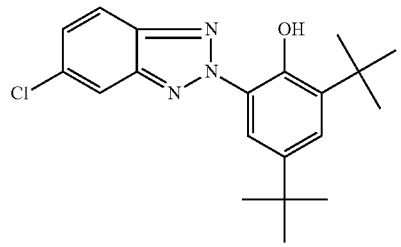 [SMILES: CC(C)(C)c1cc(-n2nc3ccc(Cl)cc3n2)c(O)c(C(C)(C)C)c1]
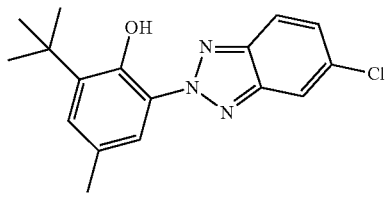 [SMILES: Cc1cc(-n2nc3ccc(Cl)cc3n2)c(O)c(C(C)(C)C)c1]
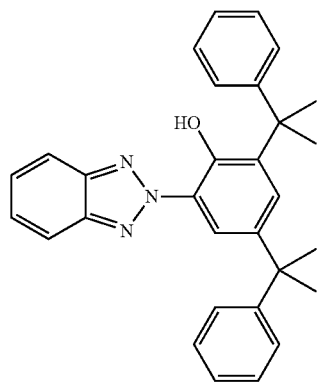 [SMILES: CC(C)(c1ccccc1)c1cc(-n2nc3ccccc3n2)c(O)c(C(C)(C)c2ccccc2)c1]
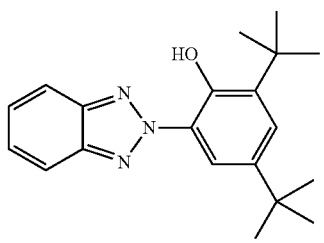 [SMILES: CC(C)(C)c1cc(-n2nc3ccccc3n2)c(O)c(C(C)(C)C)c1]
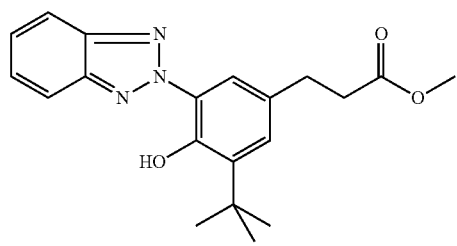 [SMILES: COC(=O)CCc1cc(-n2nc3ccccc3n2)c(O)c(C(C)(C)C)c1]

TABLE D-continued
Stabilizers which can be added, for example, to the mixtures according to the invention in amounts of 0-10% by weight are shown below.
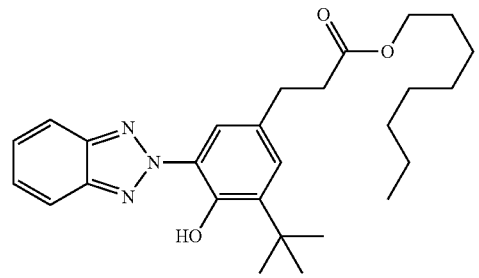 [SMILES: CCCCCCCCOC(=O)CCc1cc(-n2nc3ccccc3n2)c(O)c(C(C)(C)C)c1]
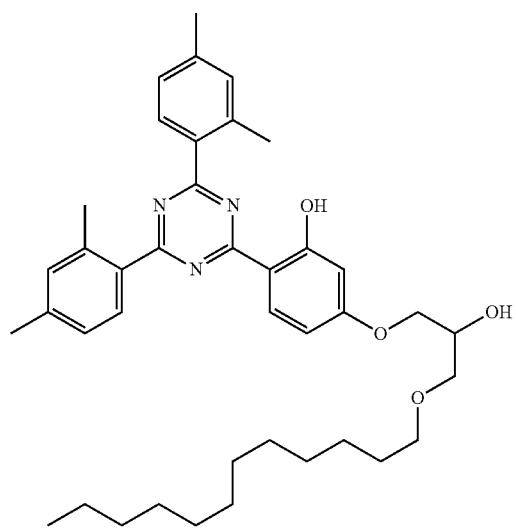 [SMILES: CCCCCCCCCCCCOCC(O)COc1ccc(-c2nc(-c3ccc(C)cc3C)nc(-c3ccc(C)cc3C)n2)c(O)c1]
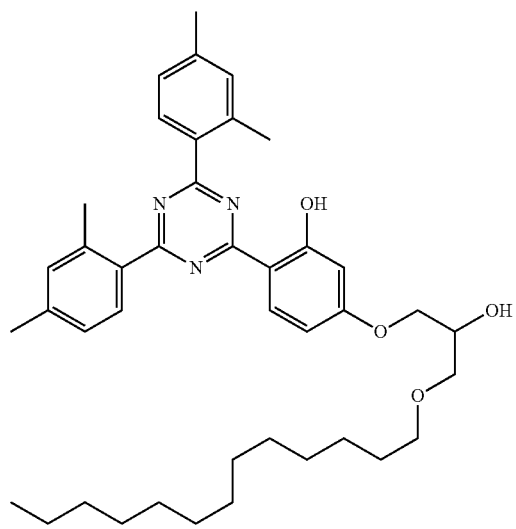 [SMILES: CCCCCCCCCCCCCOCC(O)COc1ccc(-c2nc(-c3ccc(C)cc3C)nc(-c3ccc(C)cc3C)n2)c(O)c1]

TABLE D-continued
Stabilizers which can be added, for example, to the mixtures according to the invention in amounts of 0-10% by weight are shown below.
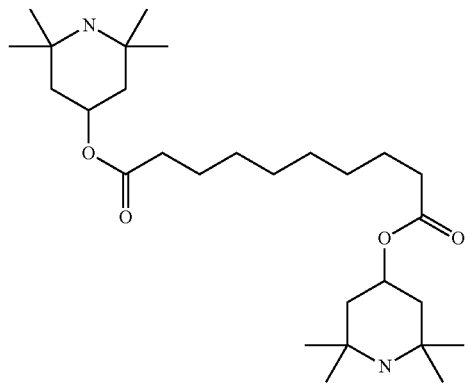
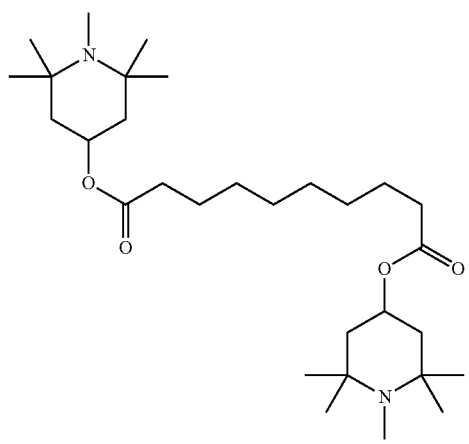
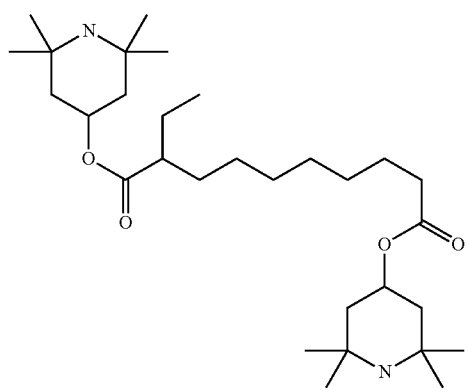

TABLE D-continued
Stabilizers which can be added, for example, to the mixtures according to the invention in amounts of 0-10% by weight are shown below.
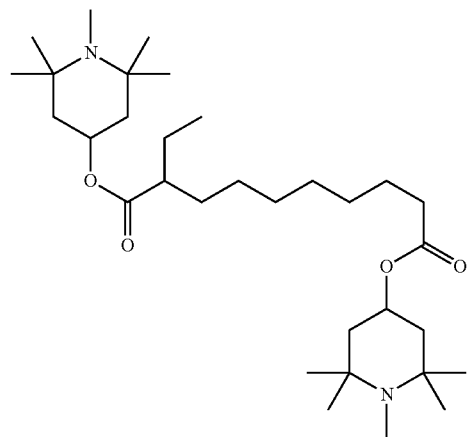
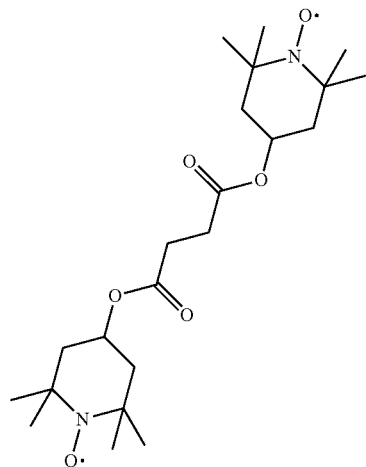
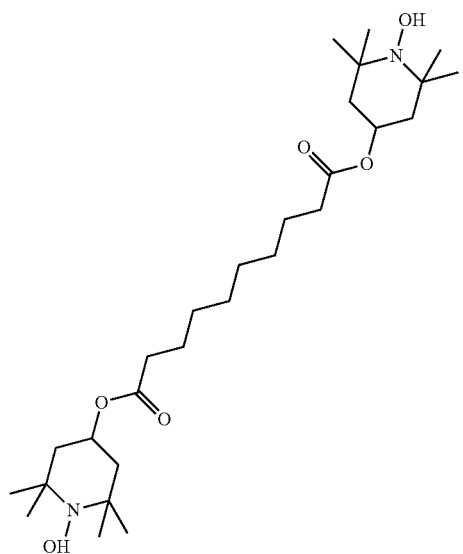

TABLE E

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

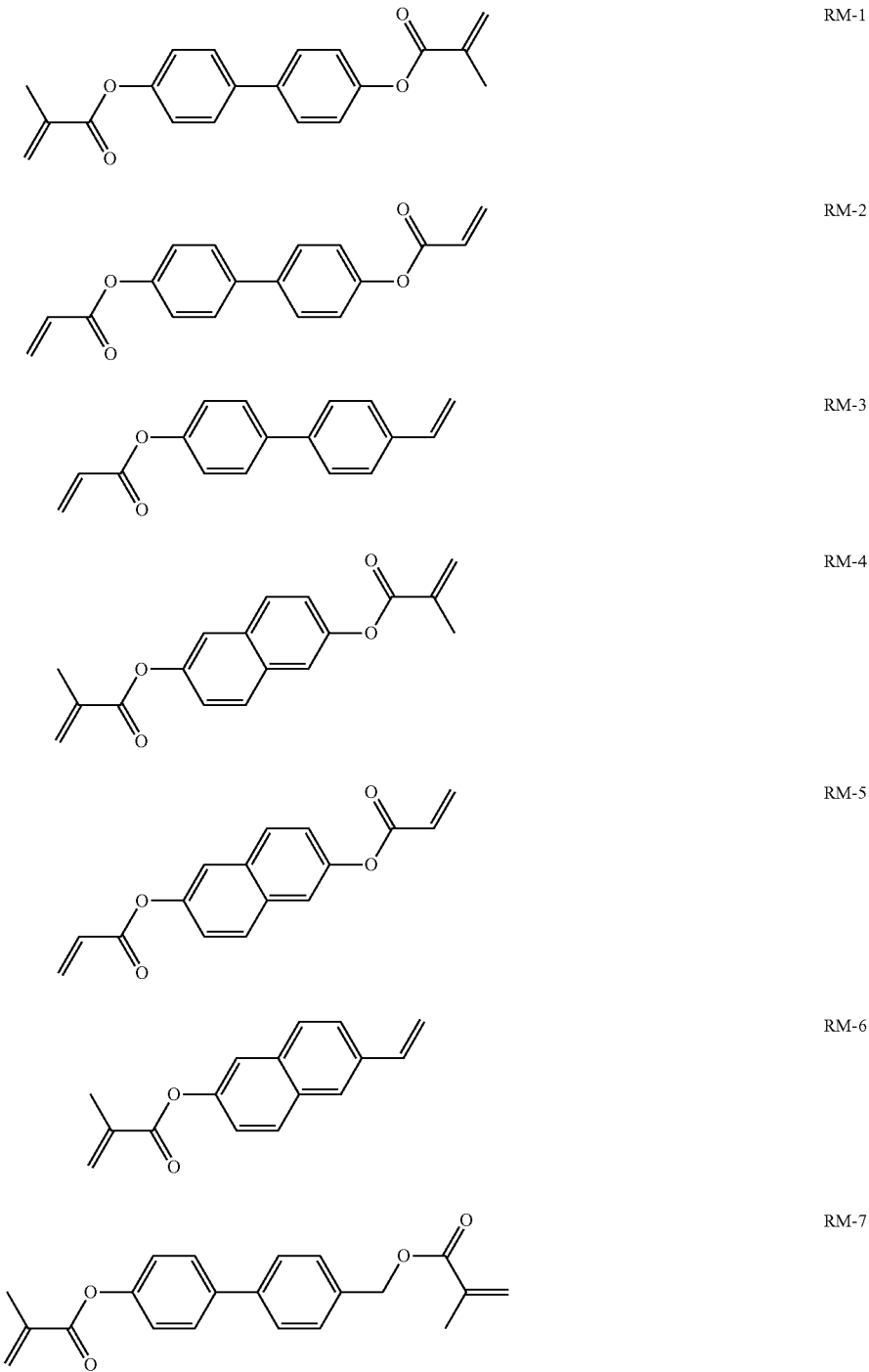

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

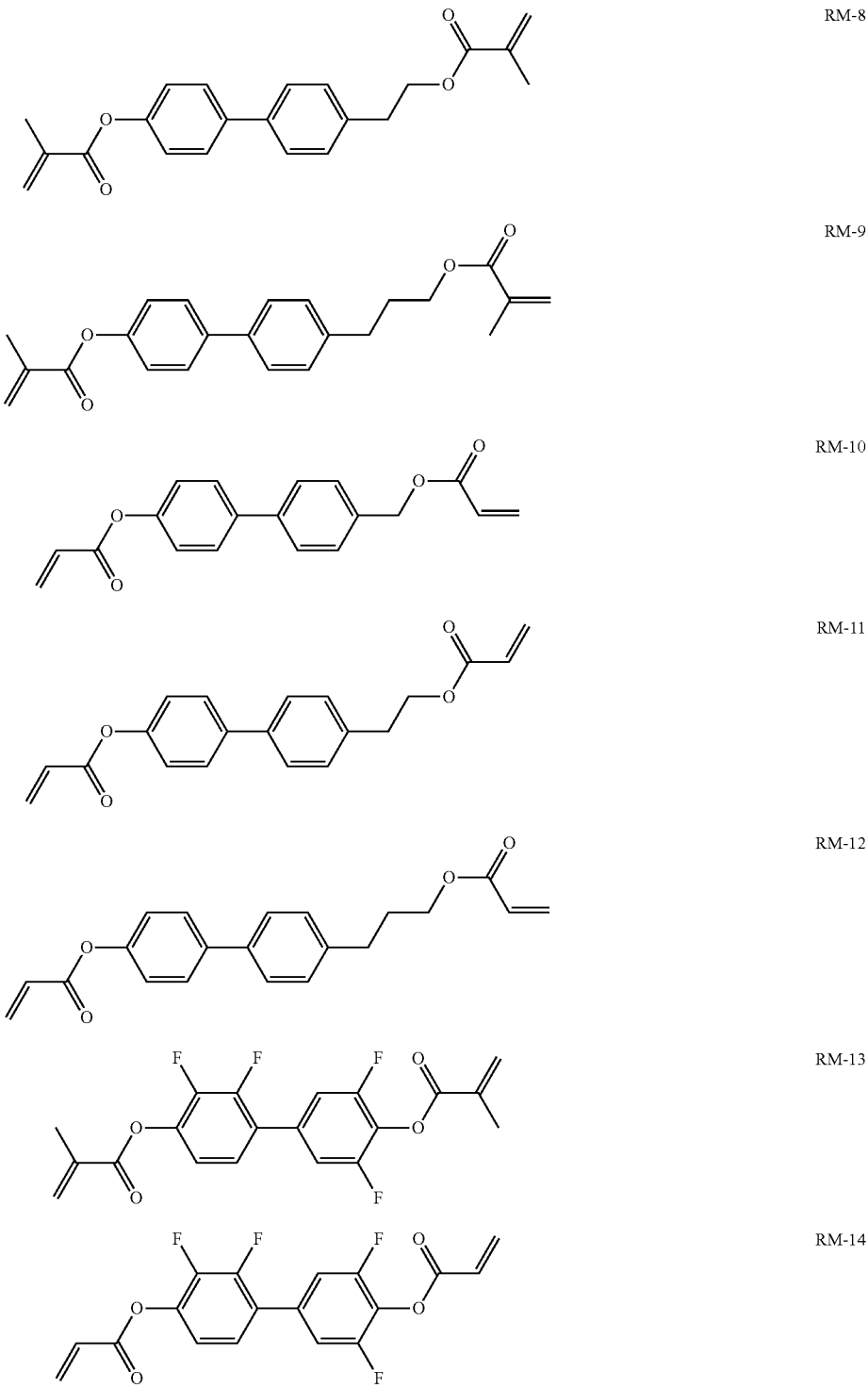

RM-8

RM-9

RM-10

RM-11

RM-12

RM-13

RM-14

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

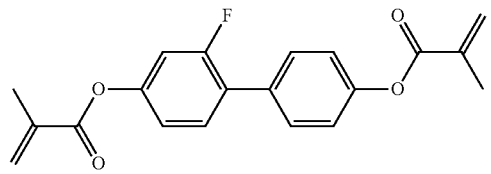 [SMILES: C=C(C)C(=O)Oc1ccc(-c2ccc(OC(=O)C(=C)C)cc2F)cc1]
RM-15

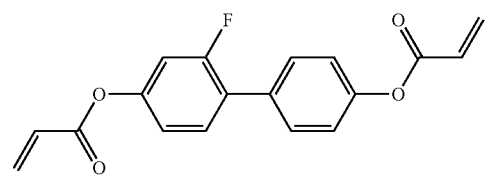 [SMILES: C=CC(=O)Oc1ccc(-c2ccc(OC(=O)C=C)cc2F)cc1]
RM-16

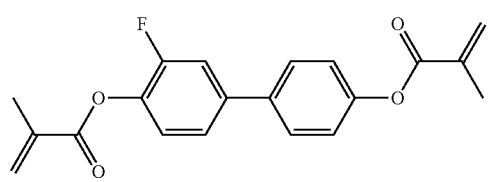 [SMILES: C=C(C)C(=O)Oc1ccc(-c2ccc(OC(=O)C(=C)C)c(F)c2)cc1]
RM-17

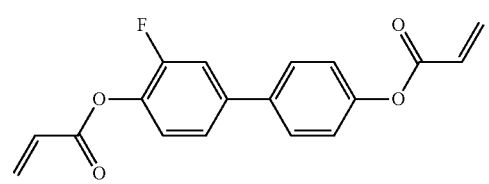
RM-18

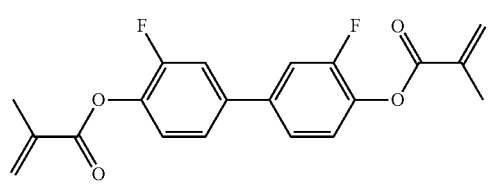 [SMILES: C=C(C)C(=O)Oc1ccc(-c2ccc(OC(=O)C(=C)C)c(F)c2)cc1F]
RM-19

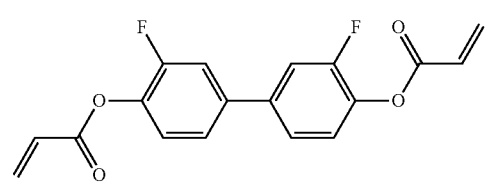 [SMILES: C=CC(=O)Oc1ccc(-c2ccc(OC(=O)C=C)c(F)c2)cc1F]
RM-20

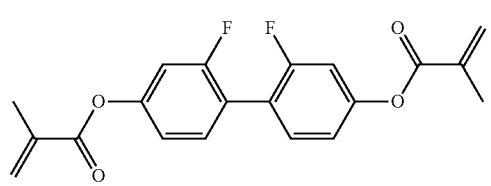 [SMILES: C=C(C)C(=O)Oc1ccc(-c2ccc(OC(=O)C(=C)C)cc2F)c(F)c1]
RM-21

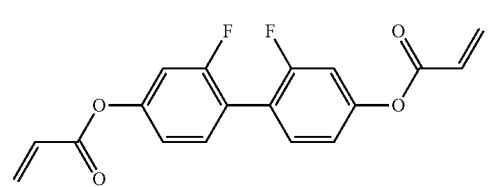 [SMILES: C=CC(=O)Oc1ccc(-c2ccc(OC(=O)C=C)cc2F)c(F)c1]
RM-22

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

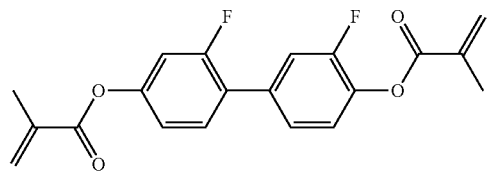

RM-23

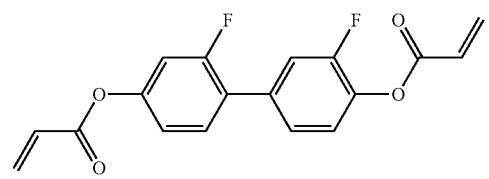 [SMILES: C=CC(=O)Oc1ccc(-c2ccc(OC(=O)C=C)c(F)c2)c(F)c1]

RM-24

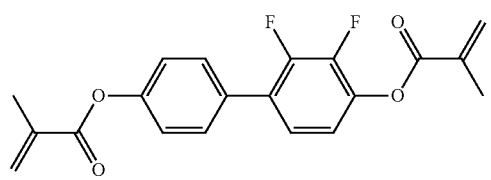 [SMILES: C=C(C)C(=O)Oc1ccc(-c2ccc(OC(=O)C(=C)C)c(F)c2F)cc1]

RM-25

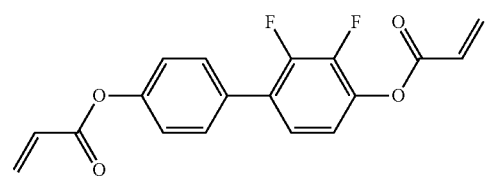 [SMILES: C=CC(=O)Oc1ccc(-c2ccc(OC(=O)C=C)c(F)c2F)cc1]

RM-26

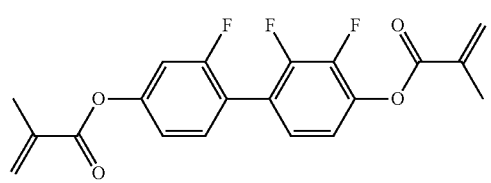 [SMILES: C=C(C)C(=O)Oc1ccc(-c2ccc(OC(=O)C(=C)C)c(F)c2F)c(F)c1]

RM-27

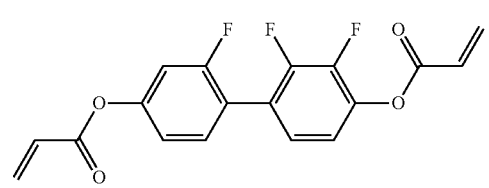

RM-28

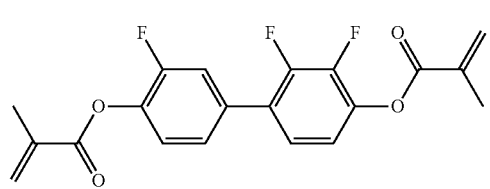

RM-29

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

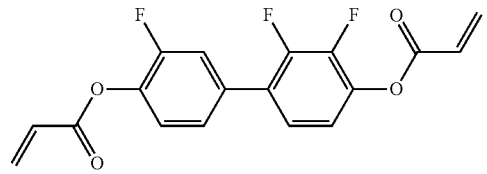 [SMILES: C=CC(=O)Oc1ccc(-c2ccc(OC(=O)C=C)c(F)c2F)cc1F]
RM-30

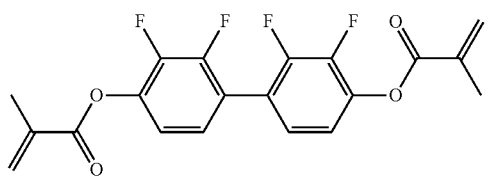 [SMILES: C=C(C)C(=O)Oc1ccc(-c2ccc(OC(=O)C(=C)C)c(F)c2F)c(F)c1F]
RM-31

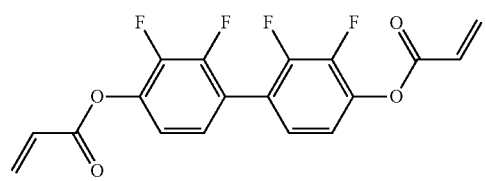
RM-32

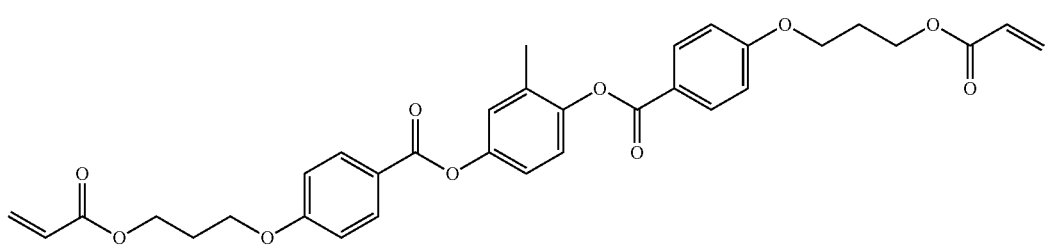 [SMILES: C=CC(=O)OCCCOc1ccc(C(=O)Oc2ccc(OC(=O)c3ccc(OCCCOC(=O)C=C)cc3)c(C)c2)cc1]
RM-33

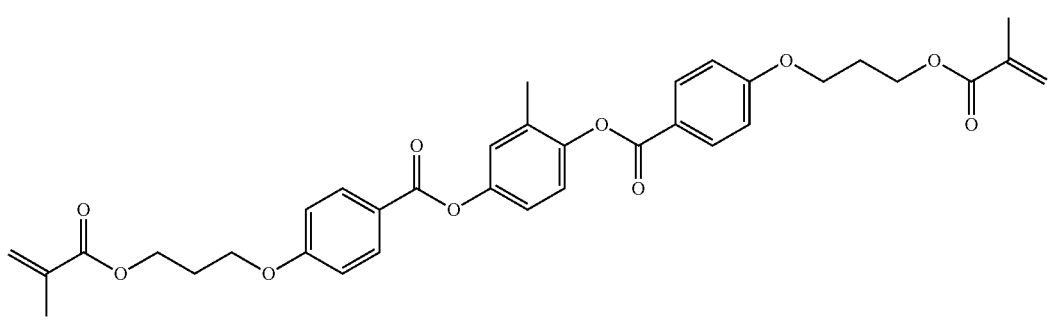 [SMILES: C=C(C)C(=O)OCCCOc1ccc(C(=O)Oc2ccc(OC(=O)c3ccc(OCCCOC(=O)C(=C)C)cc3)c(C)c2)cc1]
RM-34

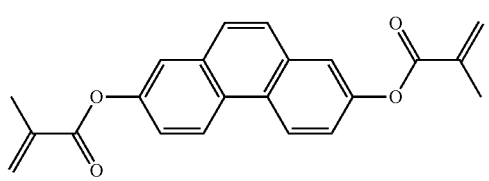 [SMILES: C=C(C)C(=O)Oc1ccc2c(ccc3cc(OC(=O)C(=C)C)ccc32)c1]
RM-35

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

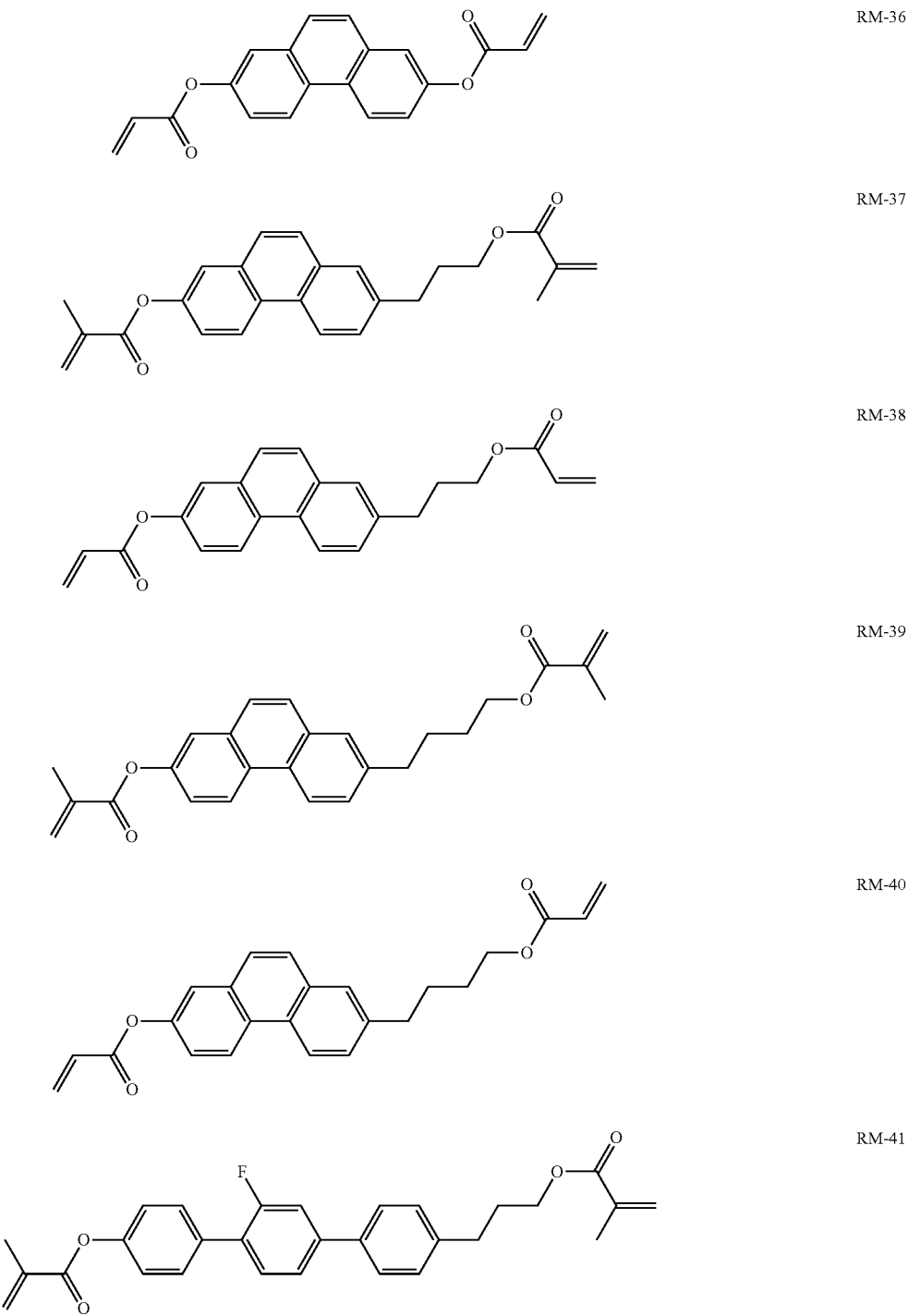

RM-36

RM-37

RM-38

RM-39

RM-40

RM-41

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

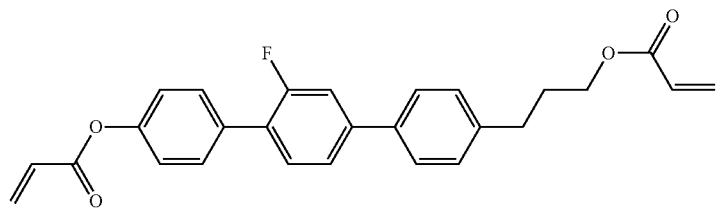 [SMILES: C=CC(=O)OCCCc1ccc(-c2ccc(-c3ccc(OC(=O)C=C)cc3)c(F)c2)cc1]

RM-42

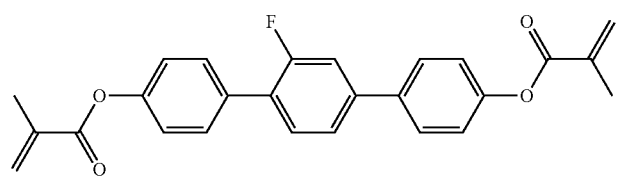 [SMILES: C=C(C)C(=O)Oc1ccc(-c2ccc(-c3ccc(OC(=O)C(=C)C)cc3)c(F)c2)cc1]

RM-43

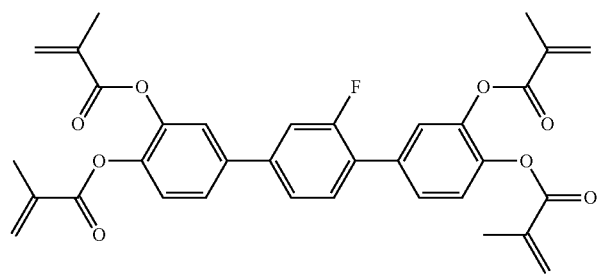 [SMILES: C=C(C)C(=O)Oc1ccc(-c2ccc(-c3ccc(OC(=O)C(=C)C)c(OC(=O)C(=C)C)c3)c(F)c2)cc1OC(=O)C(=C)C]

RM-44

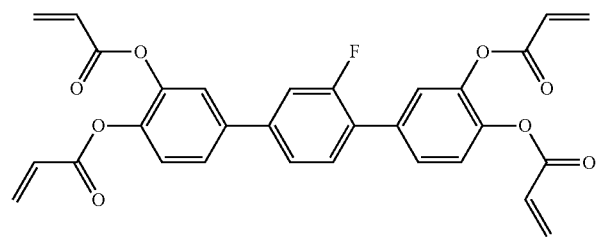 [SMILES: C=CC(=O)Oc1ccc(-c2ccc(-c3ccc(OC(=O)C=C)c(OC(=O)C=C)c3)c(F)c2)cc1OC(=O)C=C]

RM-45

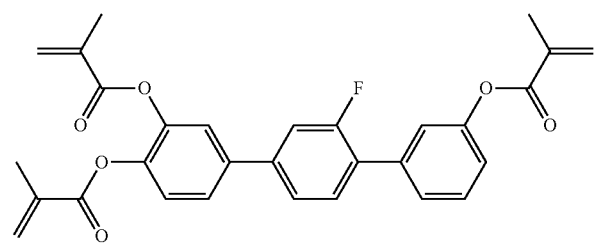 [SMILES: C=C(C)C(=O)Oc1cccc(-c2ccc(-c3ccc(OC(=O)C(=C)C)c(OC(=O)C(=C)C)c3)cc2F)c1]

RM-46

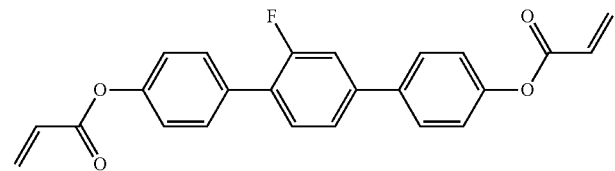

RM-47

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

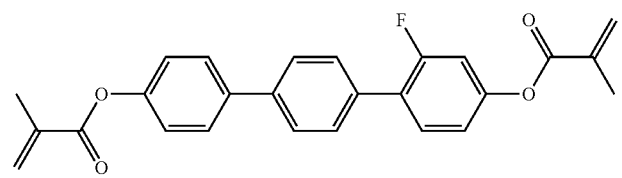
RM-48

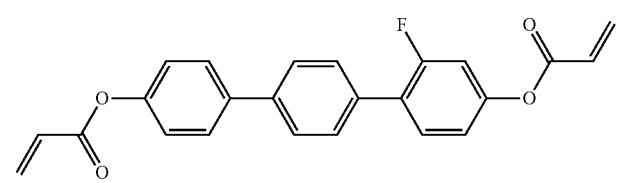 [SMILES: C=CC(=O)Oc1ccc(-c2ccc(-c3ccc(OC(=O)C=C)cc3F)cc2)cc1]
RM-49

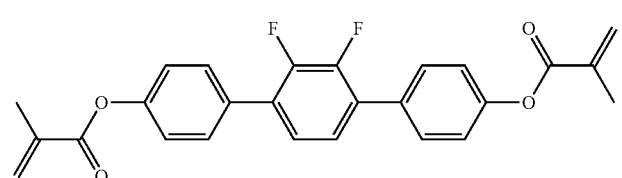
RM-50

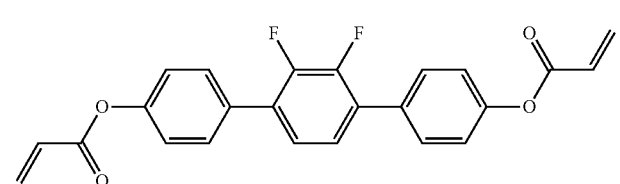
RM-51

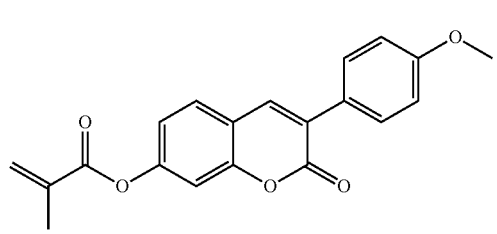 [SMILES: C=C(C)C(=O)Oc1ccc2cc(-c3ccc(OC)cc3)c(=O)oc2c1]
RM-52

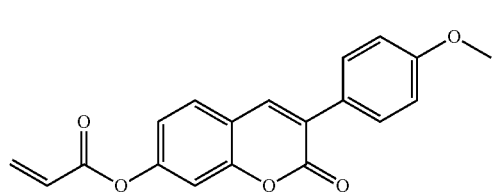 [SMILES: C=CC(=O)Oc1ccc2cc(-c3ccc(OC)cc3)c(=O)oc2c1]
RM-53

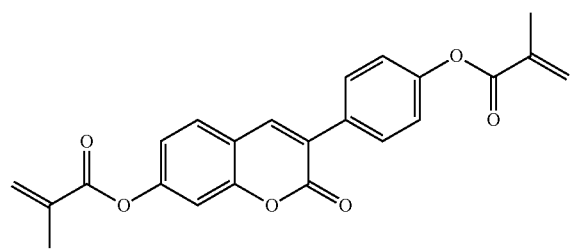 [SMILES: C=C(C)C(=O)Oc1ccc(-c2cc3ccc(OC(=O)C(=C)C)cc3oc2=O)cc1]
RM-54

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

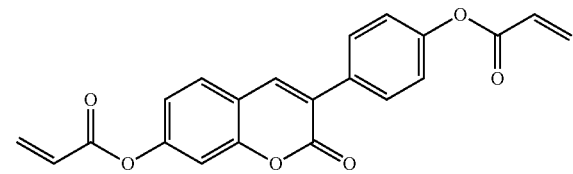 [SMILES: C=CC(=O)Oc1ccc(-c2cc3ccc(OC(=O)C=C)cc3oc2=O)cc1]

RM-55

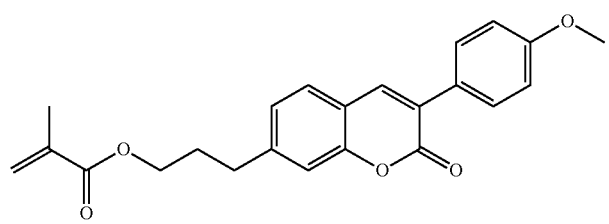 [SMILES: C=C(C)C(=O)OCCCc1ccc2cc(-c3ccc(OC)cc3)c(=O)oc2c1]

RM-56

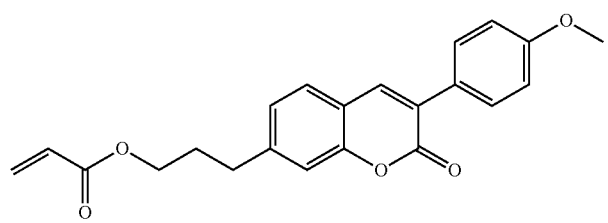 [SMILES: C=CC(=O)OCCCc1ccc2cc(-c3ccc(OC)cc3)c(=O)oc2c1]

RM-57

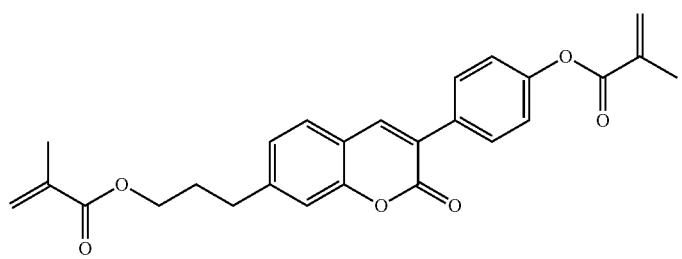 [SMILES: C=C(C)C(=O)OCCCc1ccc2cc(-c3ccc(OC(=O)C(=C)C)cc3)c(=O)oc2c1]

RM-58

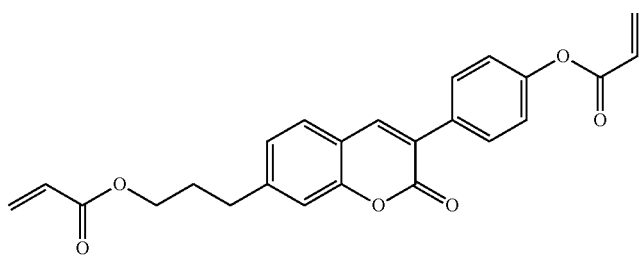 [SMILES: C=CC(=O)OCCCc1ccc2cc(-c3ccc(OC(=O)C=C)cc3)c(=O)oc2c1]

RM-59

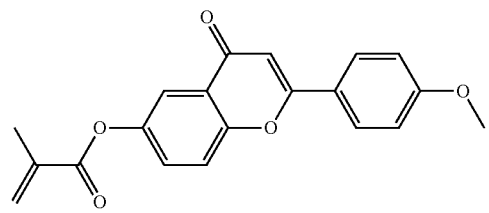 [SMILES: C=C(C)C(=O)Oc1ccc2oc(-c3ccc(OC)cc3)cc(=O)c2c1]

RM-60

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

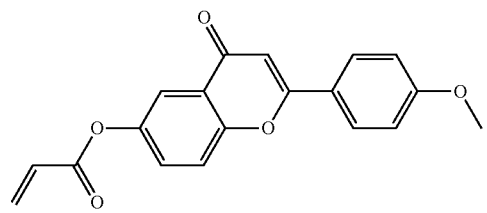 [SMILES: C=CC(=O)Oc1ccc2oc(-c3ccc(OC)cc3)cc(=O)c2c1]

RM-61

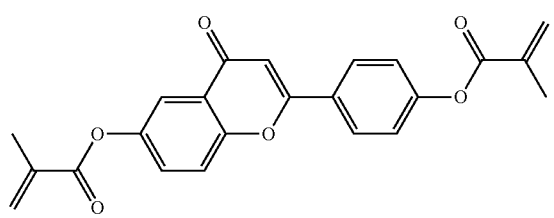 [SMILES: C=C(C)C(=O)Oc1ccc(-c2cc(=O)c3cc(OC(=O)C(=C)C)ccc3o2)cc1]

RM-62

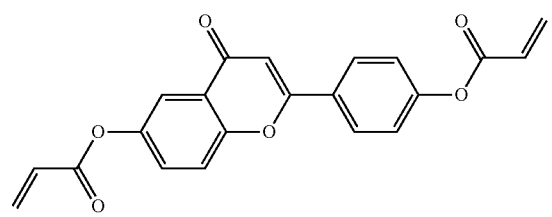 [SMILES: C=CC(=O)Oc1ccc(-c2cc(=O)c3cc(OC(=O)C=C)ccc3o2)cc1]

RM-63

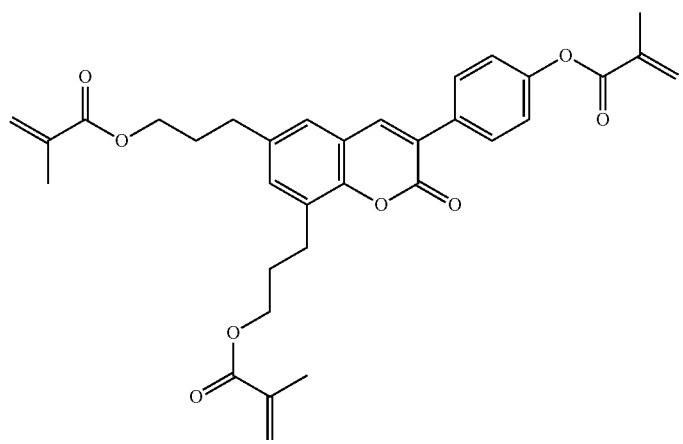 [SMILES: C=C(C)C(=O)OCCCc1cc(CCCOC(=O)C(=C)C)c2oc(=O)c(-c3ccc(OC(=O)C(=C)C)cc3)cc2c1]

RM-64

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

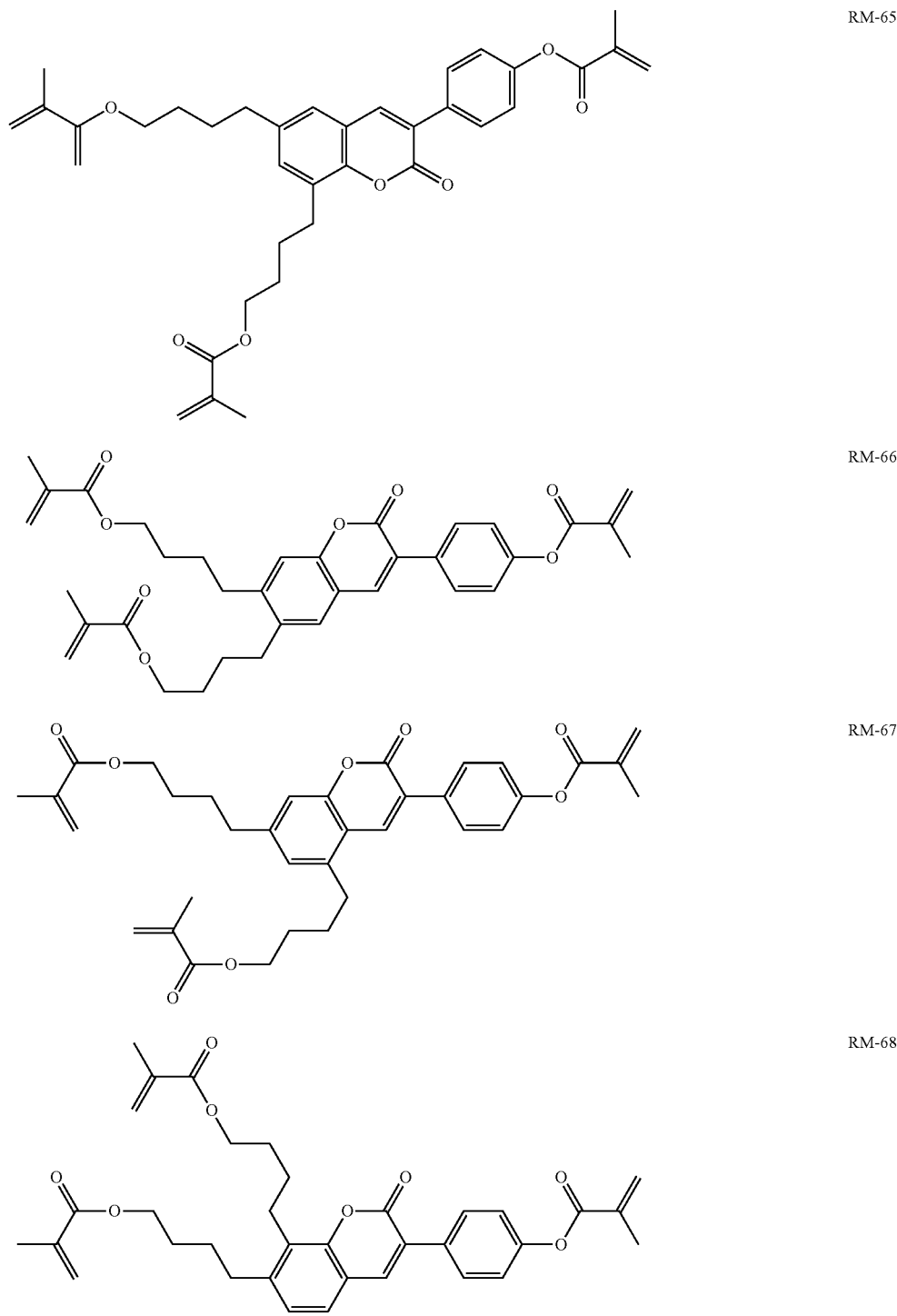

RM-65

RM-66

RM-67

RM-68

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

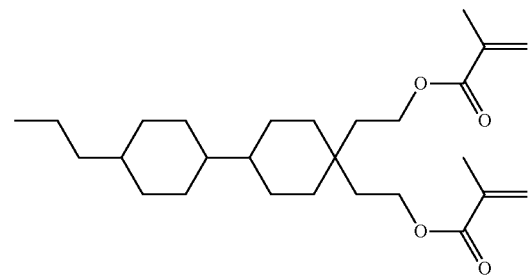 [SMILES: C=C(C)C(=O)OCCC1(CCOC(=O)C(=C)C)CCC(C2CCC(CCC)CC2)CC1]

RM-69

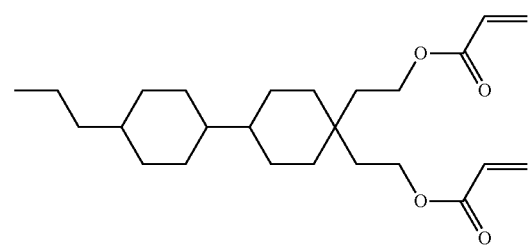 [SMILES: C=CC(=O)OCCC1(CCOC(=O)C=C)CCC(C2CCC(CCC)CC2)CC1]

RM-70

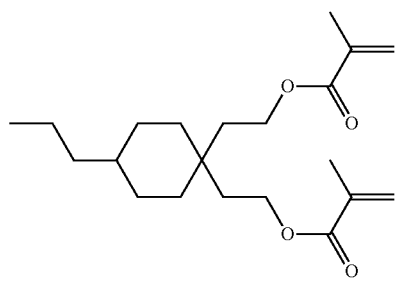 [SMILES: C=C(C)C(=O)OCCC1(CCOC(=O)C(=C)C)CCC(CCC)CC1]

RM-71

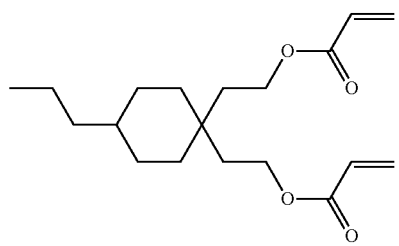 [SMILES: C=CC(=O)OCCC1(CCOC(=O)C=C)CCC(CCC)CC1]

RM-72

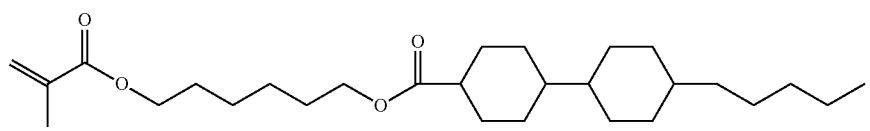 [SMILES: C=C(C)C(=O)OCCCCCCOC(=O)C1CCC(C2CCC(CCCCC)CC2)CC1]

RM-73

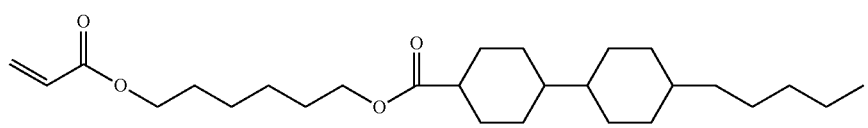 [SMILES: C=CC(=O)OCCCCCCOC(=O)C1CCC(C2CCC(CCCCC)CC2)CC1]

RM-74

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

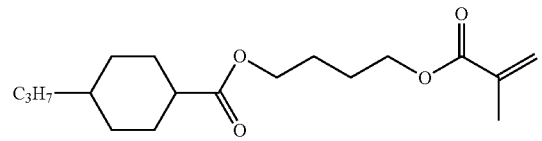

RM-75

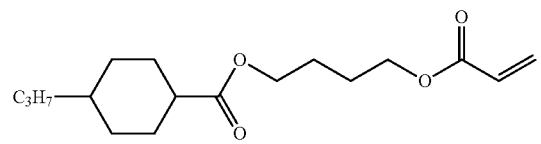

RM-76

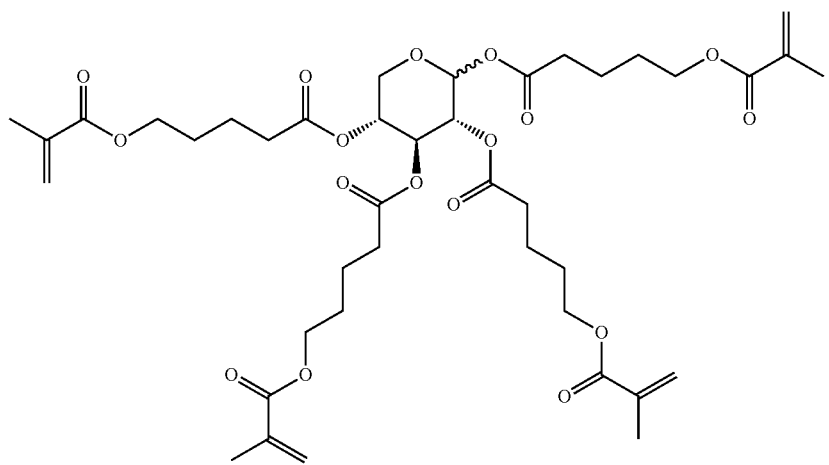 [SMILES: C=C(C)C(=O)OCCCCC(=O)OC1OC[C@@H](OC(=O)CCCCOC(=O)C(=C)C)[C@H](OC(=O)CCCCOC(=O)C(=C)C)[C@H]1OC(=O)CCCCOC(=O)C(=C)C]

RM-77

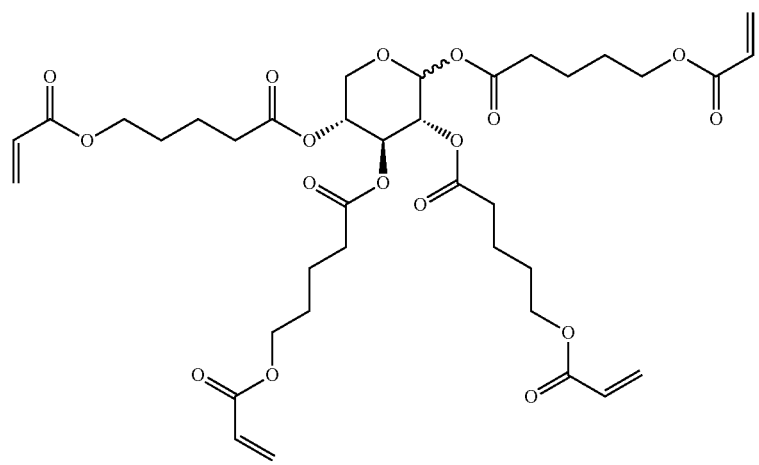 [SMILES: C=CC(=O)OCCCCC(=O)OC1OC[C@@H](OC(=O)CCCCOC(=O)C=C)[C@H](OC(=O)CCCCOC(=O)C=C)[C@H]1OC(=O)CCCCOC(=O)C=C]

RM-78

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

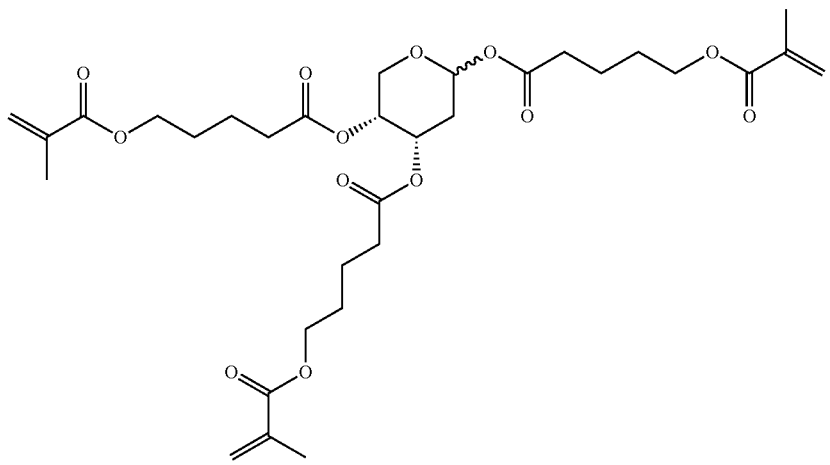 [SMILES: C=C(C)C(=O)OCCCCC(=O)OC1C[C@H](OC(=O)CCCCOC(=O)C(=C)C)[C@H](OC(=O)CCCCOC(=O)C(=C)C)CO1]
RM-79

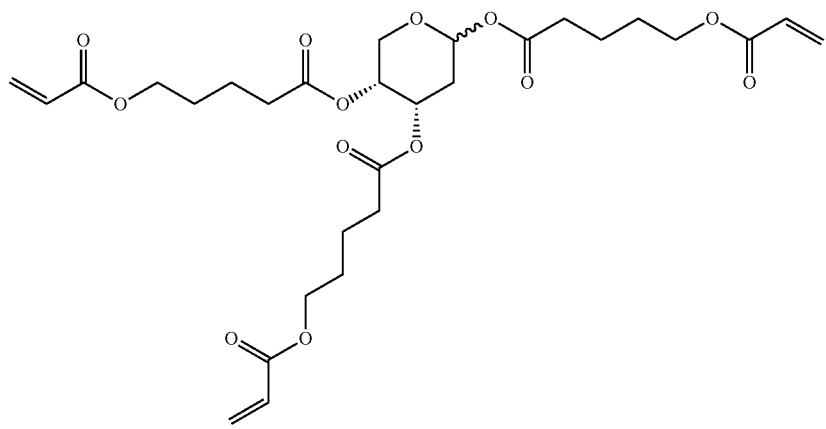 [SMILES: C=CC(=O)OCCCCC(=O)OC1C[C@H](OC(=O)CCCCOC(=O)C=C)[C@H](OC(=O)CCCCOC(=O)C=C)CO1]
RM-80

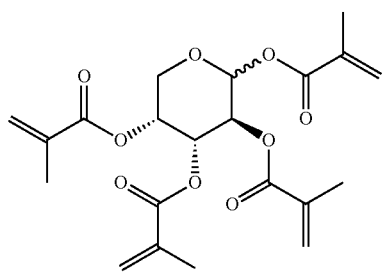 [SMILES: C=C(C)C(=O)OC1OC[C@@H](OC(=O)C(=C)C)[C@@H](OC(=O)C(=C)C)[C@@H]1OC(=O)C(=C)C]
RM-81

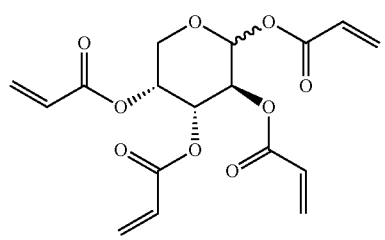 [SMILES: C=CC(=O)OC1OC[C@@H](OC(=O)C=C)[C@@H](OC(=O)C=C)[C@@H]1OC(=O)C=C]
RM-82

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

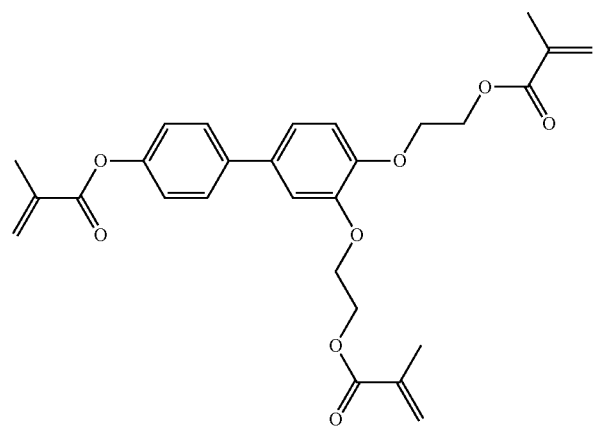 [SMILES: C=C(C)C(=O)OCCOc1ccc(-c2ccc(OC(=O)C(=C)C)cc2)cc1OCCOC(=O)C(=C)C]

RM-83

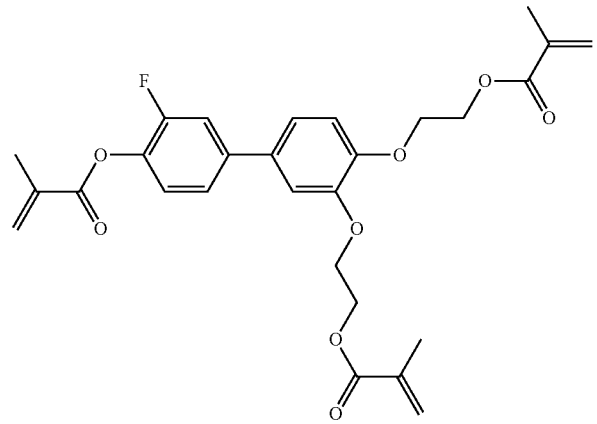 [SMILES: C=C(C)C(=O)OCCOc1ccc(-c2ccc(OC(=O)C(=C)C)c(F)c2)cc1OCCOC(=O)C(=C)C]

RM-84

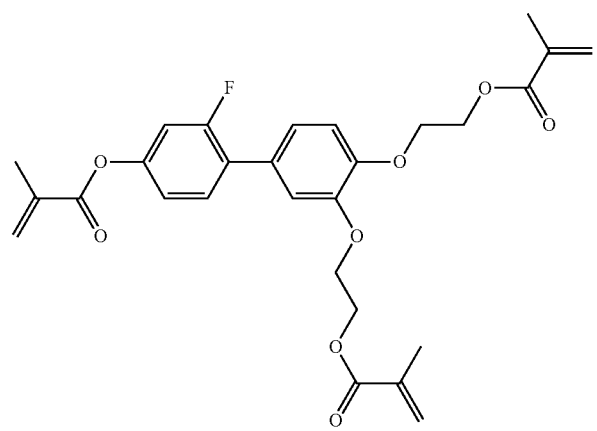 [SMILES: C=C(C)C(=O)OCCOc1ccc(-c2ccc(OC(=O)C(=C)C)cc2F)cc1OCCOC(=O)C(=C)C]

RM-85

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

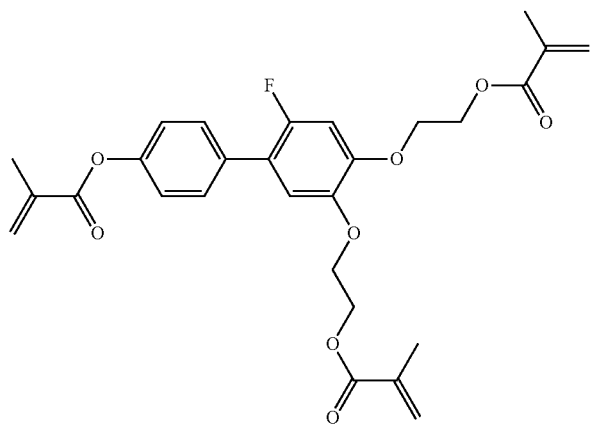 [SMILES: C=C(C)C(=O)OCCOc1cc(F)c(-c2ccc(OC(=O)C(=C)C)cc2)cc1OCCOC(=O)C(=C)C]
RM-86

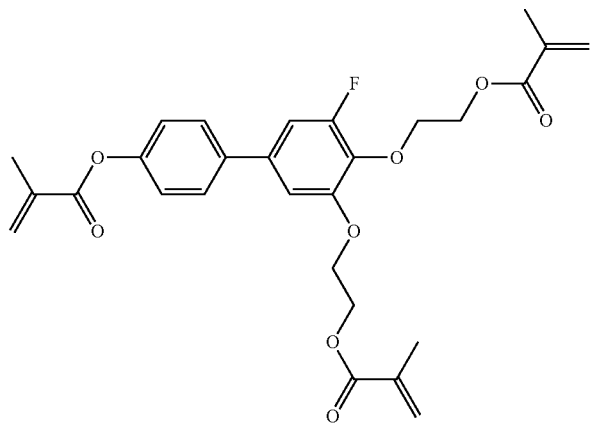 [SMILES: C=C(C)C(=O)OCCOc1cc(-c2ccc(OC(=O)C(=C)C)cc2)cc(F)c1OCCOC(=O)C(=C)C]
RM-87

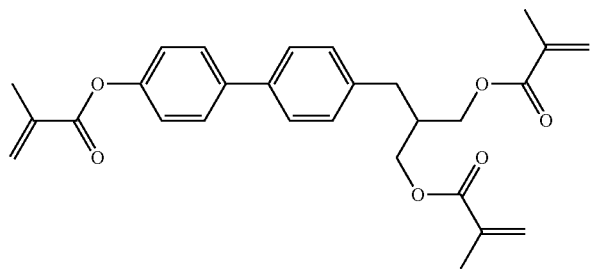 [SMILES: C=C(C)C(=O)OCC(COC(=O)C(=C)C)Cc1ccc(-c2ccc(OC(=O)C(=C)C)cc2)cc1]
RM-88

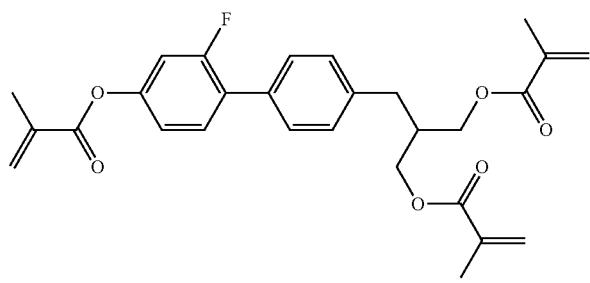 [SMILES: C=C(C)C(=O)OCC(COC(=O)C(=C)C)Cc1ccc(-c2ccc(OC(=O)C(=C)C)cc2F)cc1]
RM-89

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

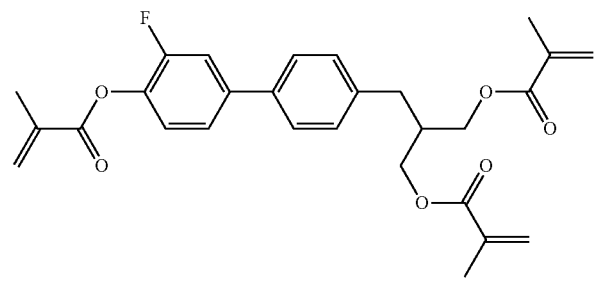 [SMILES: C=C(C)C(=O)OCC(COC(=O)C(=C)C)Cc1ccc(-c2ccc(OC(=O)C(=C)C)c(F)c2)cc1]

RM-90

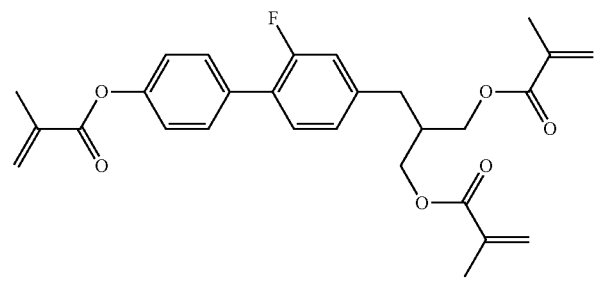 [SMILES: C=C(C)C(=O)OCC(COC(=O)C(=C)C)Cc1ccc(-c2ccc(OC(=O)C(=C)C)cc2)c(F)c1]

RM-91

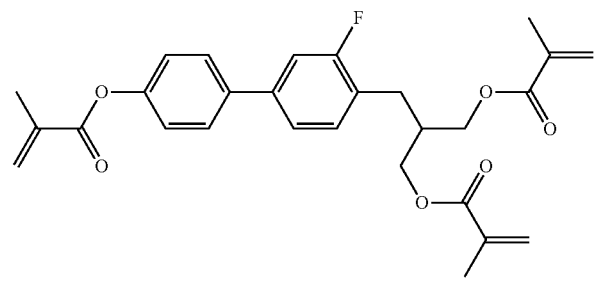 [SMILES: C=C(C)C(=O)OCC(COC(=O)C(=C)C)Cc1ccc(-c2ccc(OC(=O)C(=C)C)cc2)cc1F]

RM-92

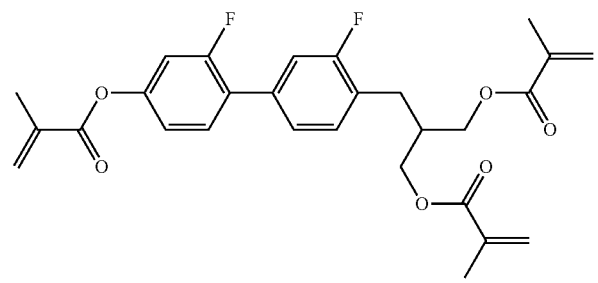 [SMILES: C=C(C)C(=O)OCC(COC(=O)C(=C)C)Cc1ccc(-c2ccc(OC(=O)C(=C)C)cc2F)cc1F]

RM-93

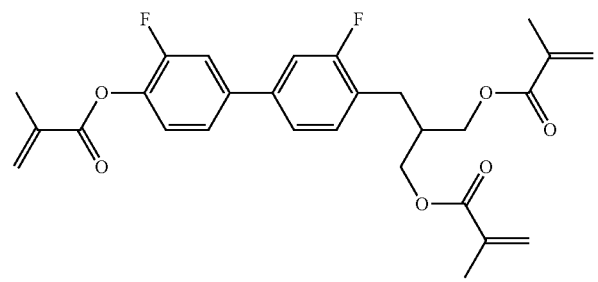 [SMILES: C=C(C)C(=O)OCC(COC(=O)C(=C)C)Cc1ccc(-c2ccc(OC(=O)C(=C)C)c(F)c2)cc1F]

RM-94

TABLE E-continued

Table E shows example compounds which can preferably be used as reactive mesogenic compounds in the LC media in accordance with the present invention. If the mixtures according to the invention comprise one or more reactive compounds, they are preferably employed in amounts of 0.01-5% by weight. It may also be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

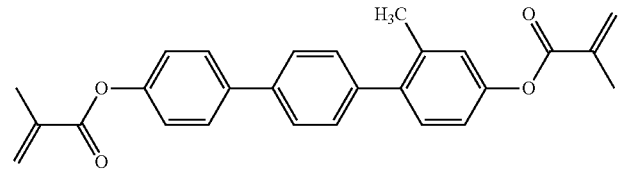 [SMILES: C=C(C)C(=O)Oc1ccc(-c2ccc(-c3ccc(OC(=O)C(=C)C)cc3C)cc2)cc1]

RM-95

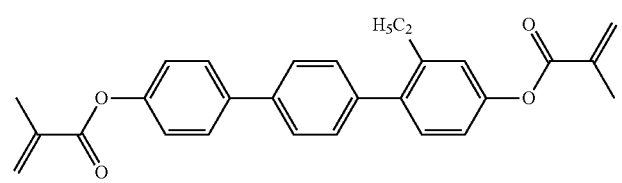

RM-96

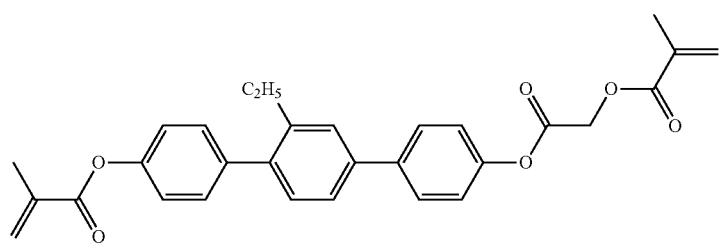 [SMILES: C=C(C)C(=O)OCC(=O)Oc1ccc(-c2ccc(-c3ccc(OC(=O)C(=C)C)cc3)c(CC)c2)cc1]

RM-97

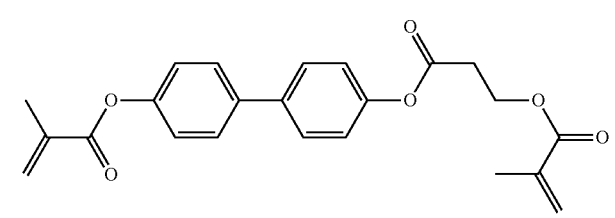 [SMILES: C=C(C)C(=O)OCCC(=O)Oc1ccc(-c2ccc(OC(=O)C(=C)C)cc2)cc1]

RM-98

In a preferred embodiment, the mixtures according to the invention comprise one or more polymerizable compounds, preferably selected from the polymerizable compounds of the formulae RM-1 to RM-98. Media of this type are suitable, in particular, for PS-FFS and PS-IPS applications. Of the reactive mesogens shown in Table E, compounds RM-1, RM-2, RM-3, RM-4, RM-5, RM-11, RM-17, RM-35, RM-41, RM-44, RM-62 and RM-81 are particularly preferred.

WORKING EXAMPLES

The following examples are intended to explain the invention without limiting it. In the examples, m.p. denotes the melting point and C denotes the clearing point of a liquid-crystalline substance in degrees Celsius; boiling temperatures are denoted by m.p. Furthermore: C denotes crystalline solid state, S denotes smectic phase (the index denotes the phase type), N denotes nematic state, Ch denotes cholesteric phase, I denotes isotropic phase, $T_g$ denotes glass-transition temperature. The number between two symbols indicates the conversion temperature in degrees Celsius an.

The host mixture used for determination of the optical anisotropy Δn of the compounds of the formula I is the commercial mixture ZLI-4792 (Merck KGaA). The dielectric anisotropy Δ∈ is determined using commercial mixture ZLI-2857. The physical data of the compound to be investigated are obtained from the change in the dielectric constants of the host mixture after addition of the compound to be investigated and extrapolation to 100% of the compound employed. In general, 10% of the compound to be investigated are dissolved in the host mixture, depending on the solubility.

Unless indicated otherwise, parts or percent data denote parts by weight or percent by weight.

Above and below:

$V_0$ denotes threshold voltage, capacitive [V] at 20° C., $n_e$ denotes extraordinary refractive index at 20° C. and 589 nm, $n_o$ denotes ordinary refractive index at 20° C. and 589 nm, Δn denotes optical anisotropy at 20° C. and 589 nm, ∈⊥ denotes dielectric permittivity perpendicular to the director at 20° C. and 1 kHz, ∈∥ denotes dielectric permittivity parallel to the director at 20° C. and 1 kHz, Δε denotes dielectric anisotropy at 20° C. and 1 kHz,
cl.p., T(N,I) denotes clearing point [° C.],
γ₁ denotes rotational viscosity measured at 20° C. [mPa·s], determined by the rotation method in a magnetic field,
K₁ denotes elastic constant, "splay" deformation at 20° C. [pN],
K₂ denotes elastic constant, "twist" deformation at 20° C. [pN],
K₃ denotes elastic constant, "bend" deformation at 20° C. [pN],
LTS denotes low-temperature stability (nematic phase), determined in test cells.

Unless explicitly noted otherwise, all values indicated in the present application for temperatures, such as, for example, the melting point T(C,N), the transition from the smectic (S) to the nematic (N) phase T(S,N) and the clearing point T(N,I), are indicated in degrees Celsius (° C.). M.p. denotes melting point, cl.p.=clearing point. Furthermore, Tg=glass state, C=crystalline state, N=nematic phase, S=smectic phase and I=isotropic phase. The numbers between these symbols represent the transition temperatures.

All physical properties are and have been determined in accordance with "Merck Liquid Crystals, Physical Properties of Liquid Crystals", Status November 1997, Merck KGaA, Germany, and apply for a temperature of 20° C., and Δn is determined at 589 nm and Δε at 1 kHz, unless explicitly indicated otherwise in each case.

The term "threshold voltage" for the present invention relates to the capacitive threshold ($V_0$), also called the Freedericksz threshold, unless explicitly indicated otherwise. In the examples, as is generally usual, the optical threshold can also be indicated for 10% relative contrast ($V_{10}$).

The display used for measurement of the capacitive threshold voltage consists of two plane-parallel glass outer plates at a separation of 20 μm, which each have on the insides an electrode layer and an unrubbed polyimide alignment layer on top, which cause a homeotropic edge alignment of the liquid-crystal molecules.

The display or test cell used for measurement of the tilt angle consists of two plane-parallel glass outer plates at a separation of 4 μm, which each have on the insides an electrode layer and a polyimide alignment layer on top, where the two polyimide layers are rubbed antiparallel to one another and cause a homeotropic edge alignment of the liquid-crystal molecules.

The polymerizable compounds are polymerized in the display or test cell by irradiation with UVA light (usually 365 nm) of a defined intensity for a pre-specified time, with a voltage simultaneously being applied to the display (usually 10 V to 30 V alternating current, 1 kHz). In the examples, unless indicated otherwise, a 50 mW/cm² mercury vapor lamp is used, and the intensity is measured using a standard UV meter (make Ushio UNI meter) fitted with a 365 nm band-pass filter.

The tilt angle is determined by a rotational crystal experiment (Autronic-Melchers TBA-105). A low value (i.e. a large deviation from the 90° angle) corresponds to a large tilt here.

The VHR value is measured as follows: 0.3% of a polymerizable monomeric compound is added to the LC host mixture, and the resultant mixture is introduced into TN-VHR test cells (rubbed at 90°, alignment layer TN polyimide, layer thickness d≈6 μm). The HR value is determined after 5 min at 100° C. before and after UV exposure for 2 h (sun test) at 1 V, 60 Hz, 64 μs pulse (measuring instrument: Autronic-Melchers VHRM-105).

In order to investigate the low-temperature stability, also known as "LTS", i.e. the stability of the LC mixture to spontaneous crystallization-out of individual components at low temperatures, bottles containing 1 g of LC/RM mixture are stored at −10° C., and it is regularly checked whether the mixtures have crystallized out.

The so-called "HTP" denotes the helical twisting power of an optically active or chiral substance in an LC medium (in μm). Unless indicated otherwise, the HTP is measured in the commercially available nematic LC host mixture MLD-6260 (Merck KGaA) at a temperature of 20° C.

Unless explicitly noted otherwise, all concentrations in the present application are indicated in percent by weight and relate to the corresponding mixture as a whole, comprising all solid or liquid-crystalline components, without solvents. All physical properties are determined in accordance with "Merck Liquid Crystals, Physical Properties of Liquid Crystals", Status November 1997, Merck KGaA, Germany, and apply for a temperature of The following mixture examples having negative dielectric anisotropy are suitable, in particular, for liquid-crystal displays which have at least one planar alignment layer, such as, for example, IPS and FFS displays, in particular UB-FFS (=ultra-bright FFS), and for VA displays.

The following mixture examples may additionally comprise a stabilizer, for example Tinuvin 770 (=bis(2,2,6,6-tetraethyl-4-piperidyl) sebacate), preferably in amounts of 0-1%.

MIXTURE EXAMPLES

Example M1

| | | | |
|---|---|---|---|
| CC-3-V | 38.00% | Clearing point [° C.]: | 74.5 |
| CC-3-V1 | 7.00% | Δn [589 nm, 20° C.]: | 0.1078 |
| CY-3-O2 | 1.00% | Δε [1 kHz, 20° C.]: | −3.0 |
| CCY-3-O1 | 5.00% | K₁ [pN, 20° C.]: | 13.8 |
| CCY-3-O2 | 11.00% | K₃ [pN, 20° C.]: | 15.6 |
| CPY-2-O2 | 4.00% | V₀ [20° C., V]: | 2.40 |
| CPY-3-O2 | 11.50% | γ₁ [mPa · s, 20° C.]: | 83 |
| PY-3-O2 | 17.00% | | |
| PGIY-2-O2 | 5.00% | | |
| PP-1-2V1 | 0.50% | | |

Example M2

| | | | |
|---|---|---|---|
| CC-3-V | 38.00% | Clearing point [° C.]: | 75.0 |
| CC-3-V1 | 7.00% | Δn [589 nm, 20° C.]: | 0.1087 |
| CCY-3-O1 | 5.00% | Δε [1 kHz, 20° C.]: | −3.1 |
| CCY-3-O2 | 11.00% | K₁ [pN, 20° C.]: | 14.0 |
| CPY-2-O2 | 4.00% | K₃ [pN, 20° C.]: | 15.9 |
| CPY-3-O2 | 11.50% | V₀ [20° C., V]: | 2.41 |
| PY-3-O2 | 18.50% | γ₁ [mPa · s, 20° C.]: | 85 |
| PGIY-3-O2 | 5.00% | | |

Example M3

| | | | |
|---|---|---|---|
| CC-3-V | 38.00% | Clearing point [° C.]: | 74.0 |
| CC-3-V1 | 7.00% | Δn [589 nm, 20° C.]: | 0.1082 |
| CCY-3-O1 | 5.00% | Δε [1 kHz, 20° C.]: | −2.9 |
| CCY-3-O2 | 11.00% | K₁ [pN, 20° C.]: | 13.8 |
| CPY-2-O2 | 4.00% | K₃ [pN, 20° C.]: | 15.3 |

-continued

| | | | |
|---|---|---|---|
| CPY-3-O2 | 11.50% | $V_0$ [20° C., V]: | 2.43 |
| PY-3-O2 | 17.00% | $\gamma_1$ [mPa·s, 20° C.]: | 82 |
| PGIY-2-O3 | 5.00% | | |
| PP-1-2V1 | 1.50% | | |

Example M4

| | | | |
|---|---|---|---|
| CC-3-V | 38.00% | Clearing point [° C.]: | 74.5 |
| CC-3-V1 | 7.00% | $\Delta n$ [589 nm, 20° C.]: | 0.1077 |
| CCY-3-O1 | 5.00% | $\Delta\varepsilon$ [1 kHz, 20° C.]: | −2.9 |
| CCY-3-O2 | 11.00% | $K_1$ [pN, 20° C.]: | 13.7 |
| CPY-2-O2 | 4.00% | $K_3$ [pN, 20° C.]: | 15.4 |
| CPY-3-O2 | 11.50% | $V_0$ [20° C., V]: | 2.44 |
| PY-3-O2 | 17.00% | $\gamma_1$ [mPa·s, 20° C.]: | 83 |
| PGIY-4-O3 | 5.00% | LTS bulk [−20° C.]: | >1000 h |
| PP-1-2V1 | 1.50% | | |

Example M5

| | | | |
|---|---|---|---|
| CC-3-V | 38.00% | Clearing point [° C.]: | 74.5 |
| CC-3-V1 | 7.00% | $\Delta n$ [589 nm, 20° C.]: | 0.1082 |
| CCY-3-O1 | 5.00% | $\Delta\varepsilon$ [1 kHz, 20° C.]: | −3.1 |
| CCY-3-O2 | 11.00% | $K_1$ [pN, 20° C.]: | 13.9 |
| CPY-2-O2 | 4.00% | $K_3$ [pN, 20° C.]: | 15.7 |
| CPY-3-O2 | 11.50% | $V_0$ [20° C., V]: | 2.39 |
| PY-3-O2 | 18.50% | $\gamma_1$ [mPa·s, 20° C.]: | 85 |
| PGIY-1-O4 | 5.00% | LTS bulk [−20° C.]: | >1000 h |

Example M6

| | | | |
|---|---|---|---|
| CC-3-V | 37.50% | Clearing point [° C.]: | 75.5 |
| CC-3-V1 | 7.00% | $\Delta n$ [589 nm, 20° C.]: | 0.1080 |
| CCY-3-O1 | 6.00% | $\Delta\varepsilon$ [1 kHz, 20° C.]: | −3.0 |
| CCY-3-O2 | 11.00% | $K_1$ [pN, 20° C.]: | 13.8 |
| CPY-2-O2 | 4.50% | $K_3$ [pN, 20° C.]: | 15.5 |
| CPY-3-O2 | 11.00% | $V_0$ [20° C., V]: | 2.41 |
| PY-3-O2 | 17.00% | $\gamma_1$ [mPa·s, 20° C.]: | 84 |
| PGIY-2-O4 | 5.00% | LTS bulk [−30° C.]: | >1000 h |
| PP-1-2V1 | 1.00% | | |

Example M7

| | | | |
|---|---|---|---|
| CC-3-V | 39.00% | Clearing point [° C.]: | 75.0 |
| CC-3-V1 | 7.00% | $\Delta n$ [589 nm, 20° C.]: | 0.1088 |
| CY-3-O2 | 1.50% | $\Delta\varepsilon$ [1 kHz, 20° C.]: | −3.0 |
| CCY-3-O2 | 5.00% | $K_1$ [pN, 20° C.]: | 14.0 |
| CLY-3-O2 | 9.00% | $K_3$ [pN, 20° C.]: | 15.5 |
| CPY-2-O2 | 6.00% | $V_0$ [20° C., V]: | 2.41 |
| CPY-3-O2 | 11.50% | $\gamma_1$ [mPa·s, 20° C.]: | 82 |
| PY-3-O2 | 16.00% | | |
| PGIY-2-O4 | 5.00% | | |

Example M8

| | | | |
|---|---|---|---|
| CC-3-V | 37.50% | Clearing point [° C.]: | 75.5 |
| CC-3-V1 | 7.00% | $\Delta n$ [589 nm, 20° C.]: | 0.1089 |
| CCY-3-O1 | 5.00% | $\Delta\varepsilon$ [1 kHz, 20° C.]: | −3.0 |
| CCY-3-O2 | 11.00% | $K_1$ [pN, 20° C.]: | 14.0 |
| CPY-2-O2 | 4.00% | $K_3$ [pN, 20° C.]: | 15.9 |
| CPY-3-O2 | 12.00% | $V_0$ [20° C., V]: | 2.44 |
| PY-3-O2 | 17.50% | $\gamma_1$ [mPa·s, 20° C.]: | 87 |
| PGIY-3-O4 | 5.00% | LTS bulk [−20° C.]: | >1000 h |
| PP-1-2V1 | 1.00% | | |

Example M9

| | | | |
|---|---|---|---|
| CC-3-V | 38.00% | Clearing point [° C.]: | 75.0 |
| CCY-3-O2 | 7.00% | $\Delta n$ [589 nm, 20° C.]: | 0.1086 |
| CLY-3-O2 | 7.00% | $\Delta\varepsilon$ [1 kHz, 20° C.]: | −3.2 |
| CPY-3-O2 | 12.00% | $K_1$ [pN, 20° C.]: | 13.5 |
| CY-3-O2 | 5.00% | $K_3$ [pN, 20° C.]: | 15.5 |
| PY-3-O2 | 20.00% | $V_0$ [20° C., V]: | 2.33 |
| CCVC-3-V | 6.00% | $\gamma_1$ [mPa·s, 20° C.]: | 88 |
| PGIY-3-O4 | 5.00% | | |

Example M10

| | | | |
|---|---|---|---|
| PY-3-O2 | 10.00% | Clearing point [° C.]: | 74.0 |
| CY-3-O2 | 11.00% | $\Delta n$ [589 nm, 20° C.]: | 0.1075 |
| CCY-3-O1 | 4.50% | $\Delta\varepsilon$ [1 kHz, 20° C.]: | −3.0 |
| CPY-2-O2 | 12.00% | $K_1$ [pN, 20° C.]: | 12.5 |
| CPY-3-O2 | 13.00% | $K_3$ [pN, 20° C.]: | 14.2 |
| CC-3-V | 39.50% | $V_0$ [20° C., V]: | 2.31 |
| CCVC-3-V | 4.50% | $\gamma_1$ [mPa·s, 20° C.]: | 86 |
| PGIY-3-O4 | 5.00% | | |
| PPGU-3-F | 0.50% | | |

Example M11

| | | | |
|---|---|---|---|
| CCH-23 | 20.00% | Clearing point [° C.]: | 73.0 |
| CCH-34 | 6.00% | $\Delta n$ [589 nm, 20° C.]: | 0.0970 |
| CCH-35 | 5.50% | $\Delta\varepsilon$ [1 kHz, 20° C.]: | −2.4 |
| CCP-3-1 | 14.00% | $K_1$ [pN, 20° C.]: | 15.1 |
| CCP-3-3 | 5.50% | $K_3$ [pN, 20° C.]: | 14.6 |
| CCY-3-O1 | 6.50% | $V_0$ [20° C., V]: | 2.62 |
| CCY-3-O2 | 11.00% | $\gamma_1$ [mPa·s, 20° C.]: | 88 |
| CPY-3-O2 | 4.00% | | |
| PY-3-O2 | 8.50% | | |
| Y-4O-O4 | 8.00% | | |
| PP-1-3 | 6.00% | | |
| PGIY-3-O2 | 5.00% | | |

Example M12

| | | | |
|---|---|---|---|
| CC-3-V | 33.00% | Clearing point [° C.]: | 75.5 |
| CC-3-2V1 | 5.00% | $\Delta n$ [589 nm, 20° C.]: | 0.1059 |
| CCY-3-O1 | 5.50% | $\Delta\varepsilon$ [1 kHz, 20° C.]: | −3.5 |
| CCY-3-O2 | 11.00% | $K_1$ [pN, 20° C.]: | 13.9 |
| CCY-4-O2 | 5.00% | $K_3$ [pN, 20° C.]: | 16.1 |
| CPY-3-O2 | 11.00% | $V_0$ [20° C., V]: | 2.27 |
| PY-3-O2 | 11.50% | $\gamma_1$ [mPa·s, 20° C.]: | 97 |
| PY-1-O4 | 3.00% | | |
| CY-3-O2 | 7.00% | | |
| PP-1-2V1 | 3.00% | | |
| PGIY-3-O2 | 5.00% | | |

Example M13

| | | | |
|---|---|---|---|
| CC-3-V | 36.00% | Clearing point [° C.]: | 75.5 |
| CC-3-V1 | 7.00% | Δn [589 nm, 20° C.]: | 0.111 |
| CCY-V-O2 | 5.00% | Δε [1 kHz, 20° C.]: | −3.1 |
| CCY-V-O4 | 11.00% | $K_1$ [pN, 20° C.]: | 13.7 |
| CPY-2-O2 | 7.00% | $K_3$ [pN, 20° C.]: | 15.8 |
| CPY-3-O2 | 11.50% | $V_0$ [20° C., V]: | 2.4 |
| PY-3-O2 | 17.50% | $\gamma_1$ [mPa · s, 20° C.]: | 86 |
| PGIY-3-O2 | 5.00% | | |

Example M14

| | | | |
|---|---|---|---|
| CC-3-V | 37.00% | Clearing point [° C.]: | 74.5 |
| CC-3-V1 | 7.00% | Δn [589 nm, 20° C.]: | 0.1092 |
| CCY-3-O1 | 6.00% | Δε [1 kHz, 20° C.]: | −3.1 |
| CCY-3-O2 | 11.00% | $K_1$ [pN, 20° C.]: | 13.8 |
| CPY-V-O2 | 6.00% | $K_3$ [pN, 20° C.]: | 15.8 |
| CPY-V-O4 | 10.00% | $V_0$ [20° C., V]: | 2.41 |
| PY-3-O2 | 18.00% | $\gamma_1$ [mPa · s, 20° C.]: | 87 |
| PGIY-3-O2 | 5.00% | | |

Example M15

| | | | |
|---|---|---|---|
| CC-3-V | 37.00% | Clearing point [° C.]: | 75.5 |
| CC-3-V1 | 7.00% | Δn [589 nm, 20° C.]: | 0.1102 |
| CCY-3-O1 | 6.00% | Δε [1 kHz, 20° C.]: | −3.1 |
| CCY-3-O2 | 11.00% | $K_1$ [pN, 20° C.]: | 13.8 |
| CPY-2-O2 | 4.00% | $K_3$ [pN, 20° C.]: | 15.9 |
| CPY-3-O2 | 10.50% | $V_0$ [20° C., V]: | 2.41 |
| PY-3-O2 | 10.50% | $\gamma_1$ [mPa · s, 20° C.]: | 85 |
| PY-V2-O2 | 9.00% | | |
| PGIY-3-O2 | 5.00% | | |

Example M16

| | | | |
|---|---|---|---|
| CC-3-V | 36.00% | Clearing point [° C.]: | 75 |
| CC-3-V1 | 7.00% | Δn [589 nm, 20° C.]: | 0.1061 |
| CCY-3-O1 | 5.00% | Δε [1 kHz, 20° C.]: | −3.0 |
| CCY-3-O2 | 11.00% | $K_1$ [pN, 20° C.]: | 13.7 |
| CPY-2-O2 | 6.00% | $K_3$ [pN, 20° C.]: | 15.9 |
| CPY-3-O2 | 11.50% | $V_0$ [20° C., V]: | 2.4 |
| PY-3-O2 | 11.50% | $\gamma_1$ [mPa · s, 20° C.]: | 86 |
| CY-V-O4 | 6.00% | | |
| PP-1-5 | 1.00% | | |
| PGIY-3-O2 | 5.00% | | |

Example M17

| | | | |
|---|---|---|---|
| CC-3-V | 35.50% | Clearing point [° C.]: | 74.5 |
| CC-3-V1 | 8.00% | Δn [589 nm, 20° C.]: | 0.1072 |
| CCY-3-O1 | 6.00% | Δε [1 kHz, 20° C.]: | −3.0 |
| CCY-3-O2 | 11.50% | $\varepsilon_\parallel$ [1 kHz, 20° C.]: | 3.5 |
| CCY-4-O2 | 3.00% | $K_1$ [pN, 20° C.]: | 14.5 |
| CPY-3-O2 | 8.00% | $K_3$ [pN, 20° C.]: | 15.9 |
| CY-3-O2 | 2.50% | $\gamma_1$ [mPa · s, 20° C.]: | 82 |
| PY-3-O2 | 12.00% | $V_0$ [20° C., V]: | 2.42 |
| PGIY-2-O4 | 4.50% | | |
| PP-1-2V1 | 5.00% | | |
| B(S)-2O-O5 | 4.00% | | |

Example M18

| | | | |
|---|---|---|---|
| CC-3-V1 | 8.00% | Clearing point [° C.]: | 75.0 |
| CCH-23 | 15.00% | Δn [589 nm, 20° C.]: | 0.1080 |
| CCH-34 | 6.00% | Δε [1 kHz, 20° C.]: | −3.3 |
| CCP-3-1 | 13.00% | $\varepsilon_\parallel$ [1 kHz, 20° C.]: | 3.5 |
| CCP-3-3 | 8.00% | $K_1$ [pN, 20° C.]: | 15.6 |
| CCY-3-O2 | 6.00% | $K_3$ [pN, 20° C.]: | 15.6 |
| CY-3-O2 | 18.00% | $\gamma_1$ [mPa · s, 20° C.]: | 99 |
| PY-3-O2 | 5.00% | $V_0$ [20° C., V]: | 2.31 |
| PYP-2-3 | 2.00% | | |
| PGIY-2-O4 | 5.50% | | |
| B(S)-2O-O5 | 10.00% | | |
| PP-1-2V1 | 3.50% | | |

Example M19

| | | | |
|---|---|---|---|
| CY-3-O2 | 11.00% | Clearing point [° C.]: | 74.0 |
| CY-3-O4 | 4.00% | Δn [589 nm, 20° C.]: | 0.1084 |
| CCY-3-O2 | 6.00% | Δε [1 kHz, 20° C.]: | −3.3 |
| CCY-4-O2 | 6.00% | $\varepsilon_\parallel$ [1 kHz, 20° C.]: | 3.9 |
| CCH-34 | 10.00% | $K_1$ [pN, 20° C.]: | 14.8 |
| CCH-35 | 5.00% | $K_3$ [pN, 20° C.]: | 14.4 |
| CCP-3-1 | 16.00% | $\gamma_1$ [mPa · s, 20° C.]: | 115 |
| CCP-3-3 | 12.00% | $V_0$ [20° C., V]: | 2.20 |
| PYP-2-3 | 7.00% | | |
| PP-1-3 | 5.00% | | |
| PGIY-2-O4 | 5.00% | | |
| Y-4O-O4 | 9.00% | | |
| B-2O-O5 | 4.00% | | |

Example M20

| | | | |
|---|---|---|---|
| CC-3-V | 35.50% | Clearing point [° C.]: | 74.5 |
| CC-3-V1 | 8.00% | Δn [589 nm, 20° C.]: | 0.1071 |
| CCY-3-O1 | 7.00% | Δε [1 kHz, 20° C.]: | −3.1 |
| CCY-3-O2 | 11.50% | $\varepsilon_\parallel$ [1 kHz, 20° C.]: | 3.5 |
| CCY-4-O2 | 4.00% | $K_1$ [pN, 20° C.]: | 14.3 |
| CPY-3-O2 | 7.50% | $K_3$ [pN, 20° C.]: | 15.8 |
| PY-3-O2 | 13.00% | $\gamma_1$ [mPa · s, 20° C.]: | 84 |
| PGIY-2-O4 | 4.50% | $V_0$ [20° C., V]: | 2.40 |
| PP-1-2V1 | 5.00% | | |
| B-2O-O5 | 4.00% | | |

Example M21

| | | | |
|---|---|---|---|
| CC-3-V | 41.00% | Clearing point [° C.]: | 80.5 |
| CY-3-O2 | 3.00% | Δn [589 nm, 20° C.]: | 0.1070 |
| CCY-3-O1 | 4.00% | Δε [1 kHz, 20° C.]: | −3.8 |
| CCY-3-O2 | 11.00% | $\varepsilon_\parallel$ [1 kHz, 20° C.]: | 3.7 |
| CCY-4-O2 | 6.00% | $K_1$ [pN, 20° C.]: | 14.1 |
| CPY-2-O2 | 6.00% | $K_3$ [pN, 20° C.]: | 15.4 |
| CPY-3-O2 | 10.00% | $\gamma_1$ [mPa · s, 20° C.]: | 99 |
| PGIY-2-O4 | 5.00% | $V_0$ [20° C., V]: | 2.11 |
| PY-3-O2 | 9.00% | | |
| B-2O-O5 | 5.00% | | |

Example M22

| | | | |
|---|---|---|---|
| CY-3-O2 | 15.50% | Clearing point [° C.]: | 86.5 |
| CCY-3-O1 | 8.00% | Δn [589 nm, 20° C.]: | 0.1026 |

-continued

| | | | |
|---|---|---|---|
| CCY-3-O2 | 11.00% | Δε [1 kHz, 20° C.]: | −4.9 |
| CCY-4-O2 | 11.00% | ε∥ [1 kHz, 20° C.]: | 3.9 |
| CPY-2-O2 | 4.00% | K₁ [pN, 20° C.]: | 14.4 |
| CPY-3-O2 | 10.00% | K₃ [pN, 20° C.]: | 16.7 |
| CC-3-V | 31.50% | γ₁ [mPa · s, 20° C.]: | 136 |
| B-2O-O5 | 4.00% | V₀ [20° C., V]: | 1.95 |
| B-3-O2 | 2.00% | | |
| PGIY-2-O4 | 3.00% | | |

Example M23

| | | | |
|---|---|---|---|
| CC-3-V | 38.50% | Clearing point [° C.]: | 75.0 |
| CC-3-V1 | 7.00% | Δn [589 nm, 20° C.]: | 0.1082 |
| CCY-3-O1 | 3.00% | Δε [1 kHz, 20° C.]: | −2.9 |
| CCY-3-O2 | 10.50% | ε∥ [1 kHz, 20° C.]: | 3.5 |
| PY-3-O2 | 5.00% | K₁ [pN, 20° C.]: | 13.8 |
| B-2O-O5 | 4.00% | K₃ [pN, 20° C.]: | 15.3 |
| PGIY-2-O4 | 5.00% | γ₁ [mPa · s, 20° C.]: | 76 |
| PP-1-2V1 | 5.00% | V₀ [20° C., V]: | 2.42 |
| PY-V2-O2 | 5.00% | | |
| CPY-V-O2 | 6.00% | | |
| CPY-V-O4 | 5.00% | | |
| CCY-V-O2 | 6.00% | | |

Example M24

For the preparation of a PS-VA mixture, 99.7% of the mixture according to Example M1 is mixed with 0.3% of the polymerizable compound of the formula

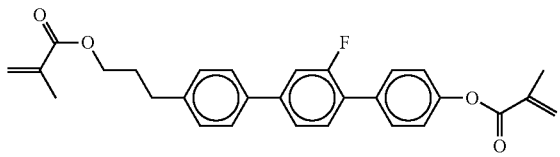

Example M25

For the preparation of a PS-VA mixture, 99.75% of the mixture according to Example M1 is mixed with 0.25% of the polymerizable compound of the formula

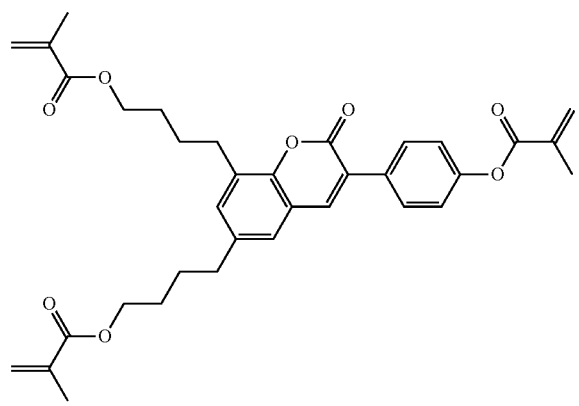 [SMILES: C=C(C)C(=O)OCCCCc1cc(CCCCOC(=O)C(=C)C)c2oc(=O)c(-c3ccc(OC(=O)C(=C)C)cc3)cc2c1]

Example M26

For the preparation of a PS-VA mixture, 99.8% of the mixture according to Example M1 is mixed with 0.2% of the polymerizable compound of the formula

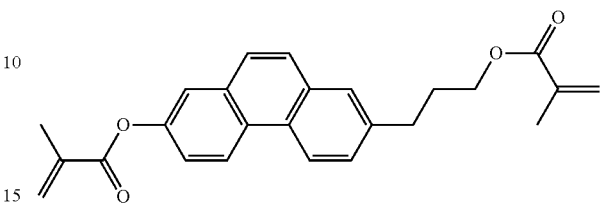

Example M27

For the preparation of a PS-VA mixture, 99.75% of the mixture according to Example M5 is mixed with 0.25% of the polymerizable compound of the formula

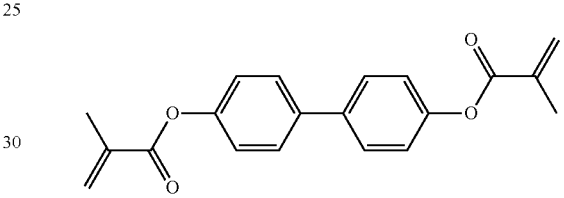

Example M28

For the preparation of a PS-VA mixture, 99.75% of the mixture according to Example M11 is mixed with 0.25% of the polymerizable compound of the formula

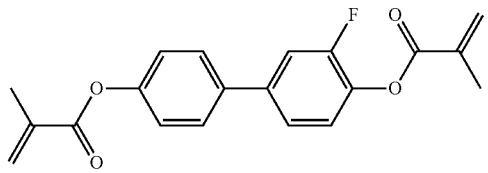

Example M29

For the preparation of a PS-VA mixture, 99.75% of the mixture according to Example M17 is mixed with 0.25% of the polymerizable compound of the formula

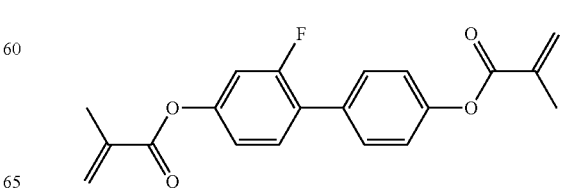

Example M30

For the preparation of a PS-VA mixture, 99.8% of the mixture according to Example M18 is mixed with 0.2% of the polymerizable compound of the formula

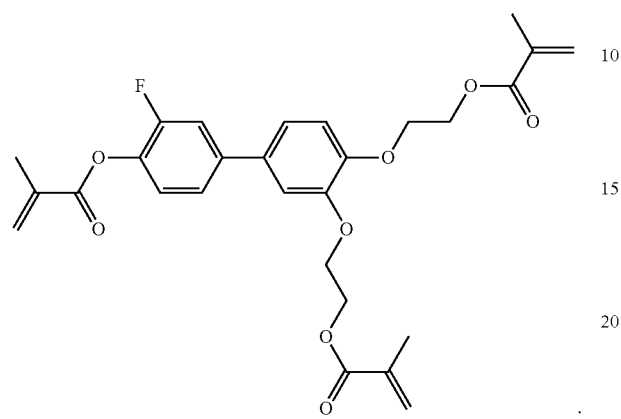

Example M31

For the preparation of a PS-VA mixture, 99.8% of the mixture according to Example M19 is mixed with 0.2% of the polymerizable compound of the formula

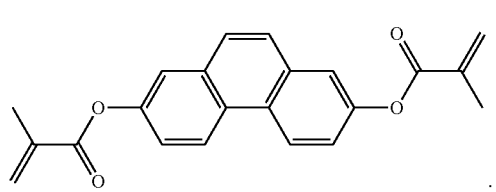 [SMILES: C=C(C)C(=O)Oc1ccc2c(ccc3cc(OC(=O)C(=C)C)ccc32)c1]

Example M32

For the preparation of a PS-VA mixture, 99.75% of the mixture according to Example M20 is mixed with 0.25% of the polymerizable compound of the formula

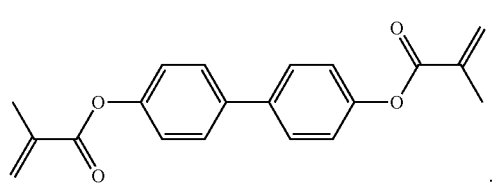 [SMILES: C=C(C)C(=O)Oc1ccc(-c2ccc(OC(=O)C(=C)C)cc2)cc1]

Example M33

For the preparation of a PS-VA mixture, 99.7% of the mixture according to Example M21 is mixed with 0.3% of the polymerizable compound of the formula

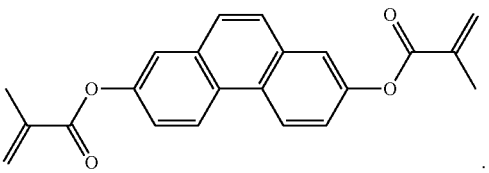 [SMILES: C=C(C)C(=O)Oc1ccc2c(ccc3cc(OC(=O)C(=C)C)ccc32)c1]

Example M34

For the preparation of a PS-VA mixture, 99.7% of the mixture according to Example M2 is mixed with 0.3% of the polymerizable compound of the formula

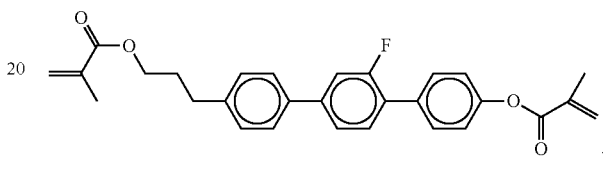

Example M35

For the preparation of a PS-VA mixture, 99.75% of the mixture according to Example M2 is mixed with 0.25% of the polymerizable compound of the formula

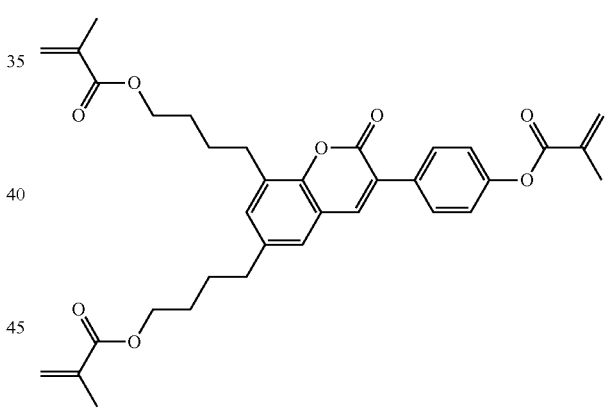

Example M36

For the preparation of a PS-VA mixture, 99.7% of the mixture according to Example M2 is mixed with 0.3% of the polymerizable compound of the formula

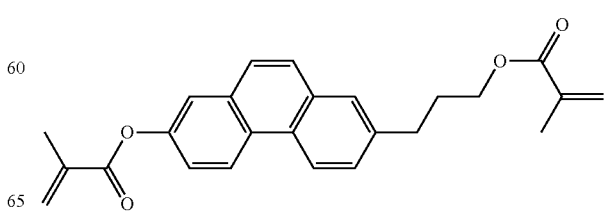

Example M37

For the preparation of a PS-VA mixture, the mixture according to Example M2 are mixed with the polymerizable compound RM-1 of the formula

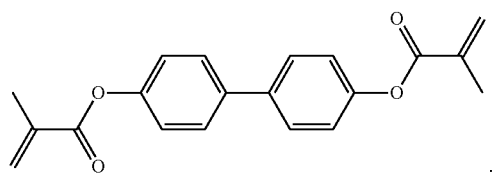

| UV time/min | Tilt/° |
|---|---|
| 0 | 88.9 |
| 1 | 86.2 |
| 2 | 80.5 |
| 3 | 77.4 |
| 5 | 75.1 |
| 10 | 72.9 |

| UV time/min | RM-1 conc./wt. % |
|---|---|
| 0 | 0.30 |
| 1 | 0.21 |
| 3 | 0.11 |
| 5 | 0.06 |
| 10 | 0.03 |
| 15 | 0.02 |
| 20 | 0.01 |

Compared with the prior art, the mixtures according to the invention exhibit significantly higher polymerization rates and at the same time faster establishment of the tilt angle.

Example M38

For the preparation of a PS-VA mixture, 99.75% of the mixture according to Example M2 is mixed with 0.25% of the polymerizable compound of the formula

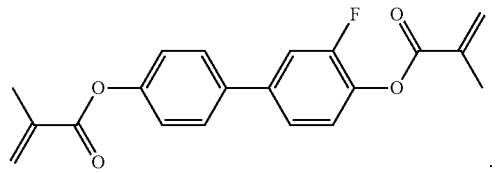 [SMILES: C=C(C)C(=O)Oc1ccc(-c2ccc(OC(=O)C(=C)C)c(F)c2)cc1]

Example M39

For the preparation of a PS-VA mixture, the mixture according to Example M2 are mixed with the polymerizable compound RM-88 of the formula

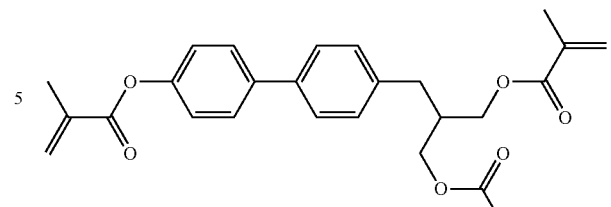

| UV time/min | Tilt/° |
|---|---|
| 0 | 88.9 |
| 1 | 83.0 |
| 2 | 79.4 |
| 3 | 78.1 |
| 5 | 75.7 |
| 10 | 73.9 |

| UV time/min | RM-88 conc./wt. % |
|---|---|
| 0 | 0.30 |
| 1 | 0.22 |
| 3 | 0.13 |
| 5 | 0.10 |
| 10 | 0.04 |
| 15 | 0.03 |
| 20 | 0.04 |

Compared with the prior art, the mixtures according to the invention exhibit significantly higher polymerization rates and at the same time faster establishment of the tilt angle.

Example M40

For the preparation of a PS-VA mixture, 99.75% of the mixture according to Example M3 is mixed with 0.25% of the polymerizable compound of the formula

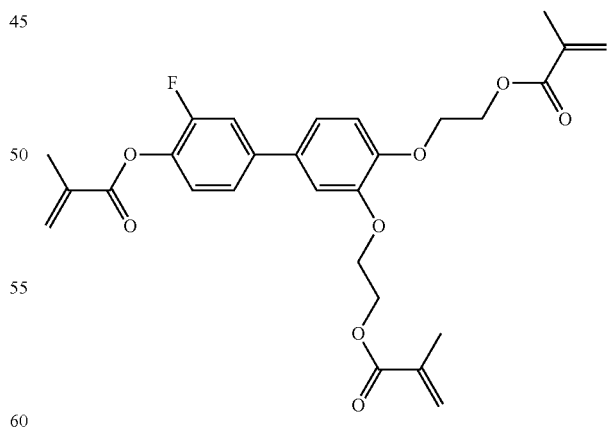

Example M41

For the preparation of a PS-VA mixture, 99.8% of the mixture according to Example M3 is mixed with 0.2% of the polymerizable compound of the formula

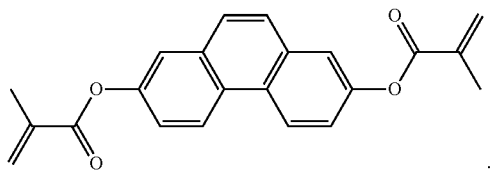 [SMILES: C=C(C)C(=O)Oc1ccc2c(ccc3cc(OC(=O)C(=C)C)ccc32)c1]

Example M42

For the preparation of a PS-VA mixture, 99.7% of the mixture according to Example M3 is mixed with 0.3% of the polymerizable compound of the formula

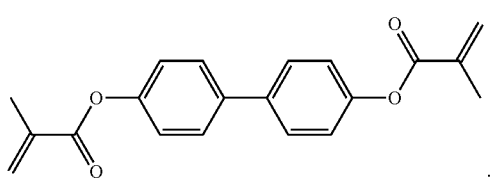 [SMILES: C=C(C)C(=O)Oc1ccc(-c2ccc(OC(=O)C(=C)C)cc2)cc1]

Example M43

For the preparation of a PS-VA mixture, 99.7% of the mixture according to Example M3 is mixed with 0.3% of the polymerizable compound of the formula

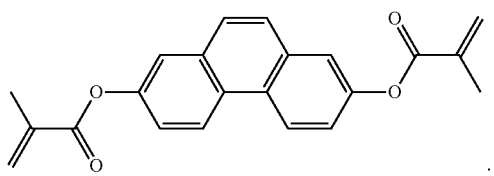 [SMILES: C=C(C)C(=O)Oc1ccc2c(ccc3cc(OC(=O)C(=C)C)ccc32)c1]

Example M44

For the preparation of a PS-VA mixture, 99.7% of the mixture according to Example M3 is mixed with 0.3% of the polymerizable compound of the formula

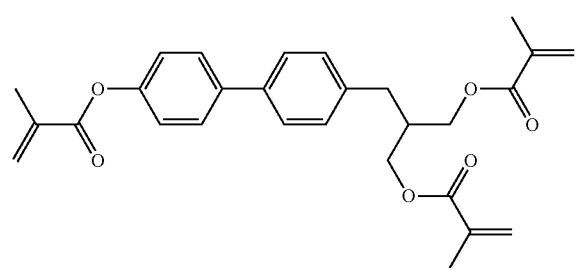

Example M45

For the preparation of a PS-VA mixture, 99.7% of the mixture according to Example M3 is mixed with 0.3% of the polymerizable compound of the formula

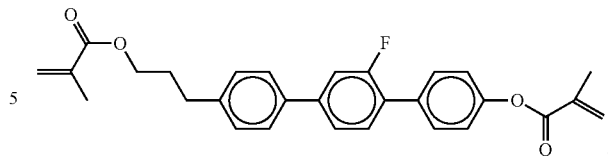

Example M46

For the preparation of a PS-VA mixture, 99.7% of the mixture according to Example M4 is mixed with 0.3% of the polymerizable compound of the formula

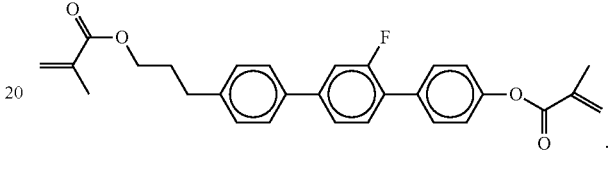

Example M47

For the preparation of a PS-VA mixture, 99.75% of the mixture according to Example M4 is mixed with 0.25% of the polymerizable compound of the formula

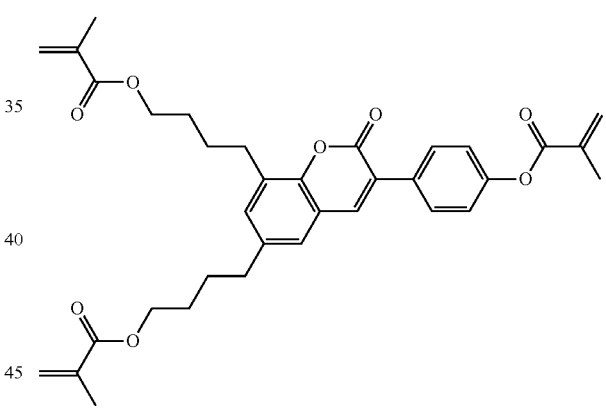

Example M48

For the preparation of a PS-VA mixture, 99.75% of the mixture according to Example M4 is mixed with 0.25% of the polymerizable compound of the formula

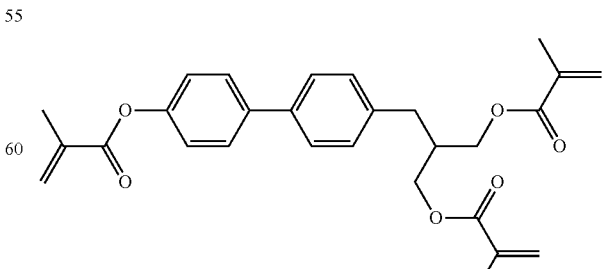

Example M49

For the preparation of a PS-VA mixture, 99.7% of the mixture according to Example M4 is mixed with 0.3% of the polymerizable compound of the formula

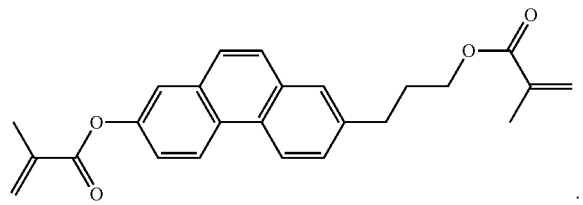 [SMILES: C=C(C)C(=O)OCCCc1ccc2c(ccc3cc(OC(=O)C(=C)C)ccc32)c1]

Example M50

For the preparation of a PS-VA mixture, 99.75% of the mixture according to Example M5 is mixed with 0.25% of the polymerizable compound of the formula

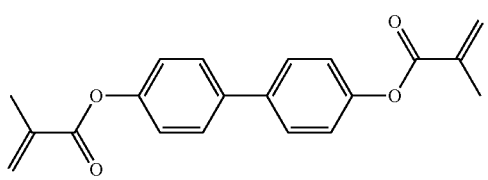

Example M51

For the preparation of a PS-VA mixture, the mixture according to Example M6 are mixed with the polymerizable compound RM-1 of the formula

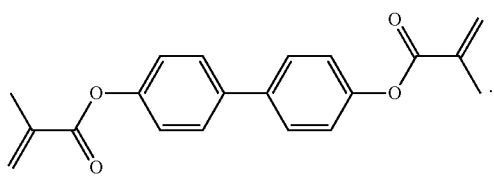

| UV time/min | Tilt/° |
|---|---|
| 0 | 88.9 |
| 1 | 86.5 |
| 2 | 80.4 |
| 3 | 77.5 |
| 5 | 75.3 |
| 10 | 73.7 |

| UV time/min | RM-1 conc./wt. % |
|---|---|
| 0 | 0.30 |
| 1 | 0.20 |
| 3 | 0.13 |
| 5 | 0.09 |
| 10 | 0.05 |
| 15 | 0.02 |
| 20 | 0.01 |

Compared with the prior art, the mixtures according to the invention exhibit significantly higher polymerization rates and at the same time faster establishment of the tilt angle.

Example M52

For the preparation of a PS-VA mixture, 99.7% of the mixture according to Example M6 is mixed with 0.3% of the polymerizable compound of the formula

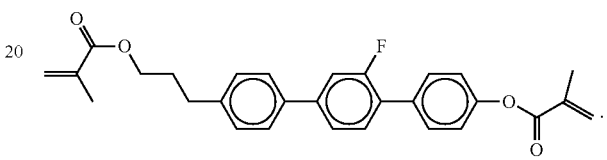

Example M53

For the preparation of a PS-VA mixture, 99.75% of the mixture according to Example M8 is mixed with 0.25% of the polymerizable compound of the formula

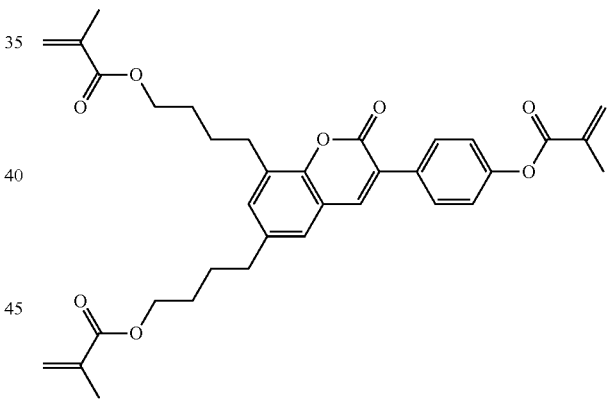

Example M54

For the preparation of a PS-VA mixture, 99.8% of the mixture according to Example M8 is mixed with 0.2% of the polymerizable compound of the formula

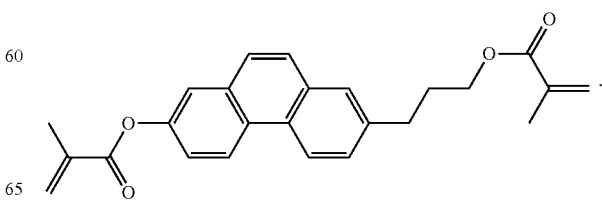

Example M55

For the preparation of a PS-VA mixture, 99.75% of the mixture according to Example M9 is mixed with 0.25% of the polymerizable compound of the formula

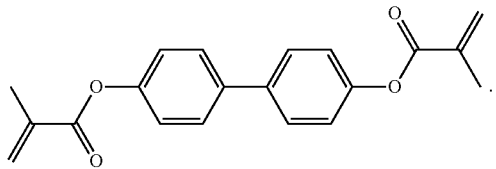

Example M56

For the preparation of a PS-VA mixture, 99.75% of the mixture according to Example M10 is mixed with 0.25% of the polymerizable compound of the formula

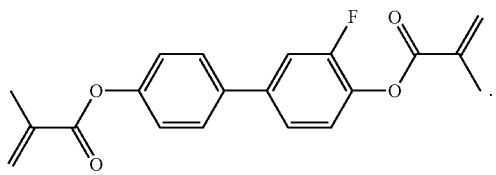 [SMILES: C=C(C)C(=O)Oc1ccc(-c2ccc(OC(=O)C(=C)C)c(F)c2)cc1]

Example M57

For the preparation of a PS-VA mixture, 99.75% of the mixture according to Example M12 is mixed with 0.25% of the polymerizable compound of the formula

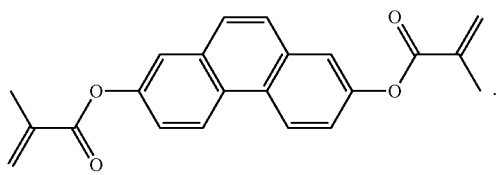 [SMILES: C=C(C)C(=O)Oc1ccc2c(ccc3cc(OC(=O)C(=C)C)ccc32)c1]

Example M58

For the preparation of a PS-VA mixture, 99.75% of the mixture according to Example M12 is mixed with 0.25% of the polymerizable compound of the formula

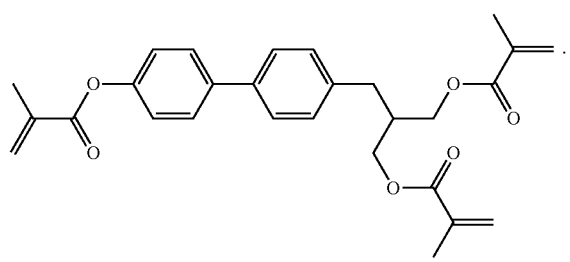 [SMILES: C=C(C)C(=O)OCC(COC(=O)C(=C)C)Cc1ccc(-c2ccc(OC(=O)C(=C)C)cc2)cc1]

Example M59

| | | | |
|---|---|---|---|
| BCH-32 | 15.50% | Clearing point [° C.]: | 109.4 |
| BCH-52 | 14.00% | Δn [589 nm, 20° C.]: | 0.1502 |
| CCY-3-O1 | 5.00% | Δε [1 kHz, 20° C.]: | −4.2 |
| CCY-3-O2 | 8.00% | $K_1$ [pN, 20° C.]: | 19.5 |
| CCY-3-O3 | 8.00% | $K_3$ [pN, 20° C.]: | 17.3 |
| CCY-4-O2 | 8.00% | $V_0$ [20° C., V]: | 2.14 |
| CCY-5-O2 | 1.50% | LTS bulk [−20° C.]: | >1000 h |
| CY-3-O2 | 13.50% | | |
| PGIY-2-O4 | 8.00% | | |
| PY-3-O2 | 8.00% | | |
| PY-4-O2 | 5.50% | | |
| PYP-2-3 | 3.00% | | |
| PYP-2-4 | 2.00% | | |

Example M60

| | | | |
|---|---|---|---|
| BCH-32 | 12.00% | Clearing point [° C.]: | 108.6 |
| BCH-52 | 13.00% | Δn [589 nm, 20° C.]: | 0.1498 |
| CCY-3-O1 | 5.00% | Δε [1 kHz, 20° C.]: | −4.2 |
| CCY-3-O2 | 8.00% | $K_1$ [pN, 20° C.]: | 18.3 |
| CCY-4-O2 | 8.00% | $K_3$ [pN, 20° C.]: | 17.0 |
| CCY-5-O2 | 6.00% | $V_0$ [20° C., V]: | 2.13 |
| CY-3-O4 | 25.00% | | |
| PGIY-2-O4 | 10.00% | | |
| PYP-2-3 | 8.00% | | |
| PYP-2-4 | 5.00% | | |

Example M61

| | | | |
|---|---|---|---|
| CC-3-V | 35.50% | Clearing point [° C.]: | 86.1 |
| CCY-3-O1 | 5.00% | Δn [589 nm, 20° C.]: | 0.1124 |
| CCY-3-O3 | 8.00% | Δε [1 kHz, 20° C.]: | −3.9 |
| CCY-4-O2 | 3.50% | $K_1$ [pN, 20° C.]: | 15.1 |
| CPY-2-O2 | 8.00% | $K_3$ [pN, 20° C.]: | 15.9 |
| CPY-3-O2 | 10.00% | $γ_1$ [mPa·s, 20° C.]: | 120 |
| CLY-3-O2 | 10.00% | $V_0$ [20° C., V]: | 2.11 |
| PY-3-O2 | 10.00% | | |
| Y-4O-O4 | 3.00% | | |
| PGIY-2-O4 | 7.00% | | |

Example M62

| | | | |
|---|---|---|---|
| BCH-32 | 5.00% | Clearing point [° C.]: | 80.4 |
| CC-3-V | 32.50% | Δn [589 nm, 20° C.]: | 0.1120 |
| CCY-3-O1 | 5.00% | Δε [1 kHz, 20° C.]: | −3.9 |
| CCY-3-O2 | 8.00% | $K_1$ [pN, 20° C.]: | 14.0 |
| CCY-4-O2 | 2.50% | $K_3$ [pN, 20° C.]: | 15.0 |
| CLY-3-O2 | 8.00% | $V_0$ [20° C., V]: | 2.05 |
| CPY-2-O2 | 7.00% | $γ_1$ [mPa·s, 20° C.]: | 108 |
| CPY-3-O2 | 10.00% | | |
| PGIY-2-O4 | 7.00% | | |
| PY-3-O2 | 7.00% | | |
| Y-4O-O4 | 8.00% | | |

Example M63

| | | | |
|---|---|---|---|
| B-2O-O5 | 5.00% | Clearing point [° C.]: | 80.1 |
| BCH-32 | 7.00% | Δn [589 nm, 20° C.]: | 0.1121 |

| | | | |
|---|---|---|---|
| CC-3-V | 34.50% | Δε [1 kHz, 20° C.]: | −3.9 |
| CCP-V-1 | 2.00% | K₁ [pN, 20° C.]: | 14.0 |
| CCY-3-O1 | 5.00% | K₃ [pN, 20° C.]: | 14.5 |
| CCY-3-O2 | 4.00% | V₀ [20° C., V]: | 2.03 |
| CCY-4-O2 | 2.00% | γ₁ [mPa·s, 20° C.]: | 104 |
| CLY-3-O2 | 8.00% | | |
| CPY-2-O2 | 10.00% | | |
| CPY-3-O2 | 7.00% | | |
| PGIY-2-O4 | 6.00% | | |
| PY-3-O2 | 2.00% | | |
| Y-4O-O4 | 7.50% | | |

Example M64

| | | | |
|---|---|---|---|
| B-2O-O5 | 5.00% | Clearing point [° C.]: | 80 |
| CC-3-V | 37.00% | Δε [1 kHz, 20° C.]: | −3.9 |
| CCP-V-1 | 4.50% | γ₁ [mPa·s, 20° C.]: | 106 |
| CCY-3-O1 | 5.00% | | |
| CCY-3-O2 | 6.00% | | |
| CCY-4-O2 | 5.00% | | |
| CLY-3-O2 | 8.00% | | |
| CPY-2-O2 | 9.50% | | |
| PGIY-2-O4 | 6.00% | | |
| PY-3-O2 | 14.00% | | |

Example M65

| | | | |
|---|---|---|---|
| BCH-32 | 5.00% | Clearing point [° C.]: | 75 |
| CC-3-V | 32.50% | Δn [589 nm, 20° C.]: | 0.1283 |
| CCP-V-1 | 7.00% | Δε [1 kHz, 20° C.]: | −2.3 |
| CCY-3-O2 | 9.00% | K₁ [pN, 20° C.]: | 14.9 |
| CPY-3-O2 | 12.00% | K₃ [pN, 20° C.]: | 15.8 |
| PY-3-O2 | 15.00% | V₀ [20° C., V]: | 2.76 |
| PY-4-O2 | 1.50% | γ₁ [mPa·s, 20° C.]: | 86 |
| PYP-2-3 | 5.00% | LTS bulk [−30° C.]: | >1000 h |
| PP-1-2V1 | 8.00% | | |
| PGIY-2-O4 | 5.00% | | |

Example M66

| | | | |
|---|---|---|---|
| CC-3-V | 35.00% | Clearing point [° C.]: | 80.7 |
| CCY-3-O1 | 5.00% | Δn [589 nm, 20° C.]: | 0.1100 |
| CCY-3-O2 | 5.00% | Δε [1 kHz, 20° C.]: | −3.9 |
| CCY-4-O2 | 5.00% | ε∥ [1 kHz, 20° C.]: | 3.8 |
| CLY-3-O2 | 8.00% | ε⊥ [1 kHz, 20° C.]: | 7.7 |
| CPY-2-O2 | 10.00% | K₁ [pN, 20° C.]: | 13.0 |
| CPY-3-O2 | 10.00% | K₃ [pN, 20° C.]: | 14.2 |
| PGIY-2-O4 | 7.00% | V₀ [20° C., V]: | 2.03 |
| PY-3-O2 | 10.00% | γ₁ [mPa·s, 20° C.]: | 114 |
| Y-4O-O4 | 5.00% | | |

Example M67

| | | | |
|---|---|---|---|
| CC-3-V | 37.50% | Clearing point [° C.]: | 80.2 |
| CCY-3-O1 | 5.00% | Δn [589 nm, 20° C.]: | 0.1097 |
| CCY-3-O2 | 3.00% | Δε [1 kHz, 20° C.]: | −3.9 |
| CCY-4-O2 | 7.00% | ε∥ [1 kHz, 20° C.]: | 3.7 |
| CLY-3-O2 | 8.00% | ε⊥ [1 kHz, 20° C.]: | 7.6 |
| CPY-2-O2 | 10.00% | K₁ [pN, 20° C.]: | 13.5 |
| CPY-3-O2 | 8.00% | K₃ [pN, 20° C.]: | 14.5 |
| PY-1-O4 | 3.50% | V₀ [20° C., V]: | 2.05 |
| PY-3-O2 | 12.00% | γ₁ [mPa·s, 20° C.]: | 110 |
| PGIY-2-O4 | 2.00% | | |
| B-2O-O5 | 4.00% | | |

Example M68

| | | | |
|---|---|---|---|
| BCH-32 | 0.50% | Clearing point [° C.]: | 80.4 |
| CC-3-V | 37.00% | Δn [589 nm, 20° C.]: | 0.1195 |
| CCY-3-O1 | 5.00% | Δε [1 kHz, 20° C.]: | −3.9 |
| CCY-3-O2 | 3.50% | ε∥ [1 kHz, 20° C.]: | 3.8 |
| CLY-3-O2 | 8.00% | ε⊥ [1 kHz, 20° C.]: | 7.7 |
| CPY-2-O2 | 10.00% | K₁ [pN, 20° C.]: | 13.5 |
| CPY-3-O2 | 10.00% | K₃ [pN, 20° C.]: | 14.5 |
| PY-3-O2 | 14.00% | V₀ [20° C., V]: | 2.04 |
| PGIY-2-O4 | 8.00% | γ₁ [mPa·s, 20° C.]: | 114 |
| B-2O-O5 | 4.00% | | |

Example M69

| | | | |
|---|---|---|---|
| CC-3-V | 35.00% | Clearing point [° C.]: | 86.0 |
| CCY-3-O1 | 5.00% | Δn [589 nm, 20° C.]: | 0.1208 |
| CCY-3-O2 | 7.50% | Δε [1 kHz, 20° C.]: | −4.2 |
| CLY-3-O2 | 8.00% | ε∥ [1 kHz, 20° C.]: | 3.8 |
| CPY-2-O2 | 10.00% | ε⊥ [1 kHz, 20° C.]: | 8.0 |
| CPY-3-O2 | 10.00% | K₁ [pN, 20° C.]: | 14.3 |
| PY-3-O2 | 12.50% | K₃ [pN, 20° C.]: | 15.6 |
| PGIY-2-O4 | 8.00% | V₀ [20° C., V]: | 2.04 |
| B-2O-O5 | 4.00% | γ₁ [mPa·s, 20° C.]: | 129 |

Example M70

| | | | |
|---|---|---|---|
| BCH-32 | 8.00% | Clearing point [° C.]: | 80.6 |
| CC-3-V | 28.00% | Δn [589 nm, 20° C.]: | 0.1194 |
| CCY-3-O1 | 5.00% | Δε [1 kHz, 20° C.]: | −3.9 |
| CCY-3-O2 | 6.00% | ε∥ [1 kHz, 20° C.]: | 4.0 |
| CLY-3-O2 | 8.00% | ε⊥ [1 kHz, 20° C.]: | 7.9 |
| CPY-2-O2 | 10.00% | K₁ [pN, 20° C.]: | 13.0 |
| CPY-3-O2 | 10.00% | K₃ [pN, 20° C.]: | 14.0 |
| PGIY-2-O4 | 8.00% | V₀ [20° C., V]: | 2.00 |
| PY-3-O2 | 9.00% | γ₁ [mPa·s, 20° C.]: | 120 |
| Y-4O-O4 | 8.00% | | |

Example M71

| | | | |
|---|---|---|---|
| CY-3-O4 | 20.50% | Clearing point [° C.]: | 71.6 |
| CCY-3-O1 | 6.00% | Δn [589 nm, 20° C.]: | 0.1196 |
| CCY-3-O3 | 8.00% | Δε [1 kHz, 20° C.]: | −7.2 |
| CCY-4-O2 | 8.00% | ε∥ [1 kHz, 20° C.]: | 5.0 |
| CCY-5-O2 | 3.00% | ε⊥ [1 kHz, 20° C.]: | 12.2 |
| CPY-2-O2 | 10.00% | K₁ [pN, 20° C.]: | 11.8 |
| CCY-2-1 | 9.00% | K₃ [pN, 20° C.]: | 12.4 |
| PYP-2-4 | 3.50% | V₀ [20° C., V]: | 1.38 |
| CLY-3-O2 | 8.00% | γ₁ [mPa·s, 20° C.]: | 245 |
| PY-1-O4 | 8.00% | | |
| Y-4O—O4 | 8.00% | | |
| PGIY-2-O4 | 8.00% | | |

Example M72

| | | | |
|---|---|---|---|
| CY-3-O2 | 15.00% | Clearing point [° C.]: | 86.6 |
| CY-3-O4 | 6.50% | $\Delta n$ [589 nm, 20° C.]: | 0.1205 |
| CY-5-O2 | 10.00% | $\Delta \varepsilon$ [1 kHz, 20° C.]: | −8.0 |
| CCY-3-O1 | 4.00% | $\varepsilon_\parallel$ [1 kHz, 20° C.]: | 4.8 |
| CCY-3-O2 | 6.00% | $\varepsilon_\perp$ [1 kHz, 20° C.]: | 12.8 |
| CCY-3-O3 | 6.00% | $K_1$ [pN, 20° C.]: | 14.4 |
| CCY-4-O2 | 6.00% | $K_3$ [pN, 20° C.]: | 16.6 |
| CCY-5-O2 | 6.00% | $V_0$ [20° C., V]: | 1.51 |
| CCY-3-1 | 2.50% | $\gamma_1$ [mPa · s, 20° C.]: | 311 |
| CPY-2-O2 | 8.00% | | |
| CPY-3-O2 | 10.00% | | |
| CLY-3-O2 | 7.00% | | |
| Y-4O—O4 | 6.00% | | |
| PGIY-2-O4 | 7.00% | | |

Example M73

| | | | |
|---|---|---|---|
| CY-3-O2 | 9.00% | Clearing point [° C.]: | 69.7 |
| CPY-2-O2 | 8.00% | $\Delta n$ [589 nm, 20° C.]: | 0.1277 |
| CPY-3-O2 | 10.00% | $\Delta \varepsilon$ [1 kHz, 20° C.]: | −1.6 |
| PYP-2-3 | 10.00% | $\varepsilon_\parallel$ [1 kHz, 20° C.]: | 3.3 |
| PGIY-2-O4 | 6.00% | $\varepsilon_\perp$ [1 kHz, 20° C.]: | 4.9 |
| CC-3-V | 15.50% | $K_1$ [pN, 20° C.]: | 12.8 |
| CC-4-V | 17.50% | $K_3$ [pN, 20° C.]: | 11.8 |
| BCH-32 | 12.00% | $V_0$ [20° C., V]: | 2.81 |
| PP-1-4 | 12.00% | $\gamma_1$ [mPa · s, 20° C.]: | 76 |

Example M74

| | | | |
|---|---|---|---|
| CY-3-O2 | 10.00% | Clearing point [° C.]: | 70.7 |
| CPY-2-O2 | 8.00% | $\Delta n$ [589 nm, 20° C.]: | 0.1278 |
| CPY-3-O2 | 8.50% | $\Delta \varepsilon$ [1 kHz, 20° C.]: | −1.7 |
| PYP-2-3 | 10.00% | $\varepsilon_\parallel$ [1 kHz, 20° C.]: | 3.2 |
| PGIY-2-O4 | 6.00% | $\varepsilon_\perp$ [1 kHz, 20° C.]: | 4.9 |
| CCH-23 | 20.00% | $K_1$ [pN, 20° C.]: | 13.7 |
| CCH-34 | 6.00% | $K_3$ [pN, 20° C.]: | 12.0 |
| CCH-35 | 2.50% | $V_0$ [20° C., V]: | 2.81 |
| BCH-32 | 15.00% | $\gamma_1$ [mPa · s, 20° C.]: | 90 |
| PP-1-4 | 11.00% | | |
| PCH-53 | 3.00% | | |

Example M75

| | | | |
|---|---|---|---|
| CC-3-V | 28.50% | Clearing point [° C.]: | 74.8 |
| CC-3-V1 | 9.00% | $\Delta n$ [589 nm, 20° C.]: | 0.1095 |
| CCY-3-O1 | 7.00% | $\Delta \varepsilon$ [1 kHz, 20° C.]: | −3.8 |
| CCY-3-O2 | 10.50% | $\varepsilon_\parallel$ [1 kHz, 20° C.]: | 3.7 |
| CPY-2-O2 | 8.00% | $\varepsilon_\perp$ [1 kHz, 20° C.]: | 7.5 |
| CPY-3-O2 | 10.00% | $K_1$ [pN, 20° C.]: | 14.1 |
| PY-3-O2 | 16.50% | $K_3$ [pN, 20° C.]: | 15.8 |
| CY-3-O2 | 7.00% | $V_0$ [20° C., V]: | 2.15 |
| PGIY-2-O4 | 3.50% | $\gamma_1$ [mPa · s, 20° C.]: | 104 |

Example M76

| | | | |
|---|---|---|---|
| CC-3-V | 32.50% | Clearing point [° C.]: | 75.0 |
| CC-3-V1 | 5.50% | $\Delta n$ [589 nm, 20° C.]: | 0.1093 |
| CCY-3-O1 | 8.50% | $\Delta \varepsilon$ [1 kHz, 20° C.]: | −3.8 |
| CCY-3-O2 | 6.00% | $\varepsilon_\parallel$ [1 kHz, 20° C.]: | 3.7 |
| CLY-3-O2 | 10.00% | $\varepsilon_\perp$ [1 kHz, 20° C.]: | 7.5 |
| CPY-3-O2 | 6.50% | $K_1$ [pN, 20° C.]: | 14.1 |
| PY-3-O2 | 15.50% | $K_3$ [pN, 20° C.]: | 15.7 |
| CY-3-O2 | 7.50% | $V_0$ [20° C., V]: | 2.15 |
| PGIY-2-O4 | 8.00% | $\gamma_1$ [mPa · s, 20° C.]: | 99 |

Example M77

| | | | |
|---|---|---|---|
| CCY-3-O1 | 7.50% | Clearing point [° C.]: | 80.5 |
| CLY-3-O2 | 10.00% | $\Delta n$ [589 nm, 20° C.]: | 0.1149 |
| CPY-2-O2 | 10.00% | $\Delta \varepsilon$ [1 kHz, 20° C.]: | −4.0 |
| CPY-3-O2 | 11.00% | $\varepsilon_\parallel$ [1 kHz, 20° C.]: | 3.7 |
| PGIY-2-O4 | 5.00% | $\varepsilon_\perp$ [1 kHz, 20° C.]: | 7.7 |
| PYP-2-3 | 2.00% | $K_1$ [pN, 20° C.]: | 14.4 |
| CC-3-V | 31.00% | $K_3$ [pN, 20° C.]: | 15.8 |
| CY-3-O2 | 11.00% | $V_0$ [20° C., V]: | 2.10 |
| PY-1-O4 | 4.00% | $\gamma_1$ [mPa · s, 20° C.]: | 116 |
| PY-3-O2 | 5.00% | | |
| CC-3-V1 | 3.50% | | |

Example M78

| | | | |
|---|---|---|---|
| CC-3-V | 37.00% | Clearing point [° C.]: | 75.0 |
| CC-3-V1 | 7.00% | $\Delta n$ [589 nm, 20° C.]: | 0.1090 |
| CCY-3-O2 | 5.00% | $\Delta \varepsilon$ [1 kHz, 20° C.]: | −3.2 |
| CLY-3-O2 | 10.00% | $\varepsilon_\parallel$ [1 kHz, 20° C.]: | 3.5 |
| CPY-2-O2 | 10.50% | $\varepsilon_\perp$ [1 kHz, 20° C.]: | 6.7 |
| CPY-3-O2 | 10.50% | $K_1$ [pN, 20° C.]: | 13.8 |
| PY-1-O4 | 10.00% | $K_3$ [pN, 20° C.]: | 15.7 |
| PY-3-O2 | 9.00% | $V_0$ [20° C., V]: | 2.34 |
| PGIY-2-O4 | 1.00% | $\gamma_1$ [mPa · s, 20° C.]: | 87 |

Example M79

| | | | |
|---|---|---|---|
| CC-3-V | 43.50% | Clearing point [° C.]: | 74.9 |
| CC-3-V1 | 10.00% | $\Delta n$ [589 nm, 20° C.]: | 0.1093 |
| CLY-3-O2 | 10.00% | $\Delta \varepsilon$ [1 kHz, 20° C.]: | −2.1 |
| CPY-2-O2 | 2.50% | $\varepsilon_\parallel$ [1 kHz, 20° C.]: | 3.2 |
| CPY-3-O2 | 10.50% | $\varepsilon_\perp$ [1 kHz, 20° C.]: | 5.3 |
| PY-1-O4 | 1.50% | $K_1$ [pN, 20° C.]: | 13.9 |
| PY-3-O2 | 9.00% | $K_3$ [pN, 20° C.]: | 15.3 |
| PYP-2-3 | 8.00% | $V_0$ [20° C., V]: | 2.87 |
| PGIY-2-O4 | 5.00% | $\gamma_1$ [mPa · s, 20° C.]: | 71 |

Example M80

| | | | |
|---|---|---|---|
| CC-3-V | 28.50% | Clearing point [° C.]: | 65.1 |
| CC-3-V1 | 10.00% | $\Delta n$ [589 nm, 20° C.]: | 0.1091 |
| CCY-3-O1 | 5.50% | $\Delta \varepsilon$ [1 kHz, 20° C.]: | −3.6 |
| CCY-3-O2 | 8.00% | $\varepsilon_\parallel$ [1 kHz, 20° C.]: | 3.7 |
| CLY-3-O2 | 10.00% | $\varepsilon_\perp$ [1 kHz, 20° C.]: | 7.3 |
| CPY-3-O2 | 3.50% | $K_1$ [pN, 20° C.]: | 13.4 |
| CY-3-O2 | 2.00% | $K_3$ [pN, 20° C.]: | 14.3 |
| PY-3-O2 | 20.00% | $V_0$ [20° C., V]: | 2.11 |
| PY-4-O2 | 7.50% | $\gamma_1$ [mPa · s, 20° C.]: | 86 |
| PYP-2-3 | 3.00% | | |
| PGIY-2-O4 | 2.00% | | |

Example M81

| | | | |
|---|---|---|---|
| CY-3-O2 | 10.00% | Clearing point [° C.]: | 70.7 |
| CPY-2-O2 | 8.00% | Δn [589 nm, 20° C.]: | 0.1278 |
| CPY-3-O2 | 8.50% | Δε [1 kHz, 20° C.]: | −1.7 |
| PYP-2-3 | 10.00% | $\varepsilon_\parallel$ [1 kHz, 20° C.]: | 3.2 |
| PGIY-2-O4 | 6.00% | $\varepsilon_\perp$ [1 kHz, 20° C.]: | 4.9 |
| CCH-23 | 20.00% | $K_1$ [pN, 20° C.]: | 13.7 |
| CCH-34 | 6.00% | $K_3$ [pN, 20° C.]: | 12.0 |
| CCH-35 | 2.50% | $V_0$ [20° C., V]: | 2.81 |
| BCH-32 | 15.00% | $\gamma_1$ [mPa · s, 20° C.]: | 90 |
| PP-1-4 | 11.00% | | |
| PCH-53 | 3.00% | | |

Example M82

| | | | |
|---|---|---|---|
| CCY-3-O1 | 3.50% | Clearing point [° C.]: | 80 |
| CLY-3-O2 | 10.00% | Δn [589 nm, 20° C.]: | 0.1152 |
| CPY-2-O2 | 10.00% | Δε [1 kHz, 20° C.]: | −3.5 |
| CPY-3-O2 | 11.00% | $\varepsilon_\parallel$ [1 kHz, 20° C.]: | 3.6 |
| PGIY-2-O4 | 4.00% | $\varepsilon_\perp$ [1 kHz, 20° C.]: | 7.2 |
| PYP-2-3 | 9.00% | $K_1$ [pN, 20° C.]: | 13.6 |
| CC-3-V | 35.00% | $K_3$ [pN, 20° C.]: | 15.5 |
| CY-3-O2 | 14.50% | $V_0$ [20° C., V]: | 2.19 |
| CY-5-O2 | 3.00% | $\gamma_1$ [mPa · s, 20° C.]: | 108 |

Example M83

| | | | |
|---|---|---|---|
| CC-3-V | 31.50% | Clearing point [° C.]: | 80.0 |
| CCY-3-O1 | 6.00% | Δn [589 nm, 20° C.]: | 0.1151 |
| CLY-3-O2 | 10.00% | Δε [1 kHz, 20° C.]: | −3.9 |
| CPY-2-O2 | 9.50% | $\varepsilon_\parallel$ [1 kHz, 20° C.]: | 3.7 |
| CPY-3-O2 | 10.50% | $\varepsilon_\perp$ [1 kHz, 20° C.]: | 7.6 |
| CY-3-O2 | 14.50% | $K_1$ [pN, 20° C.]: | 13.9 |
| CY-3-O4 | 1.00% | $K_3$ [pN, 20° C.]: | 15.4 |
| CY-5-O2 | 5.00% | $V_0$ [20° C., V]: | 2.08 |
| PYP-2-3 | 8.00% | $\gamma_1$ [mPa · s, 20° C.]: | 118 |
| PGIY-2-O4 | 4.00% | | |

Example M84

| | | | |
|---|---|---|---|
| CCY-3-O1 | 7.50% | Clearing point [° C.]: | 80.0 |
| CLY-3-O2 | 10.00% | Δn [589 nm, 20° C.]: | 0.1150 |
| CPY-2-O2 | 10.00% | Δε [1 kHz, 20° C.]: | −4.0 |
| CPY-3-O2 | 10.00% | $\varepsilon_\parallel$ [1 kHz, 20° C.]: | 3.7 |
| PGIY-2-O4 | 2.50% | $\varepsilon_\perp$ [1 kHz, 20° C.]: | 7.7 |
| CC-3-V | 35.00% | $K_1$ [pN, 20° C.]: | 14.9 |
| PY-1-O4 | 9.00% | $K_3$ [pN, 20° C.]: | 15.7 |
| PY-3-O2 | 8.00% | $V_0$ [20° C., V]: | 2.09 |
| PY-4-O2 | 3.00% | $\gamma_1$ [mPa · s, 20° C.]: | 114 |
| CCY-3-O2 | 5.00% | | |

Example M85

| | | | |
|---|---|---|---|
| CBC-33 | 3.00% | Clearing point [° C.]: | 108.5 |
| CBC-33F | 3.00% | Δn [589 nm, 20° C.]: | 0.2051 |
| CCY-3-O1 | 9.00% | Δε [1 kHz, 20° C.]: | −5.0 |
| CPY-2-O2 | 12.00% | $\varepsilon_\parallel$ [1 kHz, 20° C.]: | 4.2 |
| CPY-3-O2 | 12.00% | $\varepsilon_\perp$ [1 kHz, 20° C.]: | 9.2 |
| PGIGI-3-F | 8.00% | $K_1$ [pN, 20° C.]: | 17.1 |
| PGIY-2-O4 | 5.00% | $K_3$ [pN, 20° C.]: | 21.1 |
| PY-3-O2 | 20.00% | $V_0$ [20° C., V]: | 2.17 |
| PYP-2-3 | 14.00% | $\gamma_1$ [mPa · s, 20° C.]: | 478 |
| PYP-2-4 | 14.00% | | |

Example M86

| | | | |
|---|---|---|---|
| CCY-3-O1 | 9.00% | Clearing point [° C.]: | 97.6 |
| CCY-3-O2 | 11.00% | Δn [589 nm, 20° C.]: | 0.1596 |
| CCY-5-O2 | 10.00% | Δε [1 kHz, 20° C.]: | −7.3 |
| CPY-2-O2 | 12.00% | $\varepsilon_\parallel$ [1 kHz, 20° C.]: | 4.5 |
| CPY-3-O2 | 12.00% | $\varepsilon_\perp$ [1 kHz, 20° C.]: | 11.8 |
| CY-3-O2 | 12.00% | $K_1$ [pN, 20° C.]: | 17.6 |
| PGIGI-3-F | 5.00% | $K_3$ [pN, 20° C.]: | 21.2 |
| PGIY-2-O4 | 5.00% | $V_0$ [20° C., V]: | 1.78 |
| PY-3-O2 | 20.00% | $\gamma_1$ [mPa · s, 20° C.]: | 435 |
| PYP-2-3 | 4.00% | | |

Example M87

| | | | |
|---|---|---|---|
| B-2O-O5 | 5.00% | Clearing point [° C.]: | 80.0 |
| CC-3-V | 37.00% | Δn [589 nm, 20° C.]: | 0.1094 |
| CCP-V-1 | 4.50% | Δε [1 kHz, 20° C.]: | −3.7 |
| CCY-3-O1 | 5.00% | $\varepsilon_\parallel$ [1 kHz, 20° C.]: | 3.7 |
| CCY-3-O2 | 6.00% | $\varepsilon_\perp$ [1 kHz, 20° C.]: | 7.4 |
| CCY-4-O2 | 5.00% | $K_1$ [pN, 20° C.]: | 13.9 |
| CLY-3-O2 | 8.00% | $K_3$ [pN, 20° C.]: | 14.4 |
| CPY-2-O2 | 9.50% | $V_0$ [20° C., V]: | 2.09 |
| PGIY-2-O4 | 6.00% | $\gamma_1$ [mPa · s, 20° C.]: | 106 |
| PY-3-O2 | 14.00% | | |

Example M88

| | | | |
|---|---|---|---|
| CC-3-V | 34.00% | Clearing point [° C.]: | 74.6 |
| CC-3-V1 | 10.00% | Δn [589 nm, 20° C.]: | 0.1089 |
| CCY-3-O1 | 8.50% | Δε [1 kHz, 20° C.]: | −3.2 |
| CCY-3-O2 | 3.50% | $\varepsilon_\parallel$ [1 kHz, 20° C.]: | 3.6 |
| CLY-3-O2 | 10.00% | $\varepsilon_\perp$ [1 kHz, 20° C.]: | 6.8 |
| CPY-3-O2 | 6.50% | $K_1$ [pN, 20° C.]: | 14.0 |
| PY-1-O4 | 9.00% | $K_3$ [pN, 20° C.]: | 15.7 |
| PY-3-O2 | 10.50% | $V_0$ [20° C., V]: | 2.33 |
| PGIY-2-O4 | 8.00% | $\gamma_1$ [mPa · s, 20° C.]: | 89 |

Example M89

| | | | |
|---|---|---|---|
| CC-3-V | 32.50% | Clearing point [° C.]: | 75.1 |
| CC-3-V1 | 4.00% | Δn [589 nm, 20° C.]: | 0.1087 |
| CCY-3-O1 | 9.00% | Δε [1 kHz, 20° C.]: | −3.8 |
| CCY-3-O2 | 8.50% | $\varepsilon_\parallel$ [1 kHz, 20° C.]: | 3.7 |
| CLY-3-O2 | 10.00% | $\varepsilon_\perp$ [1 kHz, 20° C.]: | 7.5 |
| CPY-3-O2 | 4.50% | $\gamma_1$ [mPa · s, 20° C.]: | 100 |
| PY-3-O2 | 16.00% | | |
| CY-3-O2 | 7.50% | | |
| PGIY-2-O4 | 5.00% | | |
| PYP-2-3 | 3.00% | | |

Example M90

For the preparation of a PS-VA mixture, 99.7% of the mixture according to Example M61 is mixed with 0.3% of the polymerizable compound of the formula

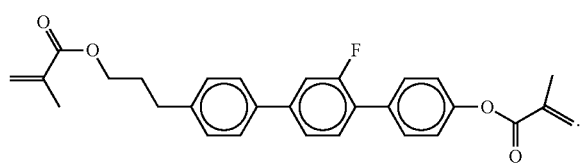

Example M91

For the preparation of a PS-VA mixture, 99.75% of the mixture according to Example M64 is mixed with 0.25% of the polymerizable compound of the formula

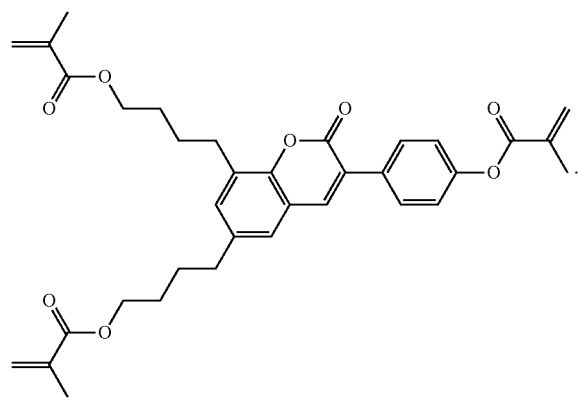 [SMILES: C=C(C)C(=O)OCCCCc1cc(CCCCOC(=O)C(=C)C)c2oc(=O)c(-c3ccc(OC(=O)C(=C)C)cc3)cc2c1]

Example M92

For the preparation of a PS-VA mixture, 99.8% of the mixture according to Example M68 is mixed with 0.2% of the polymerizable compound of the formula

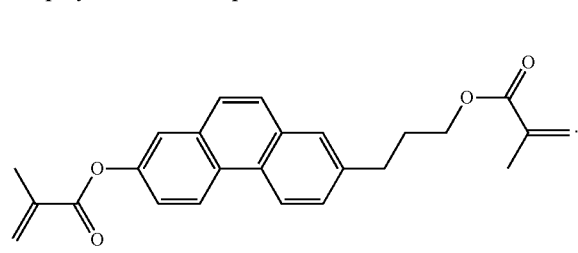

Example M93

For the preparation of a PS-VA mixture, 99.75% of the mixture according to Example M69 is mixed with 0.25% of the polymerizable compound of the formula

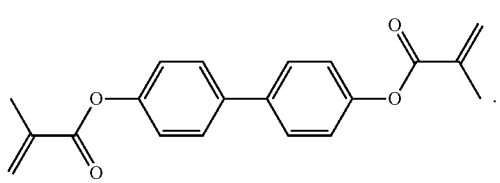 [SMILES: C=C(C)C(=O)Oc1ccc(-c2ccc(OC(=O)C(=C)C)cc2)cc1]

Example M94

For the preparation of a PS-VA mixture, 99.75% of the mixture according to Example M70 is mixed with 0.25% of the polymerizable compound of the formula

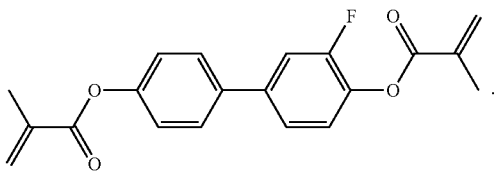 [SMILES: C=C(C)C(=O)Oc1ccc(-c2ccc(OC(=O)C(=C)C)c(F)c2)cc1]

Example M95

For the preparation of a PS-VA mixture, 99.75% of the mixture according to Example M72 is mixed with 0.25% of the polymerizable compound of the formula

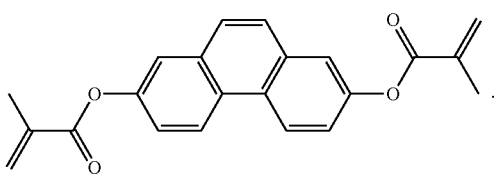 [SMILES: C=C(C)C(=O)Oc1ccc2c(ccc3cc(OC(=O)C(=C)C)ccc32)c1]

Example M96

For the preparation of a PS-VA mixture, 99.75% of the mixture according to Example M72 is mixed with 0.25% of the polymerizable compound of the formula

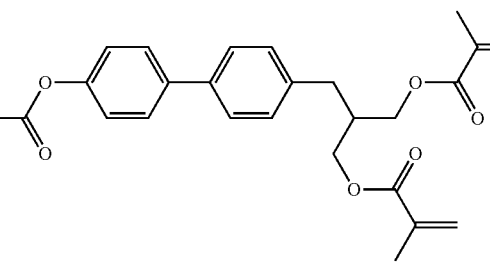

Example M97

| CC-3-V | 27.50% | Clearing point [° C.]: | 78.5 |
|---|---|---|---|
| CC-3-V1 | 8.00% | Δn [589 nm, 20° C.]: | 0.1025 |
| CCY-3-O1 | 10.00% | Δε [1 kHz, 20° C.]: | −3.8 |
| CCY-3-O2 | 6.00% | $\varepsilon_\parallel$ [1 kHz, 20° C.]: | 3.7 |
| CCY-4-O2 | 7.00% | $\varepsilon_\perp$ [1 kHz, 20° C.]: | 7.5 |
| CPY-2-O2 | 9.00% | $K_1$ [pN, 20° C.]: | 13.5 |
| CPY-3-O2 | 6.00% | $K_3$ [pN, 20° C.]: | 14.8 |
| CY-3-O4 | 13.00% | $V_0$ [20° C., V]: | 2.09 |
| PGIY-2-O4 | 5.00% | $\gamma_1$ [mPa·s, 20° C.]: | 112 |
| PY-1-O4 | 4.00% | | |
| PY-4-O2 | 4.50% | | |

Example M98

| | | | |
|---|---|---|---|
| CC-3-V | 38.00% | Clearing point [° C.]: | 80 |
| CCOY-2-O2 | 6.00% | Δn [589 nm, 20° C.]: | 0.1035 |
| CCOY-3-O2 | 10.00% | Δε [1 kHz, 20° C.]: | −4.4 |
| CLY-3-O2 | 7.00% | $\varepsilon_\parallel$ [1 kHz, 20° C.]: | 3.7 |
| CLY-3-O3 | 2.00% | $\varepsilon_\perp$ [1 kHz, 20° C.]: | 8.1 |
| CPY-2-O2 | 7.00% | $K_1$ [pN, 20° C.]: | 14.2 |
| CPY-3-O2 | 10.00% | $K_3$ [pN, 20° C.]: | 16.4 |
| COY-3-O2 | 5.00% | $V_0$ [20° C., V]: | 2.05 |
| CY-3-O2 | 2.00% | $\gamma_1$ [mPa · s, 20° C.]: | 109 |
| PY-3-O2 | 11.00% | LTS bulk [−25° C.]: | >1000 h |
| PGIY-2-O4 | 2.00% | | |

Example M99

| | | | |
|---|---|---|---|
| CC-3-V | 42.50% | Clearing point [° C.]: | 80 |
| PY-3-O2 | 9.00% | Δn [589 nm, 20° C.]: | 0.1080 |
| CCOY-2-O2 | 5.50% | Δε [1 kHz, 20° C.]: | −3.8 |
| CCOY-3-O2 | 10.00% | $\varepsilon_\parallel$ [1 kHz, 20° C.]: | 3.7 |
| CCP-3-1 | 4.50% | $\varepsilon_\perp$ [1 kHz, 20° C.]: | 7.4 |
| CPY-2-O2 | 8.50% | $K_1$ [pN, 20° C.]: | 14.4 |
| CPY-3-O2 | 10.00% | $K_3$ [pN, 20° C.]: | 15.7 |
| PGIY-2-O4 | 5.00% | $V_0$ [20° C., V]: | 2.16 |
| B-2O-O5 | 5.00% | $\gamma_1$ [mPa · s, 20° C.]: | 99 |

Example M100

| | | | |
|---|---|---|---|
| CC-3-V | 42.50% | Clearing point [° C.]: | 80 |
| CCOY-2-O2 | 6.00% | Δn [589 nm, 20° C.]: | 0.1036 |
| CCOY-3-O2 | 10.00% | Δε [1 kHz, 20° C.]: | −4.5 |
| CLY-3-O2 | 6.00% | $\varepsilon_\parallel$ [1 kHz, 20° C.]: | 3.8 |
| CPY-2-O2 | 8.50% | $\varepsilon_\perp$ [1 kHz, 20° C.]: | 8.3 |
| CPY-3-O2 | 10.00% | $K_1$ [pN, 20° C.]: | 14.4 |
| COY-3-O2 | 5.00% | $K_3$ [pN, 20° C.]: | 16.1 |
| PY-3-O2 | 7.50% | $V_0$ [20° C., V]: | 2.00 |
| PGIY-2-O4 | 2.00% | $\gamma_1$ [mPa · s, 20° C.]: | 106 |
| B-2O-O5 | 4.00% | | |

Example M101

For the preparation of a PS-VA mixture, 99.75% of the mixture according to Example M97 is mixed with 0.25% of the polymerizable compound of the formula

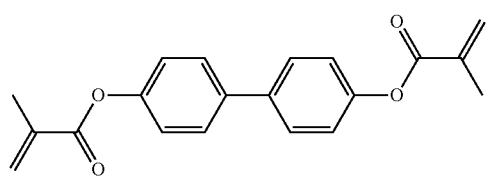

Example M102

For the preparation of a PS-VA mixture, 99.75% of the mixture according to Example M98 is mixed with 0.25% of the polymerizable compound of the formula

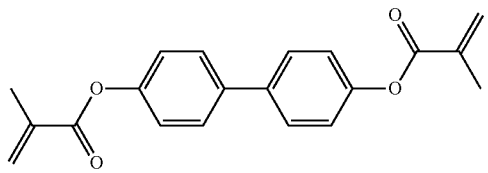

Example M103

For the preparation of a PS-VA mixture, 99.75% of the mixture according to Example M99 is mixed with 0.25% of the polymerizable compound of the formula

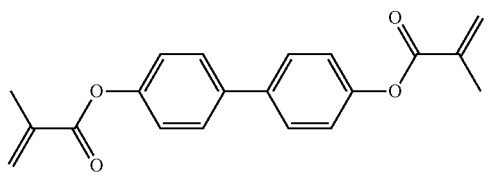

Example M104

For the preparation of a PS-VA mixture, 99.7% of the mixture according to Example M99 is mixed with 0.3% of the polymerizable compound of the formula

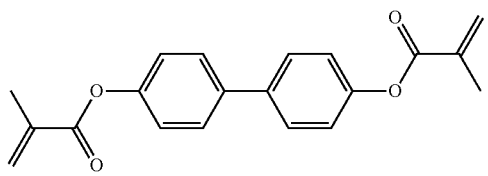

Example M105

For the preparation of a PS-VA mixture, 99.7% of the mixture according to Example M100 is mixed with 0.3% of the polymerizable compound of the formula

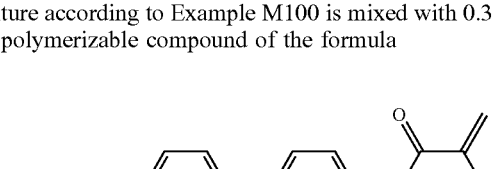

Example M106

| | | | |
|---|---|---|---|
| CCY-3-O1 | 6.50% | Clearing point ° C.]: | 86.5 |
| CCY-3-O2 | 8.00% | Δn [589 nm, 20° C.]: | 0.1020 |
| CCY-4-O2 | 8.50% | Δε [1 kHz, 20° C.]: | −4.6 |
| CCY-5-O2 | 7.00% | $\varepsilon_\parallel$ [1 kHz, 20° C.]: | 3.7 |
| CLY-3-O2 | 10.00% | $\varepsilon_\perp$ [1 kHz, 20° C.]: | 8.3 |
| PGIY-2-O4 | 1.50% | $K_1$ [pN, 20° C.]: | 16.5 |

| | | | |
|---|---|---|---|
| B-2O-O5 | 5.00% | $K_3$ [pN, 20° C.]: | 17.9 |
| CC-3-V | 26.50% | $V_0$ [20° C., V]: | 2.08 |
| CC-3-V1 | 8.00% | $\gamma_1$ [mPa · s, 20° C.]: | 134 |
| CY-5-O2 | 6.50% | | |
| PY-3-O2 | 12.50% | | |

Example M107

| | | | |
|---|---|---|---|
| CCY-3-1 | 6.50% | Clearing point [° C.]: | 93.5 |
| CCY-3-O1 | 7.00% | Δn [589 nm, 20° C.]: | 0.1077 |
| CCY-3-O2 | 8.00% | Δε [1 kHz, 20° C.]: | −4.8 |
| CCY-4-O2 | 8.00% | $\varepsilon_\parallel$ [1 kHz, 20° C.]: | 3.7 |
| CCY-5-O2 | 7.00% | $\varepsilon_\perp$ [1 kHz, 20° C.]: | 8.5 |
| CLY-3-O2 | 10.00% | $K_1$ [pN, 20° C.]: | 17.8 |
| PGIY-2-O4 | 2.00% | $K_3$ [pN, 20° C.]: | 19.4 |
| B-2O-O5 | 5.00% | $V_0$ [20° C., V]: | 2.12 |
| CC-3-V | 22.50% | $\gamma_1$ [mPa · s, 20° C.]: | 161 |
| CC-3-V1 | 8.00% | | |
| CY-5-O2 | 1.50% | | |
| PY-3-O2 | 14.50% | | |

Example M108

| | | | |
|---|---|---|---|
| CCY-3-O1 | 7.00% | Clearing point [° C.]: | 96.5 |
| CCY-3-O2 | 8.00% | Δn [589 nm, 20° C.]: | 0.1018 |
| CCY-4-O2 | 8.00% | Δε [1 kHz, 20° C.]: | −4.9 |
| CCY-5-O2 | 6.50% | $\varepsilon_\parallel$ [1 kHz, 20° C.]: | 3.7 |
| CLY-3-O2 | 10.00% | $\varepsilon_\perp$ [1 kHz, 20° C.]: | 8.6 |
| CPY-3-O2 | 4.00% | $K_1$ [pN, 20° C.]: | 17.5 |
| PGIY-2-O4 | 4.50% | $K_3$ [pN, 20° C.]: | 19.2 |
| B-2O-O5 | 5.00% | $V_0$ [20° C., V]: | 2.07 |
| CC-3-V | 23.00% | $\gamma_1$ [mPa · s, 20° C.]: | 171 |
| CC-3-V1 | 8.00% | | |
| CY-3-O2 | 1.50% | | |
| CY-5-O2 | 14.50% | | |

Example M109

For the preparation of a PS-VA mixture, 99.75% of the mixture according to Example M108 is mixed with 0.3% of the polymerizable compound of the formula

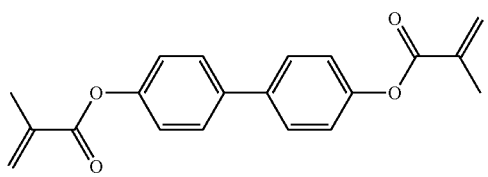

Example M110

| | | | |
|---|---|---|---|
| CCY-3-O1 | 6.50% | Clearing point [° C.]: | 75 |
| CCY-3-O2 | 8.00% | Δn [589 nm, 20° C.]: | 0.1043 |
| CCY-4-O2 | 8.00% | Δε [1 kHz, 20° C.]: | −5.0 |
| CCY-5-O2 | 2.00% | $\varepsilon_\parallel$ [1 kHz, 20° C.]: | 4.0 |
| CLY-3-O2 | 10.00% | $\varepsilon_\perp$ [1 kHz, 20° C.]: | 9.0 |
| PGIY-2-O4 | 5.00% | $K_1$ [pN, 20° C.]: | 13.7 |
| B-2O-O5 | 5.00% | $K_3$ [pN, 20° C.]: | 15.2 |
| CC-3-V | 31.50% | $V_0$ [20° C., V]: | 1.84 |
| CY-3-O2 | 11.50% | $\gamma_1$ [mPa · s, 20° C.]: | 118 |
| PY-3-O2 | 12.50% | | |

Example M111

| | | | |
|---|---|---|---|
| CC-3-V | 19.00% | Clearing point [° C.]: | 104.7 |
| CC-3-V1 | 7.00% | Δn [589 nm, 20° C.]: | 0.1102 |
| CCP-3-1 | 6.00% | Δε [1 kHz, 20° C.]: | −4.7 |
| CCY-3-O1 | 5.00% | $\varepsilon_\parallel$ [1 kHz, 20° C.]: | 3.6 |
| CCY-3-O2 | 6.00% | $\varepsilon_\perp$ [1 kHz, 20° C.]: | 8.3 |
| CCY-4-O2 | 3.50% | $K_1$ [pN, 20° C.]: | 17.7 |
| CCY-5-O2 | 3.00% | $K_3$ [pN, 20° C.]: | 19.6 |
| CLY-2-O4 | 2.50% | $V_0$ [20° C., V]: | 2.15 |
| CLY-3-O2 | 7.50% | $\gamma_1$ [mPa · s, 20° C.]: | 196 |
| CLY-3-O3 | 7.00% | | |
| CPY-3-O2 | 11.50% | | |
| CY-3-O2 | 10.00% | | |
| CY-5-O2 | 3.00% | | |
| PGIY-2-O4 | 4.00% | | |
| B-2O-O5 | 5.00% | | |

Example M112

| | | | |
|---|---|---|---|
| CC-3-V | 7.00% | Clearing point [° C.]: | 105.1 |
| CC-3-V1 | 7.00% | Δn [589 nm, 20° C.]: | 0.1105 |
| CCP-3-1 | 15.00% | Δε [1 kHz, 20° C.]: | −5.0 |
| CCP-V2-1 | 9.00% | $\varepsilon_\parallel$ [1 kHz, 20° C.]: | 3.9 |
| CCY-3-O1 | 5.00% | $\varepsilon_\perp$ [1 kHz, 20° C.]: | 8.9 |
| CCY-3-O2 | 8.00% | $K_1$ [pN, 20° C.]: | 18.7 |
| CCY-5-O2 | 5.00% | $K_3$ [pN, 20° C.]: | 20.3 |
| CLY-3-O2 | 8.00% | $V_0$ [20° C., V]: | 2.14 |
| CLY-3-O3 | 7.00% | $\gamma_1$ [mPa · s, 20° C.]: | 200 |
| CPY-3-O2 | 5.00% | | |
| CY-3-O2 | 5.00% | | |
| PGIY-2-O4 | 3.00% | | |
| B-2O-O5 | 7.00% | | |
| Y-4O-O4 | 9.00% | | |

Example M113

| | | | |
|---|---|---|---|
| CC-3-V | 17.50% | Clearing point [° C.]: | 110 |
| CC-3-V1 | 7.00% | Δn [589 nm, 20° C.]: | 0.1103 |
| CCP-3-1 | 11.00% | Δε [1 kHz, 20° C.]: | −4.5 |
| CCY-3-O1 | 5.00% | $\varepsilon_\parallel$ [1 kHz, 20° C.]: | 3.5 |
| CCY-3-O2 | 8.00% | $\varepsilon_\perp$ [1 kHz, 20° C.]: | 8.0 |
| CCY-4-O2 | 3.00% | $K_1$ [pN, 20° C.]: | 18.8 |
| CLY-2-O4 | 4.50% | $K_3$ [pN, 20° C.]: | 20.9 |
| CLY-3-O2 | 7.50% | $V_0$ [20° C., V]: | 2.28 |
| CLY-3-O3 | 6.50% | $\gamma_1$ [mPa · s, 20° C.]: | 206 |
| CPY-3-O2 | 11.00% | | |
| CY-3-O2 | 11.00% | | |
| PGIY-2-O4 | 3.00% | | |
| B-2O-O5 | 5.00% | | |

Example M114

For the preparation of a PS-VA mixture, 99.75% of the mixture according to Example M113 is mixed with 0.3% of the polymerizable compound of the formula

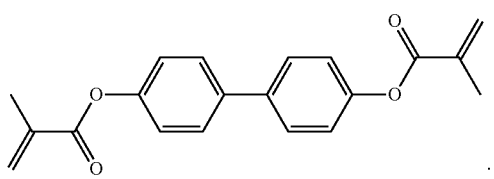 [SMILES: C=C(C)C(=O)Oc1ccc(-c2ccc(OC(=O)C(=C)C)cc2)cc1]

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The entire disclosures of all applications, patents and publications, cited herein and of corresponding German Application 102014008624.0, filed Jun. 17, 2014, and DE Application 102014012565, filed Aug. 29, 2014, are incorporated by reference herein.

The invention claimed is:

1. A liquid-crystalline medium comprising:
at least one compound of formula I,

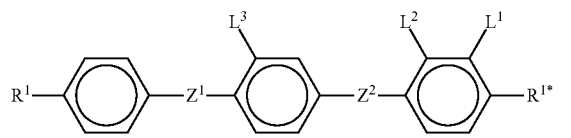

I in which
$R^1$ and
$R^{1*}$ each, independently of one another, denote an alkyl or alkoxy radical having 1 to 15 C atoms, where, in addition, one or more $CH_2$ groups in these radicals may each optionally be replaced, independently of one another, by —C≡C—, —$CF_2$O—, —CH=CH—,

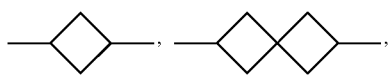

—O—, —CO—O—, —O—CO— in such a way that O atoms are not linked directly to one another, and in which, in addition, one or more H atoms may each optionally be replaced by halogen,
$Z^1$ and $Z^2$ each, independently of one another, denote a single bond, —$CH_2CH_2$—, —CH=CH—, —$CH_2$O—, —O$CH_2$—, —$CF_2$O—, —O$CF_2$—, —COO—, —OCO—, —$C_2F_4$—, —C≡C—, —CF=CF—, or —CH=CHCHO—, and
$L^{1-3}$ each, independently of one another, denote F, Cl, $CF_3$, $OCF_3$ or $CHF_2$; and 20-50%, based on the total weight of the medium, of the compound of formula CC-3-V

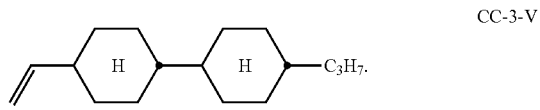

CC-3-V

2. The liquid-crystalline medium according to claim 1, wherein said medium comprises at least one compound of formulae I-a to I-h,

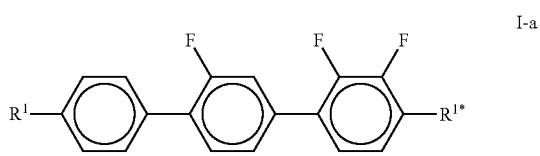

I-a

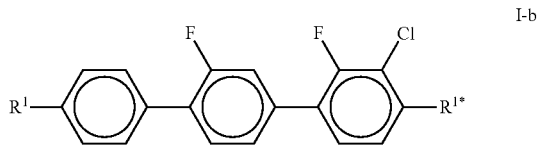

I-b

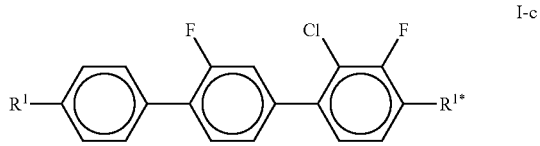

I-c

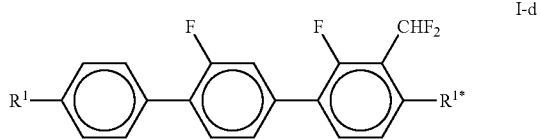

I-d

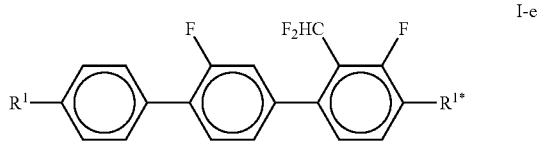

I-e

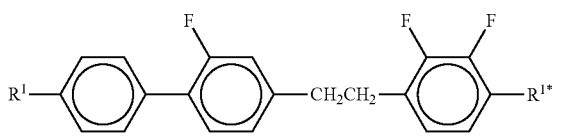

I-f

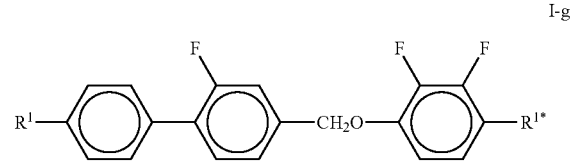

I-g

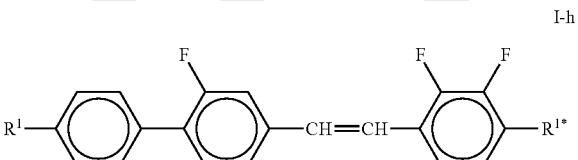

I-h in which $R^1$ and $R^{1*}$ have the meanings indicated in claim 1.

3. The liquid-crystalline medium according to claim 1, wherein said medium comprises at least one compound of formulae I-a-1 to I-a-36

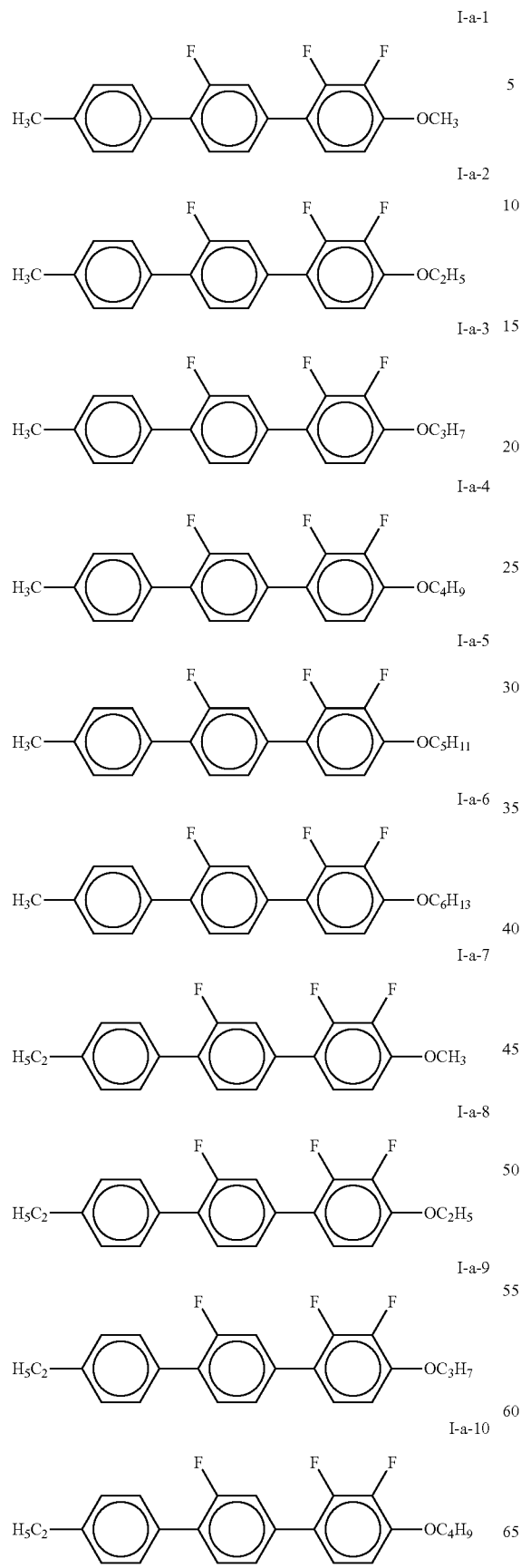
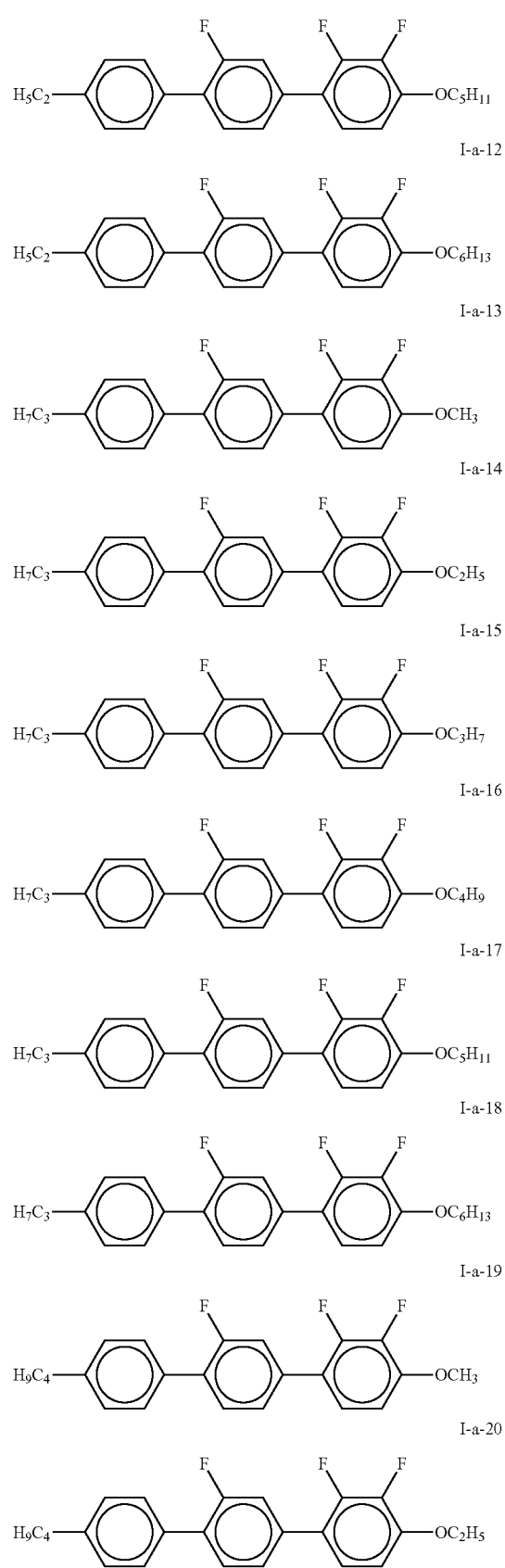

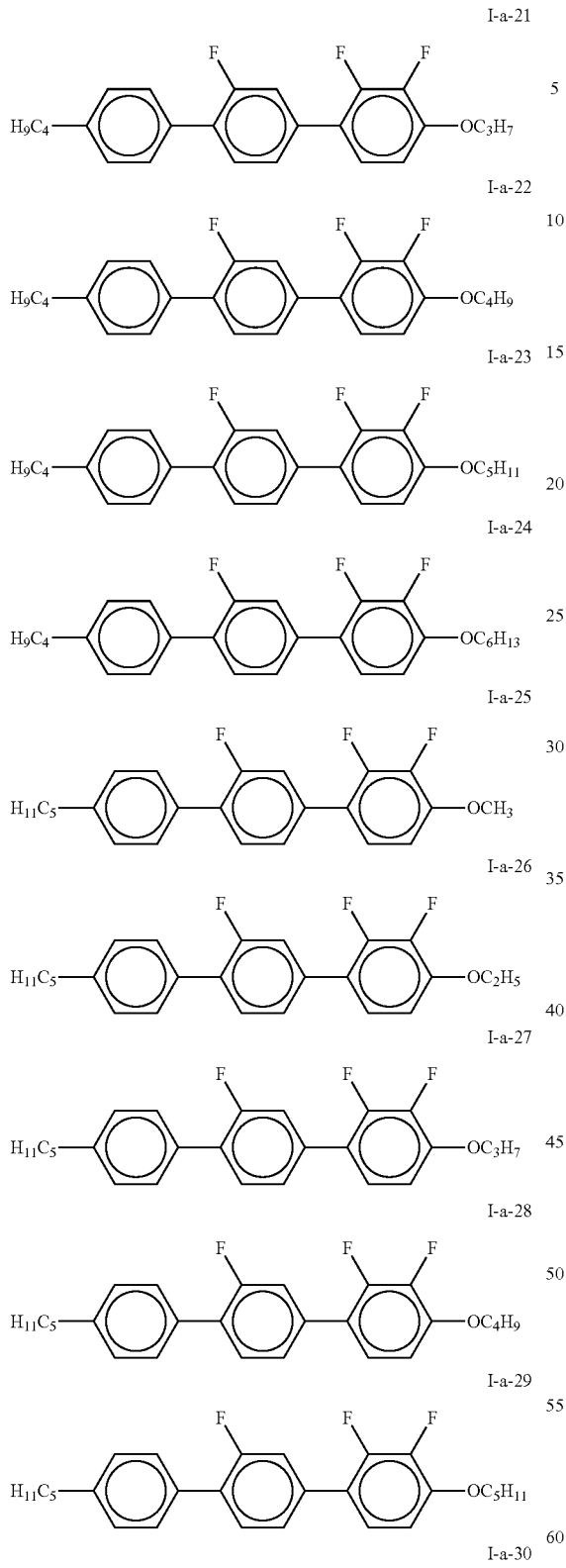
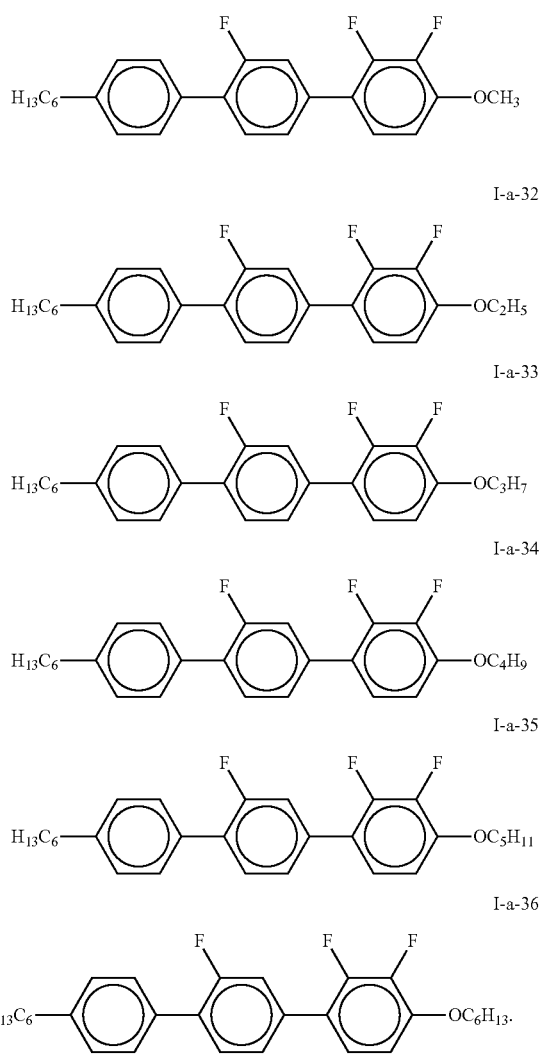
4. The liquid-crystalline medium according to claim 1, wherein the proportion of the compound(s) of formula I in the medium as a whole is 1-30% by weight.
5. The liquid-crystalline medium according to claim 1, wherein said medium further comprises one or more compounds selected from the group of the compounds of formulae IIA, IIB and IIC,
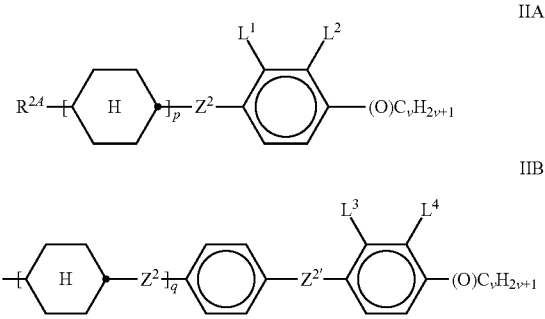

-continued

IIC

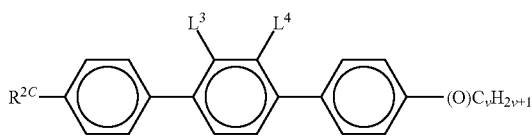

in which
R²ᴬ, R²ᴮ and R²ᶜ each, independently of one another, denote H, an alkyl or alkenyl radical having up to 15 C atoms which is unsubstituted, monosubstituted by CN or CF₃ or at least monosubstituted by halogen, where, in addition, one or more CH₂ groups in these radicals may each optionally be replaced by —O—, —S—,

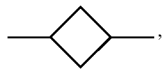

—C≡C—, —CF₂O—, —OCF₂—, —OC—O— or —O—CO— in such a way that O atoms are not linked directly to one another,
L¹⁻⁴ each, independently of one another, denote F, Cl, CF₃ or CHF₂,
Z² and Z²′ each, independently of one another, denote a single bond, —CH₂CH₂—, —CH=CH—, —CF₂O—, —OCF₂—, —CH₂O—, —OCH₂—, —COO—, —OCO—, —C₂F₄—, —CF=CF—, or —CH=CHCH₂O—,
(O) denotes a single bond or —O—,
p denotes 0, 1 or 2,
q denotes 0 or 1, and
v denotes 1 to 6.

6. The liquid-crystalline medium according to claim 1, wherein said medium further comprises one or more compounds of formula III,

III

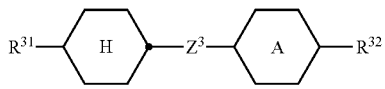

in which
R³¹ and R³² each, independently of one another, denote a straight-chain alkyl, alkenyl, alkoxy, alkoxyalkyl or alkenyloxy radical having up to 12 C atoms, and

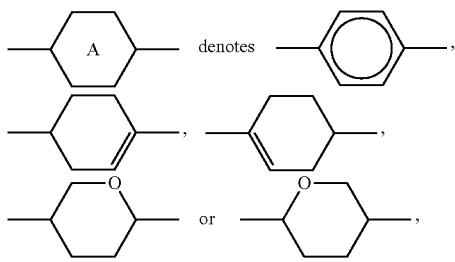

and
Z³ denotes a single bond, —CH₂CH₂—, —CH=CH—, —CF₂O—, —OCF₂—, —CH₂O—, —OCH₂—, —COO—, —OCO—, —C₂F₄—, —C₄H₉—, —C≡C—, or —CF=CF—.

7. The liquid-crystalline medium according to claim 1, wherein said medium further comprises one or more compounds of formulae L-1 to L-11,

L-1

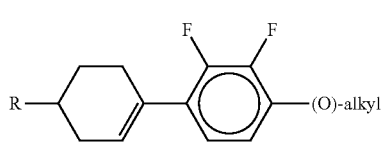

L-2

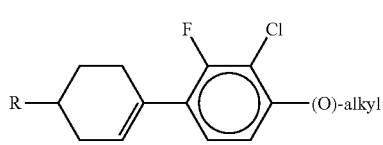

L-3

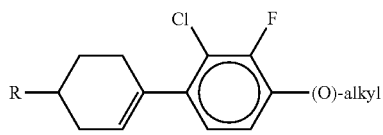

L-4

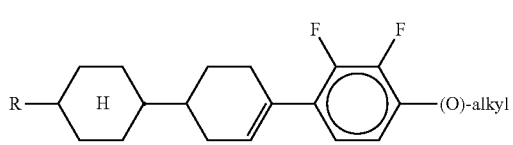

L-5

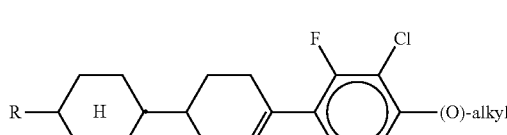

L-6

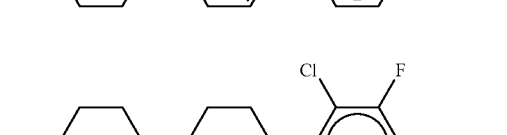

L-7

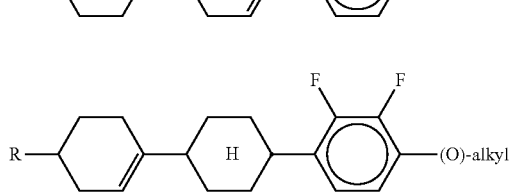

L-8

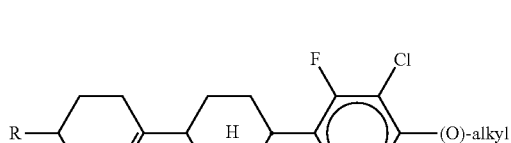

L-9

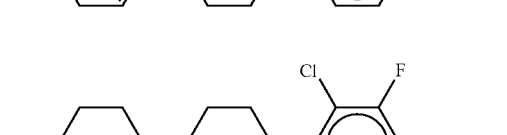

-continued

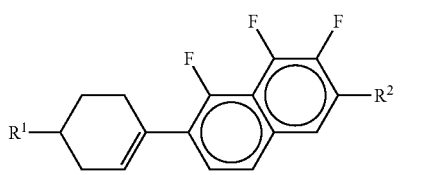
L-10

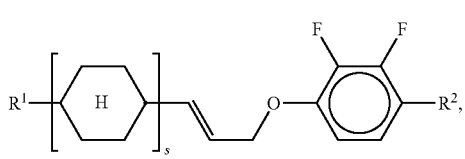
L-11 in which
R, R$^1$ and R$^2$ each, independently of one another, denotes H, an alkyl or alkenyl radical having up to 15 C atoms which is unsubstituted, monosubstituted by CN or CF$_3$ or at least monosubstituted by halogen, where, in addition, one or more CH$_2$ groups in these radicals may each optionally be replaced by —O—, —S—,

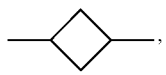

—C≡C—, —CF$_2$O—, —OCF$_2$—, —OC—O— or —O—CO— in such a way that O atoms are not linked directly to one another,
(O) denotes a single bond or —O—,
alkyl denotes an alkyl radical having 1-6 C atoms, and
s denotes 1 or 2.

8. The liquid-crystalline medium according to claim 1, wherein said medium further comprises one or more terphenyls of formulae T-1 to T-21,

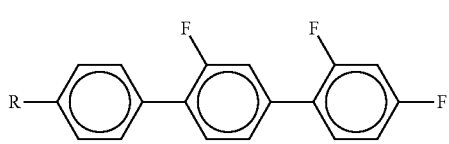
T-1

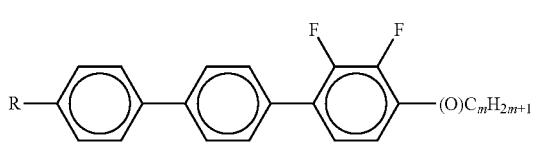
T-2

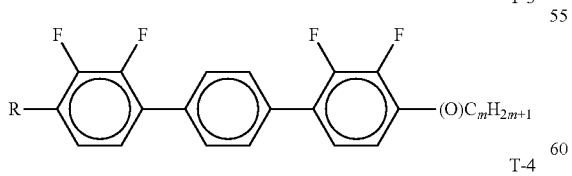
T-3

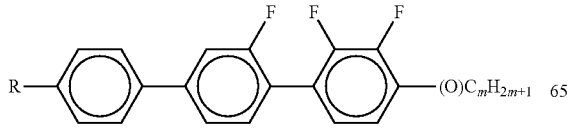
T-4

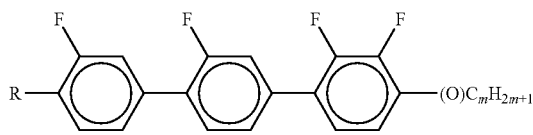
T-5

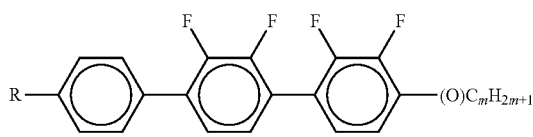
T-6

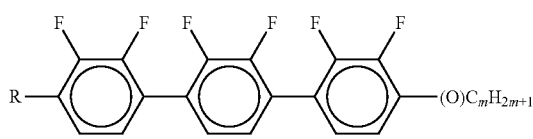
T-7

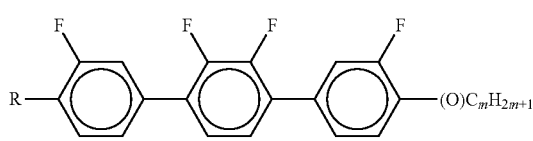
T-8

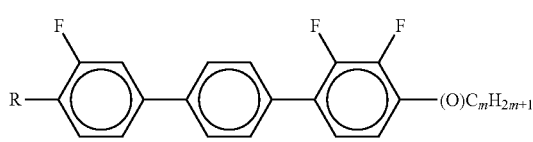
T-9

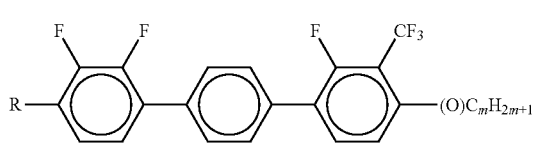
T-10

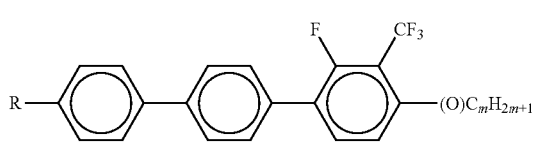
T-11

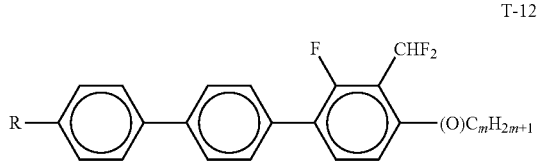
T-12

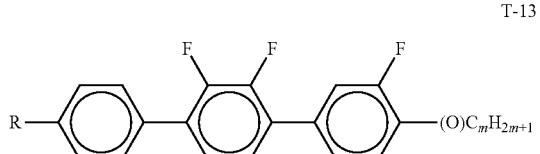
T-13

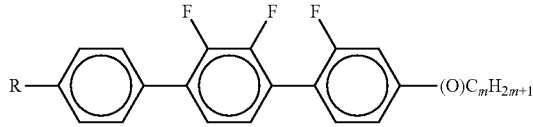
T-14

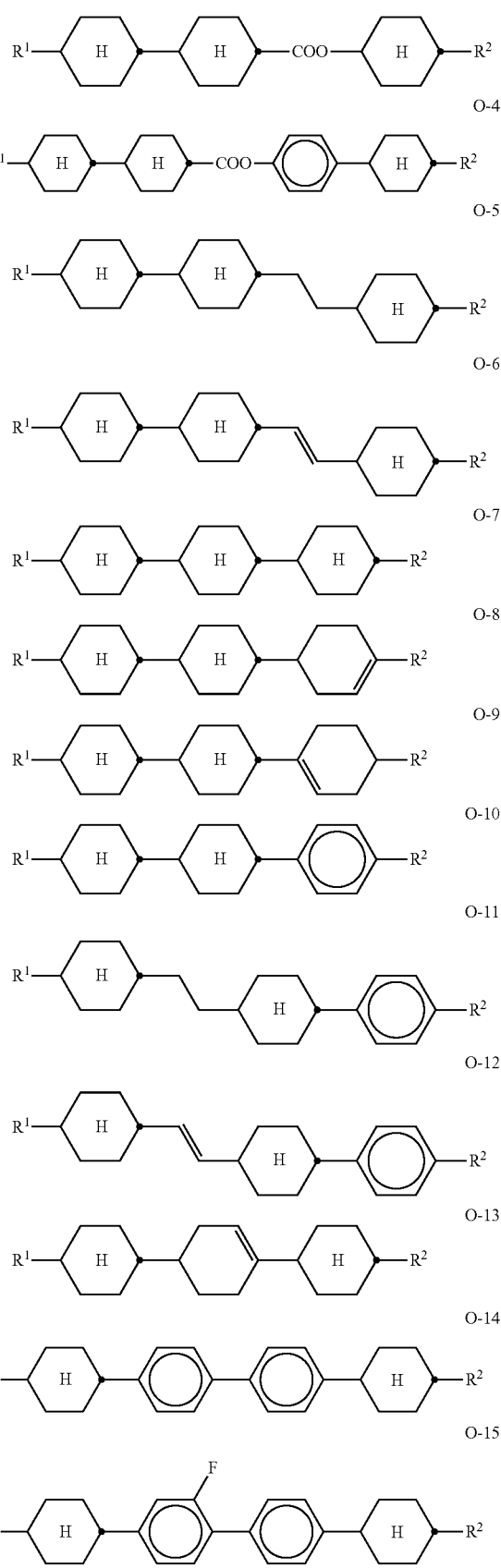
in which
R denotes a straight-chain alkyl or alkoxy radical having 1-7 C atoms,
(O) denotes a single bond or —O—,
m denotes 0, 1, 2, 3, 4, 5 or 6, and
n denotes 0, 1, 2, 3 or 4.
9. The liquid-crystalline medium according to claim 1, wherein said medium further comprises one or more compounds of formulae O-1 to O-17, -continued

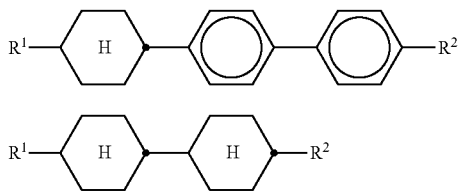

in which
R¹ and R² each, independently of one another, denotes H, an alkyl or alkenyl radical having up to 15 C atoms which is unsubstituted, monosubstituted by CN or CF₃ or at least monosubstituted by halogen, where, in addition, one or more CH₂ groups in these radicals may each optionally be replaced by —O—, —S—, $$\diamondsuit,$$

—C≡C—, —CF₂O—, —OCF₂—, —OC—O— or —O—CO— in such a way that O atoms are not linked directly to one another.

10. The liquid-crystalline medium according to claim 1, wherein said medium further comprises one or more compounds selected from the group of compounds of formulae BC, CR, PH-1, PH-2, BF-1, BF-2, BS-1 and BS-2,

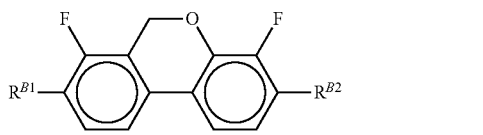  BC

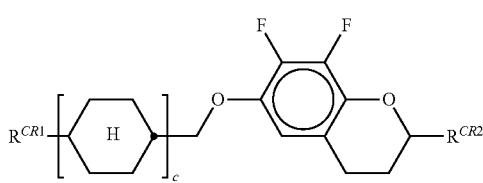  CR

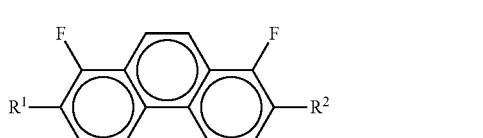  PH-1

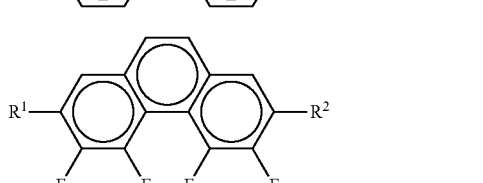  PH-2

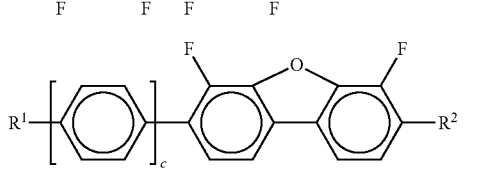  BF-1

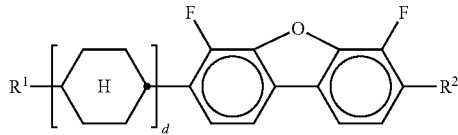  BF-2

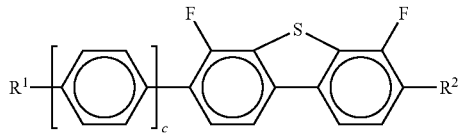  BS-1

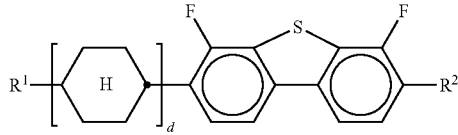  BS-2 in which
R^{B1}, R^{B2}, R^{CR1}, R^{CR2}, R¹, R² each, independently of one another, denotes H, an alkyl or alkenyl radical having up to 15 C atoms which is unsubstituted, monosubstituted by CN or CF₃ or at least monosubstituted by halogen, where, in addition, one or more CH₂ groups in these radicals may each optionally be replaced by —O—, —S—, $$\diamondsuit,$$

—C≡C—, —CF₂O—, —OCF₂—, —OC—O— or —O—CO— in such a way that O atoms are not linked directly to one another,
c denotes 0, 1 or 2, and
d denotes 1 or 2.

11. The liquid-crystalline medium according to claim 1, wherein said medium further comprises one or more compounds of the formulae

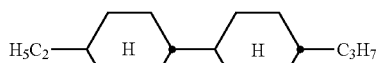
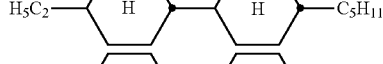
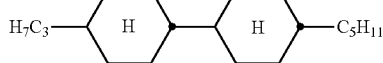
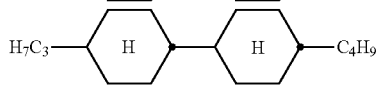
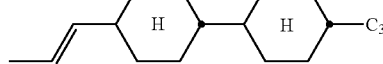
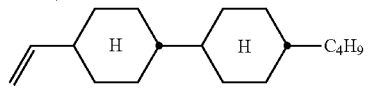

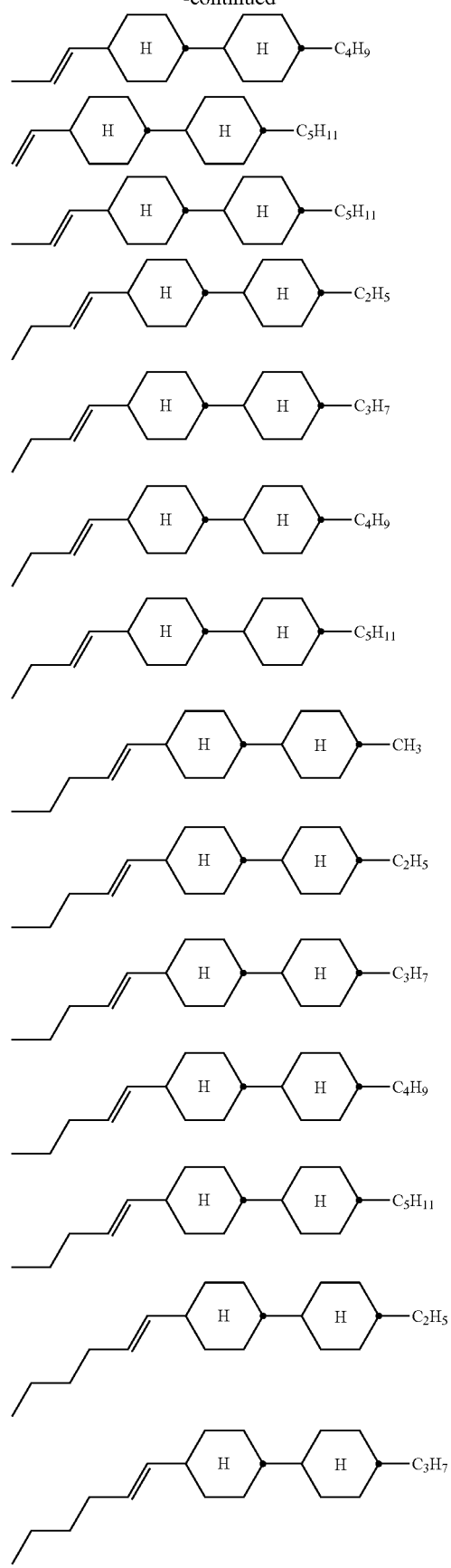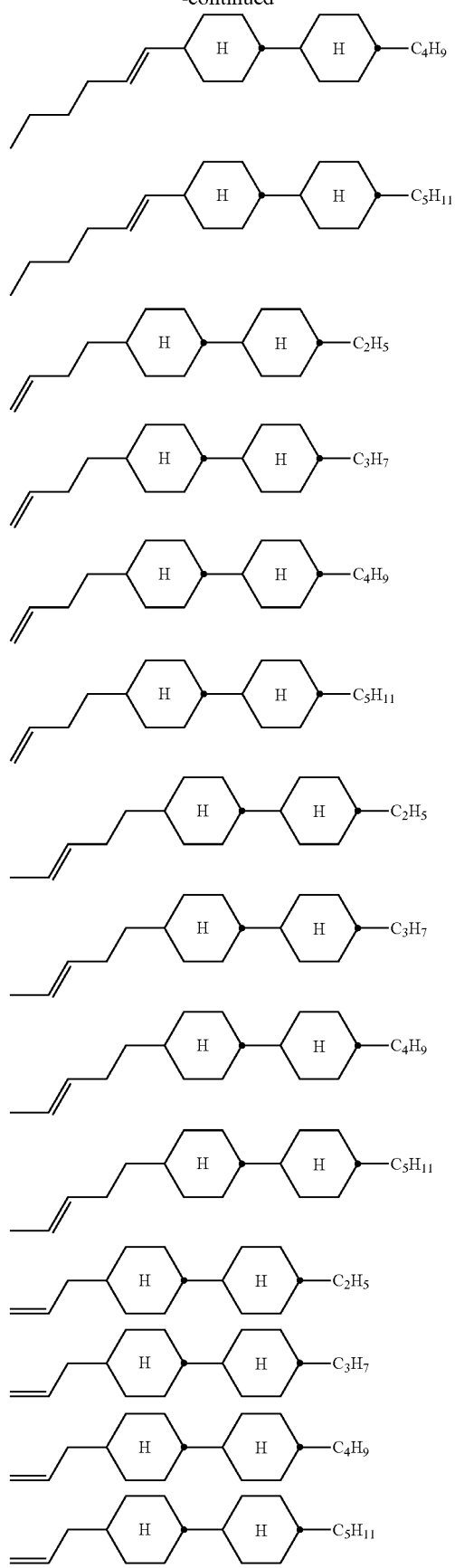

-continued

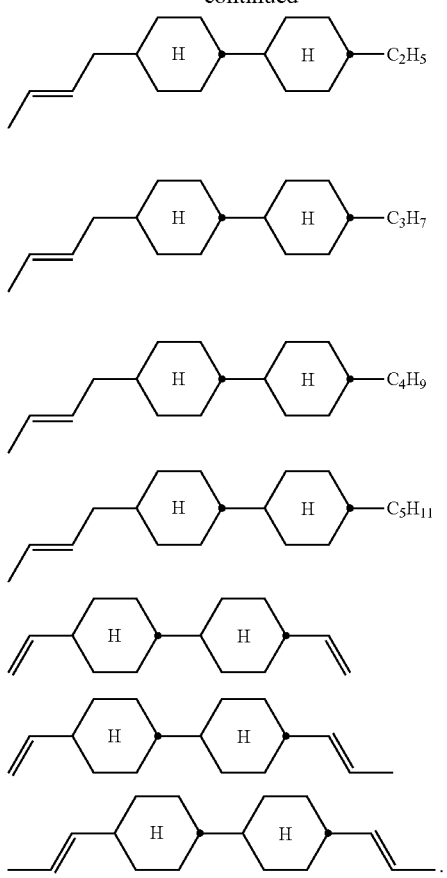

12. The liquid-crystalline medium according to claim 1, wherein said medium comprises 22.5-43.5% of the compound of the formula

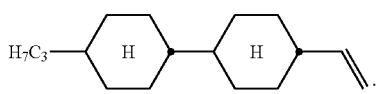

13. The liquid-crystalline medium according to claim 1, wherein said medium further comprises one or more compounds selected from the group of compounds of formulae P-1 to P-4,

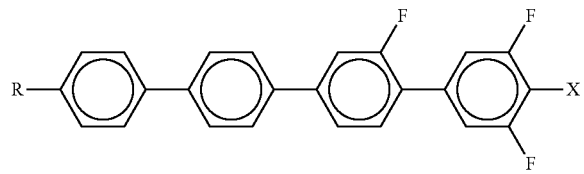

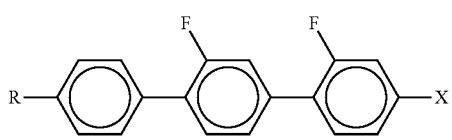

-continued

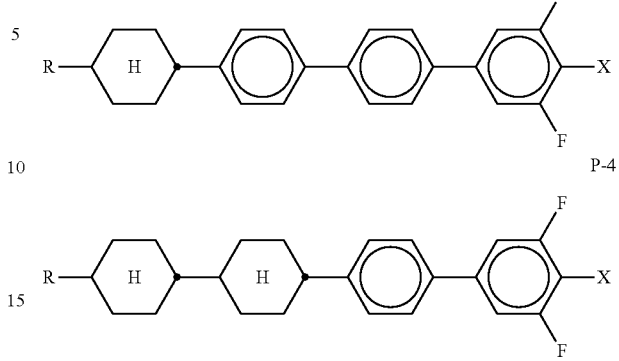

in which

R denotes straight-chain alkyl, alkoxy or alkenyl, each having 1 or 2 to 6 C atoms respectively, and X denotes F, Cl, $CF_3$, $OCF_3$, $OCHFCF_3$ or $CCF_2CHFCF_3$.

14. The liquid-crystalline medium according to claim 1, wherein said medium further comprises one or more compounds selected from the group of compounds of the formulae

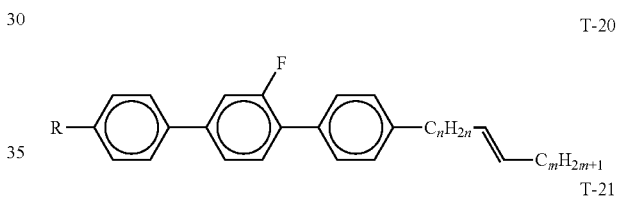

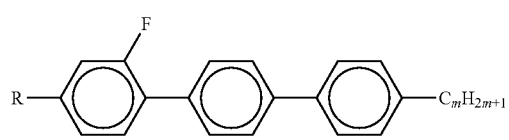

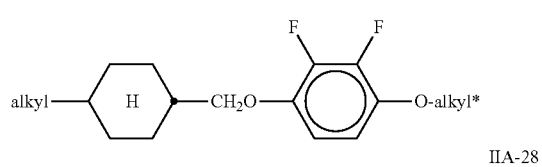

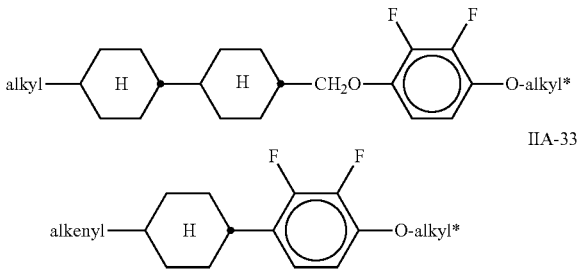

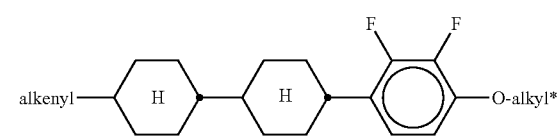

-continued

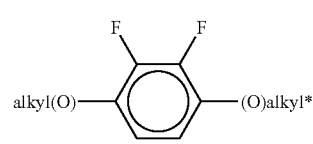
IIA-50

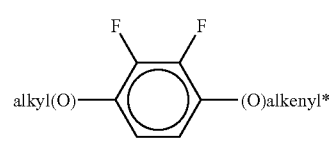
IIA-51

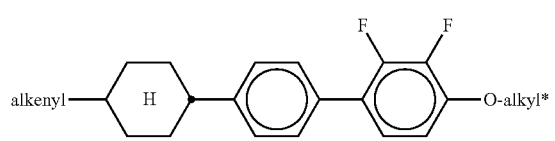
IIB-16

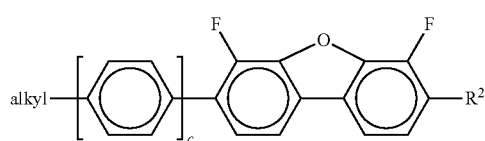
BF-1

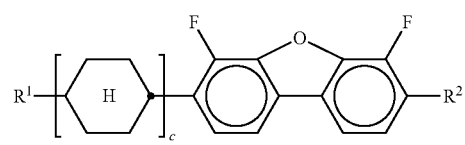
BF-2

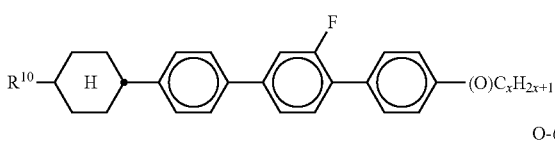
V-10

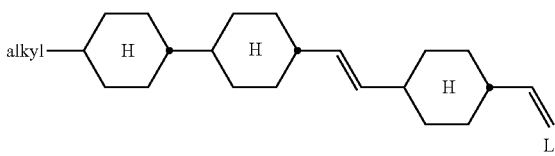
O-6a

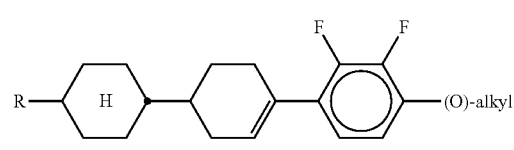
L-4

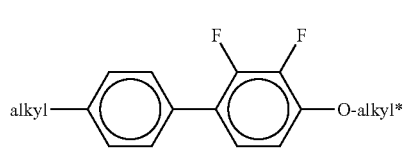
CC-3-V1

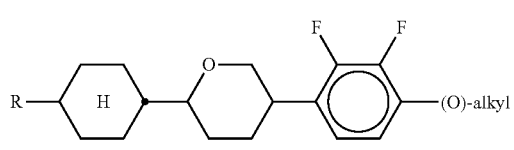
IIB-11

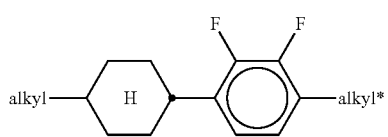
Z-9 in which
R, $R^1$, $R^2$ and $R^{10}$ each, independently of one another, denotes H, an alkyl or alkenyl radical having up to 15 C atoms which is unsubstituted, monosubstituted by CN or $CF_3$ or at least monosubstituted by halogen, where, in addition, one or more $CH_2$ groups in these radicals may each optionally be replaced by —O—, —S—,

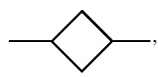

—C≡C—, —$CF_2$O—, —$OCF_2$—, —OC—O— or —O—CO— in such a way that O atoms are not linked directly to one another,
alkyl and alkyl* each, independently of one another, denote a straight-chain alkyl radical having 1-6 C atoms,
alkenyl and alkenyl* each, independently of one another, denote a straight-chain alkenyl radical having 2-6 C atoms,
(O)alkyl, (O)-alkyl and (O)alkyl* each, independently of one another, denote alkyl or O-alkyl,
(O)alkenyl* each, independently of one another, denote alkenyl or O-alkenyl,
m denotes 0, 1, 2, 3, 4, 5 or 6,
n denotes 0, 1, 2, 3 or 4,
x denotes 1 to 6,
c denotes 0, 1 or 2, and
d denotes 1 or 2.

15. The liquid-crystalline medium according to claim 1, wherein said medium comprises at least one polymerizable compound.

16. The liquid-crystalline medium according to claim 1, wherein said medium comprises one or more additives.

17. The liquid-crystalline medium according claim 16, wherein said one or more additives are selected from free-radical scavengers, antioxidants and UV stabilizers.

18. A process for the preparation of a liquid-crystalline medium according to claim 1, comprising mixing at least one compound of formula I with at least one further mesogenic compound, optionally adding one or more additives, and optionally adding at least one polymerizable compound.

19. A method of inducing an electro-optical effect comprising applying a voltage to a liquid-crystalline medium according to claim 1.

20. An electro-optical display having active-matrix addressing, said display comprising a liquid-crystalline medium according to claim 1 as dielectric.

21. The electro-optical display according to claim 20, wherein said display is a VA, PSA, PA-VA, PS-VA, PALC, IPS, PS-IPS, FFS, PS-FFS display.

22. The electro-optical display according to claim 21, wherein said display is an IPS, PS-IPS, FFS or PS-FFS display which has a planar alignment layer.

23. The liquid-crystalline medium according to claim 1, wherein said medium comprises one or more compounds of the following formulae:

IIA-1

-continued
IIA-2
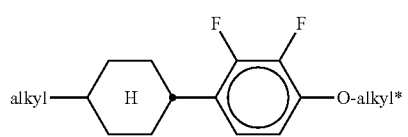
IIA-3
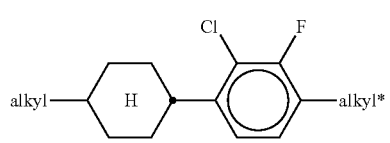
IIA-4
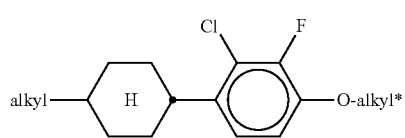
IIA-5
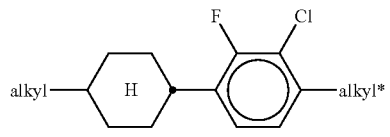
IIA-6
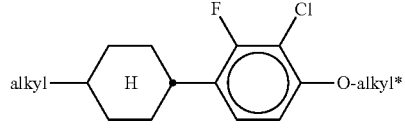
IIA-7
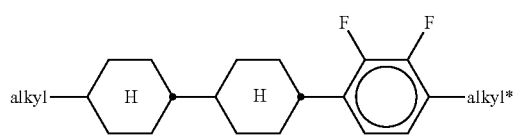
IIA-8
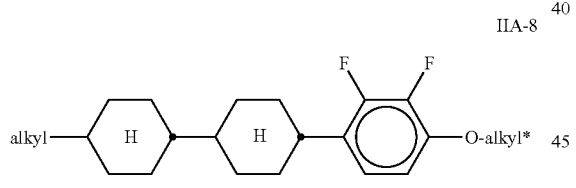
IIA-9
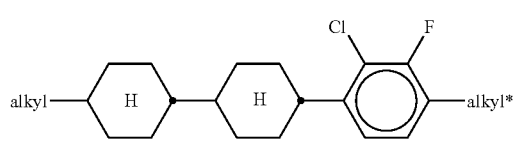
IIA-10
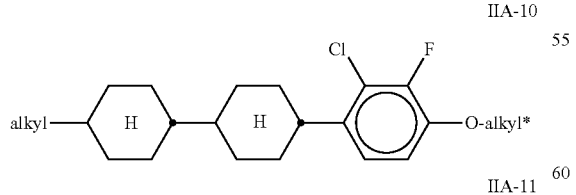
IIA-11
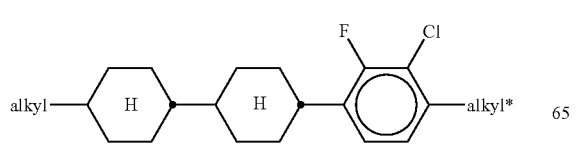
-continued
IIA-12
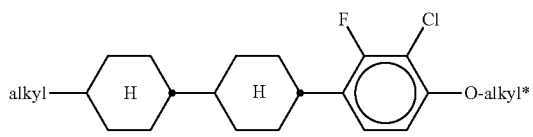
IIA-13
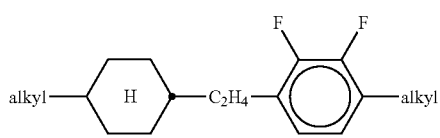
IIA-14
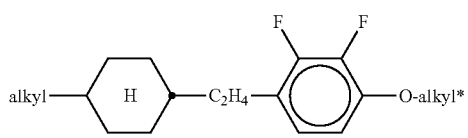
IIA-15
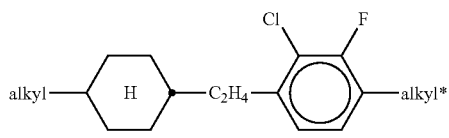
IIA-16
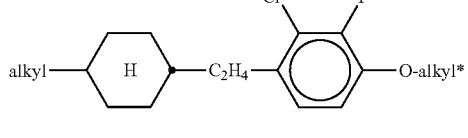
IIA-17
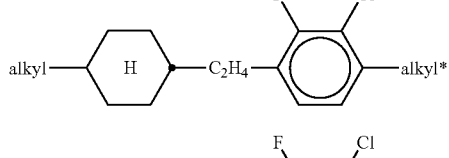
IIA-18
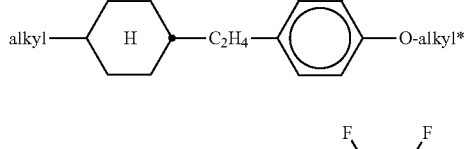
IIA-19
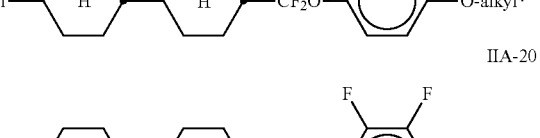
IIA-20
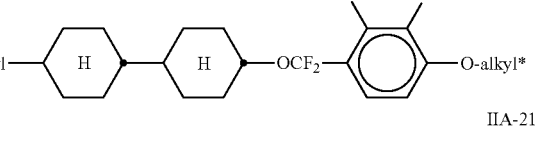
IIA-21
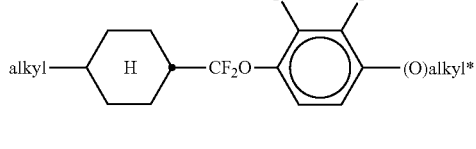
IIA-22
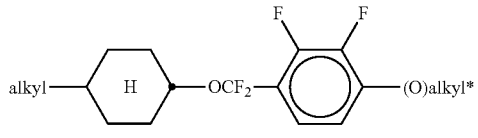

IIA-23
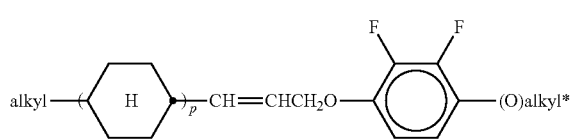
IIA-24
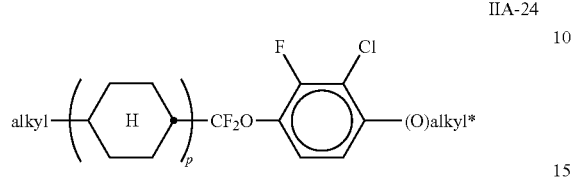
IIA-25
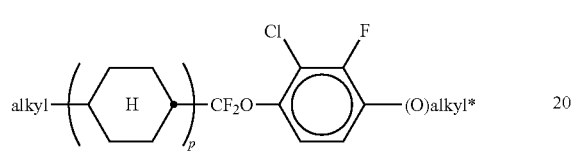
IIA-26
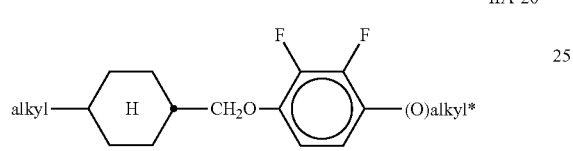
IIA-27
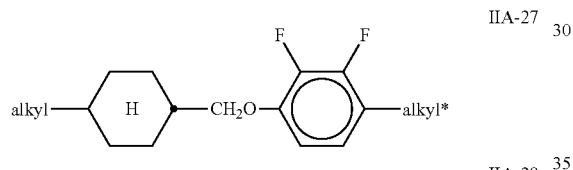
IIA-28
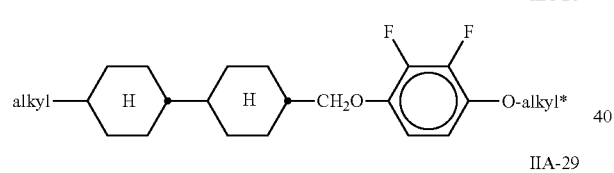
IIA-29
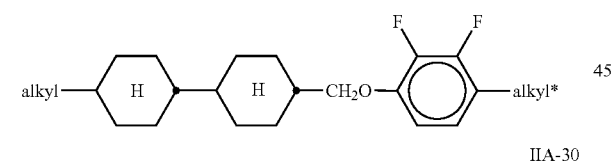
IIA-30
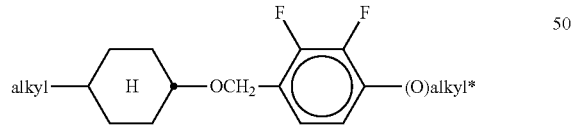
IIA-31
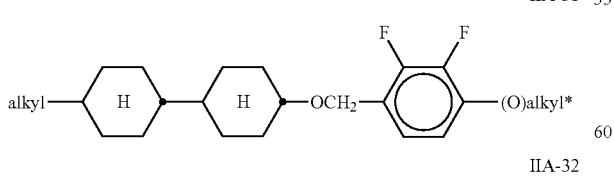
IIA-32
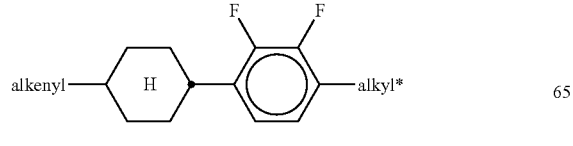
IIA-33
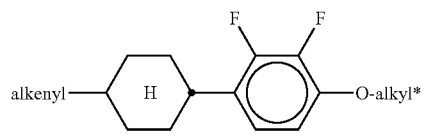
IIA-34
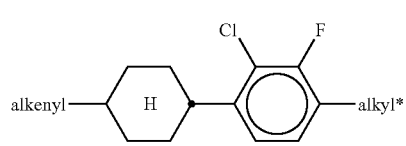
IIA-35
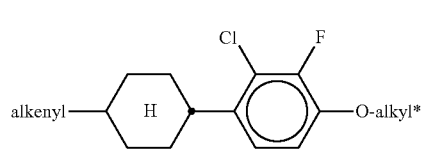
IIA-36
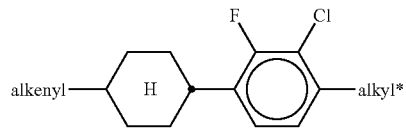
IIA-37
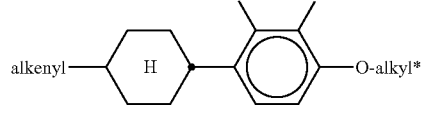
IIA-38
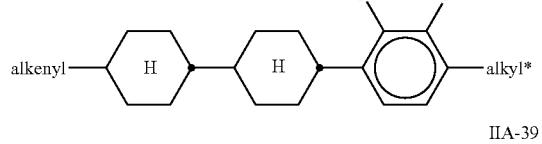
IIA-39
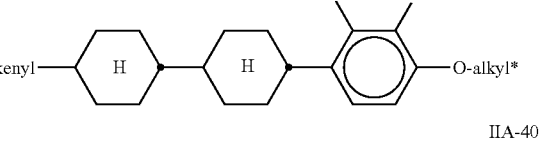
IIA-40
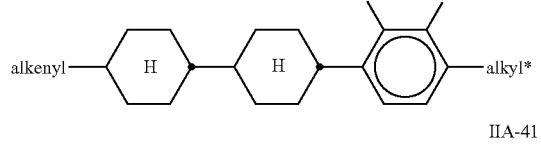
IIA-41
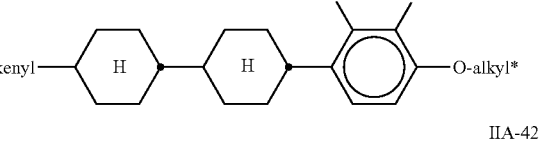
IIA-42
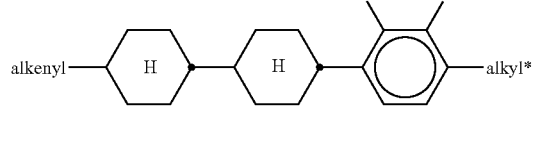

IIA-43
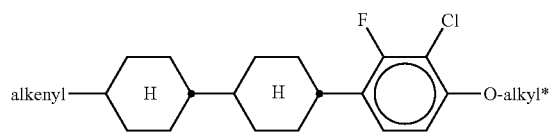
IIA-44
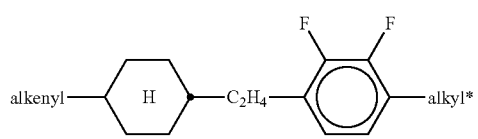
IIA-45
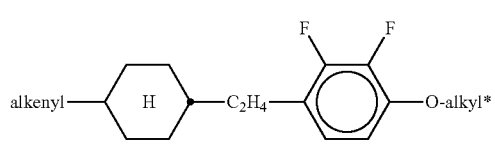
IIA-46
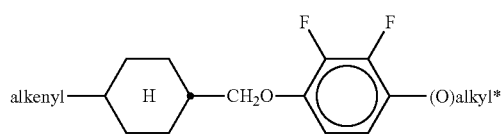
IIA-47
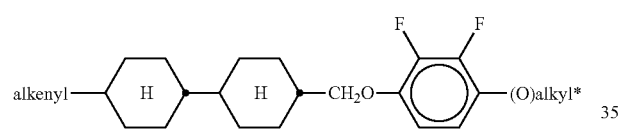
IIA-48
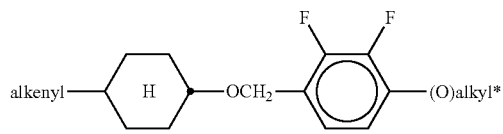
IIA-49
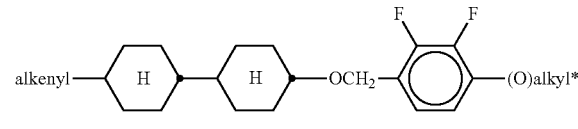
IIA-50
IIA-51
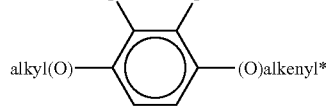
IIA-52
IIB-1
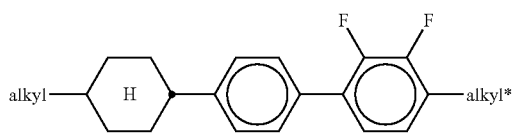
IIB-2
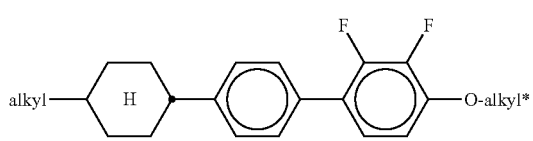
IIB-3
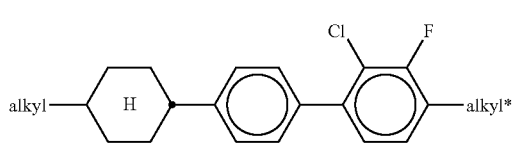
IIB-4
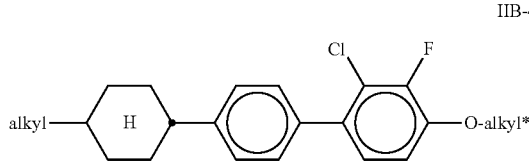
IIB-5
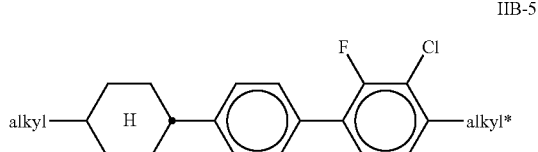
IIB-6
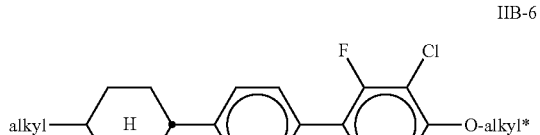
IIB-7
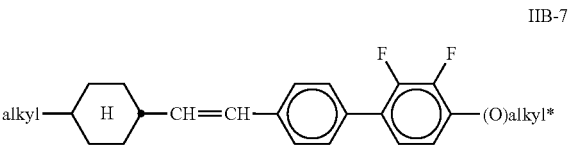
IIB-8
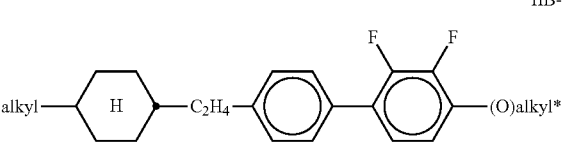
IIB-9
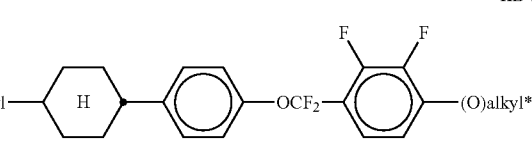
IIB-10
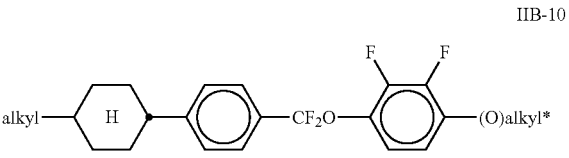

-continued

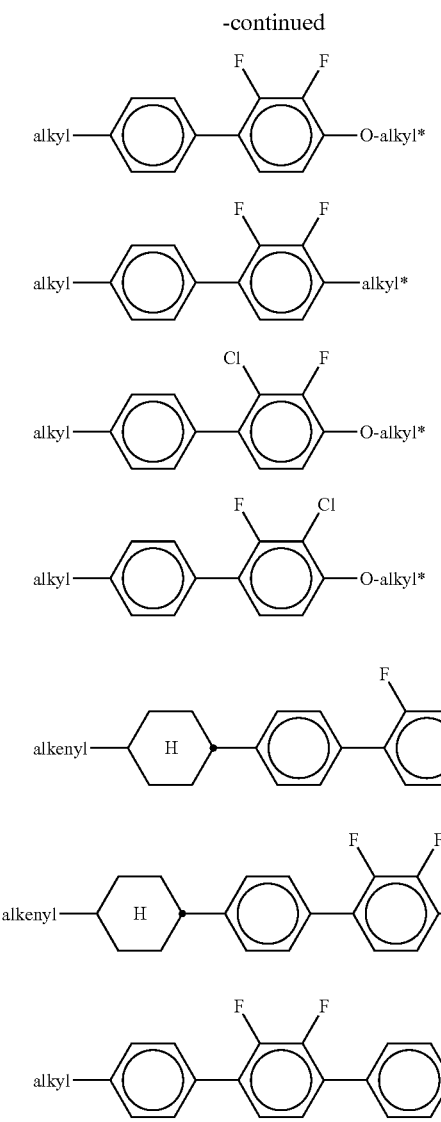

IIB-11
IIB-12
IIB-13
IIB-14
IIB-15
IIB-16
IIC-1 in which
  alkyl and alkyl* each, independently of one another, denote a straight-chain alkyl radical having 1-6 C atoms,
  alkenyl and alkenyl* each, independently of one another, denote a straight-chain alkenyl radical having 2-6 C atoms, and
  (O) denotes a single bond or —O—.

24. The liquid-crystalline medium according to claim 23, wherein said medium contains at least one compound of formula IIC-1

IIC-1

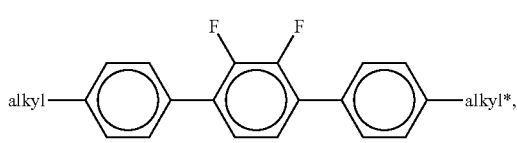

wherein alkyl and alkyl* each, independently of one another, denote a straight-chain alkyl radical having 1-6 C atom.

25. The liquid-crystalline medium according to claim 23, wherein said medium additionally comprises one or more compounds of the formula III,
  in which

III

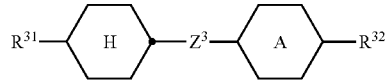

$R^{31}$ and $R^{32}$ each, independently of one another, denote a straight-chain alkyl, alkoxy, alkenyl, alkoxyalkyl or alkenyloxy radical having up to 12 C atoms, and

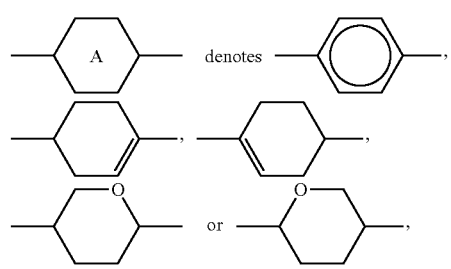

$Z^3$ denotes a single bond, —CH$_2$CH$_2$—, —CH=CH—, —CF$_2$O—, —OCF$_2$—, —CH$_2$O—, —OCH$_2$—, —COO—, —OCO—, —C$_2$F$_4$—, —C$_4$H$_8$—, —C≡C—, or —CF=CF—.

26. The liquid-crystalline medium according to claim 1, wherein said medium contains one or more biphenyls of formulae B-1 to B-3,

B-1

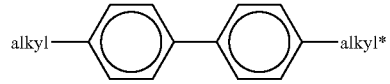

B-2

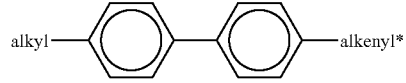

B-3

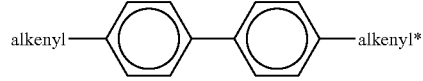

in which
  alkyl and alkyl* each, independently of one another, denote a straight-chain alkyl radical having 1-6 C atoms, and
  alkenyl and alkenyl* each, independently of one another, denote a straight-chain alkenyl radical having 2-6 C atoms.

27. The liquid-crystalline medium according to claim 1, wherein said medium contains one or more compounds of formulae Z-1 to Z-9

Z-1

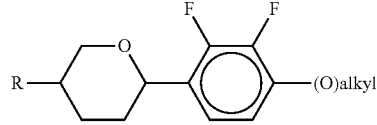

-continued

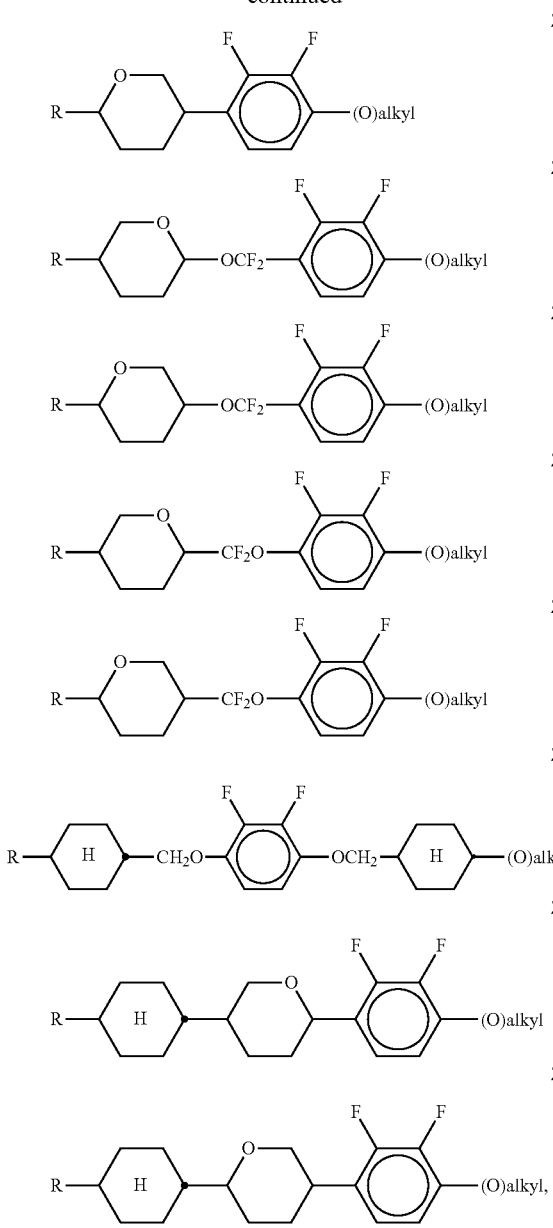

in which
R denotes H, an alkyl or alkenyl radical having up to 15 C atoms which is unsubstituted, or monosubstituted by CN or CF$_3$ or at least monosubstituted by halogen, where, in addition, one or more CH$_2$ groups in these radicals are each optionally replaced by —O—, —S—,

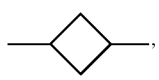

—C≡C—, —CF$_2$O—, —OCF$_2$—, —OC—O— or —O—CO— in such a way that O atoms are not linked directly to one another,
(O) denotes a single bond or —O—, and
alkyl denotes an alkyl radical having 1-6 C atoms.

28. The liquid-crystalline medium according to claim 1, wherein said medium contains one or more of the following compounds:

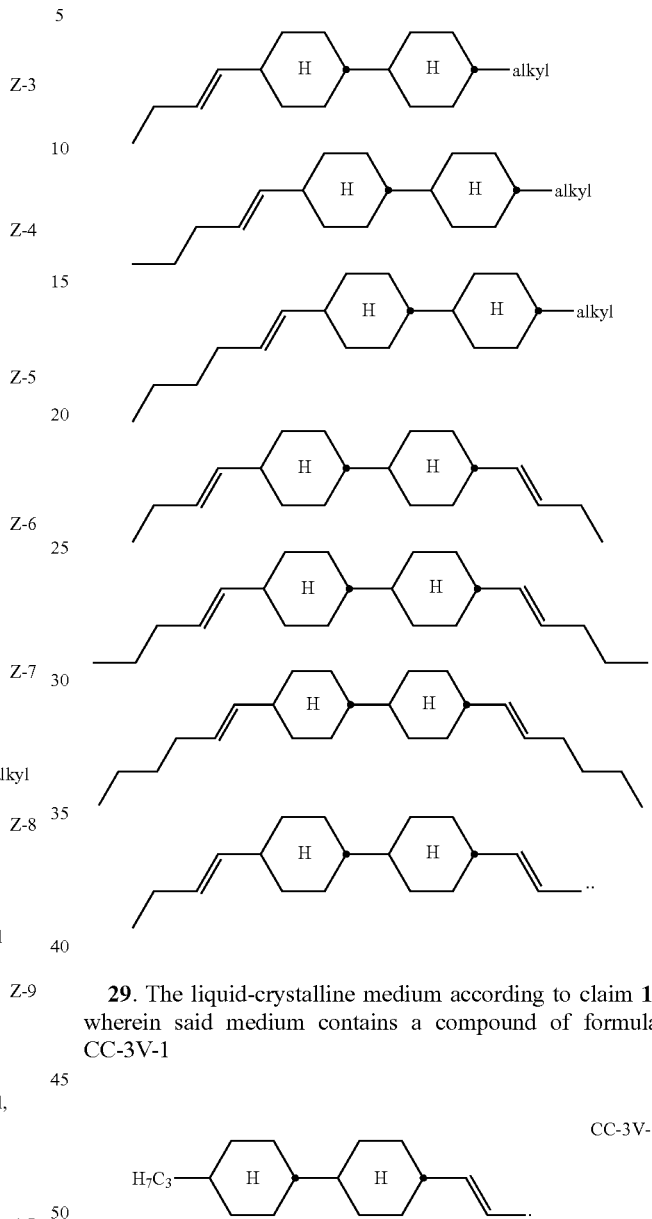

29. The liquid-crystalline medium according to claim 1, wherein said medium contains a compound of formula CC-3V-1

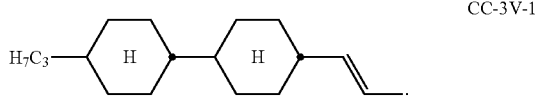

30. The liquid-crystalline medium according to claim 29, wherein the total amount of compounds CC-3-V and CC-3V-1 combined is up to 65% by weight of the medium.

31. The liquid-crystalline medium according to claim 1, wherein said medium additionally comprises at least one compound selected from formulae O-10a to O-10b and at least one compound selected from formulae O-17z to O-17d:

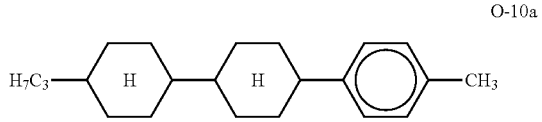

-continued

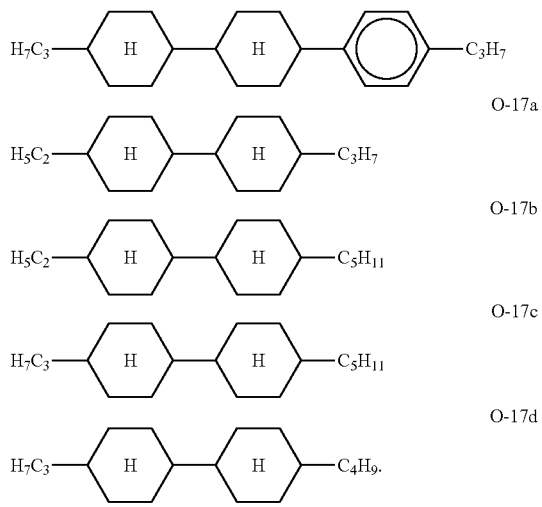

O-10b

O-17a

O-17b

O-17c

O-17d

32. The liquid-crystalline medium according to claim 31, wherein the total amount of compounds of formulae O-10a and/or O-10b and compounds of the formulae O-17a to O-17d combined is 5-40% by weight of the medium.

33. The liquid-crystalline medium according to claim 31, wherein said medium contains at least one compound of formula O-10a and at least one compound of formula O-17a.

34. The liquid-crystalline medium according to claim 33, wherein the total amount of compounds of formulae O-10a and O-17a combined is 15-35% by weight of the medium.

35. The liquid-crystalline medium according to claim 31, wherein said medium contains at least one compound of formula O-10b and at least one compound of formula O-17a.

36. The liquid-crystalline medium according to claim 35, wherein the total amount of compounds of formulae O-10b and O-17a combined is 15-35% by weight of the medium.

37. The liquid-crystalline medium according to claim 31, wherein said medium contains at least one compound of formula O-10a, at least one compound of formula O-10b, and at least one compound of formula O-17a.

38. The liquid-crystalline medium according to claim 37, wherein the total amount of compounds of formulae O-10a, O-10b and O-17a combined is 15-35% by weight of the medium.

39. The liquid-crystalline medium according to claim 1, wherein said medium additionally comprises at least one compound selected from formulae O-6, O-7, O-10, and O-17

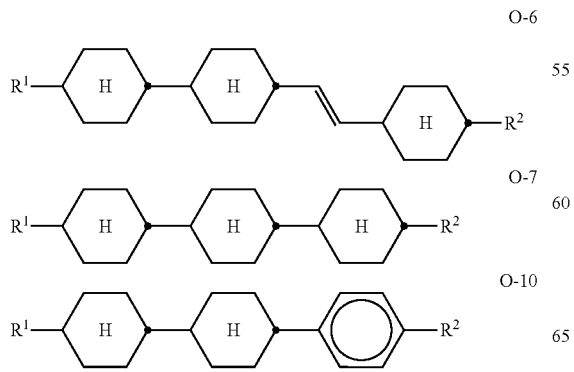

O-6

O-7

O-10

-continued

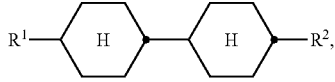

O-17 in which

R¹ and R² each, independently of one another, denotes H, an alkyl or alkenyl radical having up to 15 C atoms which is unsubstituted, monosubstituted by CN or CF₃ or at least monosubstituted by halogen, where, in addition, one or more CH₂ groups in these radicals are each optionally replaced by —O—, —S—,

—C≡C—, —CF₂O—, —OCF₂—, —OC—O— or —O—CO— in such a way that O atoms are not linked directly to one another.

40. The liquid-crystalline medium according to claim 39, wherein in the compounds formulae O-6, O-7 and O-17, R¹ is alkyl having 1-6 C atoms or alkenyl having 2-6 C atoms, and R² is alkenyl having 2-6 C atoms, and in the compounds of formula O-10, R¹ is alkyl having 1-6 C atoms or alkenyl having 2-6 C atoms, and R² is alkyl having 1-6 C atoms.

41. The liquid-crystalline medium according to claim 1, wherein the total amount of compounds of formulae BC, CR, PH-1, PH-2, BF-1, BF-2, BS-1 and BS-2 is 3 to 20% by weight of the medium.

42. The liquid-crystalline medium according to claim 1, wherein the compounds of formulae BC, CR, BF-1 and BS-1 are selected from the compounds formulae BC-1 to BC-7, CR-1 to CR-5, BF-1a to BF-1c-, BS-1a to BS-1c,

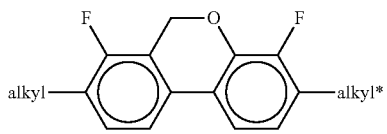

BC-1

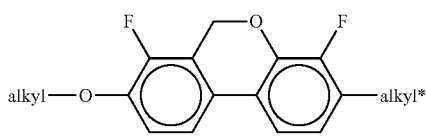

BC-2

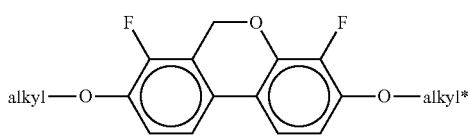

BC-3

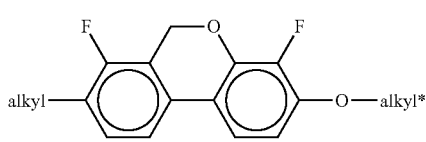

BC-4

-continued

BC-5
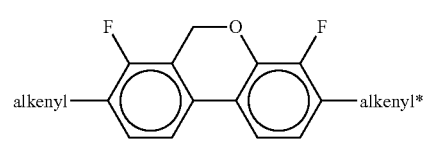

BC-6
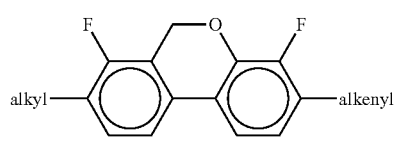

BC-7
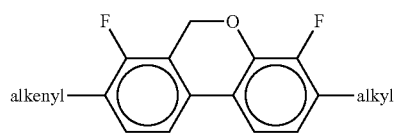

CR-1
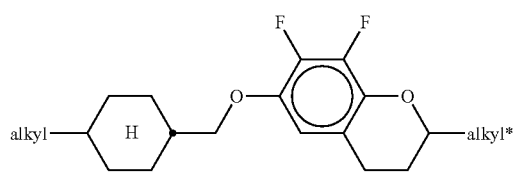

CR-2
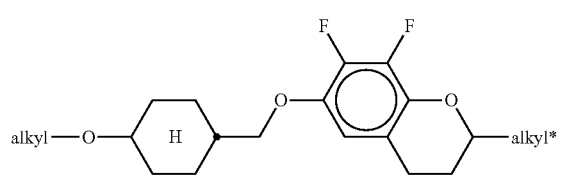

CR-3
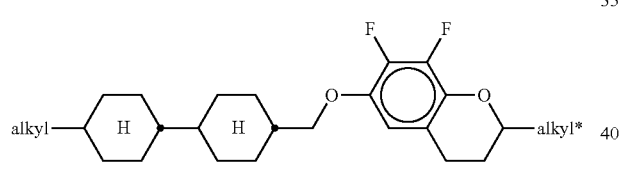

CR-4
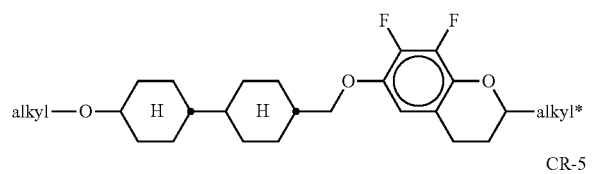

CR-5
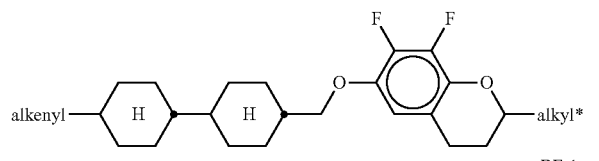

BF-1a
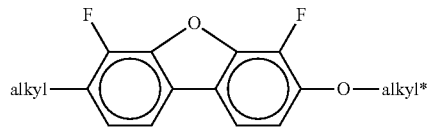

BF-1b
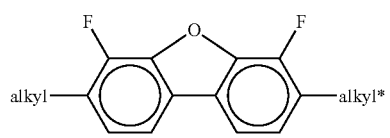

-continued

BF-1c
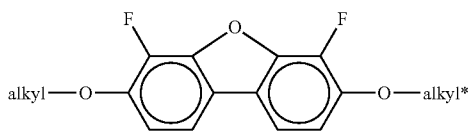

BS-1a
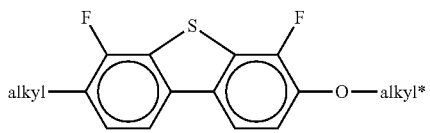

BS-1b
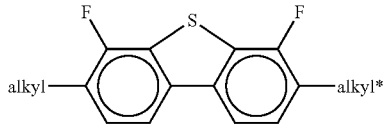

BS-1c
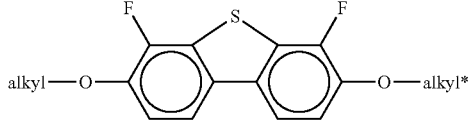

in which
  alkyl and alkyl* each, independently of one another, denote a straight-chain alkyl radical having 1-6 C atoms, and
  alkenyl and alkenyl* each, independently of one another, denote a straight-chain alkenyl radical having 2-6 C atoms.

43. The liquid-crystalline medium according to claim 1, wherein said medium comprises one, two or three compounds selected from formulae BC-2, BF-1 and BF-2.

44. The liquid-crystalline medium according to claim 1, wherein said medium comprises one or more compounds of formula In, In
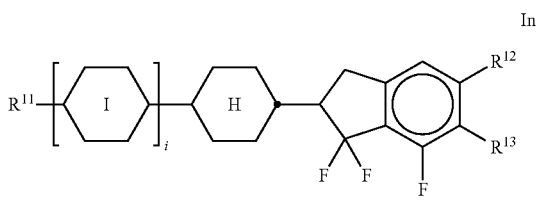

in which
  $R^{11}$, $R^{12}$, $R^{13}$ each, independently of one another, denote a straight-chain alkyl, alkoxy, alkoxyalkyl or alkenyl radical having 1-6 C atoms,
  $R^{12}$ and $R^{13}$ additionally may denote halogen,

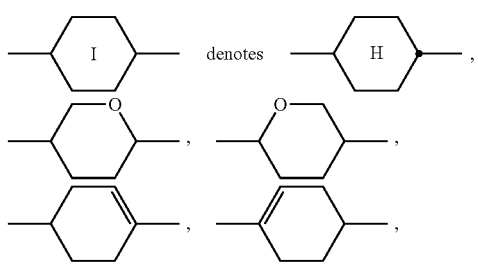

-continued

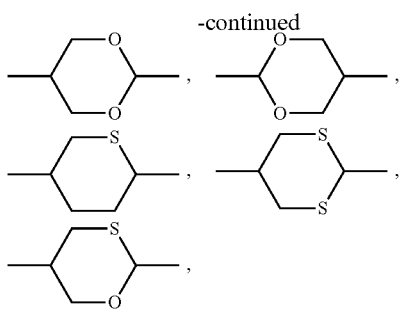

i denotes 0, 1 or 2.

45. The liquid-crystalline medium according to claim 1, wherein said medium comprises
one or more compounds of formula I in which $L^1$ is F, $L^2$ is F, and $R^1$ and $R^{1*}$ are each alkoxy;
one or more compounds of formula CPY-n-Om

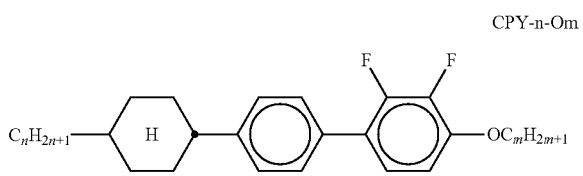
CPY-n-Om wherein m and n each denote 1-15, in concentrations >5% based on the mixture as a whole;
one or more compounds of formula CY-n-Om

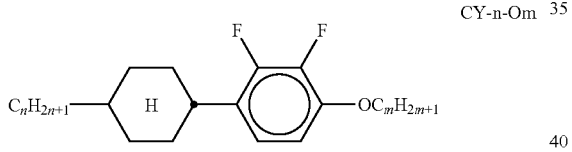
CY-n-Om wherein m and n each denote 1-15, in concentrations >5% based on the mixture as a whole;
one or more compounds of formula CCY-n-Om

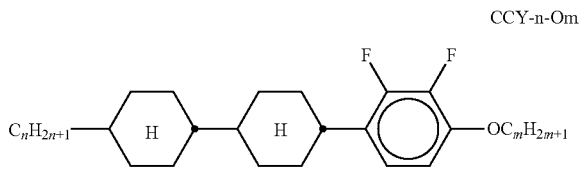
CCY-n-Om wherein m and n each denote 1-15, in concentrations >5% based on the mixture as a whole;
one or more compounds of formula CLY-n-Om

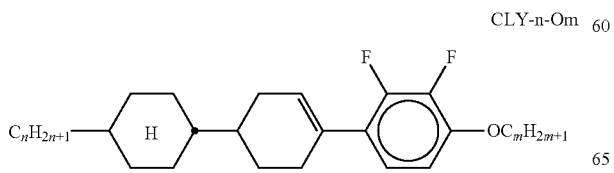
CLY-n-Om wherein m and n each denote 1-15, in concentrations >5% based on the mixture as a whole; and/or
one or more compounds of formula CK-n-F

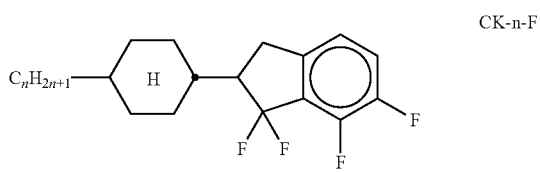
CK-n-F wherein n denotes 1-15, in concentrations >5% based on the mixture as a whole.

46. The liquid-crystalline medium according to claim 1, wherein said medium comprises
one or more compounds of formula CPY-n-Om and one or more compounds of formula CY-n-Om

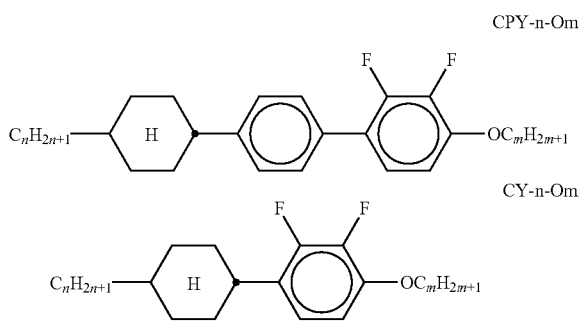
CPY-n-Om

CY-n-Om wherein m and n each denote 1-6;
one or more compounds of formula CPY-n-Om and one or more compounds of formula CK-n-F

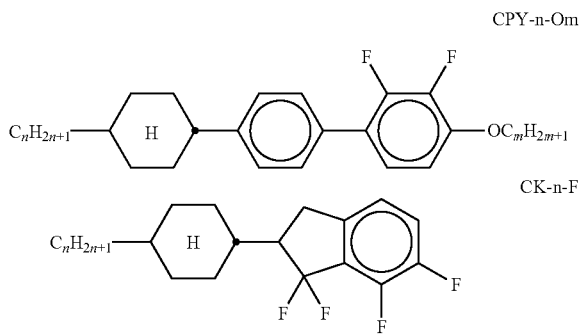
CPY-n-Om

CK-n-F wherein m and n each denote 1-6;
one or more compounds of formula Y-nO-Om

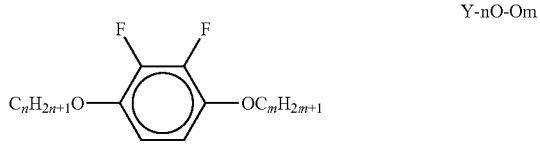
Y-nO-Om wherein m and n each denote 1-6;
one or more compounds of formula CPY-n-Om and one or more compounds of formula PY-n-Om CPY-n-Om

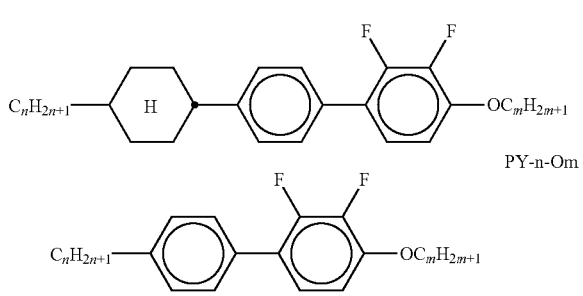

PY-n-Om wherein m and n each denote 1-6;
one or more compounds of formula CPY-n-Om and one or more compounds of formula CLY-n-Om CPY-n-Om

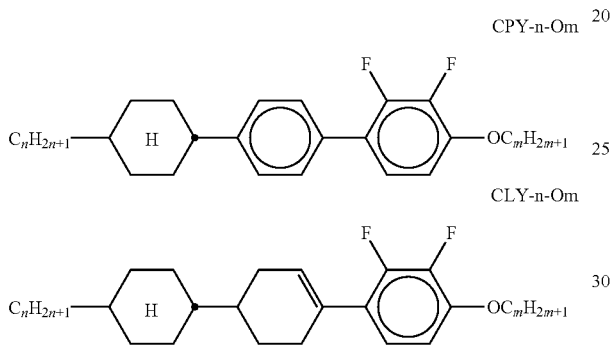

CLY-n-Om wherein m and n each denote 1-6;
one or more compounds of formula CCVC-n-V CCVC-n-V

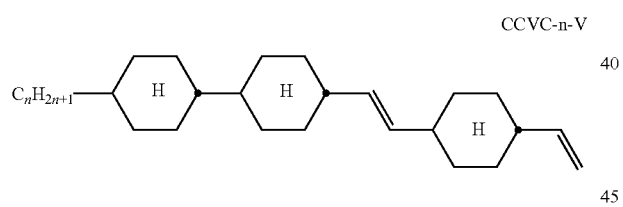

wherein n denotes 1-6;
one or more compounds of formula CCC-n-V

CCC-n-V

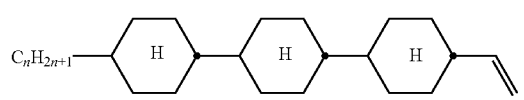

wherein n denotes 1-6; and/or
a compound of formula CC-V-V

CC-V-V

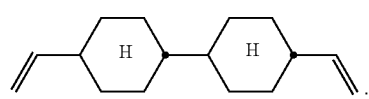

47. The liquid-crystalline medium according to claim 1, wherein said medium comprises at least one compound selected from the compounds of formulae T-20, T-21, IIA-26, IIA-28, IIIA-33, IIA-39, IIA-50, IIA-51, IIB-16, BF-1, BF-2, V-10, O-6a, L-4, CC-3-V1, IIB-11 and Z-9:

T-20

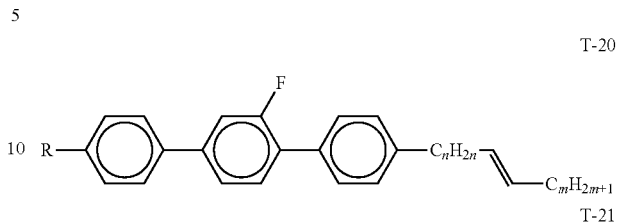

T-21

IIA-26

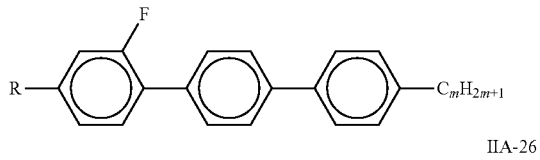

IIA-28

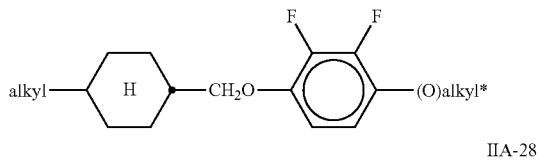

IIA-33

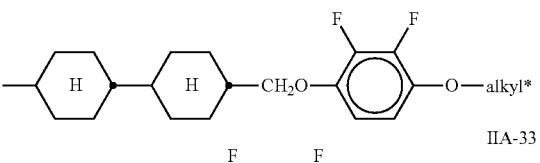

IIA-39

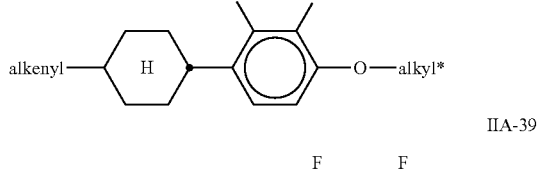

IIA-50

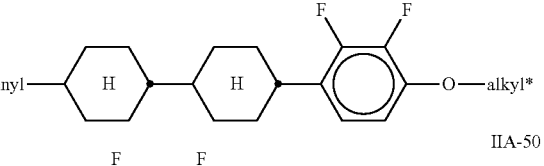

IIA-51

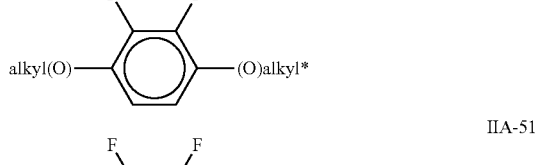

IIB-16

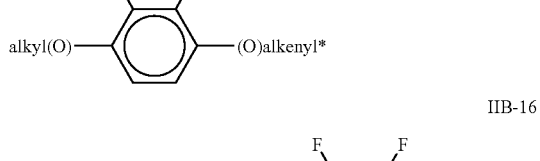

BF-1

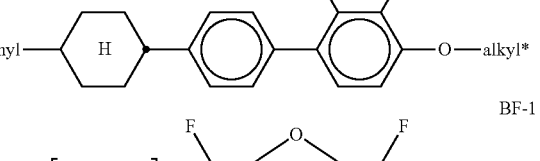

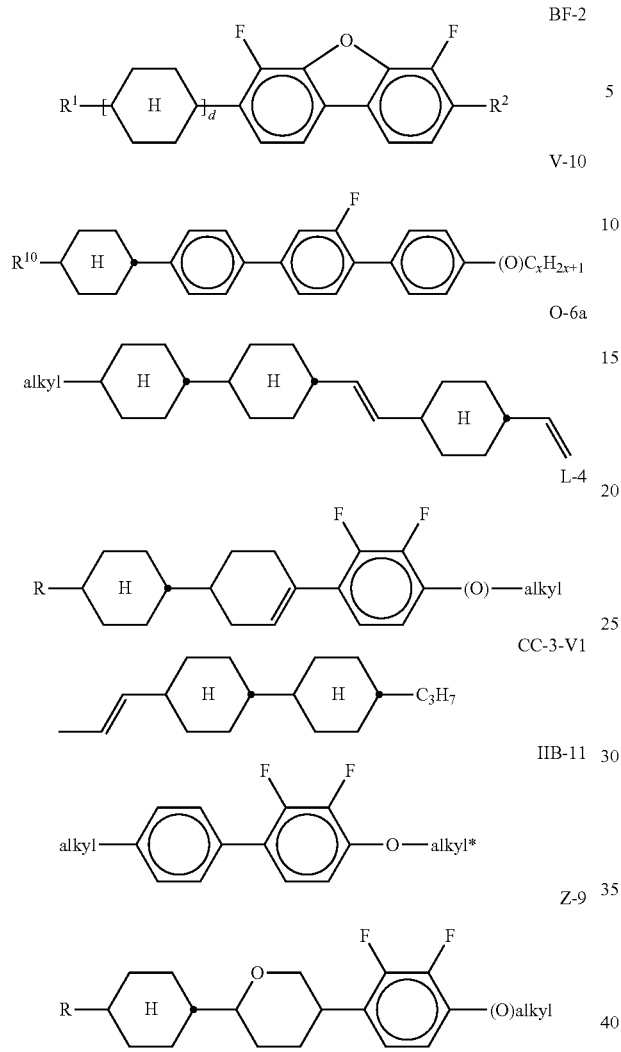

in which
R, $R^1$, $R^2$ and $R^{10}$ each, independently of one another, denote H, an alkyl or alkenyl radical having up to 15 C atoms which is unsubstituted, or monosubstituted by CN or $CF_3$ or at least monosubstituted by halogen, where, in addition, one or more $CH_2$ groups in these radicals are each optionally replaced by —O—, —S—, —C≡C—, —$CF_2$O—, —$OCF_2$—, —OC—O— or —O—CO— in such a way that O atoms are not linked directly to one another,
alkyl and alkyl* each, independently of one another, denote a straight-chain alkyl radical having 1-6 C atoms,
alkenyl and alkenyl* each, independently of one another, denote a straight-chain alkenyl radical having 2-6 C atoms,
(O)alkyl, (O)-alkyl and (O)alkyl* each, independently of one another, denote alkyl or O-alkyl, (O)alkenyl* denotes alkenyl or O-alkenyl,
m denotes 0, 1, 2, 3, 4, 5 or 6,
n denotes 0, 1, 2, 3 or 4,
x denotes 1 to 6,
c denotes 0, 1 or 2
d denotes 1 or 2.

48. The liquid-crystalline medium according to claim 1, wherein said medium further comprises one or more polymerizable compounds selected from the compounds of formula M $$R^{Ma}\text{-}A^{M1}\text{-}(Z^{M1}\text{-}A^{M2})_{m1}\text{-}R^{Mb} \qquad M$$

wherein
$R^{Ma}$ and $R^{Mb}$ each, independently of one another, denote P, P-Sp-, H, F, Cl, Br, I, —CN, —$NO_2$, —NCO, —NCS, —OCN, —SCN, $SF_5$ or an alkyl, alkenyl or alkynyl group having 1 to 25 C atoms wherein in the alkyl group one or more non-adjacent $CH_2$ groups are each optionally replaced, independently of one another, by —C($R^0$)=C($R^{00}$)—, —C≡C—, —N($R^{00}$)—, —O—, —S—, —CO—, —CO—O—, —O—CO—, —O—CO—O— in such a way that O and/or S atoms are not linked directly to one another, and in which, in addition, one or more H atoms are each optionally replaced by F, Cl, Br, I, CN, P or P-Sp-,
P denotes a polymerizable group,
Sp denotes a spacer group or a single bond,
$A^{M1}$ and $A^{M2}$ each, independently of one another, denote an aromatic, heteroaromatic, alicyclic or heterocyclic group having 4 to 25 ring atoms, which may contain annellated rings, and which are unsubstituted or mono- or polysubstituted by L,
L denotes P, P-Sp-, OH, $CH_2OH$, F, Cl, Br, I, —CN, —$NO_2$, —NCO, —NCS, —OCN, —SCN, —C(=O)N($R^x$)$_2$, —C(=O)$Y^1$, —C(=O)$R^x$, —N($R^x$)$_2$, optionally substituted silyl, optionally substituted aryl having 6 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which, in addition, one or more H atoms are each optionally replaced by F, Cl, P or P-Sp-,
$Y^1$ denotes halogen,
$Z^{M1}$ denotes —O—, —S—, —CO—, —CO—O—, —OCO—, —O—CO—O—, —$OCH_2$—, —$CH_2O$—, —$SCH_2$—, —$CH_2S$—, —$CF_2O$—, —$OCF_2$—, —$CF_2S$—, —$SCF_2$—, —$(CH_2)_{n1}$—, —$CF_2CH_2$—, —$CH_2CF_2$—, —$(CF_2)_{n1}$—, —CH=CH—, —CF=CF—, —C≡C—, —CH=CH—, —COO—, —OCO—CH=CH—, $CR^0R^{00}$ or a single bond,
$R^0$ and $R^{00}$ each, independently of one another, denote H or alkyl having 1 to 12 C atoms,
$R^x$ denotes P, P-Sp-, H, halogen, straight-chain, branched or cyclic alkyl having 1 to 25 C atoms, in which, in addition, one or more non-adjacent $CH_2$ groups are each optionally replaced by —O—, —S—, —CO—, —CO—O—, —O—CO—, or —O—CO—O— in such a way that O and/or S atoms are not linked directly to one another, and in which, in addition, one or more H atoms are each optionally replaced by F, Cl, P or P-Sp-, an optionally substituted aryl or aryloxy group having 6 to 40 C atoms, or an optionally substituted heteroaryl or heteroaryloxy group having 2 to 40 C atoms,
m1 denotes 0, 1, 2, 3 or 4 and
n1 denotes 1, 2, 3 or 4, where at least one of the groups $R^{Ma}$, $R^{Mb}$ and L present denotes a group P or P-Sp- or contains at least one group P or P-Sp-.
49. The liquid-crystalline medium according to claim 1, wherein said medium further comprises one or more polymerizable compounds selected from the following formulae:
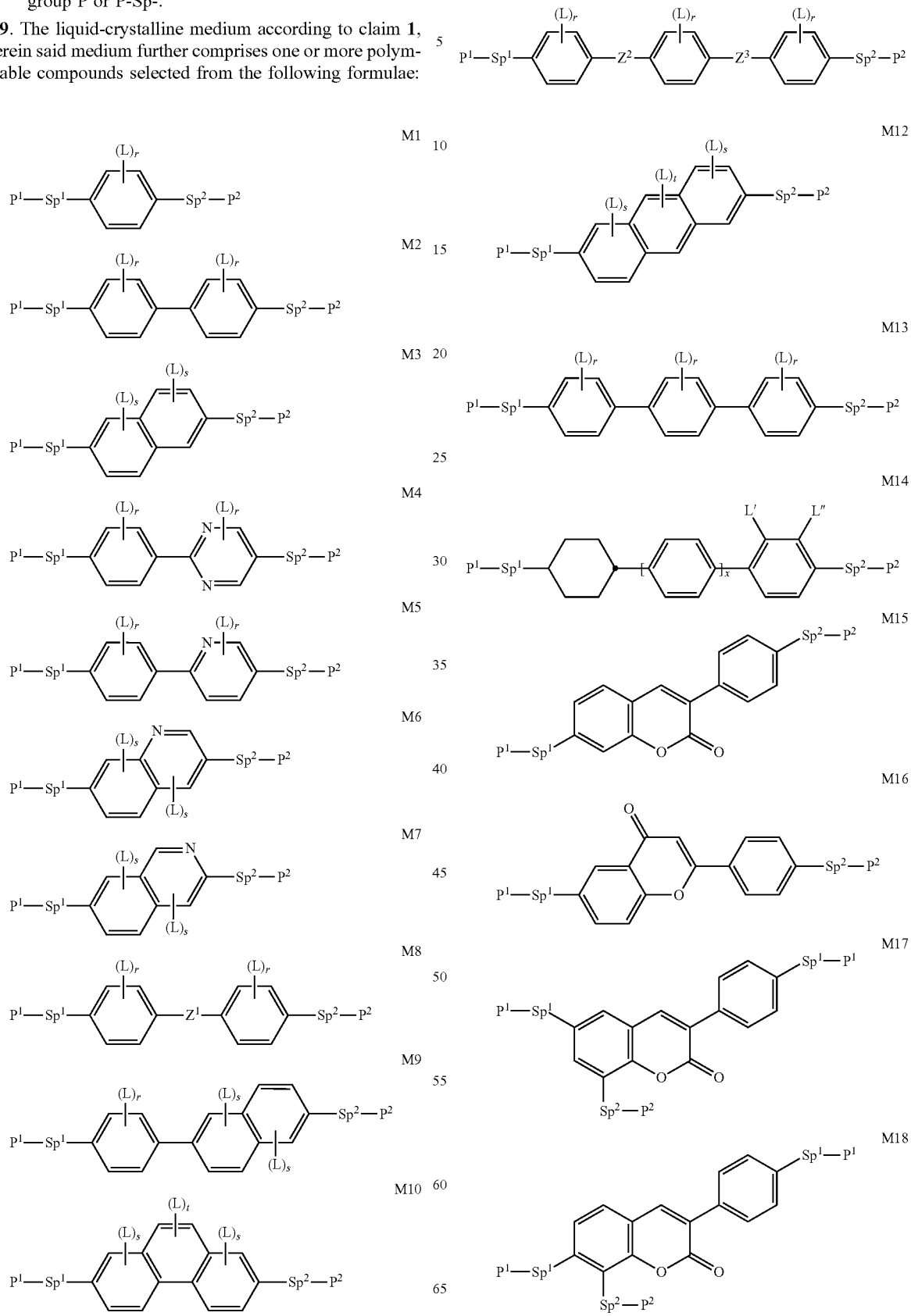

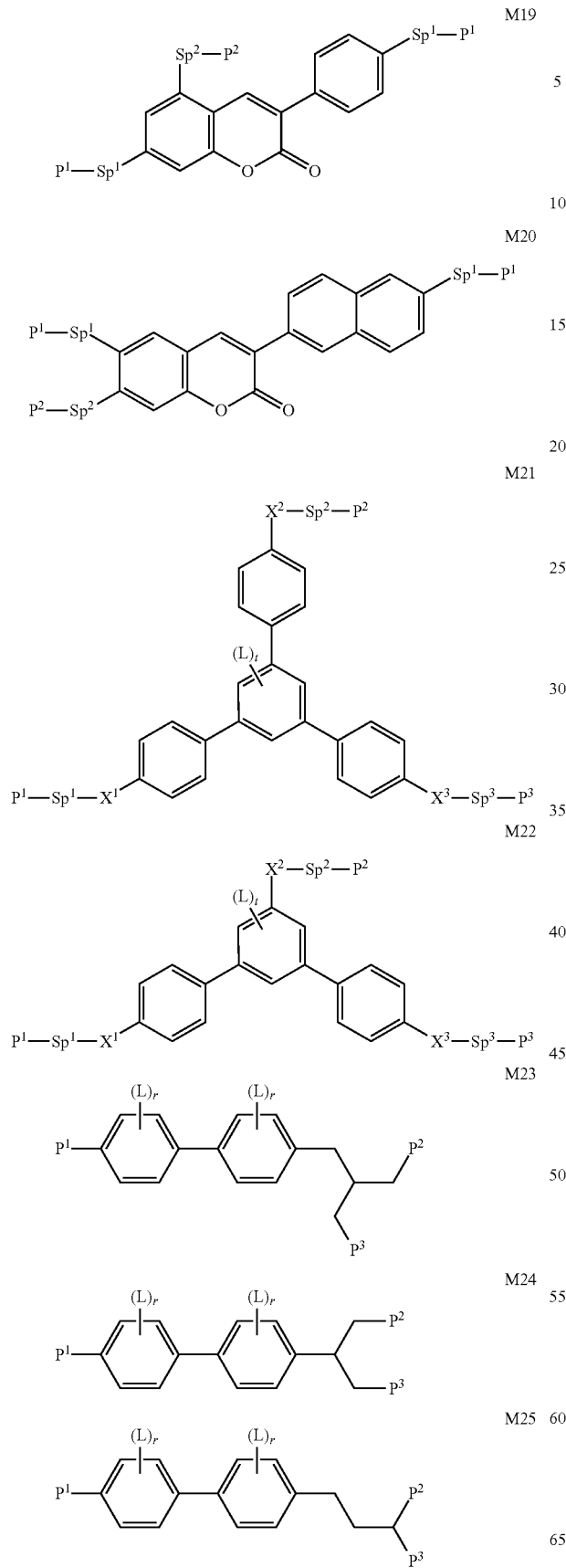
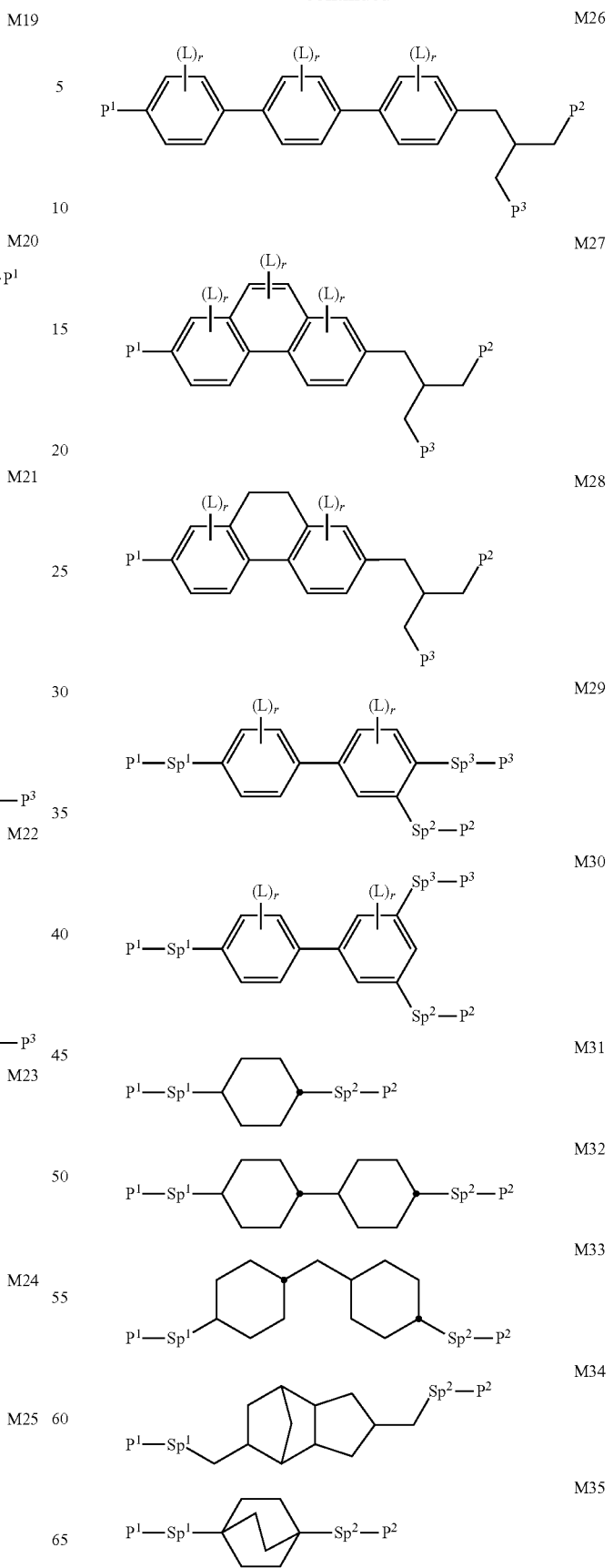

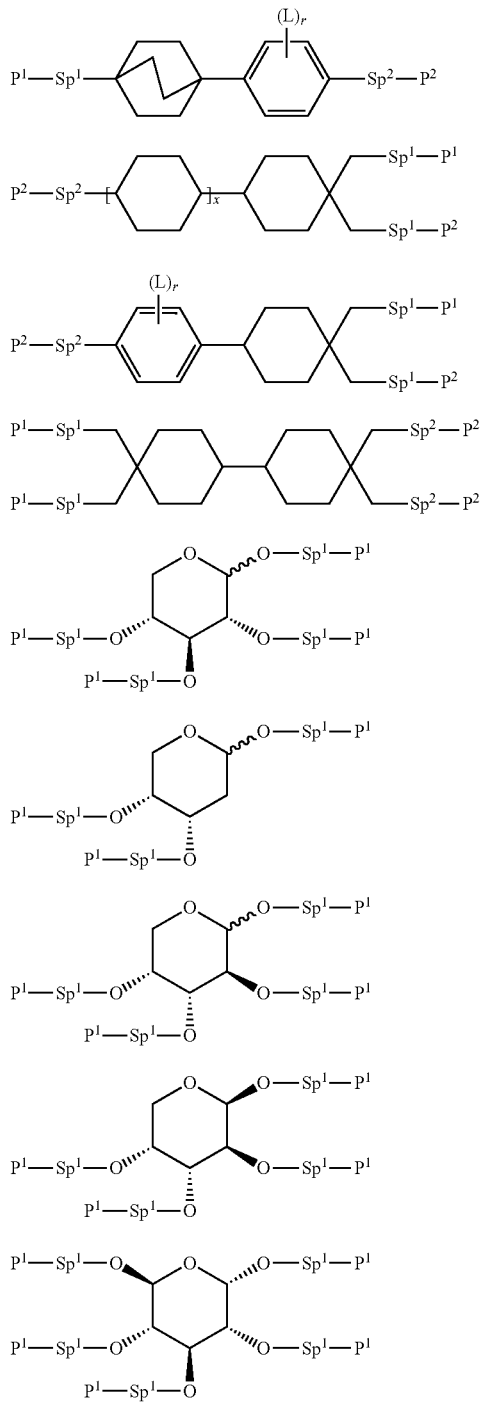

in which:
P¹, P² and P³ each, identically or differently, denote a polymerizable group, Sp¹, Sp² and Sp³ each, independently of one another, denote a single bond or a spacer group, where one or more of the radicals P¹-Sp¹-, P²-Sp²- and P³-Sp³- may also denote $R^{aa}$, with the proviso that at least one of the radicals P¹-Sp¹-, P²-Sp²- and P³-Sp³- present does not denote $R^{aa}$, $R^{aa}$ denotes H, F, Cl, CN or straight-chain or branched alkyl having 1 to 25 C atoms, in which, in addition, one or more non-adjacent $CH_2$ groups are each optionally replaced, independently of one another, by $C(R^0)=C(R^{00})-$, $-C\equiv C-$, $-N(R^0)-$, $-O-$, $-S-$, $-CO-$, $-CO-O-$, $-O-CO-$, or $-O-CO-O-$ in such a way that O and/or S atoms are not linked directly to one another, and in which, in addition, one or more H atoms are each optionally replaced by F, Cl, CN or P-Sp-, $R^0$, $R^{00}$ each, independently of one another and on each occurrence identically or differently, denote H or alkyl having 1 to 12 C atoms, X¹, X² and X³ each, independently of one another, denote $-CO-O-$, $O-CO-$ or a single bond, Z¹ denotes $-O-$, $-CO-$, $-C(R^yR^z)-$ or $-CF_2CF_2-$, $R^y$ and $R^z$ each, independently of one another, denote H, F, $CH_3$ or $CF_3$, Z² and Z³ each, independently of one another, denote $-CO-O-$, $-O-CO-$, $-CH_2O-$, $-OCH_2-$, $-CF_2O-$, $-OCF_2-$ or $-(CH_2)_n-$, where n is 2, 3 or 4, L on each occurrence, identically or differently, denotes F, Cl, CN, SCN, $SF_5$ or straight-chain or branched, optionally mono- or polyfluorinated, alkyl, alkoxy, alkenyl, alkynyl, alkylcarbonyl, alkoxycarbonyl, alkylcarbonyloxy or alkoxycarbonyloxy having up to 12 C atoms, L' and L" each, independently of one another, denote H, F or Cl, r denotes 0, 1, 2, 3 or 4, s denotes 0, 1, 2 or 3, t denotes 0, 1 or 2, x denotes 0 or 1.

50. The liquid-crystalline medium according to claim 1, wherein said medium further comprises one or more of the following stabilizers in an amount up to 10% by weight of the medium:

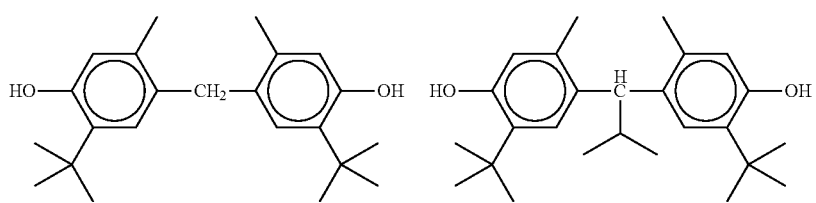

-continued
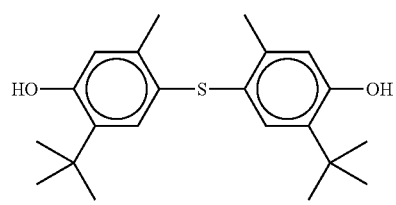
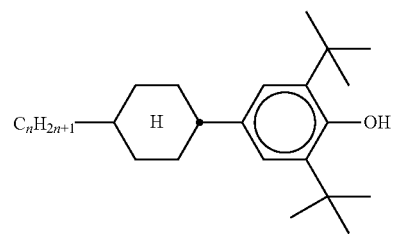
n = 1, 2, 3, 4, 5, 6 or 7
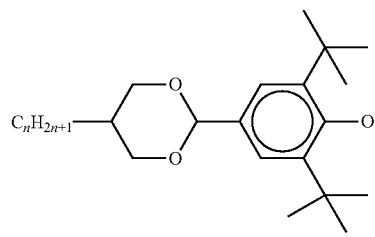
n = 1, 2, 3, 4, 5, 6 or 7
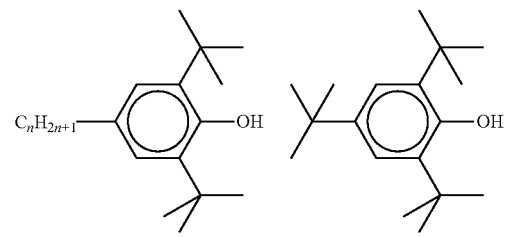
n = 1, 2, 3, 4, 5, 6 or 7
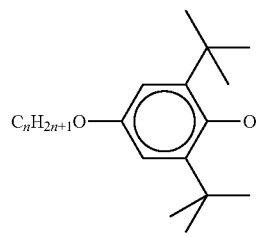
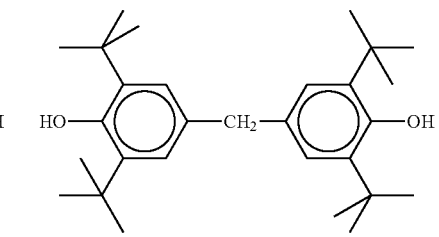
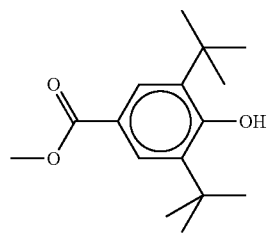
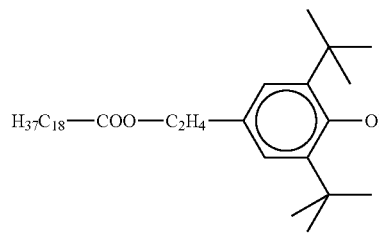
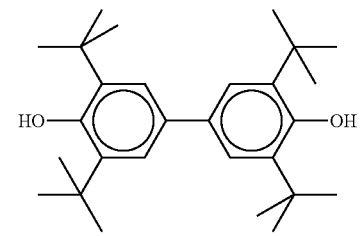
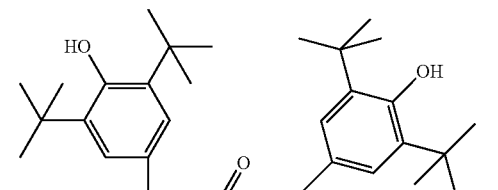
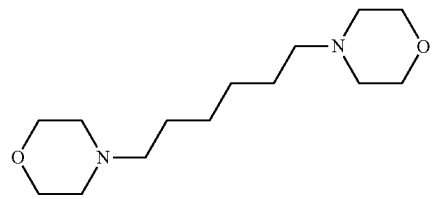
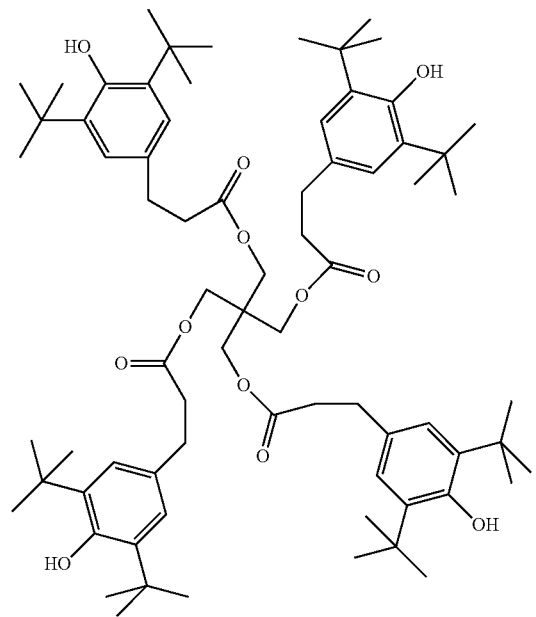

-continued
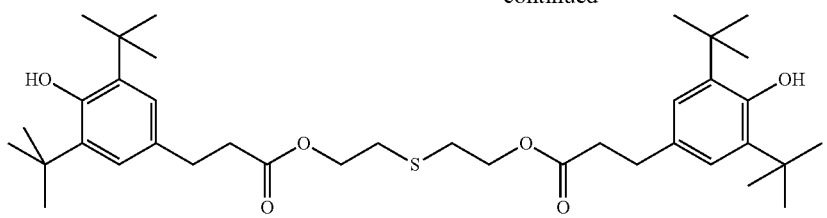
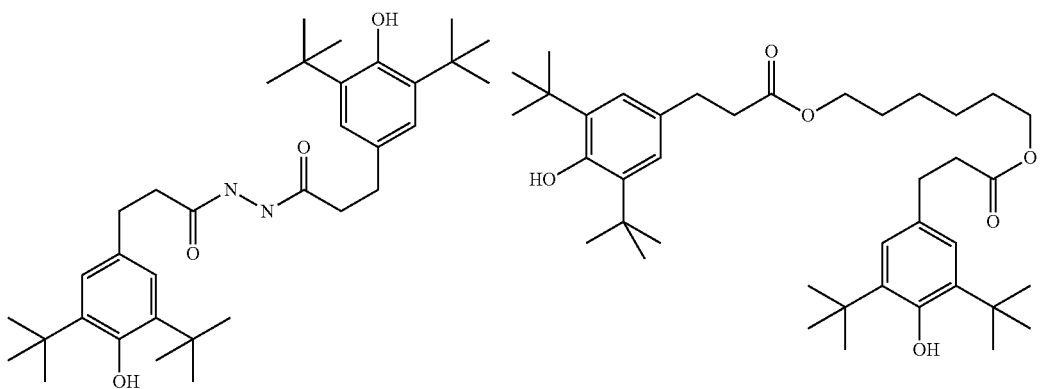
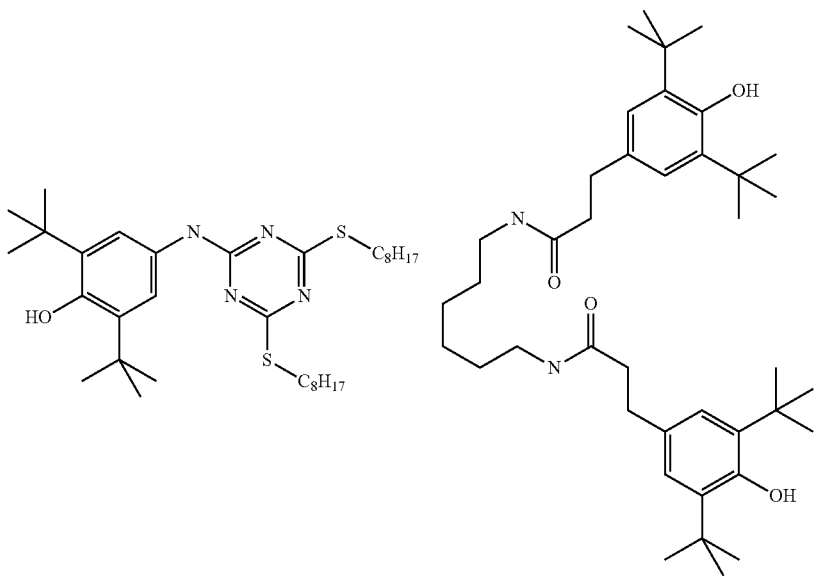
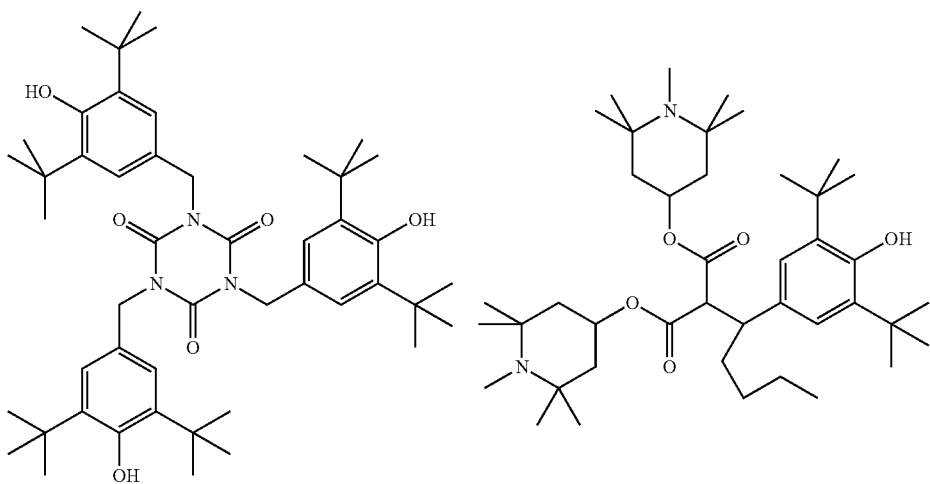

239 -continued 240
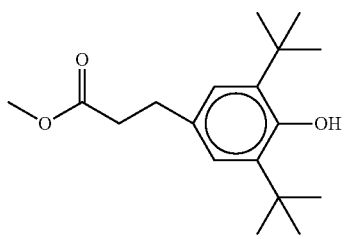 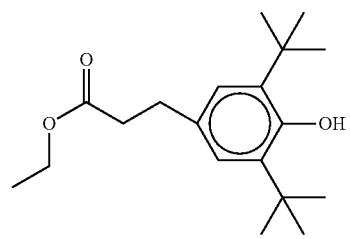 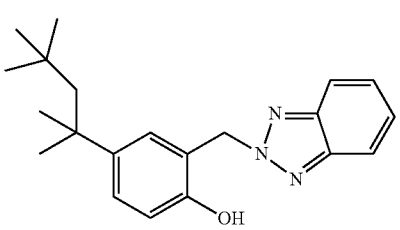
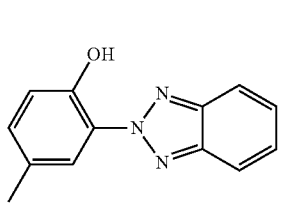 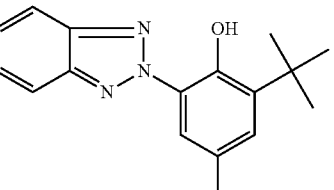 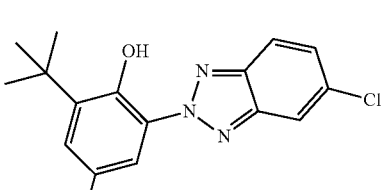
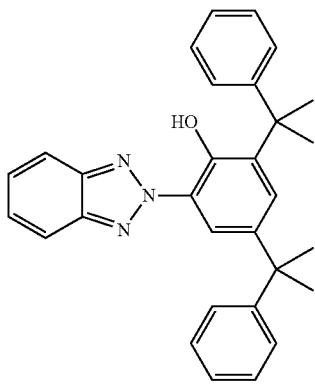 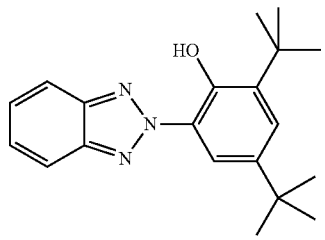 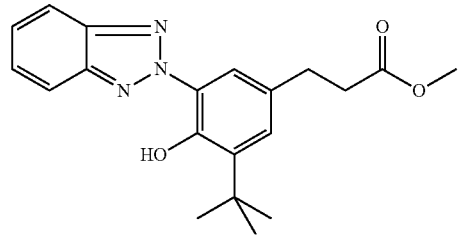
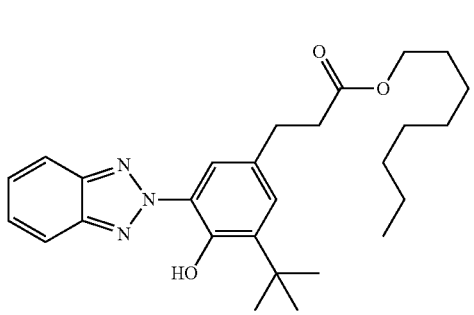 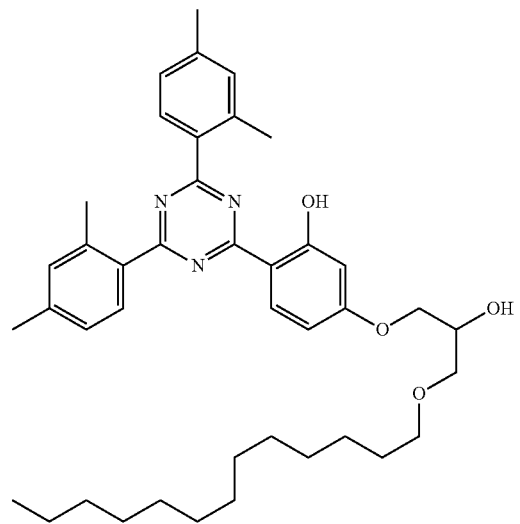

-continued
241
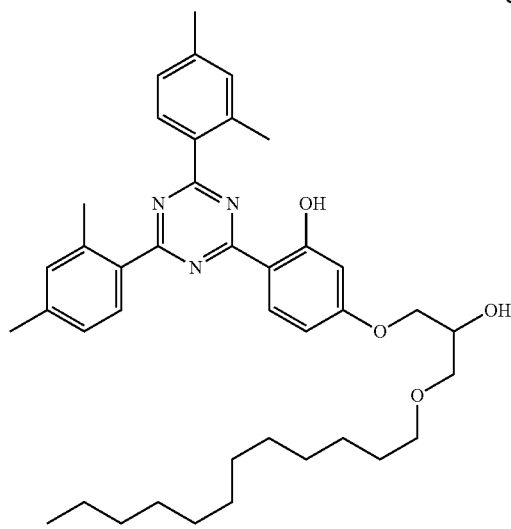
242
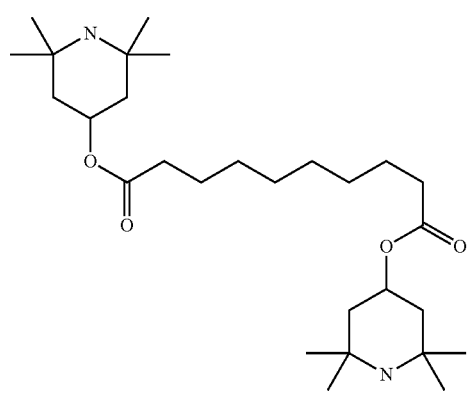
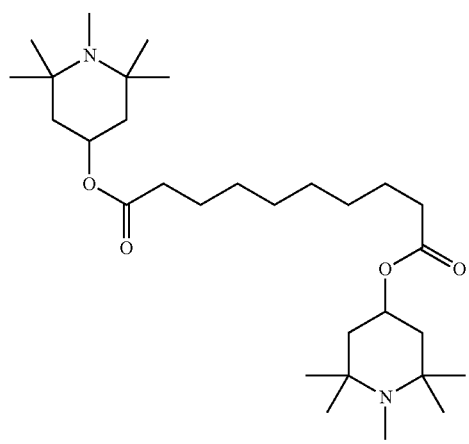
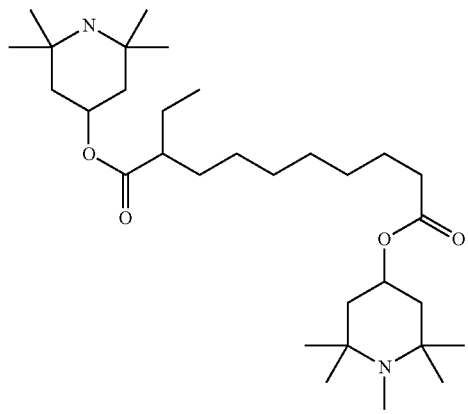
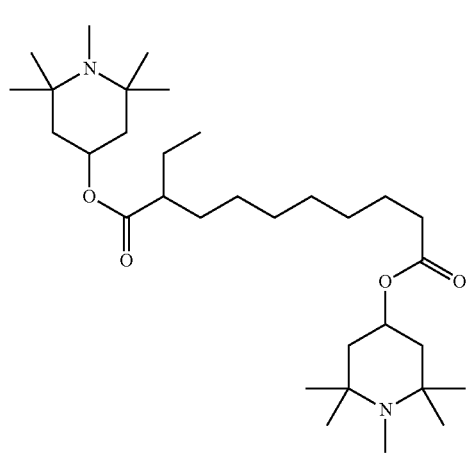
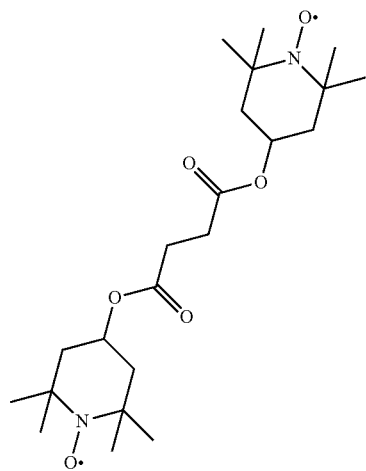

-continued
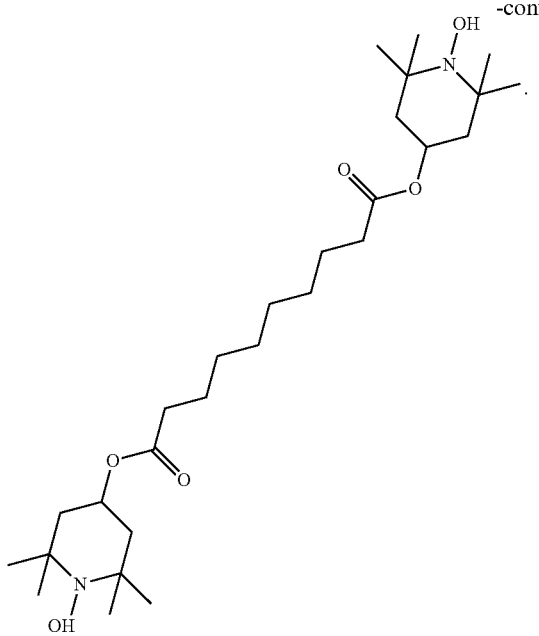
51. The liquid-crystalline medium according to claim 1, wherein said medium further comprises one or more reactive mesogenic compounds selected from the following formulae:
RM-1
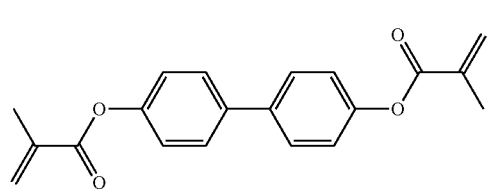
RM-2
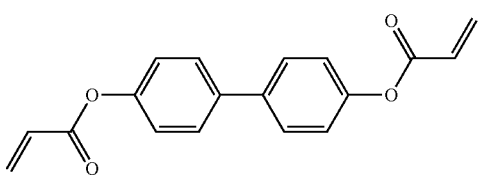
RM-3
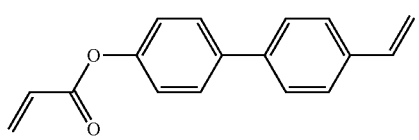
RM-4
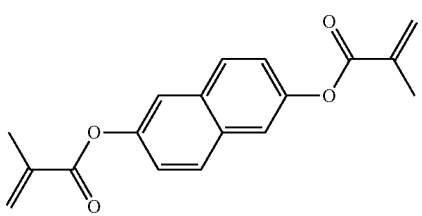
RM-5
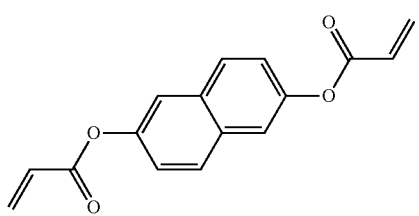
RM-6
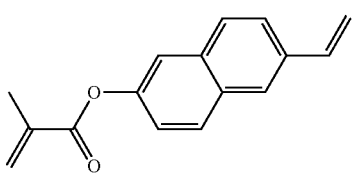
RM-7
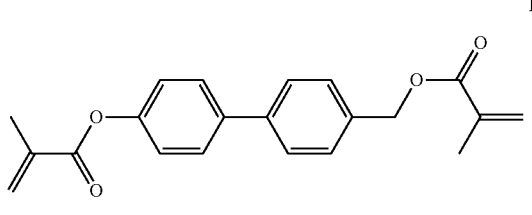
RM-8
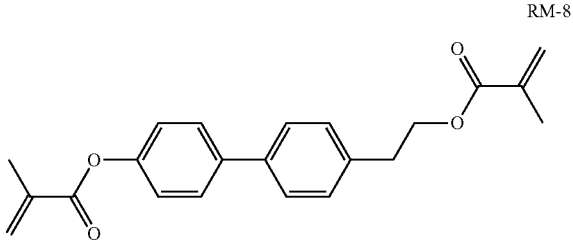

-continued
RM-9
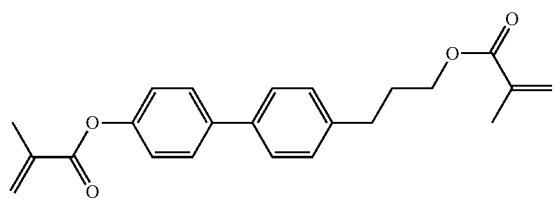
RM-10
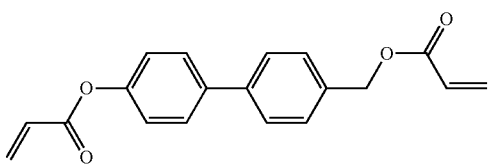
RM-11
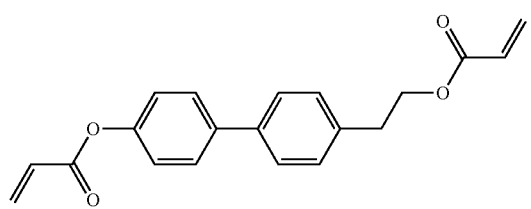
RM-12
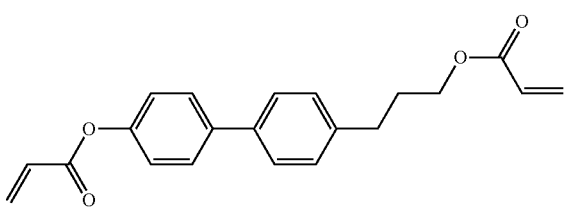
RM-13
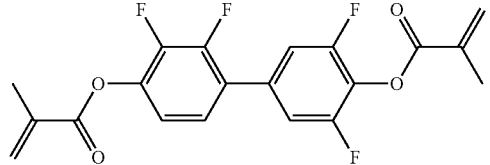
RM-14
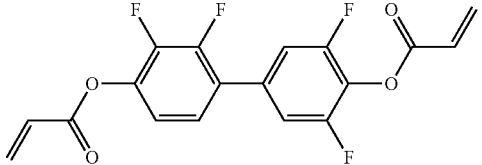
RM-15
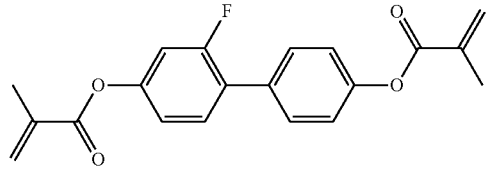
RM-16
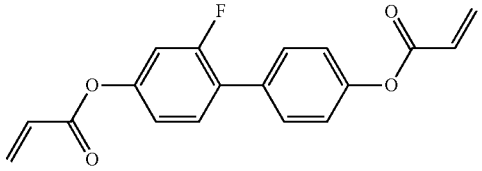
RM-17
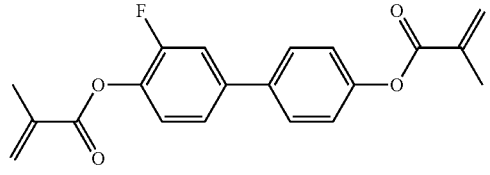
RM-18
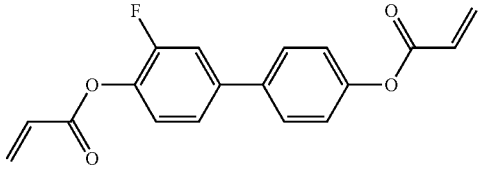
RM-19
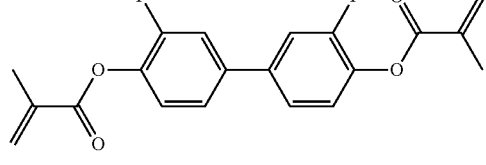
RM-20
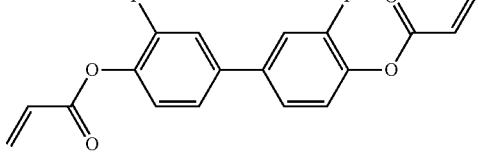
RM-21
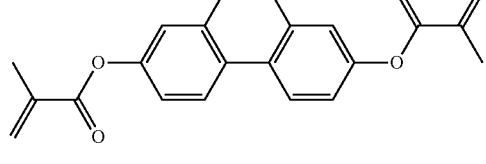
RM-22
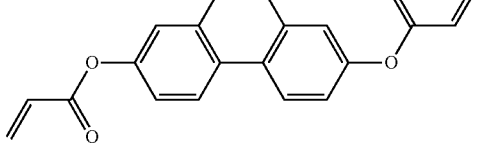
RM-23
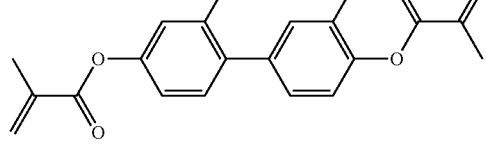
RM-24
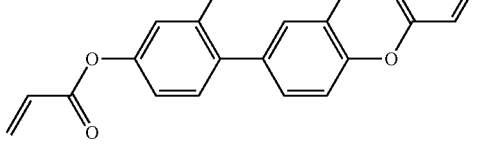

-continued
RM-25
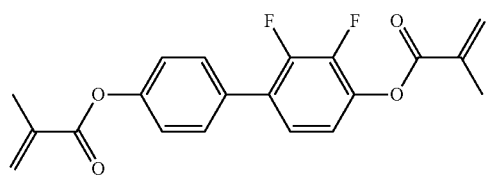
RM-26
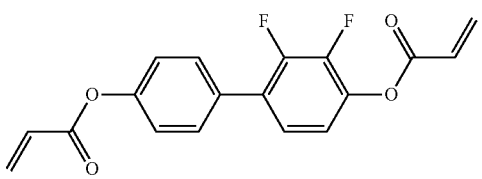
RM-27
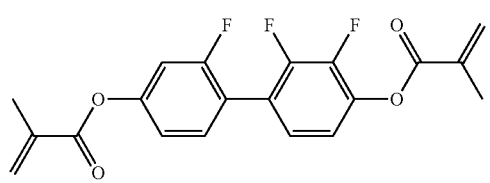
RM-28
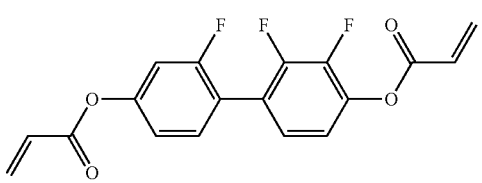
RM-29
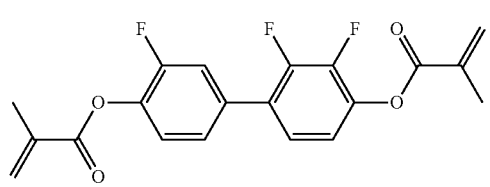
RM-30
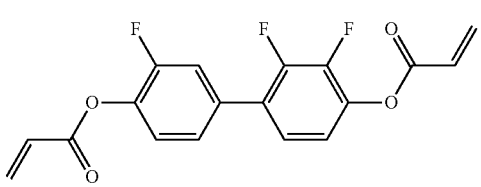
RM-31
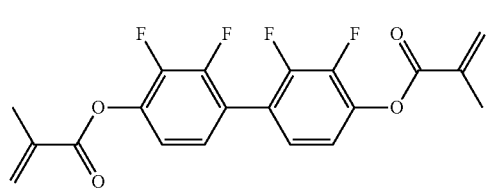
RM-32
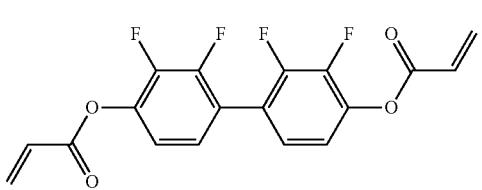
RM-33
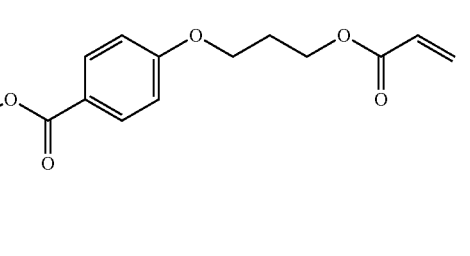
RM-34
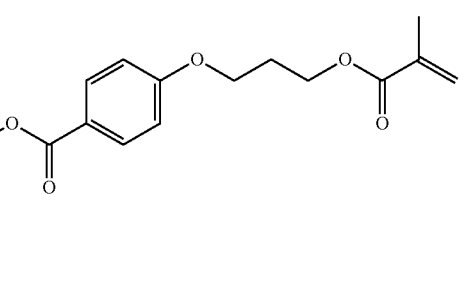
RM-35
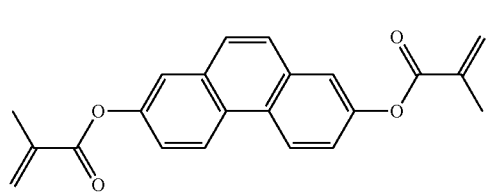
RM-36
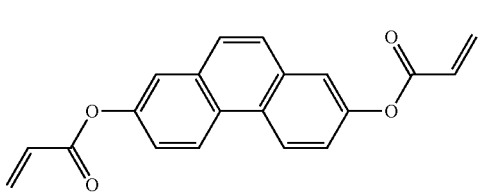

RM-37
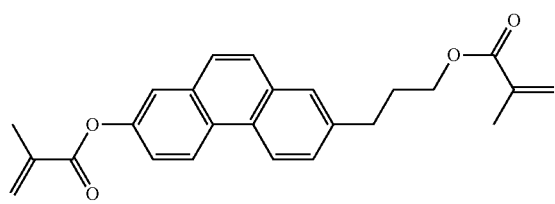
RM-38
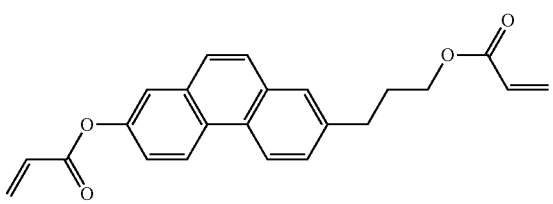
RM-39
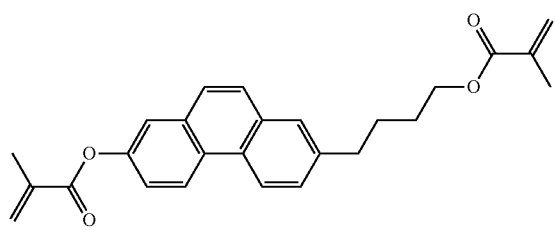
RM-40
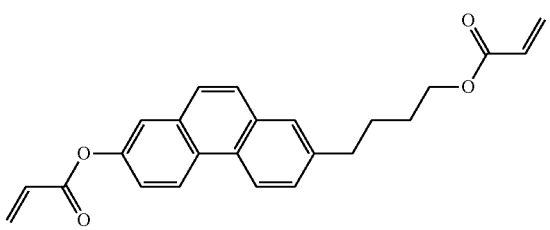
RM-41
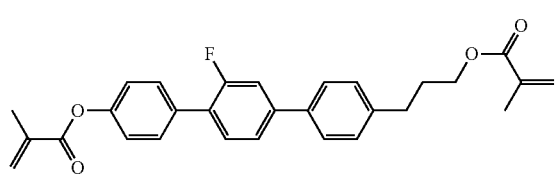
RM-42
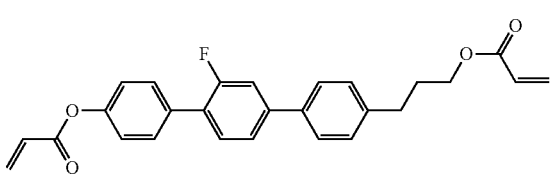
RM-43
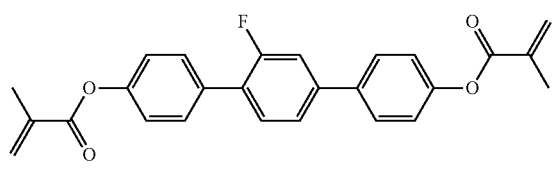
RM-44
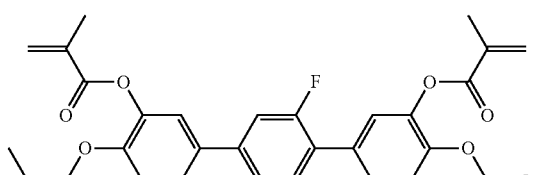
RM-45
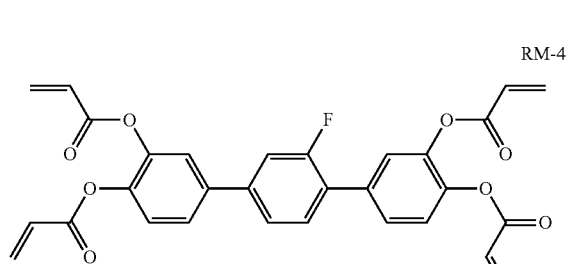
RM-46
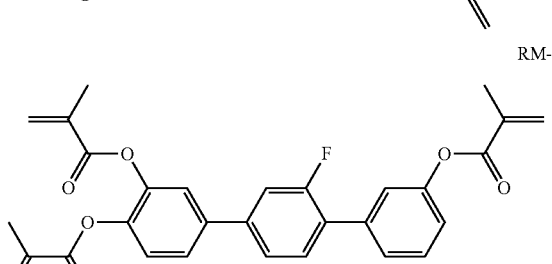
RM-47
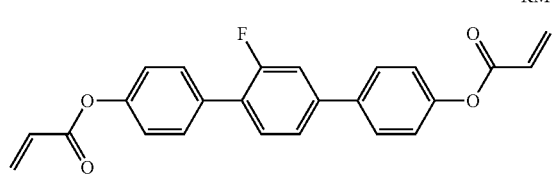
RM-48
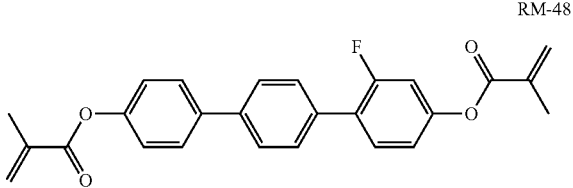
RM-49
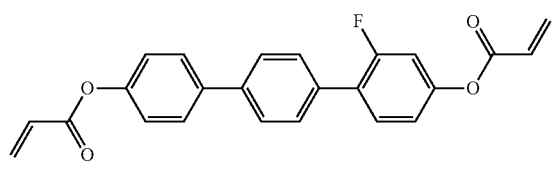
RM-50
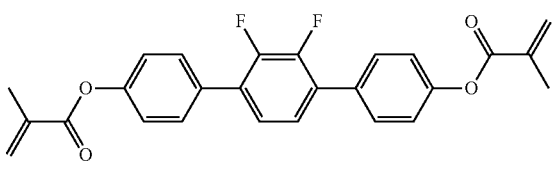

-continued
RM-51
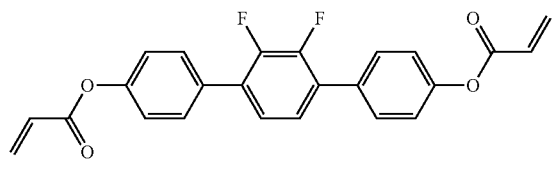
RM-52
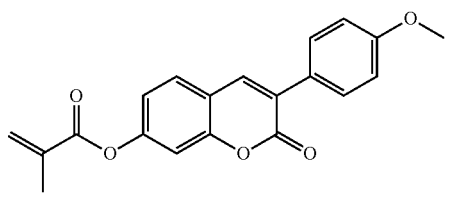
RM-53
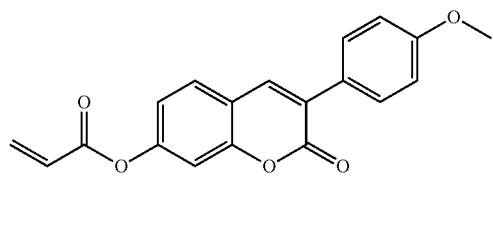
RM-54
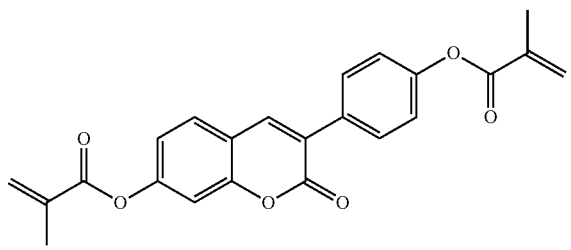
RM-55
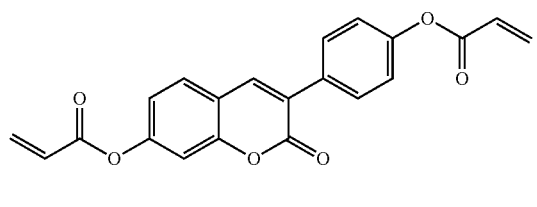
RM-56
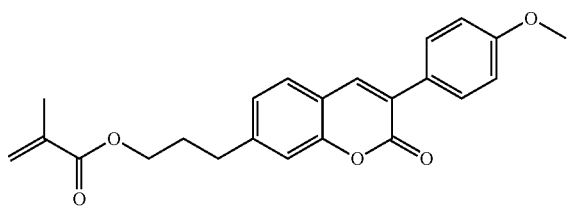
RM-57
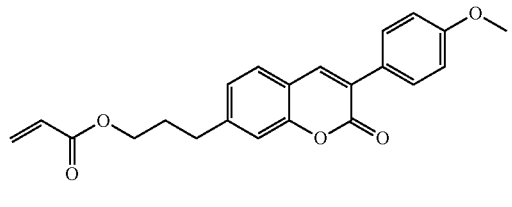
RM-58
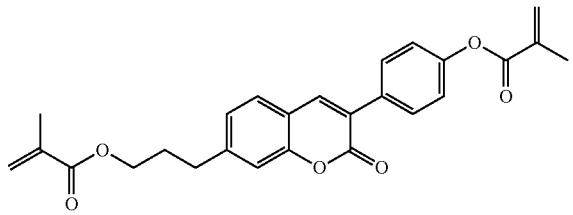
RM-59
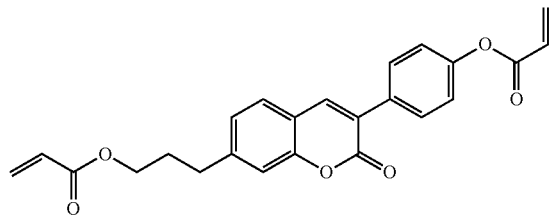
RM-60
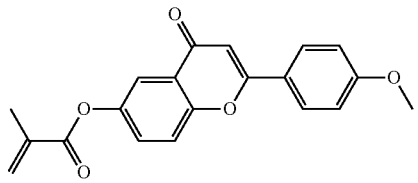
RM-61
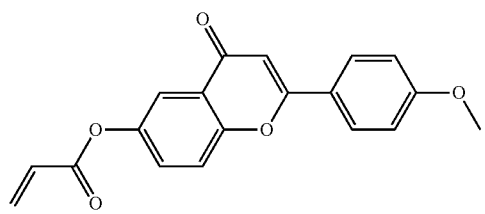
RM-62
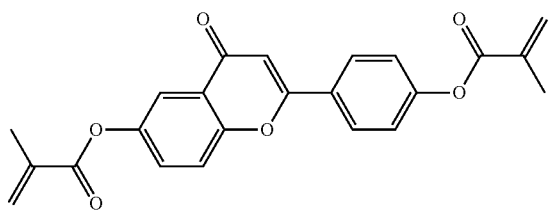

-continued
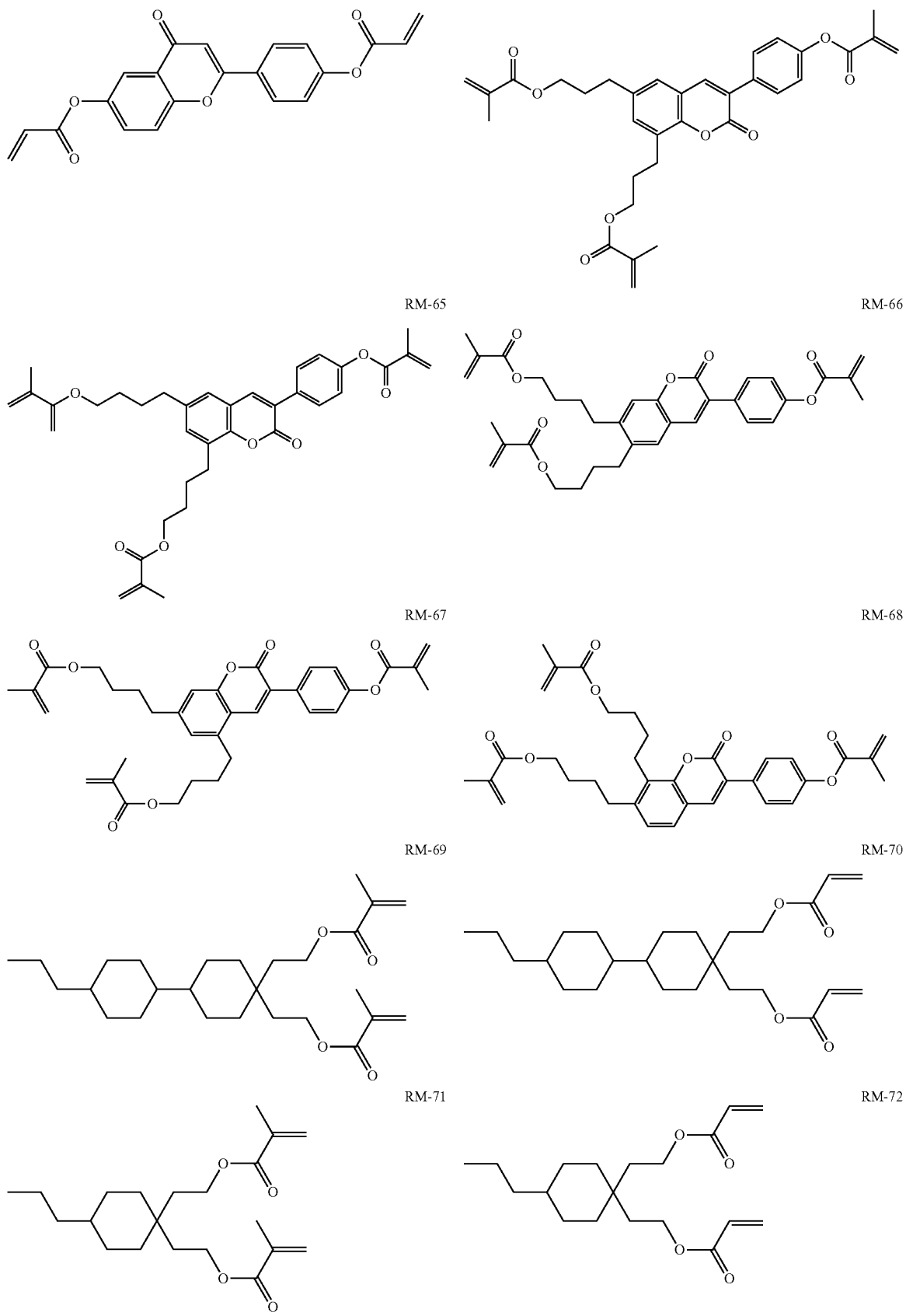

-continued
RM-73
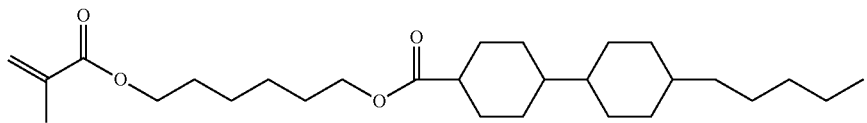
RM-74
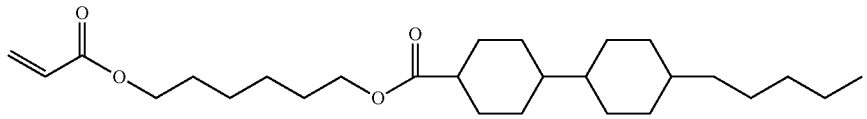
RM-75
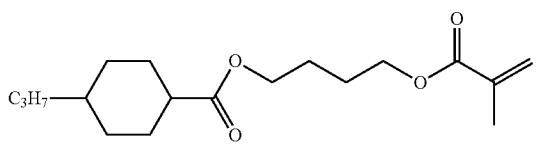
RM-76
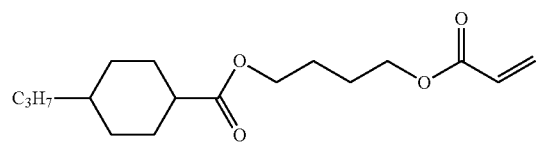
RM-77
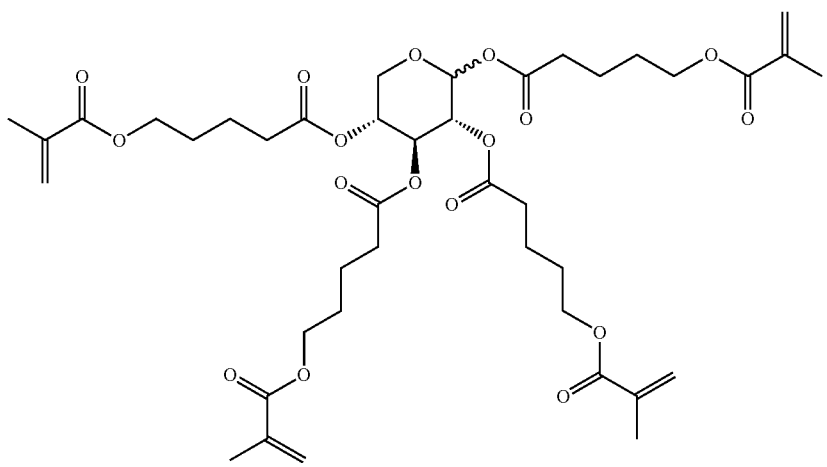
RM-78
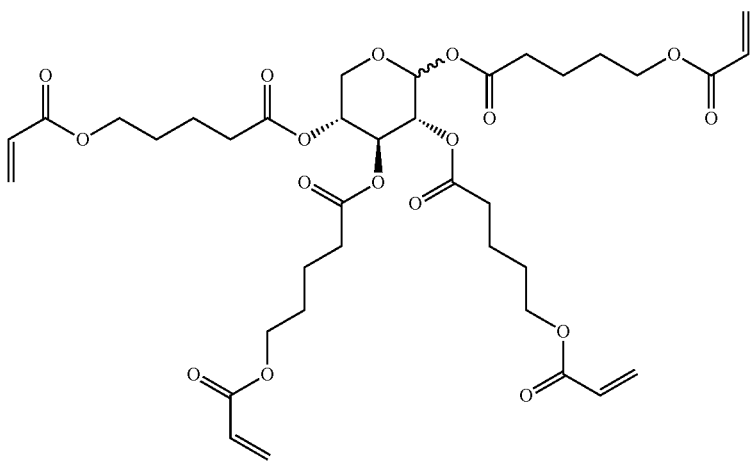

-continued
RM-79
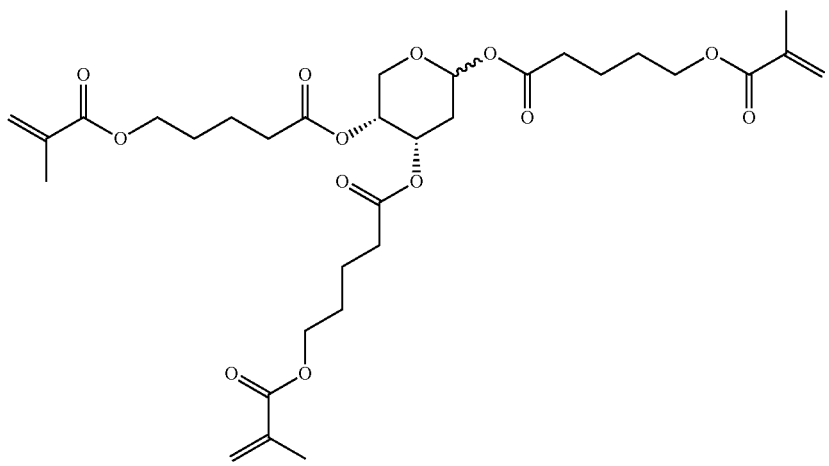
RM-80
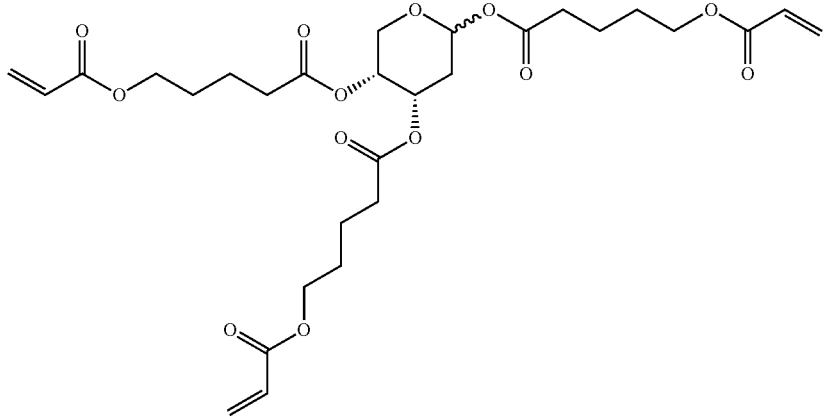
RM-81
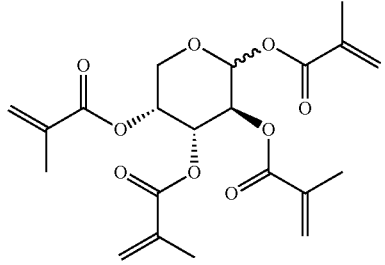
RM-82
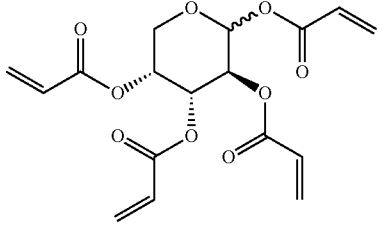
RM-83
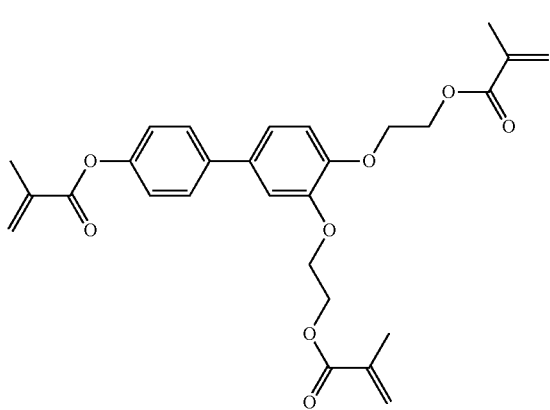
RM-84
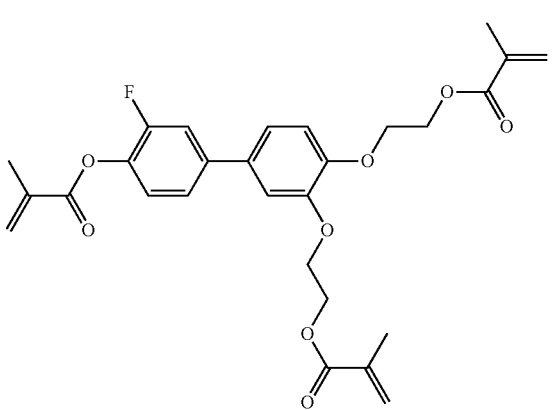

-continued
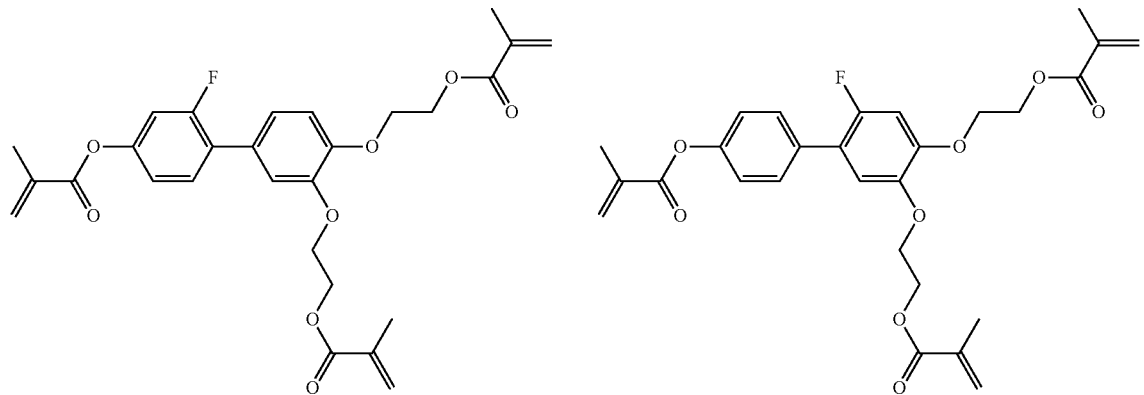
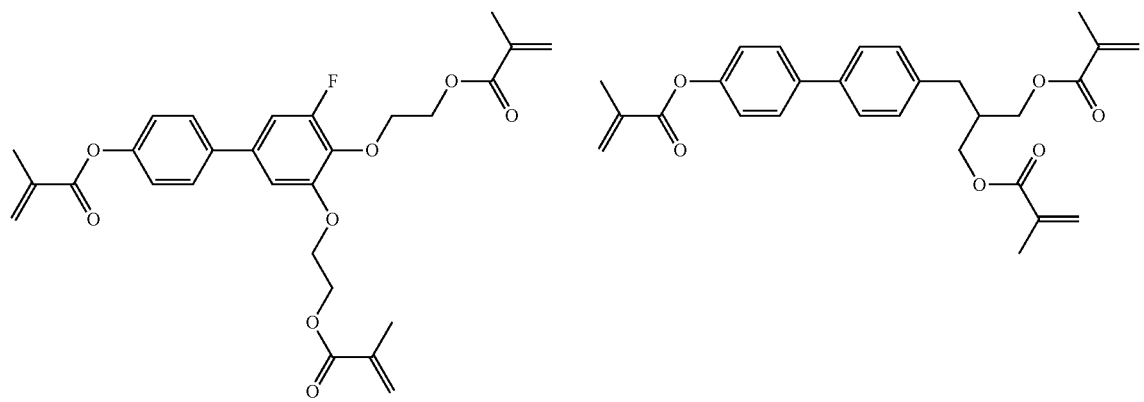
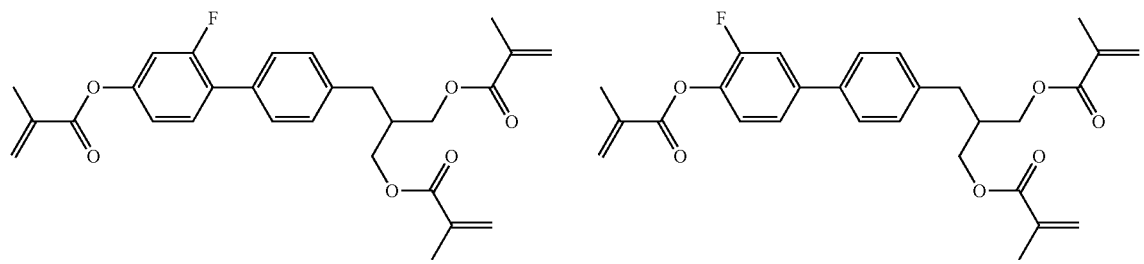
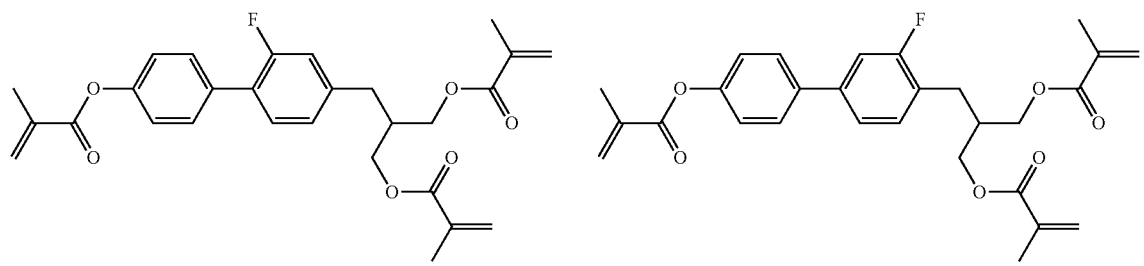

-continued

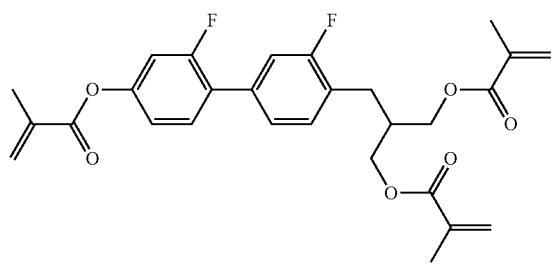
RM-93

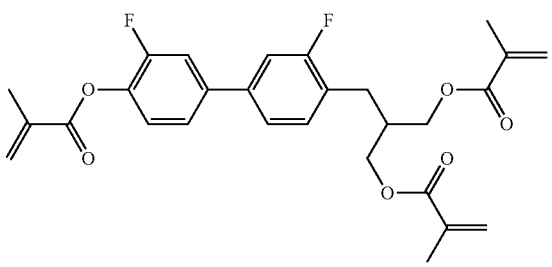
RM-94

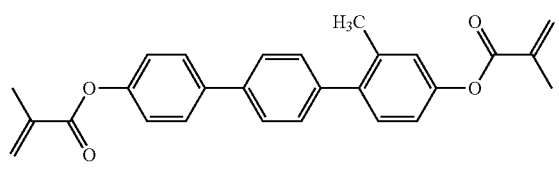
RM-95

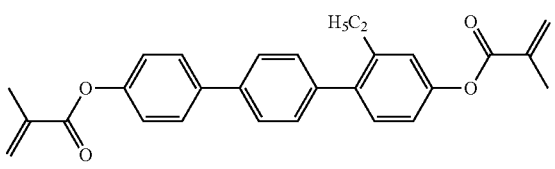
RM-96

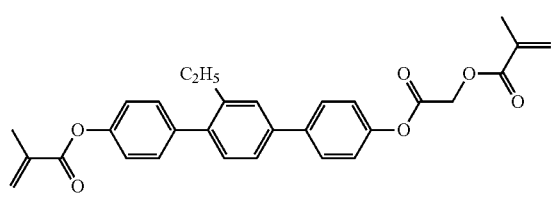
RM-97

RM-98

52. The liquid-crystalline medium according to claim 5, wherein the proportion of compounds of the formulae IIA and/or IIB in the medium as a whole is at least 20% by weight.

53. The liquid-crystalline medium according to claim 24, wherein said medium contains 5-25% by weight of at least one compound of formula IIC-1.

54. The liquid-crystalline medium according to claim 26, wherein said medium contains one or more compounds of the formulae B-1a, B-2a, B-2b, and B-2c

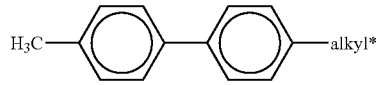
B-1a

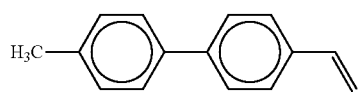
B-2a

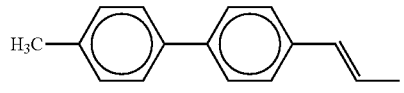
B-2b

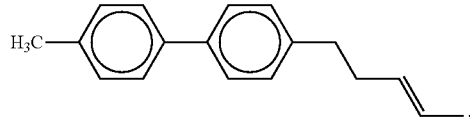
B-2c in which alkyl* denotes an alkyl radical having 1-6 C atoms.

55. The liquid-crystalline medium according to claim 26, wherein said medium contains one or more compounds of the formulae B-1a-1 and B-1a-2

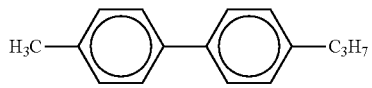
B-1a-1

B-2a-2

56. The liquid-crystalline medium according to claim 27, wherein said medium contains one or more compounds of the formula PP-n-m

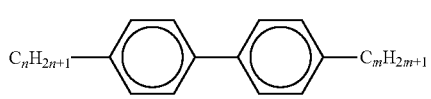
PP-n-m wherein n and m are each 1 to 6.

57. The liquid-crystalline medium according to claim 27, wherein said medium contains one or more compounds of the formula PP-n-2V1

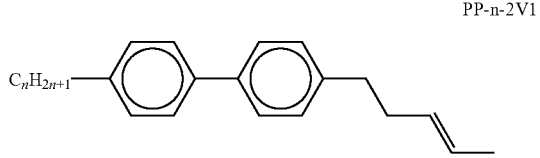
PP-n-2V1 where n and m are each 1 to 6.

* * * * *